US011883484B2

(12) United States Patent
Weiner et al.

(10) Patent No.: US 11,883,484 B2
(45) **Date of Patent: *Jan. 30, 2024**

(54) EXTREME POLYVALENCY INDUCES POTENT CROSS-CLADE CELLULAR AND HUMORAL RESPONSES IN RABBITS AND NON-HUMAN PRIMATES

(71) Applicants: THE TRUSTEES OF THE UNIVERSITY OF PENNSYLVANIA, Philadelphia, PA (US); THE WISTAR INSTITUTE OF ANATOMY AND BIOLOGY, Philadelphia, PA (US)

(72) Inventors: David Weiner, Merion, PA (US); Megan Wise, Raleigh, NC (US)

(73) Assignees: The Trustees of the University of Pennsylvania, Philadelphia, PA (US); The Wistar Institute of Anatomy and Biology, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/093,927

(22) Filed: Nov. 10, 2020

(65) Prior Publication Data

US 2021/0138061 A1 May 13, 2021

Related U.S. Application Data

(63) Continuation of application No. 15/705,549, filed on Sep. 15, 2017, now Pat. No. 10,828,363.

(60) Provisional application No. 62/395,803, filed on Sep. 16, 2016.

(51) Int. Cl.

| | |
|---|---|
| ***A61K 39/21*** | (2006.01) |
| ***C07K 14/005*** | (2006.01) |
| ***A61K 39/02*** | (2006.01) |
| *A61K 39/00* | (2006.01) |

(52) U.S. Cl.

CPC ............ *A61K 39/02* (2013.01); *C07K 14/005* (2013.01); *A61K 2039/53* (2013.01); *A61K 2039/54* (2013.01); *A61K 2039/545* (2013.01); *C12N 2740/16134* (2013.01); *C12N 2740/16171* (2013.01)

(58) Field of Classification Search

CPC .... A61K 39/12; A61K 39/21; A61K 2039/53; A61K 2039/70; A61P 31/18; A61P 31/14; C12N 2740/16111; C12N 2740/16134; C12N 2740/16122; C07K 14/005; C07K 16/32; C07K 16/10; C07K 16/1063; C07K 16/1081; C07K 2317/10; C07K 2317/55; C07K 2317/60; C07K 2317/76; C07K 2317/14; C07K 2317/21; C07K 14/05; C07K 14/705; C07K 2317/51; C07K 2317/522; C07K 2317/524; C07K 2317/526; C07K 2317/53; C07K 2317/56; C07K 2319/00; C07K 2319/02; C07K 14/1816; C07K 14/445; C07K 14/47; C07K 14/54; C07K 14/70514; C07K 14/723; C07K 14/78; C07K 16/2803; C07K 16/2809; C07K 16/2863; C07K 16/2866; C07K 16/2869; C07K 16/2878; C07K 16/3069; C07K 16/40; C07K 2317/31; C07K 2317/40; C07K 2317/52; C07K 2317/622; C07K 2317/732; C07K 2319/20; C07K 2319/30; C07K 2319/32; C07K 2319/42

See application file for complete search history.

(56) References Cited

U.S. PATENT DOCUMENTS

| | | | | |
|---|---|---|---|---|
| 8,071,107 | B2 | 12/2011 | Haynes | |
| 9,855,329 | B2 * | 1/2018 | Korber | A61K 45/06 |
| 10,828,363 | B1 * | 11/2020 | Weiner | A61K 39/21 |

OTHER PUBLICATIONS

Office Action dated Feb. 7, 2019 for U.S. Appl. No. 15/705,549 (pp. 1-7).

Long et al. AIDS Res. Human, Retrovirus 2002, vol. 18, pp. 567-576.

Office Action dated Jun. 28, 2019 for U.S. Appl. No. 15/705,549 (pp. 1-6).

Office Action dated Dec. 12, 2019 for U.S. Appl. No. 15/705,549 (p. 1-6).

Bowles et al., Comparison of Neutralizing Antibody Responses Elicited from Highly Diverse Polyvalent Heterotrimeric HIV-1 gp140 Cocktail Immunogens versus a Monovalent Counterpart in Rhesus Macaques, 2014, PLoS One 9:e114709.

Harper et al., Sustained Efficacy Up to 4.5 Years of a Bivalent L1 Virus-Like Particle Vaccine Against Human Papillomavirus Types 16 and 18: Follow-Up From a Randomised Control Trial, 2006, Lancet 367:1247-55.

Hirao et al., Comparative Analysis of Immune Responses Induced by Vaccination With SIV Antigens by Recombinant Ad5 Vector or Plasmid DNA in Rhesus Macaques, 2010, Mol Ther 18:1568-76.

Joura et al., A 9-valent HPV Vaccine Against Infection and Intraepithelial Neoplasia in Women, 2015, NEJM 372:711-23.

Kwong and Mascola, Human Antibodies That Neutralize HIV-1: Identification, Structures, and B Cell Ontogenies, 2012, Immunity 37:412-5.

Lee et al., Cryo-EM Structure of a Native, Fully Glycosylated, Cleaved HIV-1 Envelope Trimer, 2016, Science 351:1043-8.

Liao et al., A Group M Consensus Envelope Glycoprotein Induces Antibodies That Neutralize Subsets of Subtype B and C HIV-1 Primary Viruses, 2006, Virology 353:268-82.

Li et al., Genetic and neutralization properties of subtype C human immunodeficiency virus type 1 molecular env clones from acute and early heterosexually acquired infections in Southern Africa, 2006, J Virol 80:11776-90.

(Continued)

*Primary Examiner* — Bao Q Li

(74) *Attorney, Agent, or Firm* — Riverside Law LLP

(57) ABSTRACT

The present invention relates to compositions comprising two or more DNA plasmids encoding consensus and transmitted founder HIV envelope glycoproteins which expressed and induce a potent immune response.

20 Claims, 25 Drawing Sheets

Specification includes a Sequence Listing.

(56) References Cited

OTHER PUBLICATIONS

Li et al, Human immunodeficiency virus type 1 env clones from acute and early subtype B infections for standardized assessments of vaccine-elicited neutralizing antibodie 2005 J. Virol 79(16):10108-25.
Mao et al., Molecular architecture of the uncleaved HIV-1 envelope glycoprotein trimer, 2013, PNAS 110:12438-43.
Munro and Mothes, Structure and Dynamics of the Native HIV-1 Env Trimer, 2015, J Virol 89:5752-5.
Muthumani et al., "HIV-1 Env DNA Vaccine plus Protein Boost Delivered by EP Expands B- and T-Cell Responses and Neutralizing Phenotype In Vivo.", PLoS On e, (Dec. 31, 2013), vol. 8, No. 12, p. e84234.
Ortqvist et al., Randomised trial of 23-valent pneumococcal capsular polysaccharide vaccine in prevention of pneumonia in middle-aged and elderly people, 1998, Lancet 351:399-403.
Osterholm et al., Efficacy and effectiveness of influenza vaccines: a systematic review and meta-analysis, 2012, Lancet Infect Dis 12:36-44.
Paavoen et al., Efficacy of Human Papillomavirus (HPV)-16/18 AS04-adjuvanted Vaccine Against Cervical Infection and Precancer Caused by Oncogenic HPV Types (PATRICIA): Final Analysis of a Double-Blind, Randomised Study in Young Women, 2009, Lancet 374:301-14.
Santra et al., A centralized gene-based HIV-1 vaccine elicits broad cross-clade cellular immune responses in rhesus monkeys, 2008, PNAS 105:10489-94.
Sardesai and Weiner, Electroporation Delivery of DNA Vaccines: Prospects for Success, 2011, Curr Opin Immunol 23:421-9.
Sellhorn et al., Engineering, Expression, Purification, and Characterization of Stable Clade A/B Recombinant Soluble Heterotrimeric gp140 Proteins, 2012, J Virol 86:128-42.
Weaver et al., Cross-Subtype T-Cell Immune Responses Induced by a Human Immunodeficiency Virus Type 1 Group M Consensus Env Immunogen, 2006, J Virol 80:6745-56.
Wilen et al., Phenotypic and Immunologic Comparison of Clade B Transmitted/Founder and Chronic HIV-1 Envelope Glycoproteins, 2011, J Virol 85:8514-27.
Wise et al., An Enhanced Synthetic Multiclade DNA Prime Induces Improved Cross-Clade-Reactive Functional Antibodies when Combined with an Adjuvanted Protein Boost in Nonhuman Primates, 2015, J Virol 89:9154-66.
Yan et al., Immunogenicity of a Novel Engineered HIV-1 Clade C Synthetic Consensus-Based Envelope DNA Vaccine, 2011, Vaccine 29:7173-81.
Notice of Allowance dated Jun. 30, 2020 for U.S. Appl. No. 15/705,549 (pp. 1-9).

* cited by examiner

| Plasmid | Expression (%) |
|---|---|
| A1 | 14.9 |
| A2 | 12.9 |
| A3 | 13.5 |
| A4 | 15.4 |
| A5 | 10.6 |
| A6 | 3.16 |

| Plasmid | Expression (%) |
|---|---|
| B1 | 17.8 |
| B2 | 14.7 |
| B3 | 9.90 |
| B4 | 26.4 |
| B5 | |
| B6 | 13.6 |
| B7 | 14.0 |
| B8 | |
| B9 | |
| B10 | 14.1 |

| plasmid | Expression (%) |
|---|---|
| C1 | 16.6 |
| C2 | 13.3 |
| C3 | 15.3 |
| C4 | 14.5 |
| C5 | 2.85 |
| C6 | 5.62 |
| C7 | 5.50 |
| C8 | 12.4 |
| C9 | 14.7 |
| C10 | 12.4 |
| C11 | 12.6 |

A Week
0
3
6
9
12
pA1, A2, A3, A4, A5, A6
pC1, C3, C5, C6, C7
pB1, B2, B5, B6, B7
pC2, C4, C8, C9, C10, C11
B
Clade A
Clade B
Clade C
Endpoint titers to gp120 92RW020
Endpoint titer to gp120 SF162
Endpoint titer to gp120 ZM197
weeks
C
ID50 Titer
Weeks
MN.3
MW965.26
Q23.17

A Week
0
3
6
9
12
pA1, A2, A3, A4, A5, A6
pA1, A2, A3, A4, A5, A6
pB3, B4, B8, B9
pB1, B2, B5, B6, B7
B
Clade A
Clade B
Clade C
Endpoint titers to gp120 92RW020
Endpoint titer to gp120 SF162
Endpoint titer to gp120 ZM197
weeks
C
ID50 Titer
Weeks
MN.3
MW965.26
Q23.17

Mixing of plasmids together drives binding titers against peptides from the V3 region of gp160.

| Name | Insert | Clade | Tier | Accession # | Transmission | Stage |
|---|---|---|---|---|---|---|
| A1 | Q769ENVd22 | A | 2 | AF407158 | FSW | acute early |
| A2 | Q168ENVe2 | A | 2 | AF407148 | FSW | acute early |
| A3 | Q842ENVd12 | A | 2 | AF407160 | FSW | acute early |
| A4 | Q461ENVe2 | A | 2 | AF407156 | FSW | acute early |
| A5 | Q23ENV17 | A | 2 | AF004885 | FSW | Fiebig IV |
| A6 | Q259d2.17 | A | 2 | AF407152 | FSW | acute early |
| B1 | WITO4160.33 | B | 2 | AY835451 | F-M | Fiebig II |
| B2 | REJO4541.67 | B | 2 | AY835449 | F-M | Fiebig II |
| B3 | RHPA4259.7 | B | 2 | AY835447 | | Fiebig < V |
| B4 | TRJO4551.58 | B | 3 | AY835450 | M-M | Fiebig II |
| B5 | CAAN5342.A2 | B | 2 | AY835452 | M-M | |
| B6 | PVO.4 | B | 3 | AY83544 | M-M | Fiebig III |
| B7 | TRO.11 | B | 2 | AY835445 | M-M | Fiebig III |
| B8 | AC10.0.29 | B | 2 | AY835446 | M-M | Fiebig III |
| B9 | QHO692.42 | B | 2 | AY835439 | F-M | Fiebig V |
| C1 | Cap45.2.00.G3 | C | 2 | DQ435682 | FSW | |
| C2 | Cap210.2.00.E8 | C | 2 | DQ435683 | FSW | |
| C3 | Du422.1 | C | 2 | DQ411854 | FSW | Fiebig V |
| C4 | ZM53M.PB12 | C | 2 | AY423984 | F-M | |
| C5 | ZM233M.PB6 | C | 2 | DQ388517 | F-M | |
| C6 | ZM249M.PL1 | C | 2 | DQ388514 | F-M | |
| C7 | ZM214M.PL15 | C | 2 | DQ388516 | F-M | |
| C8 | Du123.6 | C | 2 | DQ411850 | FSW | Fiebig VI |
| C9 | Du151.2 | C | 2 | DQ411851 | FSW | Fiebig V |
| C10 | Du156.12 | C | 2 | DQ411852 | FSW | Fiebig <IV |
| C11 | Du172.17 | C | 2 | DQ411853 | FSW | Fiebig VI |

Figure 24

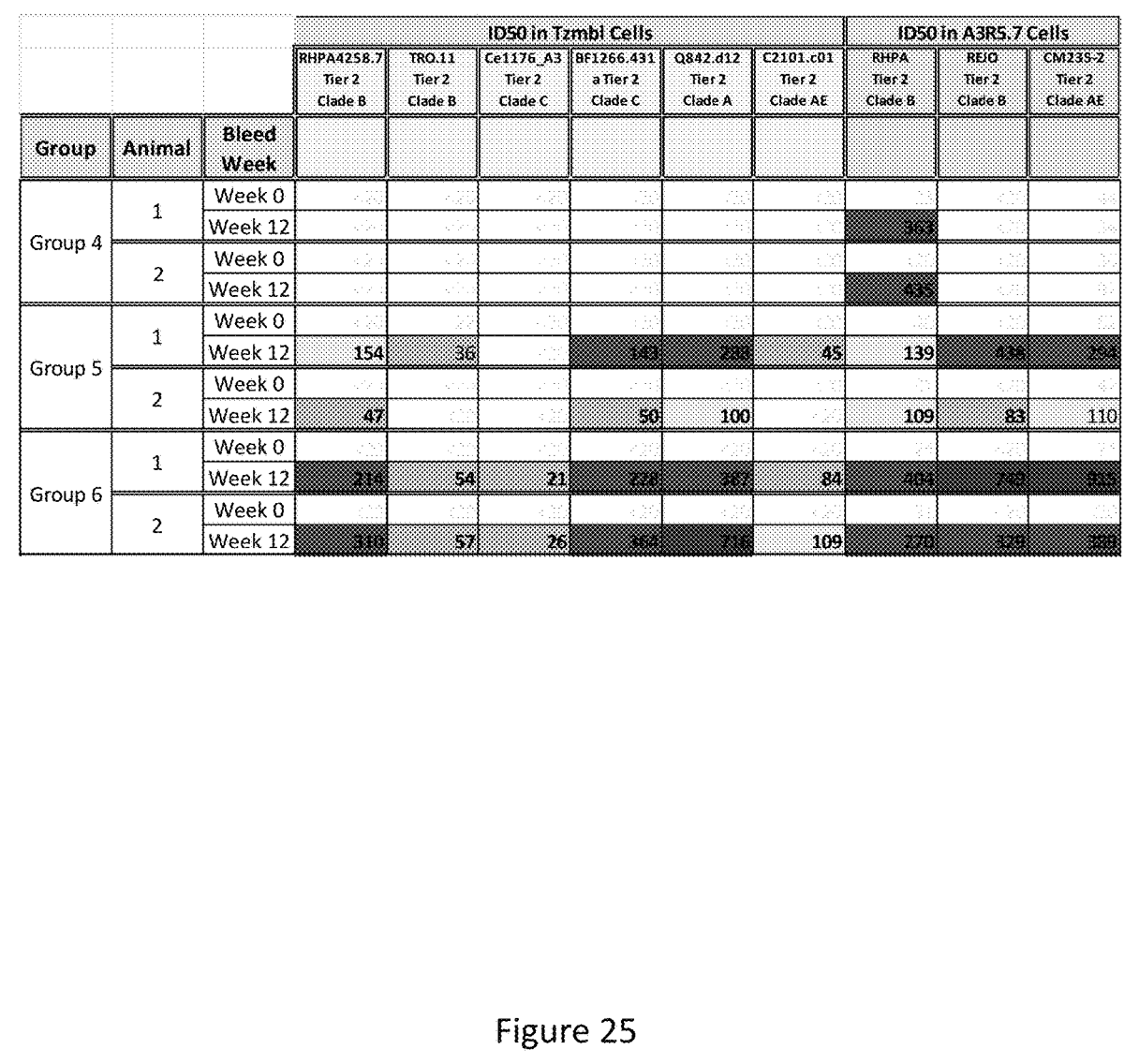

| | | | ID50 in Tzmbl Cells | | | | | | ID50 in A3R5.7 Cells | | |
|---|---|---|---|---|---|---|---|---|---|---|---|
| | | | RHPA4258.7 Tier 2 Clade B | TRO.11 Tier 2 Clade B | Ce1176_A3 Tier 2 Clade C | BF1266.431 a Tier 2 Clade C | Q842.d12 Tier 2 Clade A | C2101.c01 Tier 2 Clade AE | RHPA Tier 2 Clade B | REJO Tier 2 Clade B | CM235-2 Tier 2 Clade AE |
| **Group** | **Animal** | **Bleed Week** | | | | | | | | | |
| Group 4 | 1 | Week 0 | | | | | | | | | |
| | | Week 12 | | | | | | | 363 | | |
| | 2 | Week 0 | | | | | | | | | |
| | | Week 12 | | | | | | | 435 | | |
| Group 5 | 1 | Week 0 | | | | | | | | | |
| | | Week 12 | 154 | 36 | | 143 | 288 | 45 | 139 | 438 | 294 |
| | 2 | Week 0 | | | | | | | | | |
| | | Week 12 | 47 | | | 50 | 100 | | 109 | 83 | 110 |
| Group 6 | 1 | Week 0 | | | | | | | | | |
| | | Week 12 | 214 | 54 | 21 | 228 | 387 | 84 | 404 | 740 | 915 |
| | 2 | Week 0 | | | | | | | | | |
| | | Week 12 | 310 | 57 | 26 | 464 | 716 | 109 | 270 | 320 | 380 |

Figure 25

EXTREME POLYVALENCY INDUCES POTENT CROSS-CLADE CELLULAR AND HUMORAL RESPONSES IN RABBITS AND NON-HUMAN PRIMATES

CROSS-REFERENCE TO RELATED APPLICATIONS

The present application is a continuation of U.S. patent application Ser. No. 15/705,549, filed Sep. 15, 2017, which is entitled to priority under 35 U.S.C § 119(e) to U.S. Provisional Patent Application No. 62/395,803, filed Sep. 16, 2016, each of which applications are incorporated by reference herein in their entireties.

FIELD OF THE INVENTION

The present invention relates to treating and preventing symptoms of an HIV associated infection using a priming vaccine containing a DNA encoding the antigen, and a second vaccine for boosting the response to the first vaccine using the same or different antigen than the first vaccine.

BACKGROUND OF THE INVENTION

A major obstacle for vaccine development is the diversity of HIV and creating an immunogen that is able to produce responses which will be broad enough to encompass the global or even regional diversity of the virus. Consensus immunogens have displayed considerable potential in driving T cell responses which exhibit cross clade reactivity when compared to wild-type HIV immunogens (Muthumani et al., 2013, PLoS One 8:e84234; Yan et al., 2011, Vaccine 29:7173-81; Wise et al., 2015, J Virol 89:9154-66; Liao et al., 2006, Virology 353:268-82; Weaver et al., 2006, J Virol 80:6745-56; Santra et al., 2008, PNAS 105:10489-94). However, this coverage is limited to cellular responses and fails to induce a potent and broad neutralizing antibody response. Recently, it has been reported that guinea pigs vaccinated with transmitted founder gp140 Envelope proteins are able to induce low but broad neutralizing antibodies to both tier 1 and tier 2 viruses (Liao et al., 2013, J Virol 87:4185-201). This general induction of coverage may be ideal for a priming immunization, establishing a response which is able to be boosted with the addition of either chronic or consensus Envelopes.

Given the above requirement, DNA vaccination may be the optimal platform for a successful HIV vaccine. Advances in technology including codon and RNA optimization as well as electroporation, can induce anti-HIV cellular responses comparable with viral vectors (Hirao et al., 2010, Mol Ther 18:1568-76). In addition, this platform would allow for the expression of full length gp160 protein and could allow for the presentation of the native trimer to the immune system. Cryo-EM structures of Envelopes have highlighted the differences between gp120 and gp140 structures and the potential for off target effects if the proper immunogen is not provided (Lee et al., 2016, Science 351:1043-8; Mao et al., 2013, PNAS 110:12438-43; Munro and Mothes, 2015, J Virol 89:5752-5). DNA vaccination also allows for multiple difference plasmids to be delivered simultaneously, increasing the coverage of the immunization. However, while DNA vaccines against HIV are able to induce potent cellular immunity, antibody titers have remained low, and they are limited in functional antibody titers, and usually require a boost.

There is a need in the art for DNA vaccines which induce both binding and neutralizing antibodies. The present invention addresses this unmet need in the art.

SUMMARY OF THE INVENTION

In one embodiment, the invention provides a composition comprising two or more nucleic acid molecules encoding an HIV immunogen, wherein each nucleic acid has a sequence independently selected from the group consisting of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a fragment of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a sequence that is 90% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a fragment of a sequence that is 90% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, one of SEQ ID NOs: SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61 linked to a nucleic acid encoding an IgE signal peptide, a fragment of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61 linked to a nucleic acid encoding an IgE signal peptide, a sequence that is 90% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61 linked to a nucleic acid encoding an IgE signal peptide, and a fragment of a sequence that is 90% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61 linked to a nucleic acid encoding an IgE signal peptide.

An aspect of the invention provides various immunogenic antigens of HIV selected from one or more of: Env Clade A, Env Clade B, or Env Clade C. In some embodiments the Env proteins can be selected from the following: SEQ ID NOs: 2, 4, 6, 8, 10, 12, 14, 16, 18, 20, 22, 24, 26, 28, 30, 32, 34, 36, 38, 40, 42, 44, 46, 52, 54, 56, 58, 60, or 62. In some embodiments, the vaccination of a subject can further include a HIV pol antigen, for example SEQ ID NO:48, or fragments thereof.

In one aspect, provided are various encoding nucleotide sequences that encode Env selected from one or more of: encoding sequences of Env Clade A, encoding sequences of Env Clade B, or encoding sequences of Env Clade C. The encoding sequences of Env can be selected from the following: SEQ ID NOs:1, 3, 5, 7, 9, 11, 13, 15, 17, 19, 21, 23, 25, 27, 29, 31, 33, 35, 37, 39, 41, 43, 45, 51, 53, 55, or 57; or nucleotide sequences that encode SEQ ID NOs: 2, 4, 6, 8, 10, 12, 14, 16, 18, 20, 22, 24, 26, 28, 30, 32, 34, 36, 38, 40, 42, 44, 46, 52, 54, 56, 58, 60, or 62.

In one embodiment, each nucleic acid has a sequence independently selected from the group consisting of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a fragment of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a sequence that is 95% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a fragment of a sequence that is 95% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61 linked to a nucleic acid encoding an IgE signal peptide, a fragment of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61 linked to a nucleic acid encoding an IgE signal peptide, a sequence that is 95% homologous to one of S SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61 linked to a nucleic acid encoding an IgE signal peptide, and a fragment of a sequence that is 95% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61 linked to a nucleic acid encoding an IgE signal peptide.

In one embodiment, each nucleic acid has a sequence independently selected from the group consisting of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a fragment of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a sequence that is 99% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a fragment of a sequence that is 99% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61 linked to a nucleic acid encoding an IgE signal peptide, a fragment of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61 linked to a nucleic acid encoding an IgE signal peptide, a sequence that is 99% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61 linked to a nucleic acid encoding an IgE signal peptide, and a fragment of a sequence that is 99% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61 linked to a nucleic acid encoding an IgE signal peptide.

In one embodiment, each nucleic acid has a sequence independently selected from the group consisting of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a fragment of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61 linked to a nucleic acid encoding an IgE signal peptide, and a fragment of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61 linked to a nucleic acid encoding an IgE signal peptide.

In one embodiment, the composition comprises 3 or more nucleic acid molecules. In one embodiment, the composition comprises 6 or more nucleic acid molecules. In one embodiment, the composition comprises 10 or more nucleic acid molecules. In one embodiment, the composition comprises 14 or more nucleic acid molecules.

In one embodiment, the composition comprises two or more plasmids, wherein each plasmid comprises only one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61.

In one embodiment, the composition of the invention is formulated for delivery to a subject using electroporation.

In another aspect, the invention provides a method of immunizing a subject in need thereof against HIV, the method comprising administering a first vaccine comprising one or more nucleic acid having a sequence independently selected from SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a variant thereof or a fragment thereof.

In one embodiment, the method comprises administering a second vaccine comprising one or more nucleic acid having a sequence independently selected from SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a variant thereof or a fragment thereof.

In one embodiment, the method comprises administering a third vaccine comprising one or more nucleic acid having a sequence independently selected from SEQ ID NOs: 1, 3, 5, 7, 9, 11, 13, 15, 17, 19, 21, 23, 25, 27, 29, 31, 33, 35, 37, 39, 41, 43, 45, 51, 53, 55, 57, or R 59-60, a variant thereof or a fragment thereof.

In one embodiment, the first vaccine is administered intradermally. In one embodiment, the second vaccine is administered intradermally. In one embodiment, the third vaccine is administered intramuscularly.

In one embodiment, the first vaccine is administered twice. In one embodiment, the second vaccine is administered twice. In one embodiment, the third vaccine is administered twice.

In another aspect, the invention provides a method of preventing HIV infection in an individual comprising administering a prophylactically effective amount of the composition of the invention.

BRIEF DESCRIPTION OF THE DRAWINGS

FIG. 1, comprising

FIG. 2, comprising (FIG. 2A) Guinea pigs were immunized with 25 μg of each plasmid ID followed by electroportation. (FIG. 2B) Binding titers against consensus clade A gp120. Individual titers are denoted in the shapes and geometric mean titers by the horizontal bar.

FIG. 3, comprising (FIG. 3A) Rabbits were immunized with 600 μg of each envelope construct ID followed by electroporation every three weeks for a total of 6 immunizations. (FIG. 3B) Binding titers against clade A (92RW020), clade B (SF162) and clade C (ZM197) primary gp120s. Individual titers are denoted in the shapes and geometric mean titers by the horizontal bar.

FIG. 4, comprising (FIG. 4A) Rabbits were immunized with the same six clade A envelopes as in the previous experiment but all plasmids were delivered at the same time. In order to determine if formulating the plasmids together would affect the vaccine induced responses, two separate studies were performed: one in which each plasmid was delivered at a different site and one in which all plasmids were formulated together. In both experiments, all rabbits received the same number of plasmid and amount of DNA (100 μg per plasmid for 600 μg total). All vaccinations were performed ID followed by electroporation. (FIG. 4B) Binding titers against clade A (92RW020), clade B (SF162) and clade C (ZM197) primary gp120s. Individual titers are denoted in the shapes and geometric mean titers by the horizontal bar. (FIG. 4C) Neutralization titers after final immunization were determined for a set of tier 1 viruses.

FIG. 5, comprising (FIG. 5A) Rabbits were immunized with the either six clade B envelopes or six clade C envelopes. All envelope plasmids were formulated together (100 μg of each plasmid, 600 μg total) and delivered ID followed by electroporation. Binding titers against clade A (92RW020), clade B (SF162) and clade C (ZM197) primary gp120s for clade B immunized rabbits (FIG. 5B) or clade C immunized rabbits (FIG. 5C). Individual titers are denoted in the shapes and geometric mean titers by the horizontal bar.

FIG. 6, comprising (FIG. 6A) Rabbits were immunized with two separate combinations of two clade A, two clade B, and two clade C at weeks 0, 3, 6 and 9. All envelope plasmids were formulated together (100 μg of each plasmid, 600 μg total) and delivered ID followed by electroporation. (FIG. 6B) Binding titers against clade A (92RW020), clade B (SF162) and clade C (ZM197) primary gp120s. Individual titers are denoted in the shapes and geometric mean titers by the horizontal bar. (FIG. 6C) Neutralization titers after final immunization were determined for a set of tier 1 viruses.

FIG. 7, comprising (FIG. 7A) Rabbits were immunized with different combinations of clade A, clade B, and clade C "clouds". All envelope plasmids were formulated together (100 μg of each plasmid, 500 μg-600 μg total) and delivered ID followed by electroporation. (FIG. 7B) Binding titers against clade A (92RW020), clade B (SF162) and clade C (ZM197) primary gp120s. Individual titers are denoted in the shapes and geometric mean titers by the horizontal bar. (FIG. 7C) Neutralization titers after final immunization were determined for a set of tier 1 viruses.

FIG. 8, comprising (FIG. 8A) Rabbits were immunized with different combinations of clade A and B "clouds". All envelope plasmids were formulated together (100 μg of each plasmid, 500 ug-600 μg total) and delivered ID followed by electroporation. (FIG. 8B) Binding titers against clade A (92RW020), clade B (SF162) and clade C (ZM197) primary gp120s. Individual titers are denoted in the shapes and geometric mean titers by the horizontal bar. (FIG. 8C) Neutralization titers after final immunization were determined for a set of tier 1 viruses.

FIG. 9, comprising (FIG. 9A) Eight rhesus macaques were immunized with the same envelopes as in the previous study. All envelopes (1 mg per construct) were formulated together and delivered to 4-6 sites for the first 4 ID immunization. For the two IM boosting immunizations all 15 envelopes were formulated together and delivered to 1 site IM followed by electroporation. (FIG. 9B) Interferon-γ responses were determined two weeks after each vaccination and during memory period using interferon-γ ELISpots. Cells were stimulated with consensus clade A and B peptides.

FIG. 14, comprising FIG. 14A depicts cellular responses post final vaccination as measured by IFN-γ spot forming units (SFU) after ex vivo stimulation of splenocytes with consensus clade A, B or C depending on the clade of the insert.

FIG. 14B depicts humoral antibody responses as assessed by binding to consensus clade A, B, or C gp120. FIG. 14C depicts humoral antibody responses as assessed by binding to consensus clade A, B, or C gp140. FIG. 14D depicts binding to gp41. The dotted line represents background binding level.

FIG. 15, comprising FIG. 15A depicts the immunization scheme for guinea pig vaccination with two different groups: one where all of the plasmids were mixed and formulated together and another where each plasmid was delivered into a separate site. FIG. 15B depicts binding titers against clade A (92RW020), clade B (SF162) and clade C (ZM197) primary gp120s over time. FIG. 15C depicts the avidity index of binding to 92RW020, SF162, and ZM197 at week 12. FIG. 15D depicts neutralization titers for week 12 serum were determined for a set of tier 1 viruses.

FIG. 16, comprising FIG. 16A demonstrates that expression of each individual constructs can be detected. FIG. 16B depicts an overlay of each construct demonstrating multiple constructs can be expressed form a single cell.

FIG. 17, comprising FIG. 17A depicts rabbits were immunized with six clade A, B or clade C Env plasmids. All plasmids were formulated together (100 μg of each plasmid, 600 μg total) and delivered ID followed by electroporation. FIG. 17B depicts binding titers of Group 1 immunized rabbits against clade A (92RW020), clade B (SF162) and clade C (ZM197) primary gp120s. FIG. 17C depicts binding titers of Group 2 immunized rabbits against clade A (92RW020), clade B (SF162) and clade C (ZM197) primary gp120s. FIG. 17D depicts binding titers of Group 3 immunized rabbits against clade A (92RW020), clade B (SF162) and clade C (ZM197) primary gp120s. Individual titers are denoted in the shapes, geometric mean titers by the horizontal bar and standard error by the bracket.

FIG. 18, comprising FIG. 18A through FIG. 18E depicts experimental results demonstrating clouds of Envelope plasmids increases functional humoral responses.

FIG. 19, comprising FIG. 19A depicts the experimental design. Four Indian Rhesus Macaques were immunized with a combination of 14 different plasmids expressing primary HIV Envelopes following a similar immunization protocol as in rabbit group 6. FIG. 19B depicts IFN-γ ELISpot responses in peripheral blood mononuclear cells (PBMCs) after overnight stimulation with consensus clade A and B peptides after ID immunizations. FIG. 19C depicts IFN-γ ELISpot responses in peripheral blood mononuclear cells (PBMCs) after overnight stimulation with consensus clade A and B peptides after memory and IM boost. Cellular responses were also assessed for intracellular cytokine production of IFN-γ, IL-2 and TNF-α after stimulation with consensus clade A, B or C peptides. FIG. 19D depicts cytokine production over the time course of immunizations for CD8 subset of CD3 T cells. FIG. 19E depicts cytokine production over the time course of immunizations for CD4 subset of CD3 T cells.

FIG. 20, comprising FIG. 20A depicts IFN-γ ELISpot responses over time for each individual NHP after ID immunizations. FIG. 20B depicts IFN-γ ELISpot responses over time for each individual NHP after memory and IM boost. NHP 4 died due to unrelated causes on week 80.

FIG. 21, comprising FIG. 21A depicts endpoint binding titers over time against 92RW020, SF162 and ZM197. FIG. 21B depicts avidity index against 92RW020, SF162 and ZM197 after the second, third, fourth ID immunization and each of the IM boost. FIG. 21C depicts binding to consensus and primary gp120/gp140 Envs as assessed by binding antibody multiplex assay (SAMA). FIG. 21D depicts antibody binding responses to multiple scaffolded (gp70) V1/V2 after final ID immunization and after each IM boosts.

FIG. 22, comprising

FIG. 22A depicts neutralization titers against a panel of tier 1 viruses across time. FIG. 22B depicts week 83 serum (two week post final immunization) was assessed for neutralization capacity against two infectious molecular clones: SF162P4 (tier 1) and SF162P3 (tier 2). FIG. 22C depicts antibody dependent cellular cytotoxicity (ADCC) titers were determine against targets coated with gp140 (1086c) or gp120 (WITO, JR-FL, and 92MG037.1) for serum from weeks 20 (post final ID), week 46 (post 1$^{st}$ IM) and 83 (post 2$^{nd}$ IM). FIG. 22D depicts a strong correlation between binding to 1086c gp140 as assessed by SAMA and ADCC titers against 1086c gp140.

FIG. 24 depicts the characteristics of acute/early primary Envs. For ease, each plasmid is denoted by the clade letter followed by a number throughout the paper. All inserts were RNA and codon optimized and encoded for the full gp160 Env protein.

FIG. 25 depicts serum neutralization titers against a panel of tier 2 viruses from the top two rabbits from groups 4, 5, and 6. The two rabbits with the strongest binding titers were tested for neutralization against a panel of Tier 2 viruses. Colors represent the strength of neutralization with green between baseline to 100, yellow 100-200, red 200-500 and deep red great than 500.

DETAILED DESCRIPTION

Figures 1A, 1B:
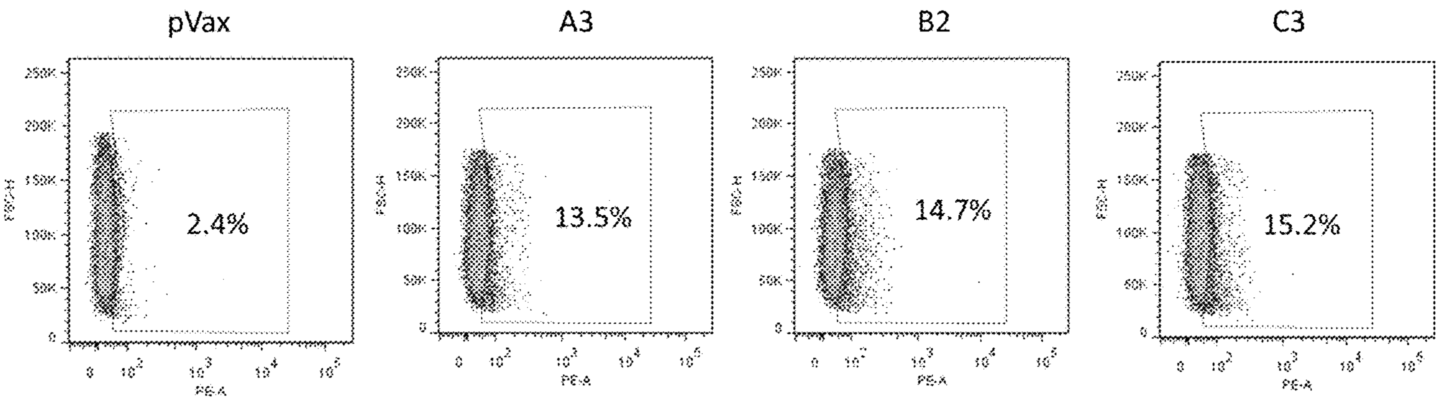
FIGS. 1A and 1B, is a series of images depicting example flow plots for in vitro expression. HEK 293T cells were transfected with each plasmid. After 48 hours cells were harvested and surface expression was determined using 2G12 anti-envelope antibody followed by anti-human antibody conjugated to PE. pVax served as the negative control. All plasmid expressed in vitro as seen in FIG. 1B.

The present invention is based in part upon the surprising discovery that delivery of multiple nucleic acid vaccines is able to induce potent antibody dependent cellular cytotoxicity against multiple HIV gp120 and gp140 coated targets. Therefore, the present invention provides compositions and methods for inducing an immune response against HIV. The nucleic acid vaccines described herein can be optimized using the following plasmid-enhancement techniques: codon optimization, RNA optimization, leader sequence addition. The nucleic acid prime can be followed by a protein boost with recombinant HIV gp120.

Groupings or "clouds" of plasmids expressing primary isolate HIV-1 envelopes are able to produce potent anti-envelope antibodies. In addition, priming with a "cloud" expressing primarily transmitted founder envelopes is able to increase the breadth of these responses. In some embodiments, immunized with two primings of the transmitted found envelope "cloud" followed by "clouds" of diverse chronic isolates develop both tier 1 and tier 2 neutralization antibodies which span multiple clades. This robust induction of antibodies has yet to be seen using other platforms and could lend itself well to being further expanded by boosting with other modalities like protein. Many successful antiviral vaccines have the ability to induce neutralizing antibodies.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Adjuvant" as used herein may mean any molecule added to the DNA plasmid vaccines described herein to enhance antigenicity of the one or more immunogens encoded by the DNA plasmids and encoding nucleic acid sequences described hereinafter.

"Antibody" may mean an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Coding sequence" or "encoding nucleic acid" as used herein may mean refers to the nucleic acid (RNA or DNA molecule) that comprise a nucleotide sequence which encodes a protein. The coding sequence may further include initiation and termination signals operably linked to regulatory elements including a promoter and polyadenylation signal capable of directing expression in the cells of an individual or mammal to whom the nucleic acid is administered. In some embodiments, the coding sequence may optionally further comprise a start codon that encodes an N terminal methionine or a signal peptide such as an IgE or IgG signal peptide.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Consensus" or "Consensus Sequence" as used herein may mean a synthetic nucleic acid sequence, or corresponding polypeptide sequence, constructed based on analysis of an alignment of multiple subtypes of a particular antigen. The sequence may be used to induce broad immunity against multiple subtypes or serotypes of a particular antigen. Synthetic antigens, such as fusion proteins, may be manipulated to consensus sequences (or consensus antigens).

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" or "immunogenic fragment" may mean a polypeptide fragment of an HIV immunogen that is capable of eliciting an immune response in a mammal against HIV by recognizing the particular HIV antigen. The fragment may be capable of eliciting an immune response in a mammal that cross reacts with a full length endogenous antigen. The HIV envelope glycoprotein immunogen may optionally include a signal peptides and/or a methionine at position 1, proteins 98% or more homologous to the consensus sequences set forth herein, proteins 99% or more homologous to the consensus sequences set forth herein, and proteins 100% identical to the sequences set forth herein, in each case with or without signal peptides and/or a methionine at position 1. A fragment may or may not for example comprise a fragment of an HIV immunogen linked to a signal peptide such as an immunoglobulin signal peptide for example IgE signal peptide or IgG signal peptide. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, or at least 240 amino acids or more of a consensus protein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acid molecules or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more filovirus consensus antigen via the provided DNA plasmid vaccines. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid molecule may be used for the same purpose as a given nucleic acid molecule. Thus, a nucleic acid molecule also encompasses substantially identical nucleic acids and complements thereof. A single strand provides a probe that may hybridize to a target sequence under stringent hybridization conditions. Thus, a nucleic acid molecule also encompasses a probe that hybridizes under stringent hybridization conditions.

Nucleic acid molecules may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acid molecules may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" as used herein may refer to a short peptide sequence, typically less than 50 amino acids long, which directs the transport of the protein in which it is incorporated. Signal peptides typically are linked to a protein at the N terminus and coding sequences encoding the signal peptide often include the initiation codon that encodes the N terminal methionine encoded by the initiation codon.

Signal peptides target the protein for transport within the cell and are involved in the secretory pathway in which the presence of the signal peptide on a protein targets the protein for transport though the secretory pathway such that the protein is secreted by the cell or otherwise targeted for release by the cell into the extracellular environment. In some embodiments, the signal peptide is an immunoglobulin signal peptide such as an IgG or IgE signal peptide. The addition of a coding sequence of a signal peptide to the coding sequences of a protein generally refers to the insertion of the coding sequence of a signal peptide including an initiation codon in place of the initiation codon of the coding sequence of the protein. That is, the addition of the coding sequence of a signal peptide to the coding sequence of the protein involves the removal of the initiation codon of the coding sequence of the protein and the insertion of the coding sequence of a signal peptide including an initiation codon. Thus, in the single peptide plus protein encoded thereby, the methionine at position 1 of the amino acid sequence of the original protein sequence is replaced by the amino acid sequence of the signal peptide which has a methionine at position 1.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5 to 10° C. lower than the thermal melting point (Tm) for the specific sequence at a defined ionic strength pH. The Tm may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

A "peptide" or "polypeptide" is a linked sequence of amino acids and can be natural, synthetic, or a modification or combination of natural and synthetic.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

"Substantially complementary" as used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 nucleotides or amino acids, or with respect to nucleic acids, if the first sequence is substantially complementary to the complement of the second sequence.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Variant" with respect to a nucleic acid sequence that encodes the same specific amino acid sequence differs in nucleotide sequence by use of different codons.

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

"Cloud" is used herein to refer to a formulation of antigens, preferably nucleotide sequences encoding HIV envelope proteins, that can be used to vaccinate a subject. Preferably, each cloud or cloud vaccine is comprised of at least 4 HIV envelope antigens, and more preferably at least 6 HIV envelope antigens. In some embodiments, each cloud is comprised of 6 HIV envelope antigens.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compositions

Provided herein are HIV immunogens that can be used to induce broad immunity against multiple subtypes or serotypes of a particular HIV antigen. HIV antigens may include sequences of any HIV glycoprotein immunogen. In one embodiment, the immunogen includes a gp160 immunogen. In one embodiment, the immunogen includes a gp120 immunogen. In one embodiment, the immunogen includes a gp41 immunogen. In one embodiment, the immunogen includes Clade A HIV glycoprotein immunogens, Clade B HIV glycoprotein immunogens, or Clade C HIV glycoprotein immunogens.

The immunogens include HIV gp160, HIV gp140, HIV gp120, HIV gp41, and variants thereof, optionally including a signal peptide such as for example an IgE or IgG signal peptide.

In some embodiments, the Env proteins can comprise an amino acid sequence selected from the following list: SEQ ID NOs: 2, 4, 6, 8, 10, 12, 14, 16, 18, 20, 22, 24, 26, 28, 30, 32, 34, 36, 38, 40, 42, 44, 46, 50, 52, 54, 56, or 58.

In some embodiments, the Env proteins can comprise an amino acid sequence that is at least 90% homologous to at least one of SEQ ID NOs: 2, 4, 6, 8, 10, 12, 14, 16, 18, 20, 22, 24, 26, 28, 30, 32, 34, 36, 38, 40, 42, 44, 46, 50, 52, 54, 56, or 58.

In some embodiments, the Env proteins can comprise a fragment of an amino acid sequence selected from the following list: SEQ ID NOs: 2, 4, 6, 8, 10, 12, 14, 16, 18, 20, 22, 24, 26, 28, 30, 32, 34, 36, 38, 40, 42, 44, 46, 50, 52, 54, 56, 58, 60 or 62.

In some embodiments, the Env proteins can comprise a fragment of an amino acid sequence that is at least 90% homologous to at least one of SEQ ID NOs: 2, 4, 6, 8, 10, 12, 14, 16, 18, 20, 22, 24, 26, 28, 30, 32, 34, 36, 38, 40, 42, 44, 46, 50, 52, 54, 56, 58, 60 or 62.

In some embodiments, the vaccination of a subject can further include a HIV pol antigen, for example a HIV pol antigen comprising the amino acid sequence of SEQ ID NO: 48, an amino acid sequence at least 90% homologous to SEQ ID NO: 48, or fragments thereof.

Also provided herein is a composition comprising two or more nucleic acid molecules encoding an HIV immunogen. In one embodiment, the nucleic acid may encode a full length HIV immunogen, a fragment of an HIV immunogen, a protein homologous to an HIV immunogen, or a protein homologous to a fragment of an HIV immunogen. Nucleic acid sequence may optionally comprise coding sequences that encode a signal peptide such as for example an IgE or IgG signal peptide.

In one embodiment, the nucleic acid comprises a sequence selected from SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a fragment of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a sequence that is 90% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, or a fragment of a sequence that is 90% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61.

In one embodiment, the nucleic acid comprises a sequence selected from SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a fragment of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a sequence that is 95% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, or a fragment of a sequence that is 95% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61.

In one embodiment, the nucleic acid comprises a sequence selected from SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a fragment of one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, a sequence that is 99% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61, or a fragment of a sequence that is 99% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61.

In one embodiment, the nucleic acid sequence comprises a sequence that encodes SEQ ID NOs: 2, 4, 6, 8, 10, 12, 14, 16, 18, 20, 22, 24, 26, 28, 30, 32, 34, 36, 38, 40, 42, 44, 46, 52, 54, 56, 58, 60 or 62.

In one embodiment, the nucleic acid sequence comprises a sequence that encodes a sequence at least 90% homologous to SEQ ID NOs: 2, 4, 6, 8, 10, 12, 14, 16, 18, 20, 22, 24, 26, 28, 30, 32, 34, 36, 38, 40, 42, 44, 46, 52, 54, 56, 58, 60 or 62.

In one embodiment, the nucleic acid comprises a sequence encoding a transmitted founder HIV immunogen. In one embodiment, the nucleic acid comprises a sequence encoding a consensus HIV immunogen. Consensus HIV immunogens are described in PCT Patent Application No. WO2008/014521, the contents of which is fully incorporated by reference.

Compositions are provided which comprise nucleic acid molecules. The compositions may comprise a plurality of copies of a single nucleic acid molecule such a single plasmid, a plurality of copies of two or more different nucleic acid molecules such as two or more different plasmids. For example a composition may comprise plurality of two, three, four, five, six, seven, eight, nine or ten or more different nucleic acid molecules. Such compositions may comprise plurality of two, three, four, five, six, or more different plasmids.

Compositions may comprise nucleic acid molecules, such as plasmids, that collectively contain coding sequence for a single HIV immunogen selected from the group consisting of one or more of a HIV gp160 envelope glycoprotein immunogen, one or more of a HIV gp120 envelope glycoprotein immunogen, one or more of a HIV gp140 envelope glycoprotein immunogen, and one or more of a HIV gp41 envelope glycoprotein immunogen.

Compositions comprise nucleic acid sequence that encode the combination of: one or more of a HIV gp160 envelope glycoprotein immunogen, one or more of a HIV gp120 envelope glycoprotein immunogen, one or more of a HIV gp140 envelope glycoprotein immunogen, and one or more of a HIV gp41 envelope glycoprotein immunogen.

Each coding sequence for each HIV immunogens is preferably included on a separate nucleic acid molecule.

In one embodiment, the composition comprises a plurality of nucleic acid sequences described herein. In one embodiment, the composition comprises 3 or more nucleic acid sequences. In one embodiment, the composition comprises 6 or more nucleic acid sequences. In one embodiment, the composition comprises 10 or more nucleic acid sequences. In one embodiment, the composition comprises 14 or more nucleic acid sequences. In one embodiment, the composition comprises 20 or more nucleic acid sequences. In one embodiment, the composition comprises 25 or more nucleic acid sequences. In one embodiment, the composition comprises 30 or more nucleic acid sequences. In one embodiment, the composition comprises 35 or more nucleic acid sequences. In one embodiment, the composition comprises 40 or more nucleic acid sequences. In one embodiment, the composition comprises two or more nucleic acid molecules, wherein each nucleic acid molecule comprises only one of SEQ ID NOs: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, or 61.

In one embodiment, the composition comprises 3 or more nucleic acid sequences, where the 3 or more nucleic acid sequences may be on a single nucleic acid molecule or on two nucleic acid molecules in any permutation, but are preferably on three separate nucleic acid molecules (e.g., three separate plasmids).

In one embodiment, the composition comprises 6 or more nucleic acid molecules, where the 6 or more nucleic acid molecules may be on a single plasmid or on two plasmids in any permutation, or on three plasmids in any permutation or on four plasmids in any permutation or on five plasmids in any permutation or, but are preferably on six separate plasmids.

In one embodiment, the composition comprises 10 or more nucleic acid molecules, where the 10 or more nucleic acid molecules be on a single plasmid or on two plasmids in any permutation, or on three plasmids in any permutation or on four plasmids in any permutation or on five plasmids in any permutation or on six plasmids in any permutation, on seven plasmids in any permutation, on eight plasmids in any permutation, on nine plasmids in any permutation, but are preferably on ten separate plasmids.

In one embodiment, the composition comprises 14 or more nucleic acid molecules, where the 14 or more nucleic acid molecules be on a single plasmid or on two plasmids in any permutation, or on three plasmids in any permutation or on four plasmids in any permutation or on five plasmids in any permutation or on six plasmids in any permutation, on seven plasmids in any permutation, on eight plasmids in any permutation, on nine plasmids in any permutation, on ten plasmids in any permutation, on eleven plasmids in any permutation, on twelve plasmids in any permutation, on thirteen plasmids in any permutation, on fourteen plasmids in any permutation, but are preferably on one plasmid or on fourteen plasmids in any permutation.

The compositions can induce potent antibody dependent cellular cytotoxicity (ADCC) against multiple gp120 and gp140 coated targets. The combination of two or more nucleic acid molecules efficiently induces cellular and humoral responses better than one nucleic acid alone.

a. Antigen

The composition may comprise an antigen. The antigen is encoded by a nucleic acid sequence. The nucleic acid sequence may be DNA or RNA. The nucleic acid may encode an antigen or a variant thereof. The antigen can be an antigen isolated from human immunodeficiency virus (HIV). The HIV antigens can include modified consensus sequences for immunogens. Genetic modifications including codon optimization, RNA optimization, and the addition of a high efficient immunoglobin leader sequence to increase the immunogenicity of constructs can be included in the modified consensus sequences. The novel immunogens can be designed to elicit stronger and broader cellular immune responses than a corresponding codon optimized immunogens.

In one embodiment, the antigen encoded by an optimized consensus sequence is capable of eliciting an immune response in a mammal. In one embodiment, the antigen encoded by an optimized consensus sequence can comprise an epitope(s) that makes it particularly effective as an immunogen against which an immune response can be induced.

The optimized consensus sequence can be a consensus sequence derived from two or more native HIV proteins or two or more HIV subtypes. The optimized consensus sequence can comprise a consensus sequence and/or modification(s) for improved expression. Modification can include codon optimization, RNA optimization, addition of a kozak sequence for increased translation initiation, and/or the addition of an immunoglobulin leader sequence to increase immunogenicity. The HIV antigen encoded by the optimized consensus sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized consensus sequence can comprise a hemagglutinin (HA) tag. The HIV antigen encoded by the optimized consensus sequence can be designed to elicit stronger cellular and/or humoral immune responses than a corresponding native antigen.

The antigen of the first vaccine may be the same antigen across different subtypes of HIV. The composition may comprise 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, or 26 or more nucleic acid sequences encoding a particular protein sequence isolated from HIV subtypes A, B, C, D, or other HIV subtypes, or a combination or variant thereof.

In some embodiments, the HIV antigen can be a subtype A consensus envelope DNA sequence construct, an IgE leader sequence linked to a consensus sequence for Subtype A envelope protein, or a subtype A consensus Envelope protein sequence.

In other embodiments, the HIV antigen can be a subtype B consensus envelope DNA sequence construct, an IgE leader sequence linked to a consensus sequence for Subtype B envelope protein, or a subtype B consensus Envelope protein sequence.

In still other embodiments, the HIV antigen can be a subtype C consensus envelope DNA sequence construct, an IgE leader sequence linked to a consensus sequence for subtype C envelope protein, or a subtype C consensus envelope protein sequence.

In further embodiments, the HIV antigen can be a subtype D consensus envelope DNA sequence construct, an IgE leader sequence linked to a consensus sequence for Subtype D envelope protein, or a subtype D consensus envelope protein sequence.

In some embodiments, the HIV antigen can be a subtype A Nef-Rev consensus envelope DNA sequence construct, an IgE leader sequence linked to a consensus sequence for Subtype A Nef-Rev protein, or a Subtype A Nef-Rev consensus protein sequence.

In some embodiments, the HIV antigen can be a subtype B Nef-Rev consensus envelope DNA sequence construct, an IgE leader sequence linked to a consensus sequence for Subtype B Nef-Rev protein, or a Subtype B Nef-Rev consensus protein sequence.

In some embodiments, the HIV antigen can be a subtype C Nef-Rev consensus envelope DNA sequence construct, an IgE leader sequence linked to a consensus sequence for Subtype C Nef-Rev protein, or a Subtype C Nef-Rev consensus protein sequence.

In some embodiments, the HIV antigen can be a subtype D Nef-Rev consensus envelope DNA sequence construct, an IgE leader sequence linked to a consensus sequence for Subtype D Nef-Rev protein, or a Subtype D Nef-Rev consensus protein sequence.

In other embodiments, the HIV antigen can be a Gag consensus DNA sequence of subtype A, B, C and D DNA sequence construct, an IgE leader sequence linked to a consensus sequence for Gag consensus subtype A, B, C and D protein, or a consensus Gag subtype A, B, C and D protein sequence.

In still other embodiments, the HIV antigen can be a MPol DNA sequence or a MPol protein sequence. The HIV antigen can be nucleic acid or amino acid sequences of Env A, Env B, Env C, Env D, B Nef-Rev, Gag, or any combination thereof.

In other embodiments, the HIV antigen may be a DNA sequence or consensus sequence of subtype A, B, C, or D encoding gp140 or consensus gp140 protein. In other embodiments, the HIV antigen may be a DNA sequence or consensus sequence of subtype A, B, C, or D encoding gp140 or consensus gp120 protein. In other embodiments, the HIV antigen gp140 peptide sequence or gp140 consensus peptide sequence of subtype A, B, C, or D. In other embodiments, the HIV antigen gp120 peptide sequence or gp140 consensus peptide sequence of subtype A, B, C, or D. In some embodiments, the HIV antigen gp160 peptide sequence or gp160 consensus peptide sequence of subtype A, B, C, or D.

The antigen can affect a mammal, which can be a human, chimpanzee, dog, cat, horse, cow, mouse, or rat. The antigen can be contained in a protein from a mammal, which can be a human, chimpanzee, dog, cat, horse, cow, pig, sheep, mouse, or rat.

b. DNA

The composition may comprise DNA. Also provided herein is a DNA that encodes the antigen as described above. The DNA can include an encoding sequence that encodes the antigen. The DNA can also include additional sequences that encode linker or tag sequences that are linked to the antigen by a peptide bond.

c. RNA

The composition may comprise RNA. Also provided herein is a RNA that encodes the antigen as described above. The RNA can include an encoding sequence that encodes the antigen. The RNA can also include additional sequences that encode linker or tag sequences that are linked to the antigen by a peptide bond.

d. Vector

The composition may comprise a vector. Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the hoses genome The vector can be capable of expressing the antigen. The vector may be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

i. Expression Vectors

The vector may be circular plasmid or a linear nucleic acid vaccine. The circular plasmid and linear nucleic acid are capable of directing expression of a particular nucleotide sequence in an appropriate subject cell. The vector may have a promoter operably linked to the antigen-encoding nucleotide sequence, which may be operably linked to termination signals. The vector may also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

ii. RNA Vectors

In one embodiment, the nucleic acid is an RNA molecule. Accordingly, in one embodiment, the invention provides an RNA molecule encoding one or more HIV antigens. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

iii. Circular and Linear Vectors

The vector may be circular plasmid, which may transform a target cell by integration into the cellular genome or exist extrachromosomally (e.g. autonomous replicating plasmid with an origin of replication).

The vector can be pVAX, pcDNA3.0, or provax, or any other expression vector capable of expressing the DNA and enabling a cell to translate the sequence to a antigen that is recognized by the immune system. The vector can be combined with antigen at a mass ratio of between 5:1 and 1:5, or of between 1:1 and 2:1.

Plasmid may comprise a nucleic acid sequence that encodes one or more of the various immunogens disclosed above including coding sequences that encode synthetic, consensus antigen capable of eliciting an immune response against HIV immunogens.

A single plasmid may contain coding sequence for a single HIV immunogen, coding sequence for two HIV immunogens, coding sequence for three HIV immunogens, coding sequence for four HIV immunogens, coding sequence for five HIV immunogens or coding sequence for six HIV immunogens. A single plasmid may contain a coding sequence for a single HIV immunogen which can be formulated together. In some embodiments, a plasmid may comprise coding sequence that encodes IL-12, IL-15 and/or IL-28.

The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, Calif.).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an Ig leader sequence. The leader sequence may be 5' of the coding sequence. The consensus antigens encoded by this sequence may comprise an N-terminal Ig leader followed by a consensus antigen protein. The N-terminal Ig leader may be IgE or IgG.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNA I or pcDNA3 (Invitrogen, San Diego, Calif.), which may be used for protein production in mammalian cells such as Chinese hamster ovary (CHO) cells.

Also provided herein is a linear nucleic acid vaccine, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid may be pNP (Puerto Rico/34) or pM2 (New Caledonia/99). See FIG. 1. The plasmid may be pVAX, pcDNA3.0, or provax, or any other expression vector capable of expressing the DNA and enabling a cell to translate the sequence to a antigen that is recognized by the immune system.

The LEC may be perM2. The LEC may be perNP. perNP and perMR may be derived from pNP (Puerto Rico/34) and pM2 (New Caledonia/99), respectively. The LEC may be combined with antigen at a mass ratio of between 5:1 and 1:5, or of between 1:1 to 2:1.

iv. Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleotide sequence encoding the antigen and signals required for efficient polyadenylation of the transcript, ribosome binding sites, and translation termination. The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

e. Vaccines

Provided herein is a vaccine capable of generating in a mammal an immune response against HIV. The vaccine may comprise each plasmid as discussed above. The vaccine may comprise a plurality of the plasmids, or combinations thereof. The vaccine may be provided to induce a therapeutic or prophylactic immune response.

Vaccines may be used to deliver nucleic acid molecules that encode consensus HIV envelope glycoprotein immunogens. Vaccines may be used to deliver nucleic acid molecules that encode transmitted founder HIV envelope glycoprotein immunogens. Vaccines may be used to deliver nucleic acid molecules that encode consensus Clade A, Clade B, Clade C, or Clade D HIV envelope glycoprotein immunogens. Vaccines may be used to deliver nucleic acid molecules that encode transmitted founder Clade A, Clade B, Clade C, or Clade D HIV envelope glycoprotein immunogens. Vaccines may be used to deliver nucleic acid molecules that encode consensus HIV gp160 envelope glycoprotein immunogens. Vaccines may be used to deliver nucleic acid molecules that encode transmitted founder HIV gp160 envelope glycoprotein immunogens. Vaccines may be used to deliver nucleic acid molecules that encode consensus HIV gp140 envelope glycoprotein immunogens. Vaccines may be used to deliver nucleic acid molecules that encode transmitted founder HIV gp140 envelope glycoprotein immunogens. Vaccines may be used to deliver nucleic acid molecules that encode consensus HIV gp120 envelope glycoprotein immunogens. Vaccines may be used to deliver nucleic acid molecules that encode transmitted founder HIV gp120 envelope glycoprotein immunogens. Vaccines may be used to deliver nucleic acid molecules that encode consensus HIV gp41 envelope glycoprotein immunogens. Vaccines may be used to deliver nucleic acid molecules that encode transmitted founder HIV gp41 envelope glycoprotein immunogens.

The vaccine may comprise the antigens and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the consensus antigen or plasmid thereof.

f. Other Components of Vaccine-Adjuvants, Excipients

The composition may further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate is may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in alternative plasmid or are delivered as proteins in combination with the plasmid above in the vaccine. The adjuvant may be selected from the group consisting of: α-interferon (IFN-α), β-interferon (IFN-β), γ-interferon, platelet derived growth factor (PDGF), TNFα, TNF3, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes that can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The composition may further comprise a genetic vaccine facilitator agent as described in U.S. Ser. No. 021,579 filed Apr. 1, 1994, which is fully incorporated by reference.

The composition can be formulated according to the mode of administration to be used. An injectable composition pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polyanions or polyanions.

2. Method of Vaccination

Provided herein is a method for delivering the vaccine for providing genetic constructs and proteins of the antigen which comprise epitopes that make them particular effective against immunogens of HIV, against which an immune response can be induced. The method of delivering the vaccine or vaccination may be provided to induce a therapeutic and prophylactic immune response. The vaccination process may generate in the mammal an immune response against HIV. The vaccine may be delivered to an individual to modulate the activity of the mammal's immune system and enhance the immune response. The delivery of the vaccine may be the transfection of the antigen as a nucleic acid molecule that is expressed in the cell and delivered to the surface of the cell upon which the immune system recognized and induces a cellular, humoral, or cellular and humoral response. The delivery of the vaccine may be used to induce or elicit and immune response in mammals against HIV by administering to the mammals the vaccine as discussed above.

Upon delivery of the vaccine and plasmid into the cells of the mammal, the transfected cells will express and secrete consensus antigens for each of the plasmids injected from the vaccine. These proteins will be recognized as foreign by the immune system and antibodies will be made against them. These antibodies will be maintained by the immune system and allow for an effective response to subsequent infections by HIV.

Also provided herein is a method of immunizing a subject against HIV to treat or prevent HIV infection using the composition. The method of immunizing a subject comprises administering a first composition comprising one or more nucleic acid molecules encoding a sequence at least 90% homologous to SEQ ID NOs: 2, 4, 6, 8, 10, 12, 14, 16, 18, 20, 22, 24, 26, 28, 30, 32, 34, 36, 38, 40, 42, 44, 46, 52, 54, 56, 58, 60, or 62, a variant thereof or a fragment thereof. In one embodiment, the first composition comprises one or more nucleic acid molecules having a sequence at least 90% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, or 61. The first composition may be given in multiple doses. In one embodiment, the first composition is administered twice. The first composition can be administered a second time within 2 days, 5 days, or 7 days of the first administration of the first composition. In one embodiment, the first composition is administered intradermally. The first composition can efficiently deliver antigen to a subject in need thereof for immune stimulation via a priming dose.

In one embodiment, the method further comprises administering a second composition comprising one or more nucleic acid molecules encoding a sequence at least 90% homologous to SEQ ID NOs: 2, 4, 6, 8, 10, 12, 14, 16, 18, 20, 22, 24, 26, 28, 30, 32, 34, 36, 38, 40, 42, 44, 46, 52, 54, 56, 58, 60, or 62, a variant thereof or a fragment thereof. In one embodiment, the second composition comprises one or more nucleic acid molecules having a sequence at least 90% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, or 61. In one embodiment, the second composition comprises nucleic acid molecules different than the nucleic acid molecules comprised within the first composition. In one embodiment, the second composition is administered at least 3 or more, 6 or more, or 12 or more weeks after the first composition is administered. The second composition may be given in multiple doses. In one embodiment, the second composition is administered twice. The second composition can be administered a second time within 1 week, 2 weeks, 4 weeks or 6 weeks of the first administration of the composition. In one embodiment the second composition is administered intradermally.

In one embodiment, the method further comprises administering a third composition comprising one more nucleic acid molecules encoding a sequence at least 90% homologous to SEQ ID NOs: 2, 4, 6, 8, 10, 12, 14, 16, 18, 20, 22, 24, 26, 28, 30, 32, 34, 36, 38, 40, 42, 44, 46, 52, 54, 56, 58, 60, or 62, a variant thereof or a fragment thereof. In one embodiment, the third composition comprises one or more nucleic acid molecules having a sequence at least 90% homologous to one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, or 61 In one embodiment, the third composition comprises each nucleic acid comprised in the first composition and the second composition. In one embodiment, the third composition is administered at least 10 or more, 15 or more, 20 or more or 25 or more weeks after the second composition is administered. The third composition may be given in multiple doses. In one embodiment, the third composition is administered twice. The third composition can be administered a second time within 25 weeks, 30 weeks, or 40 weeks of the first administration of the third composition. In one embodiment, the second composition is administered intramuscularly.

The number of composition doses for effective treatment can be 1, 2, 3, 4, 5, 6, 7, 8, 9, or 10.

The composition may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

a. Immune Response

The composition can induce an immune response in the subject administered the composition. The induced immune response can be specific for a native antigen. The induced immune response can be reactive with a native antigen related to the optimized consensus-encoded antigen. In various embodiments, related antigens include antigens having amino acid sequences having at least 90%, at least 91%, at least 92%, at least 93%, at least 94%, at least 95%, at least 96%, at least 97%, at least 98%, at least 99%, or 100% homology to the amino acid sequence of the optimized consensus-encoded antigen. In various embodiments, related antigens include antigens encoded by nucleotide sequences having at least 90%, at least 91%, at least 92%, at least 93%, at least 94%, at least 95%, at least 96%, at least 97%, at least 98%, at least 99%, or 100% homology to the optimized consensus nucleotide sequences disclosed herein.

The immunogenic composition can induce a humoral immune response in the subject administered the immunogenic composition. The induced humoral immune response can be specific for a native antigen. The induced humoral immune response can be reactive with the native antigen related to the optimized consensus-encoded antigen. The humoral immune response can be induced in the subject administered the immunogenic composition by about 1.5-fold to about 16-fold, about 2-fold to about 12-fold, or about 3-fold to about 10-fold. The humoral immune response can be induced in the subject administered the immunogenic composition by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized antigen.

The humoral immune response induced by the immunogenic composition can include an increased level of neutralizing antibodies associated with the subject administered the immunogenic composition as compared to a subject not administered the immunogenic composition. The neutralizing antibodies can be specific for a native antigen related to the optimized consensus-encoded antigen. The neutralizing antibodies can be reactive with the native antigen genetically related to the optimized consensus antigen. The neutralizing antibodies can provide protection against and/or treatment of tumor growth, metastasis or tumor associated pathologies in the subject administered the immunogenic composition.

The humoral immune response induced by the immunogenic composition can include an increased level of IgG antibodies associated with the subject administered the immunogenic composition as compared to a subject not administered the immunogenic composition. These IgG antibodies can be specific for the native antigen genetically related to the optimized consensus antigen. These IgG antibodies can be reactive with the native antigen genetically related to the optimized consensus antigen. The level of IgG antibody associated with the subject administered the immunogenic composition can be increased by about 1.5-fold to about 16-fold, about 2-fold to about 12-fold, or about 3-fold to about 10-fold as compared to the subject not administered the immunogenic composition. The level of IgG antibody associated with the subject administered the immunogenic composition can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized antigen.

The immunogenic composition can induce a cellular immune response in the subject administered the immunogenic composition. The induced cellular immune response can be specific for a native antigen related to the optimized consensus-encoded antigen. The induced cellular immune response can be reactive to the native antigen related to the optimized consensus-encoded antigen. The induced cellular immune response can include eliciting a $CD8^+$ T cell response. The elicited $CD8^+$ T cell response can be reactive with the native antigen genetically related to the optimized consensus antigen. The elicited $CD8^+$ T cell response can be polyfunctional. The induced cellular immune response can include eliciting a $CD8^+$ T cell response, in which the $CD8^+$ T cells produce interferon-gamma (IFN-γ), tumor necrosis factor alpha (TNF-α), interleukin-2 (IL-2), or a combination of IFN-γ and TNF-α.

The induced cellular immune response can include an increased $CD8^+$ T cell response associated with the subject administered the immunogenic composition as compared to the subject not administered the immunogenic composition. The $CD8^+$ T cell response associated with the subject administered the immunogenic composition can be increased by about 2-fold to about 30-fold, about 3-fold to about 25-fold, or about 4-fold to about 20-fold as compared to the subject not administered the immunogenic composition. The $CD8^+$ T cell response associated with the subject administered the immunogenic composition can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic composition or a subject administered a non-optimized antigen.

The induced cellular immune response can include an increased frequency of CD107a/IFNγ/T-bet triple-positive CD8 T cells that are reactive against the native antigen. The frequency of CD107a/IFNγ/T-bet triple-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized antigen.

The induced cellular immune response can include an increased frequency of CD107a/IFNγ double-positive CD8 T cells that are reactive against the native antigen. The frequency of CD107a/IFNγ double-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic composition or a subject administered a non-optimized antigen.

The cellular immune response induced by the immunogenic composition can include eliciting a $CD4^+$ T cell response. The elicited $CD4^+$ T cell response can be reactive with the native antigen genetically related to the optimized consensus antigen. The elicited $CD4^+$ T cell response can be polyfunctional. The induced cellular immune response can include eliciting a $CD4^+$ T cell response, in which the $CD4^+$ T cells produce IFN-γ, TNF-α, IL-2, or a combination of IFN-γ and TNF-α.

The induced cellular immune response can include an increased frequency of $CD4^+$ T cells that produce IFN-γ. The frequency of $CD4^+$ IFN-$\gamma^+$ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized antigen.

The induced cellular immune response can include an increased frequency of $CD4^+$ T cells that produce TNF-α. The frequency of $CD4^+$ TNF-$\alpha^+$ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic composition or a subject administered a non-optimized antigen.

The induced cellular immune response can include an increased frequency of $CD4^+$ T cells that produce both IFN-γ and TNF-α. The frequency of $CD4^+$IFN-$\gamma^+$TNF-$\alpha^+$ associated with the subject administered the immunogenic composition can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic composition or a subject administered a non-optimized antigen.

The immunogenic composition of the present invention can have features required of effective vaccines such as being safe so the vaccine itself does not cause illness or death; is protective against illness resulting from exposure to live pathogens such as viruses or bacteria; induces neutralizing antibody to prevent invention of cells; induces protective T cells against intracellular pathogens; and provides ease of administration, few side effects, biological stability, and low cost per dose.

The immunogenic composition can further induce an immune response when administered to different tissues such as the muscle or skin. The immunogenic composition can further induce an immune response when administered via electroporation, or injection, or subcutaneously, or intramuscularly.

b. Cloud Vaccines

The cloud vaccines can include HIV antigens, and preferably Env and more preferably Env of Clade A, Clade B, or Clade C. It is preferable to have a cloud vaccine comprised of the nucleotide sequences encoding an Env protein described herein.

Could vaccines can be comprised of one of more of the Env encoding nucleotide sequences, and can comprise at least 4, at least 5, at least 6, at least 7, at least 8, at least 9, at least 10, at least 11, or at least 12 Env.

The cloud vaccines can be one of the following groups of antigens in each cloud (referring to table 1a and 1b, below, for abbreviations):

a. A1, A2, A3, A4, A5, and A6
b. B3, B4, B8, and B9
c. B1, B2, B5, B6, and B7
d. C1, C3, C5, C6, and C7
e. A1, A2, A3, and A4
f. A2, A3, A4, and A5
g. A3, A4, A5, and A6
h. A1, A2, A3, A4, and A5
i. A2, A3, A4, A5, and A6
j. B1, B2, B3, B4, B5, and B6
k. B2, B3, B4, B5, B6 and B7
l. B3, B4, B, B5, B6, B7, and B8
m. B4, B5, B6, B7, B8, and B9
n. B5, B6, B7, B8, B9, and B10
o. B1, B2, B3, B4, B5, B6, and B7
p. B1, B2, B3, B4, B5, B6, B7, and B8
q. B1, B2, B3, B4, B5, B6, B7, B8, and B9
r. B1, B2, B3, B4, B5, B6, B7, B8, B9, and B10
s. B2, B3, B4, B5, B6, B7, B8, and B9
t. B2, B3, B4, B5, B6, B7, B8, B9, and B10
u. B3, B4, B5, B6, B7, B8, and B9
v. B3, B4, B5, B6, B7, B8, B9, and B10
w. C1, C2, C3, C4, C5, and C6
x. C2, C3, C4, C5, C6, and C7
y. C3, C4, C5, C6, C7, and C8
z. C4, C5, C6, C7, C8, and C9
aa. C5, C6, C7, C8, C9, and C10
bb. C6, C7, C8, C9, C10, and C11
cc. C1, C2, C3, C4, C5, C6, and C7
dd. C1, C2, C3, C4, C5, C6, C7, and C8
ee. C1, C2, C3, C4, C5, C6, C7, C8 and C9
ff. C1, C2, C3, C4, C5, C6, C7, C8, C9, and C10
gg. C1, C2, C3, C4, C5, C6, C7, C8, C9, C10, and C11
hh. C2, C3, C4, C5, C6, C7, and C8
ii. C2, C3, C4, C5, C6, C7, C8 and C9
jj. C2, C3, C4, C5, C6, C7, C8, C9, and C10
kk. C2, C3, C4, C5, C6, C7, C8, C9, C10, and C11
ll. C3, C4, C5, C6, C7, C8, and C9
mm. C3, C4, C5, C6, C7, C8, C9, and C10 nn. C3, C4, C5, C6, C7, C8, C9, C10, and C11
oo. C4, C5, C6, C7, C8, C9 and C10
pp. C4, C5, C6, C7, C8, C9, C10 and C11
qq. C5, C6, C7, C8, C9, C10, and C11
rr. C6, C7, C8, C9, C10, and C11 and other subcombinations of the groups, above.

The clouds will have Env antigens that are closely related, and preferably of the same clade. Preferably, within each cloud the diversity between Env antigens (intra-cloud diversity) is between 10% and 20%, preferably 12% and 18%; more preferably between 12% and 17%; between 12% and 16%; between 13% and 18%; between 13% and 17%; between 13% and 16%; between 14% and 18%; or between 14% and 17%.

Preferably, the diversity between Env antigens between clouds (inter-cloud diversity) between 12% and 25%, preferably 13% and 25%; more preferably between 14% and 25%; between 14% and 24%; between 14% and 23%; between 14% and 22%; between 14% and 21%; between 15% and 22%; or between 15% and 20%.

In some embodiments, the intracloud diversity (within each cloud) ranged from 10-20%, preferably 12.4-16.4% and intercloud diversity (between clouds) was consistently around 20%. The intracloud diversity ranged from 12-16%, preferably 13.3-14.3% and the intercloud diversity between 12-20%, preferably 14-17.6%.

Preferably, the cloud vaccines comprise groups a., b., and c., above. Most preferred is cloud vaccine of group a, above, which is comprised of SEQ ID NOs: 1, 3, 5, 7, 45, and 9.

Cloud Vaccines, above, the vaccination schedule for administering to a mammal can be chosen from the following (Table A):

TABLE A

Vaccination dosing schedules. This table is not meant to be exhaustive. Other combinations using the clouds described above, are contemplated using various prime and dose combinations.

| | Priming | | Boost | |
|---|---|---|---|---|
| Vaccination schedule no. | Number of dose | Cloud No. | Number Dose | Cloud No. |
| i. | 2x | a | 1x; 1x | b; c |
| ii. | 2x | a | 2x | b |
| iii. | 2x | a | 2x | c |
| iv. | 2x | a | 2x | d |
| v. | 2x | a | 2x | e |
| vi. | 2x | a | 2x | f. |
| vii. | 2x | b. | 1x; 1x | a; c |
| viii. | 2x | b. | 2x | a |
| ix. | 2x | b. | 2x | c |
| x. | 2x | b. | 2x | d |
| xi. | 2x | b. | 2x | e. |
| xii. | 2x | c. | 1x; 1x | a; b. |
| xiii. | 2x | c. | 2x | a. |
| xiv. | 2x | c. | 2x | b. |
| xv. | 2x | c. | 2x | d |
| xvi. | 2x | c. | 2x | e. |
| xvii. | 1x; 1x | a; b | 1x; 1x | c.; d. |
| xviii. | 1x; 1x | a; b | 2x | c |
| xix. | 1x; 1x | a; b | 2x | d. |
| xx. | 1x; 1x | a; b | 2x | e |

Preferably, vaccination schedule i. can be used to treat a subject infected with HIV virus.

c. Combination Treatments

The composition may be administered in combination with other proteins and/or genes encoding CCL20, α-interferon, γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence deleted and optionally including the different signal peptide such as the IgE signal peptide, MHC, CD80, CD86, IL-28, IL-1, IL-2, IL-4, IL-5, IL-6, IL-10, IL-18, MCP-1, MIP-1α, MIP-1β, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or combinations thereof. In some embodiments, the vaccine is administered in combination with one or more of the following nucleic acid molecules and/or proteins: nucleic acid molecules selected from the group consisting of nucleic acid molecules comprising coding sequence that encode one or more of CCL20, IL-12, IL-15, IL-28, CTACK, TECK, MEC and RANTES or functional fragments thereof, and proteins selected from the group consisting of: CCL02, IL-12 protein, IL-15 protein, IL-28 protein, CTACK protein, TECK protein, MEC protein or RANTES protein or functional fragments thereof.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal, intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The vaccine may be administered by traditional syringes, needleless injection devices, "microprojectile bombardment gone guns", or other physical methods such as electroporation ("EP"), "hydrodynamic method", or ultrasound.

d. Administration

The composition can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The composition can be administered prophylactically or therapeutically. In prophylactic administration, the vaccines can be administered in an amount sufficient to induce iTreg responses. In therapeutic applications, the vaccines are administered to a subject in need thereof in an amount sufficient to elicit a therapeutic effect. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The composition can be administered by methods well known in the art as described in Donnelly et al. (Ann. Rev. Immunol. 15:617-648 (1997)); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the vaccine can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The composition can be delivered via a variety of routes. Typical delivery routes include parenteral administration, e.g., intradermal, intramuscular or subcutaneous delivery. Other routes include oral administration, intranasal, and intravaginal routes. For the DNA of the vaccine in particular, the vaccine can be delivered to the interstitial spaces of tissues of an individual (Feigner et al., U.S. Pat. Nos. 5,580,859 and 5,703,055, the contents of all of which are incorporated herein by reference in their entirety). The vaccine can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The composition can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The composition can be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The composition can be incorporated into liposomes, microspheres or other polymer matrices (Feigner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The composition can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the composition into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520,950; 7,171,264; 6,208,893; 6,009,347; 6,120,493; 7,245,963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired composition in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Blue Bell Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so user's have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

e. Method of Preparing DNA Plasmids

Provided herein is methods for preparing the DNA plasmids that comprise the DNA vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a licensed, co-pending U.S. application Ser. No. 12/126,611, which was filed on May 23, 2008. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. application Ser. No. 12/126,611, including those described in a licensed patent, U.S. Pat. No. 7,238,522, which issued on Jul. 3, 2007. The above-referenced application and patent, U.S. application Ser. No. 12/126,611 and U.S. Pat. No. 7,238,522, respectively, are hereby incorporated in their entirety The present invention has multiple aspects, illustrated by the following non-limiting examples.

4. Examples

The present invention is further illustrated in the following Example. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Materials and Methods

Envelope Immunogens (Env)

Plasmids expressing codon and RNA optimized HIV-1 envelope glycoproteins (gp160) were made synthetically using OptimumGene Codon optimization analysis (GenScript). Inserts were then cloned into the pVAX (Invitrogen) backbone using either BamHI/XhoI or BamHI/EcoRI cloning sites. Each insert was under the control of the cytomegalovirus immediate-early promoter.

Expression of Plasmids

Each plasmid was tested in vitro for proper expression. Briefly, HEK 293T cells (ACTC) were cultured in Dulbecco's Modified Eagle Medium (Life Technologies) supplemented with 10% fetal bovin serum and 1% penicillin and streptomycin. Twenty four hours before transfection, $7.5\times10^5$ cells were plated in 1.5 mls of media in a 6 well dish. Each plasmid was used in a separate transfection with pVax empty backbone serving as a negative control. Transfection was performed using NeoFectin transfection reagent (NeoBio Labs) following manufactures protocol. Fourty-eight hours after transfection, cells were collected and washed with PBS. Cells were then incubated with 2G12 (Immune Tech) at a 1:100 dilution in Facs buffer (1% FBS in PBS) for 1 hour at room temperature. After washing the cells with PBS, mouse anti-human phycoerythrin linked antibody was added at a 1:5000 dilution for 1 hour at room temperature. Cells were then washed and fixed with 3% paraformaldehyde and run on a modified LSR II (BD Biosciences). Analysis was performed using FlowJo software (FlowJo Enterprise).

Immumization of Guinea Pigs

Female Hartley guinea pigs (300-350 grams) were immunized with 25 μg of DNA intradermal every 3 weeks with in vivo electroporation using the CELLECTA adaptive constant current electroporation device (Inovio Pharmaceuticals, Blue Bell, Pa.). Square-wave pulses were delivered with a triangular electrode array consisting of 3 26-gauge solid stainless steel electrodes. Two constant current pulses of 0.2 Amps were delivered with a 3 second delay and 52 ms length. Blood was collected for analysis before every vaccination.

Immumization of Rabbits

Female New Zealand white rabbits (1900 grams) were immunized using between 100 μg-200 μg/plasmid of DNA intradermal every 3 weeks with in vivo electroporation using the CELLECTA adaptive constant current electroporation device (Inovio Pharmaceuticals, Blue Bell, Pa.). Group 1 rabbits received 200 μg total of each plasmid delivered to two sites. Group 2 rabbits received 100 μg of each DNA plasmid injected into 6 separate sites followed by electroporation. Groups 3-6 received a mixture of 100 μg/plasmid injected into multiple sites (4-6 depending on the number of plasmids) followed by electroporation. Each site received 100 μg of mixed DNA. Blood was collected for analysis before every vaccination.

Immunization of Non-Human Primates

Eight Indian rhesus macaques were house at Bioqual (Rockville Md.) according to the standards to the American Association for Accreditation of Laboratory Animal Care and all animal protocols were IACUC approved. All animals received six vaccinations: the first four were administered intradermally, and the last two were administered intramuscularly. The first and second vaccination on weeks 0 and 6 were a combination of five clade A primary envelopes (1.0 mgs each), formulated together and delivered to 5 separate sites. The third immunization delivered on week 12 was a combination of four clade B envelopes (1.0 mgs each), formulated together and administered to four different sites. The four immunization delivered on week 18 was a combination of six clade B envelopes (1.0 mgs each), formulated together and administered to six different sites. The fifth and six vaccination were given on weeks 44 and 81, composed of all 15 envelopes (1.0 mgs each) formulated together and delivered to a single site. All DNA deliveries were followed by in vivo EP with the constant current CELLECTRA® device (Inovio Pharmaceuticals, Plymouth Meeting, Pa.) with 3 pulses at 0.5 A constant current, a 52 ms pulse length and 1s rest between pulses.

Blood Collection

Animals were bled 2 weeks following each immunization. Blood (15 ml at each time point) was collected in EDTA tubes and peripheral blood mononuclear cells (PBMCs) were isolated using standard Ficoll-Hypaque procedure with Accuspin tubes (Sigma-Aldrich, St. Louis Mo.). An additional 10 ml was collected into clot tubes for serum collection.

Rhesus IFN-Gamma Enzyme-Linked Immunospot Assay (ELISpot).

To determine cellular responses, interferon-gamma (IFN-γ) ELISpots (MabTech, Stockholm Sweden) were performed following manufactures protocols. Isolated PBMCs were stimulated overnight in the presence of either specific peptide antigens (Consensus clade A and B envelope peptides (NIH AIDS Research & Reagent Program, Germantown, Md.), R10 (negative control), or anti-CD3 (positive control). All samples were run in triplicate.

Endpoint Binding Titer ELISA

The measurement of anti-HIV 120 specific antibodies was determined by ELISA (enzyme linked immunosorbent assay). Nunc-Immuno Plates (Nalge Nunc Internaltional) were coated with 1 μg/ml of either consensus clade A, 92RW020, SF162, or ZM197M soluble gp120 (Immune Technology Corp) and incubated overnight at 4 deg C. After washing, plates were block with 10% fetal bovine serum (FBS) in 1× phosphate-buffered saline (PBS) for 1 hour at room temperature. Plates were then washed again and incubated with specific guinea pig or rabbit sera diluted with 1% FBS in 1×PBS+0.02% Tween-20 for 1 hour at room temperature. After washing, plates were incubated with ½,000 or ⅕,000 dilution of horseradish peroxidase-conjugated goat anti-guinea pig or donkey anti-rabbit IgG respectively (Santa Cruz Biotech) for 1 hour at room temperature. The reaction was developed using the SigmaFast OPD tablets and stopped with 100μ of 2N sulfuric acid/well. Plates were read on Promega Globmax Multi detection system at an OD of 450 nm. Endpoint titers were determined as previously reported (Frey et al 1998). Briefly, the upper prediction limit of Envelope specific IgG antibodies was calculated using the Student t distribution. The upper prediction limit was defined as the standard deviation multiplied by a factor based on the number of naïve controls and a 95% confidence interval. Endpoint titer was the lowest dilution that remained above the upper prediction limit.

Epitope Mapping ELISA

Consensus clade C linear 15-mer peptides with 11 amino acid overlap (NIH AIDS Research and Reference Reagent Program) were used to make pools of the variable regions of gp120 and gp41. Peptides were resuspended in 1×PBS at a concentration of 1 mg/ml of each peptide. Plates were coated with 1 μg/ml of pooled peptides and ELISA was performed as described above. Sera from groups 2, 3, 4, 5 and 6 weeks 0 and 12 were diluted 1/50.

Neutralization Assay

HIV-1 envelope pseudovirus production and titration was performed as previously described (Seaman et al., 2010, J Virol 84:1439-52). Briefly, single round infectious HIV-1 env pseudoviruess were produced by co-transfection of 293T cells with 2 μg of an HIV-1 env/rev expressing plasmid and 12 μg of HIV-1 Δenv backbone plasmid (pSG3ΔEnv) using Lipofectamine transfection reagent (Invitrogen). After 24 hours, virus containing supernatant was harvested, spun and filtered over a 0.45 μm filter. The 50% tissue culture infectious dose was determined using TZM.bl cells as previously described (Li M et al 2005 J. Virol 79(16):10108-25). Aliquoted pseudotyped virus was stored at −80° C. TZM.bl cells were used to determine the amount of sera neutralization by measuring the reduction in luciferase reporter gene expression following a single round of infection.

Results

Construction and Design of Primary Isolate HIV-1 Envelopes

A panel of plasmids expressing HIV-1 gp160 envelopes from clade A, B, and C were constructed using the pVAX backbone (Invitogen). All sequences were obtained from GenBank using the accession numbers listed in Table 1. Inserts were RNA and codon optimized to increased expression and cloned into pVAX using either BamHI/XhoI or BamHI/EcoRI. Inserts were isolated from patients that ranged in disease progress from acute/early transmitted isolates to Fiebig stage VI. To confirm the expression of each plasmid, 293T cells were transfected with individual plasmids and flow cytometry was performed using anti-HIV-1 envelope antibody 2G12. Cells were gated on live singles and expression levels were compared to pVax empty vector control. All constructs expressed on the surface of the cells (FIG. 1A and FIG. 1B).

TABLE 1a

Description of inserts used in the study

| Name | Insert | Clade | Tier | Genbank # | Transmission | Stage |
|---|---|---|---|---|---|---|
| A1 | Q769ENVd22 | A | 2 | AF407158 | F-M | acute early |
| A2 | Q168ENVe2 | A | 2 | AF407148 | F-M | acute early |
| A3 | Q842ENVd12 | A | 2 | AF407160 | F-M | acute early |
| A4 | Q461ENVe2 | A | 2 | AF407156 | F-M | acute early |
| A5 | Q23ENV17 | A | 2 | AF004885 | F-M | Fiebig IV |
| A6 | Q259d2.17 | A | 2 | AF407152 | F-M | acute early |
| B1 | WITO4160.33 | B | 2 | AY835451 | F-M | Fiebig II |
| B2 | TRJO4551.58 | B | 3 | AY835450 | M-M | Fiebig II |
| B3 | PVO.4 | B | 3 | AY83544 | M-M | Fiebig III |
| B4 | TRO.11 | B | 2 | AY835445 | M-M | Fiebig III |
| B5 | AC10.0.29 | B | 2 | AY835446 | M-M | Fiebig III |
| B6 | REJO4541.67 | B | 2 | AY835449 | F-M | Fiebig II |
| B7 | RHPA4259.7 | B | 2 | AY835447 | | Fiebig < V |
| B8 | NL43 | B | 1B | AF324493 | | |
| B9 | QHO692.42 | B | 2 | AY835439 | F-M | Fiebig V |
| B10 | CAAN5342.A2 | B | 2 | AY835452 | M-M | |
| C1 | Du123.6 | C | 2 | DQ411850 | FSW | Fiebig VI |
| C2 | ZM53M.PB12 | C | 2 | AY423984 | F-M | |
| C3 | Du422.1 | C | 2 | DQ411854 | FSW | Fiebig V |
| C4 | Cap210.2.00.E8 | C | 2 | DQ435683 | FSW | |
| C5 | Du151.2 | C | 2 | DQ411851 | FSW | Fiebig V |
| C6 | Du156.12 | C | 2 | DQ411852 | FSW | Fiebig < IV |
| C7 | Du172.17 | C | 2 | DQ411853 | FSW | Fiebig VI |
| C8 | Cap45.2.00.G3 | C | 2 | DQ435682 | FSW | |
| C9 | ZM233M.PB6 | C | 2 | DQ388517 | F-M | |
| C10 | ZM249M.PL1 | C | 2 | DQ388514 | F-M | |
| C11 | ZM214M.PL15 | C | 2 | DQ388516 | F-M | |

TABLE 1b

Showing the relationship between the insert and SEQ ID NOs. Each insert was cloned into the pVAX backbone (Invitrogen) under the control of the cytomegalovirus immediate-early promoter using either BamH1/Xho1 or BamH1/EcoR1. The insert was full length gp160 and was codon optimized to increase protein expression. All sequences were obtained from Genbank using the accession number listed.

| Name | Insert | Nucleotide SEQ ID NO | Encoded aa SEQ ID NO |
|---|---|---|---|
| A1 | Q769ENVd22 | 1 | 2 |
| A2 | Q168ENVe2 | 3 | 4 |
| A3 | Q842ENVd12 | 5 | 6 |
| A4 | Q461ENVe2 | 7 | 8 |
| A5 | Q23ENV17 | 45 | 46 |
| A6 | Q259d2.17 | 9 | 10 |
| B1 | WITO4160.33 | 11 | 12 |
| B2 | TRJO4551.58 | 13 | 14 |
| B3 | PVO.4 | 15 | 16 |
| B4 | TRO.11 | 17 | 18 |
| B5 | AC10.0.29 | 53 | 54 |
| B6 | REJO4541.67 | 19 | 20 |
| B7 | RHPA4259.7 | 21 | 22 |
| B8 | NL43 | 51 | 52 |
| B9 | QHO692.42 | 55 | 56 |
| B10 | CAAN5342.A2 | 57 | 58 |
| C1 | Du123.6 | 23 | 24 |
| C2 | ZM53M.PB12 | 25 | 26 |
| C3 | Du422.1 | 27 | 28 |
| C4 | Cap210.2.00.E8 | 29 | 30 |
| C5 | Du151.2 | 31 | 32 |
| C6 | Du156.12 | 33 | 34 |
| C7 | Du172.17 | 35 | 36 |
| C8 | Cap45.2.00.G3 | 37 | 38 |
| C9 | ZM233M.PB6 | 39 | 40 |
| C10 | ZM249M.PL1 | 41 | 42 |
| C11 | ZM214M.PL15 | 43 | 44 |

Expression of Plasmids

To confirm the expression of each plasmid, 293T cells were transfected with individual plasmids and fluorescent immunohistochemistry was performed using anti-HIV-1 envelope antibody 2G12. Analysis using gel electrophoresis and staining, showed expression of the encoded protein.

Figures 2A, 2B:
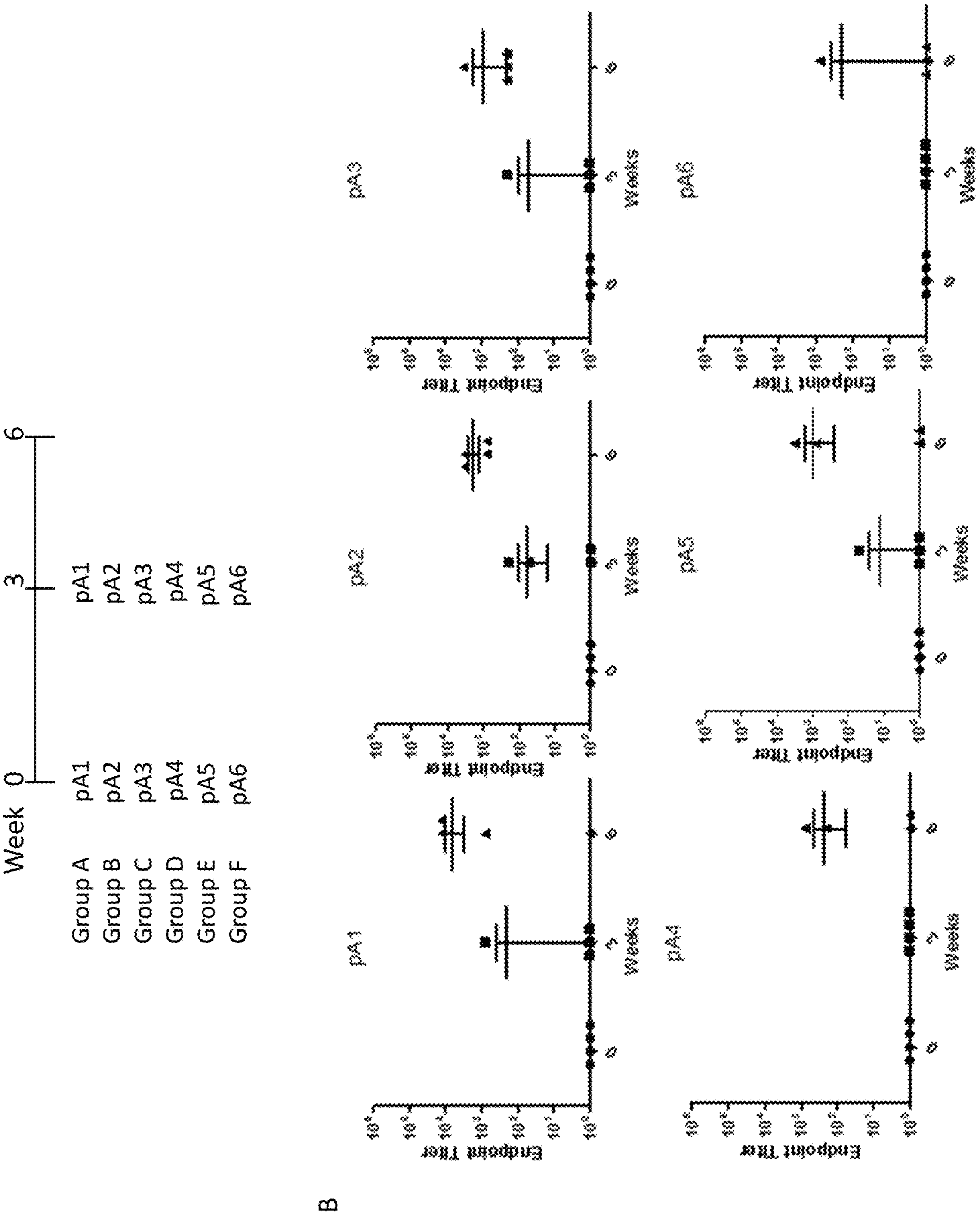
FIGS. 2A and 2B, is a series of images demonstrating that immunization of guinea pigs with plasmids containing primary isolate gp160 induce binding titers to consensus clade A gp120.

Immunization of a Single Plasmid Expressing Primary Isolate Gp160 Produces Limited Binding Titers Against a Consensus Gp120 Protein Previous experiments have shown that guinea pigs immunized with plasmids expressing consensus envelope immunogens are able to produce robust binding titers within two immunizations. To determine if plasmids expressing primary isolate envelopes could also induce binding titer responses, groups of four guinea pigs were immunized intradermal with 25 μg of plasmids A1-A6 tri-weekly followed by electroporation (FIG. 2A). Plasmids A1-A5 were able to induce anti-gp120 binding titers after two immunizations (FIG. 2B). However, this response was inconsistent as not all guinea pigs seroconverted after two immunizations. In addition, the level of binding titers was much lower than seen with consensus envelope immunogens.

Sequential Immunization of Plasmids do not Increase Antibody Responses

Figures 3A, 3B:
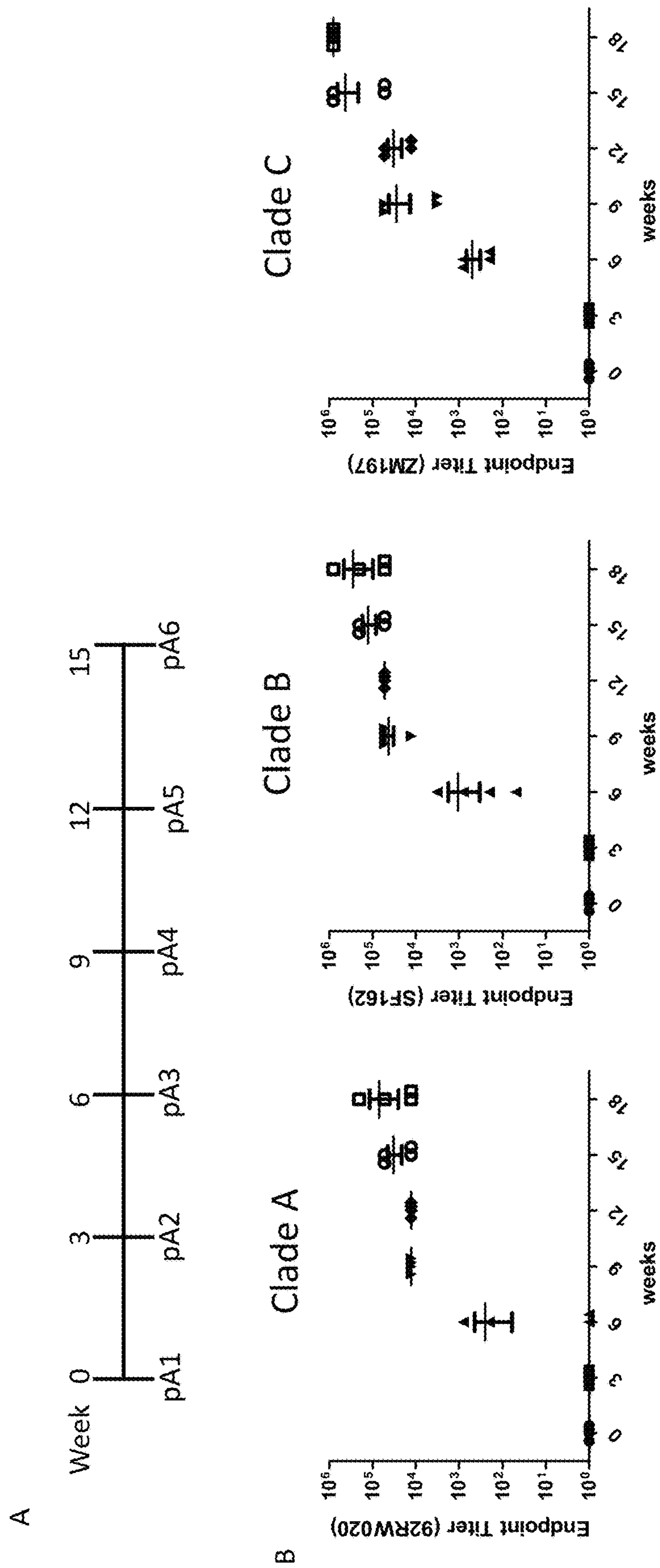
FIGS. 3A and 3B, is a series of images demonstrating that immunization of rabbits with sequential envelope plasmids induces binding titers to primary clade A, B, and C gp120s.

In order to investigate if sequential immunization of plasmids expressing different but related gp160 inserts, four rabbits were immunized with 600 μg of plasmids A1-A6 in a stepwise fashion (FIG. 3A). After three immunization, binding antibodies are detected against primary gp120 envelopes from clades A, B, and C (FIG. 3B). For clades A and B (92RW020 and SF162 respectively), binding titers were only moderately increased after the $4^{th}$ immunization. However, binding titers to clade C gp120 (ZM197) continue to increase through the final immunization. Thus, rabbits immunized with multiple different DNA constructs expressing primary gp160 envelopes are able to induce a potent binding humoral response which could induce functional antibodies.

Formulation of Plasmids Affect the Strength of the Response

Figures 4A, 4B, 4C:
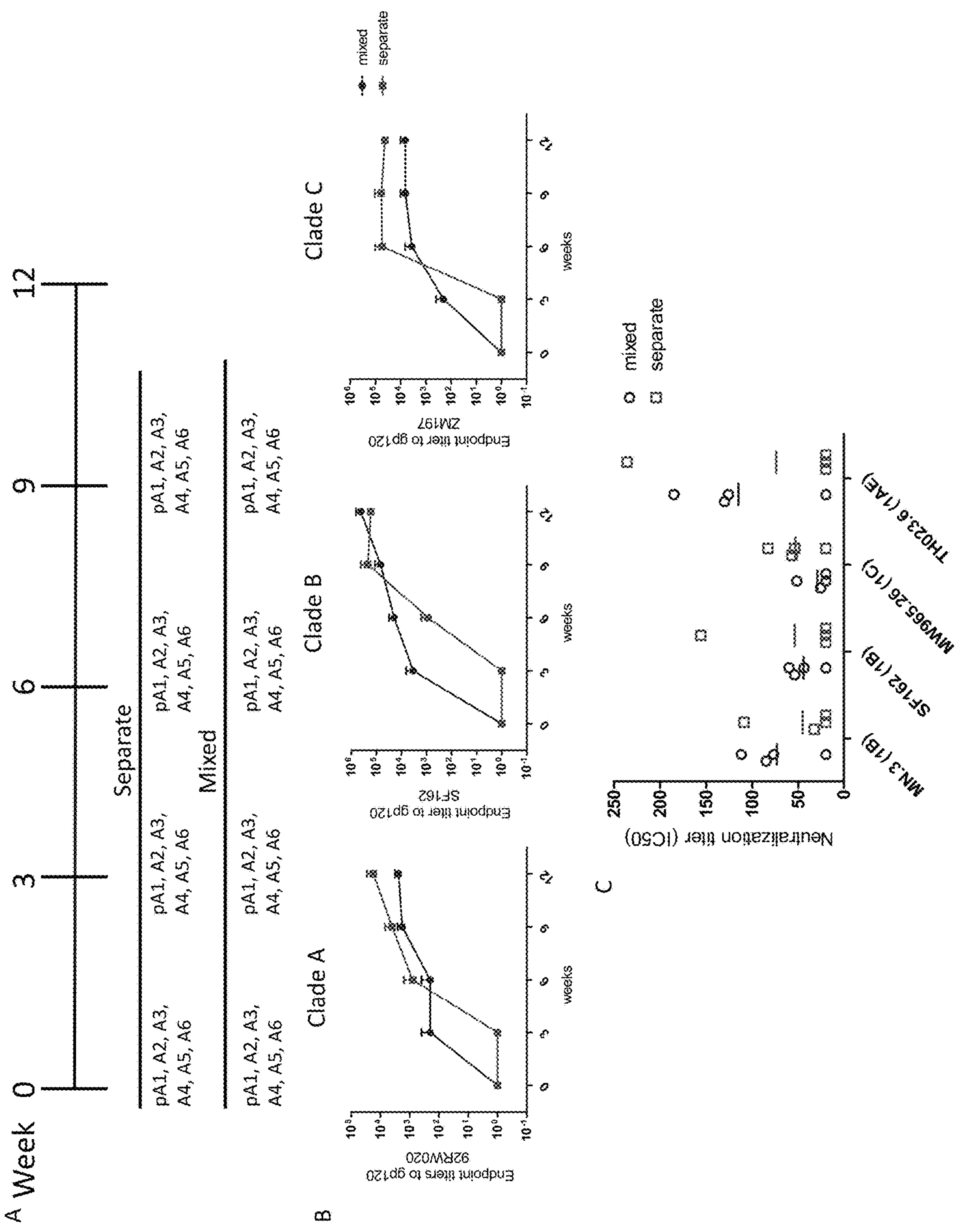
FIGS. 4A through 4C, is a series of images demonstrating that rabbits immunized with mixed envelopes more rapidly induce humoral responses compared to separate immunization.

Sequential immunization may be difficult to perform in the field due to different immunizations needed to be given at each visit. Thus we wanted to determine if these same envelopes formulated together in a vaccine could induce a similar humoral responses as seen in the sequential immunization. However, questions arose as to if there would be antigen competition between the groups of envelopes and thus, two vaccinations were performed: one where all of the plasmids were formulated together and another were each plasmid was given in a separate site. Rabbits were immunized four times with 100 μg of each plasmid ID followed by electroporation (FIG. 4A). The total amount of DNA for each immunization was the same across both groups (600 μg total–100 μg/plasmid) and the route and electroporation protocol were the same. The only difference was whether or not the plasmids were immunized separately or mixed together. In both cases, the binding titer response is similar to that induced in the sequential immunizations. Endpoint binding titers to the same primary gp120s were used to determine the induction of humoral responses. Though at the end of the vaccination (week 12) binding titers between the mixed vs separate are similar, the induction of humoral responses is quicker in the mixed group than in the separate group (FIG. 4B). In addition, post final vaccination neutralization titers were slightly, though not significantly, higher in the mix vs separate group for three different tier 1 viruses (MN.3, SF162, and TH023.6) (FIG. 4C). This data suggest that mixing the envelopes together does not dampen the humoral responses but instead, increases the initial seroconversion rate and could induce more superior functional antibody titers. Due to this and the ease mixed formulation provides for vaccine administration, all further studies were performed in this fashion.

Figures 5A, 5B, 5C:
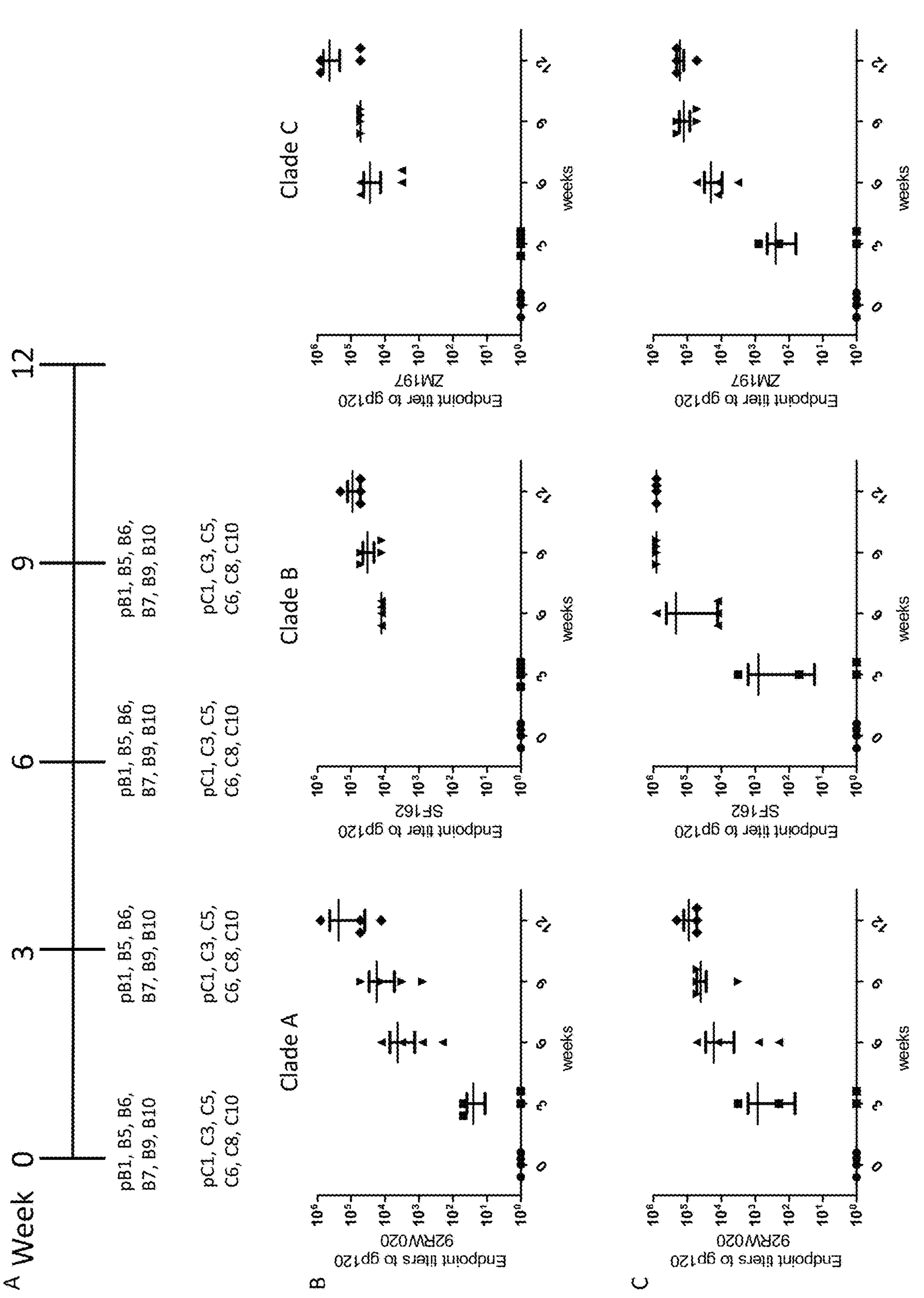
FIGS. 5A through 5C, is a series of images demonstrating that rabbits immunized with mixed clade B and C envelopes are able to induce strong humoral responses.

To further investigate the use of small groups of primary envelopes, additional rabbits were immunized with six plasmids expressing either clade B or clade C envelopes (FIG. 5A). All envelopes (100 μg/plasmid) were formulated together and delivered to six sites ID followed by electroporation. After two immunizations, half of the animals developed humoral responses in both the clade B and clade C regimen (FIG. 5B-FIG. 5C). Even though the animals are immunized with only a single clade, all rabbits induce strong cross-clade binding titers which was also seen in the clade A immunized rabbits. In fact, the clade C immunized rabbits had the highest binding titer responses to the clade B (SF162) gp120 protein. Overall, formulating multiple primary transmitter founder or acute envelopes together in a single formulation induces strong cross-clade binding titers and a limited neutralization profile.

Increasing Diversity within Group Expands Antibody Responses

Figures 6A, 6B, 6C:
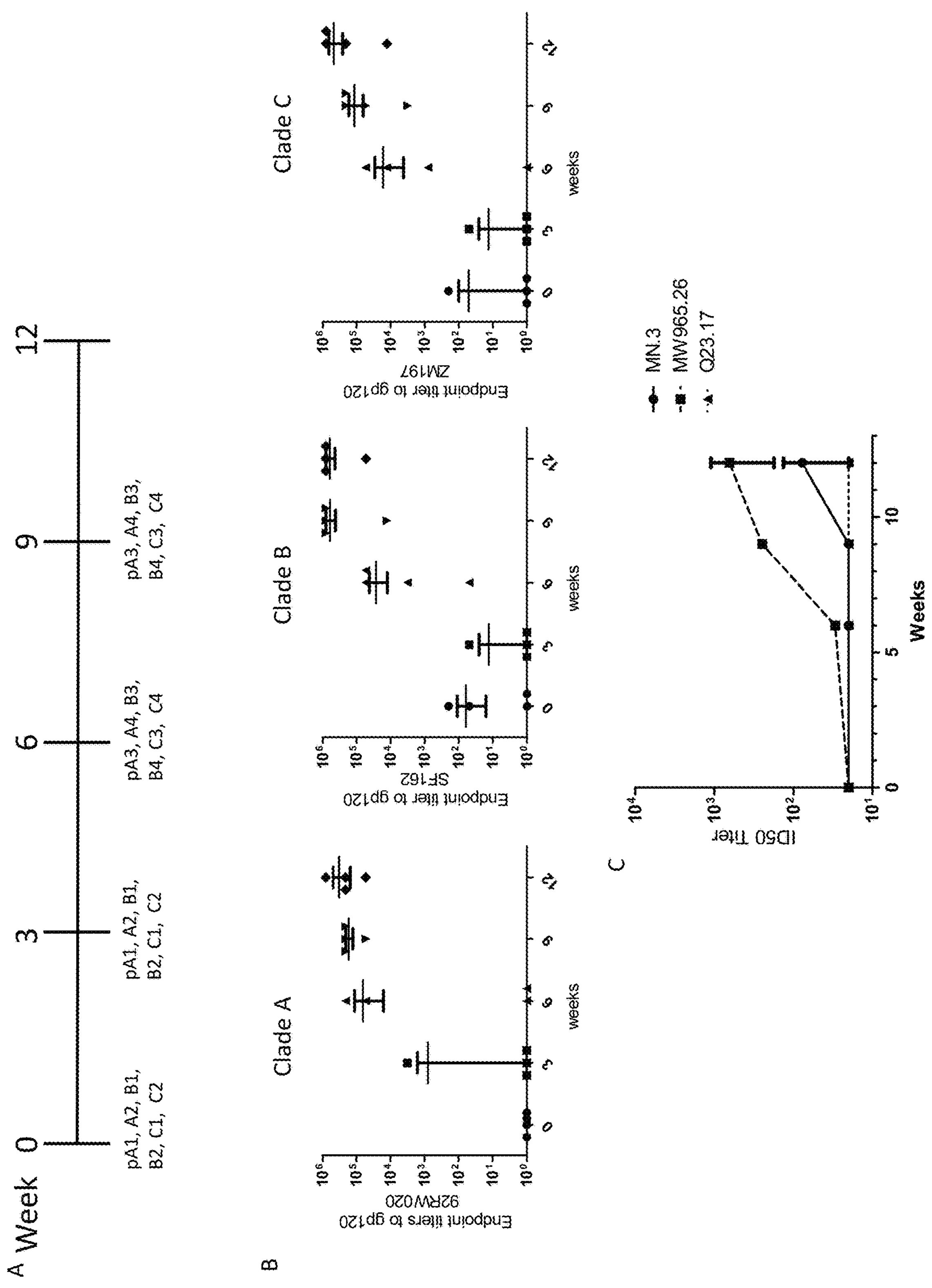
FIGS. 6A through 6C, is a series of images demonstrating that increasing the diversity of envelopes increases humoral responses.

To investigate whether the results seen in the single clade immunizations could be further expanded upon, two different groups of plasmids were used each containing two clade A, B, and C primary gp160 envelopes. Four rabbits were immunized with combination 1 (pA1, A2, B1, B2, C1, C2) twice followed by combination 2 (pA3, A4, B3, B4, C3, C4) (FIG. 6A). The plasmids were all formulated together per different combination with 100 μg (600 μg total) of DNA construct used per immunization, delivered ID followed by electroporation. The mean diversity within the groups was 22.0% and 21.0% respectively. The mean diversity intergroup was 20.6%. Once again after two immunization, there is potent induction of binding titers against primary clade A, B, and C gp120s (FIG. 6B). Neutralization of tier 1 clade B viruses is induced after immunization of combination 2 and continues to increase after the final immunization at week 9 (FIG. 6C). However, the neutralization profile of sera is still limited in breadth and there is limited neutralization of tier 2 virus in the A3R5.7 cells and no neutralization of tier 2 viruses in the TZM.bl cells (Table 2 group 5). The combination of plasmids expressing two clade A, B, and C envelope gp160s does appear to induce potent binding titers but limited neutralization breadth.

TABLE 3

Neutralization profile of serum from groups 5, 6, and 7

| Group | Group 5 | | | | Group 6 | | | | Group 7 | | | |
|---|---|---|---|---|---|---|---|---|---|---|---|---|
| Animal | 1 | | 2 | | 1 | | 2 | | 1 | | 2 | |
| Bleed Week | Wk 0 | Wk 12 | Wk 0 | Wk 12 | Wk 0 | Wk 12 | Wk 0 | Wk 12 | Wk 0 | Wk 12 | Wk 0 | Wk 12 |
| MN.3 Tier 1 Clade B | <20 | 135 | <20 | <20 | <20 | 226 | <20 | 90 | <20 | 248 | <20 | 524 |

TABLE 3-continued

| Neutralization profile of serum from groups 5, 6, and 7 | | | | | | | | | | | | |
|---|---|---|---|---|---|---|---|---|---|---|---|---|
| Group | Group 5 | | | | Group 6 | | | | Group 7 | | | |
| Animal | 1 | | 2 | | 1 | | 2 | | 1 | | 2 | |
| Bleed Week | Wk 0 | Wk 12 | Wk 0 | Wk 12 | Wk 0 | Wk 12 | Wk 0 | Wk 12 | Wk 0 | Wk 12 | Wk 0 | Wk 12 |
| MW 965.26 Tier 1 Clade C | <20 | 1113 | <20 | 177 | <20 | 530 | <20 | 630 | <20 | 862 | <20 | 287 |
| Q23.17 Tier 1 Clade A | <20 | <20 | <20 | <20 | <20 | 109 | <20 | 39 | <20 | 124 | <20 | 220 |
| RHPA4258.7 Tier 2 Clade B | <20 | <20 | <20 | <20 | <20 | 154 | <20 | 47 | <20 | 214 | <20 | 310 |
| TRO.11 Tier 2 Clade B | <20 | <20 | <20 | <20 | <20 | 36 | <20 | <20 | <20 | 54 | <20 | 57 |
| Ce1176_A3 Tier 2 Clade C | <20 | <20 | <20 | <20 | <20 | <20 | <20 | <20 | <20 | 21 | <20 | 26 |
| BF1266.431 a Tier 2 Clade C | <20 | <20 | <20 | <20 | <20 | 143 | <20 | 50 | <20 | 228 | <20 | 364 |
| Q842.d12 Tier 2 Clade A | <20 | <20 | <20 | <20 | <20 | 288 | <20 | 100 | <20 | 387 | <20 | 716 |
| C2101.c01 Tier 2 Clade AE | <20 | <20 | <20 | <20 | <20 | 45 | <20 | <20 | <20 | 84 | <20 | 109 |
| RHPA Tier 2 Clade B | 23 | 363 | <20 | 435 | 40 | 139 | 31 | 109 | 24 | 404 | 31 | 270 |
| REJO Tier 2 Clade B | <20 | <20 | <20 | <20 | <20 | 438 | <20 | 83 | <20 | 749 | <20 | 329 |
| CM234-2 Tier 2 Clade AE | 44 | 34 | 36 | 97 | 62 | 294 | 47 | 110 | 74 | 915 | <20 | 389 |

Neutralization was determined using tier 1 and 2 envelopes from clades A, B, C, and AE. In addition, neutralization was determine for a selection of tier 2 isolates in the A3R5.7 cell line.

Figures 7A, 7B, 7C:
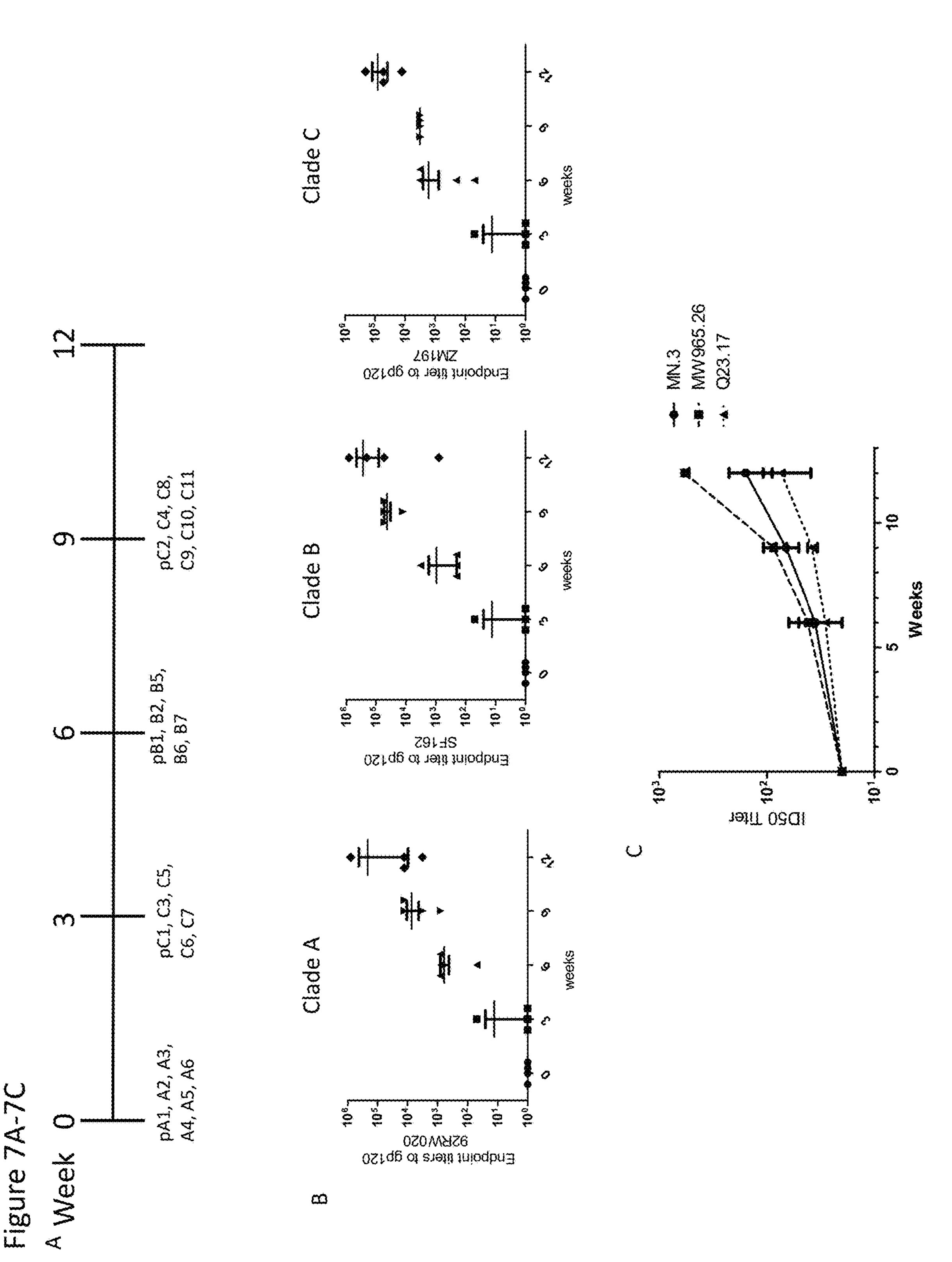
FIGS. 7A through 7C, is a series of images demonstrating that decreasing the percent of intra "cloud" diversity induces stronger humoral responses.

Creating "Clouds" with Limited Diversity Expand the Neutralization Breadth of Sera We next wanted to investigate if too much diversity within the vaccinated "cloud" could inhibit responses. Using the same primarily transmitted founder group (pA1-A6) as a priming dose, four rabbits were immunized with additional "clouds" or groups of plasmid which were more limited in diversity and stayed within clades (FIG. 7). The intra-cloud diversity ranged from 12.4-16.4% and inter-cloud was consistently around 20%. Each immunization was between 500 μg-600 μg of total DNA (100 μg of each plasmid) mixed together and administered ID to five or six separate sites followed by electroporation. Using this limited intra-cloud diversity regiment did not disrupt the ability to induce potent cross-clade binding tiers against the three primary isolate gp120 (FIG. 7B). There is a consistent boosting of titers after every immunization with the highest binding titers obtained after the final immunization at week 9. Although at a low level, as early as week 6 (post two immunizations), sera is able to neutralize tier 1 viruses from clades A, B, and C (FIG. 7C). This neutralization ability continues to rise after every immunization with final IC50 titers as high as 1/630 (Table 2 group 6). The limited diversity cloud vaccination is able to induce a more potent neutralization profile as sera is able to neutralize tier 2 viruses in A3R5.7 cells and even low but consentient neutralization of tier 2 virus in TZM.bl cells for the two rabbits tested. The ability to induce this robust of a response by DNA alone has yet to be seen and could lend itself well to further expansion by boosting with a different platform.

Highest Induction of Robust Antibody Responses in Rabbits Primed Twice with Transmitted Founder "Cloud"

Figures 8A, 8B, 8C:
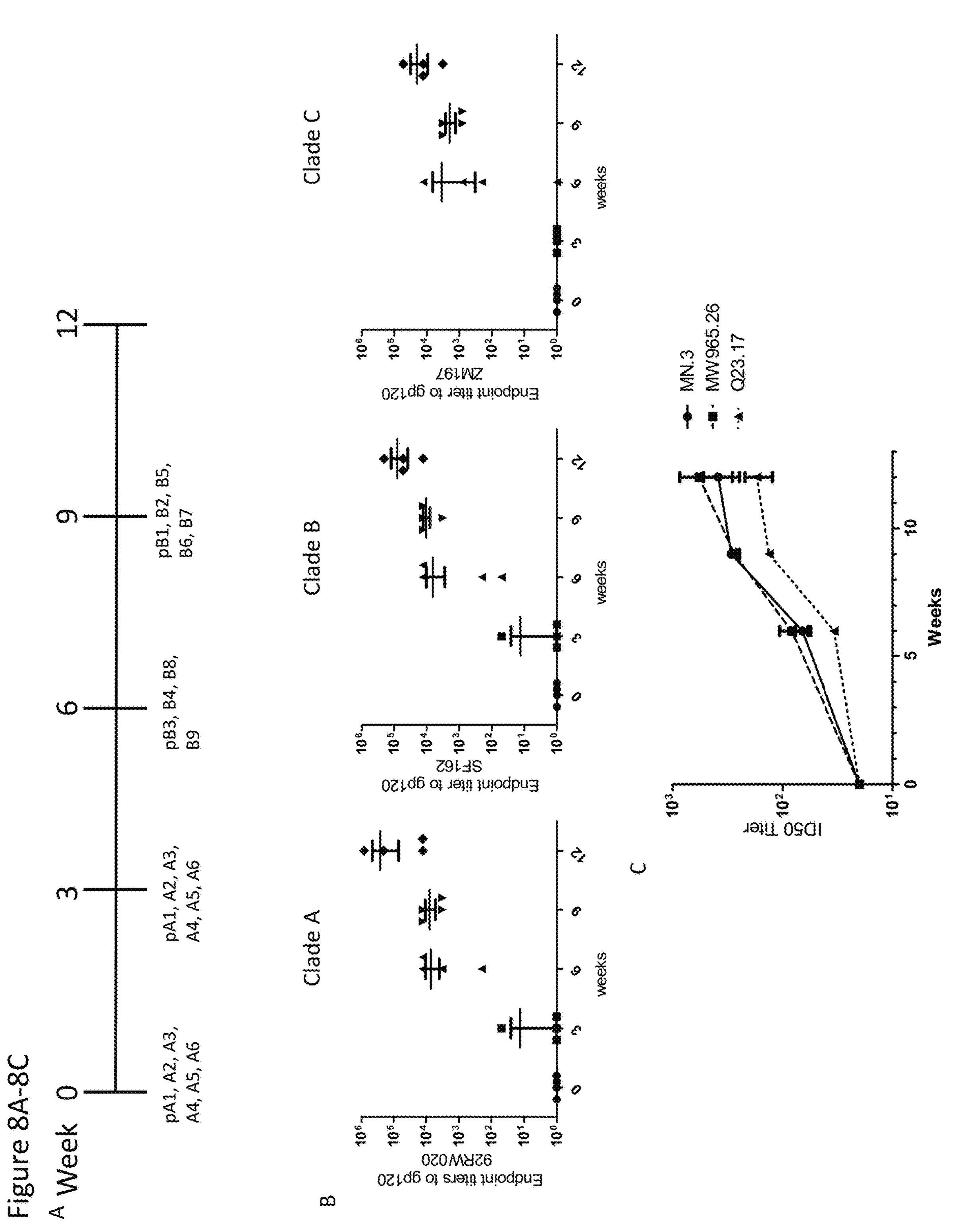
FIGS. 8A through 8C, is a series of images demonstrating that priming twice with the same cloud increases vaccine induced functional antibody titers.

The final group of rabbits looked to determine if these responses would increase by priming with the same group twice. This would allow for the immune system to potentially honing in on specific epitopes which would later be expanded by boosting with additional clouds. Rabbits were immunized twice with the transmitted founder plasmid cloud and boosted with primarily clade B immunogens (FIG. 8A). The intra-cloud diversity ranged from 13.3-14.3% and the inter-cloud diversity between 14-17.6%. Thus this regiment has the lowest diversity between the clouds compared to the other two combinations. This low intra-cloud diversity does not limit the responses as potent binding titers are induced in all animals after 3 immunizations (FIG. 8B). The highest and quickest induction of neutralization is seen for this group, with the most powerful response happening after the final immunization (FIG. 8C). In addition, sera from two rabbits were able to neutralize more isolates at higher IC50 concentrations than groups 4 and 5 (Table 2 group 7). This includes hard to neutralize tier 2 viruses where only one virus (Ce1176_A3) is not able to be neutralized. This neutralization capacity holds against clade C and clade AE viruses, both of which the rabbits never saw any isolates from either clade. Thus, priming rabbits with two immunizations of plasmids expressing primarily transmitted founder immunogens seems to focus the immune system in a way that allows for effective induction of broadly binding and neutralizing antibodies.

Figures 9A, 9B:
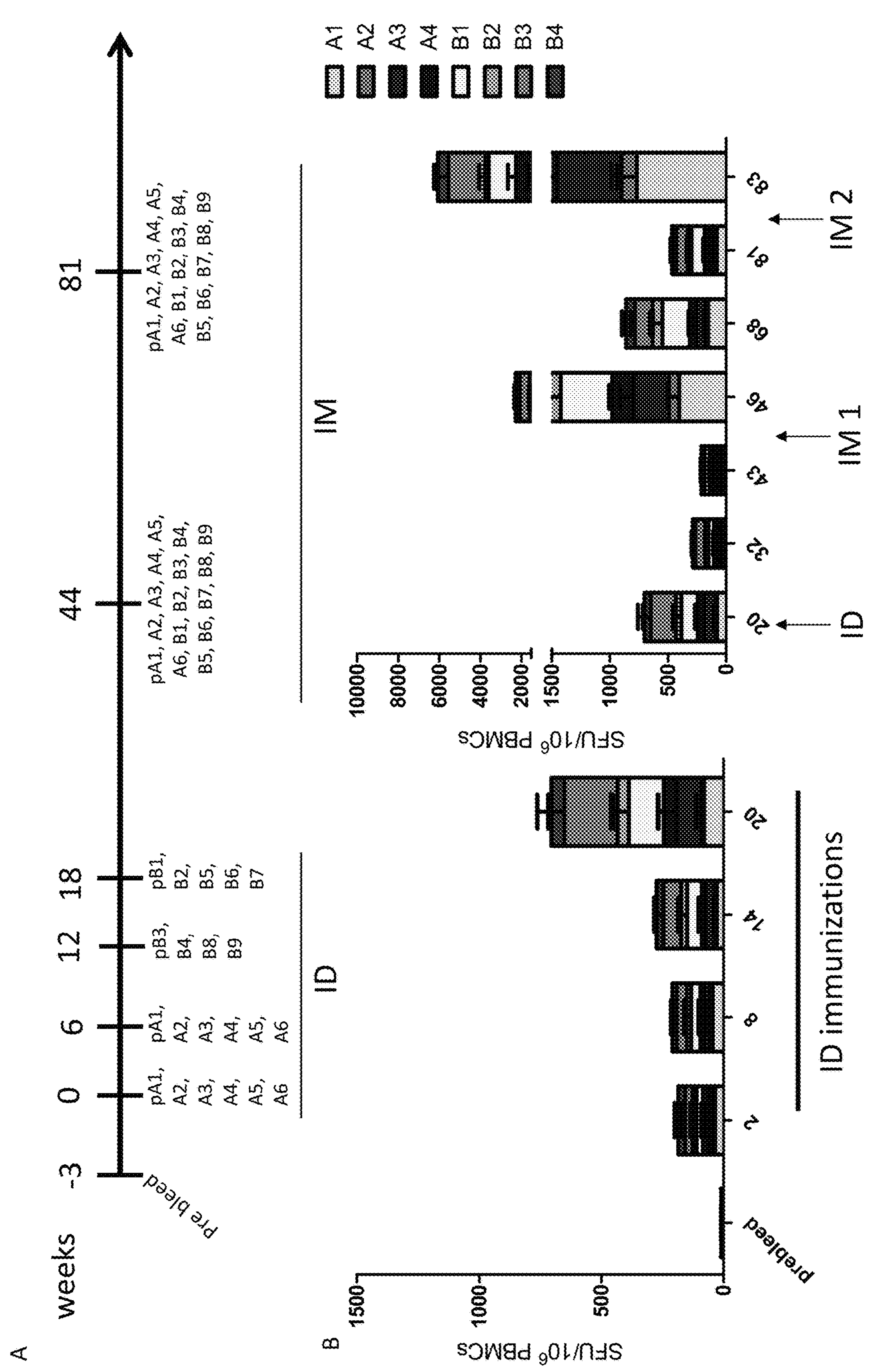
FIGS. 9A and 9B, is a series of images demonstrating that rhesus macaques immunized with primary envelopes from clades A and B induce robust cellular responses against consensus clade A and B peptides.

Non-Human Primates Immunized with "Clouds" of Primary Envelopes Induce Potent Cellular and Humoral Responses To further characterize the vaccine induced responses produced by the most potent regiment (FIG. 8A), eight rhesus macaques (RhMs) were immunized with a similar vaccine regiment. On weeks 0, 6, 12 and 18, the NHP received a mixture of different envelopes (1 mg/plasmid) formulated together and delivered ID followed by electroporation (FIG. 9A). To further expand the vaccine induced responses, at weeks 44 and 81 post first vaccination, all animals received all of the envelopes from vaccination 1-4 (1 mg/plasmid) delivered IM at a single site followed by electroporation. Cellular and humoral responses were followed two weeks after each vaccination. After only a single immunization, IFN-γ spot forming units (SFU) are detected against consensus clades A and B peptides (FIG. 9B). These responses are not boosted with the second immunization of the priming cloud but are expanded upon after the third and fourth immunization. After the final ID immunization, the average total IFN-γ SFU is around 800. Though there is contraction into the memory phase, cellular responses can still be detected against consensus clade A and B almost 6 months after final ID immunization. After the first IM boosting immunization at week 44, cellular responses expand greatly to levels over double the amount seen after final ID immunization. Over eight months after IM immunization, cellular responses have contracted but remain around the levels seen after final ID immunization. Upon second IM boost, cellular responses again expand above those seen after the previous IM immunization with IFN-γ SFU averaging around 7000. These responses are extremely high, especially since they are against unmatched peptides. In addition, since consensus peptides are used, this suggest that these small "clouds" of immunogens are able to induce potent cellular responses against conserved regions within the envelope. This could be important for the induction of cytotoxic T cells against envelope as well as providing broad CD4 T cell help.

Figure 10:
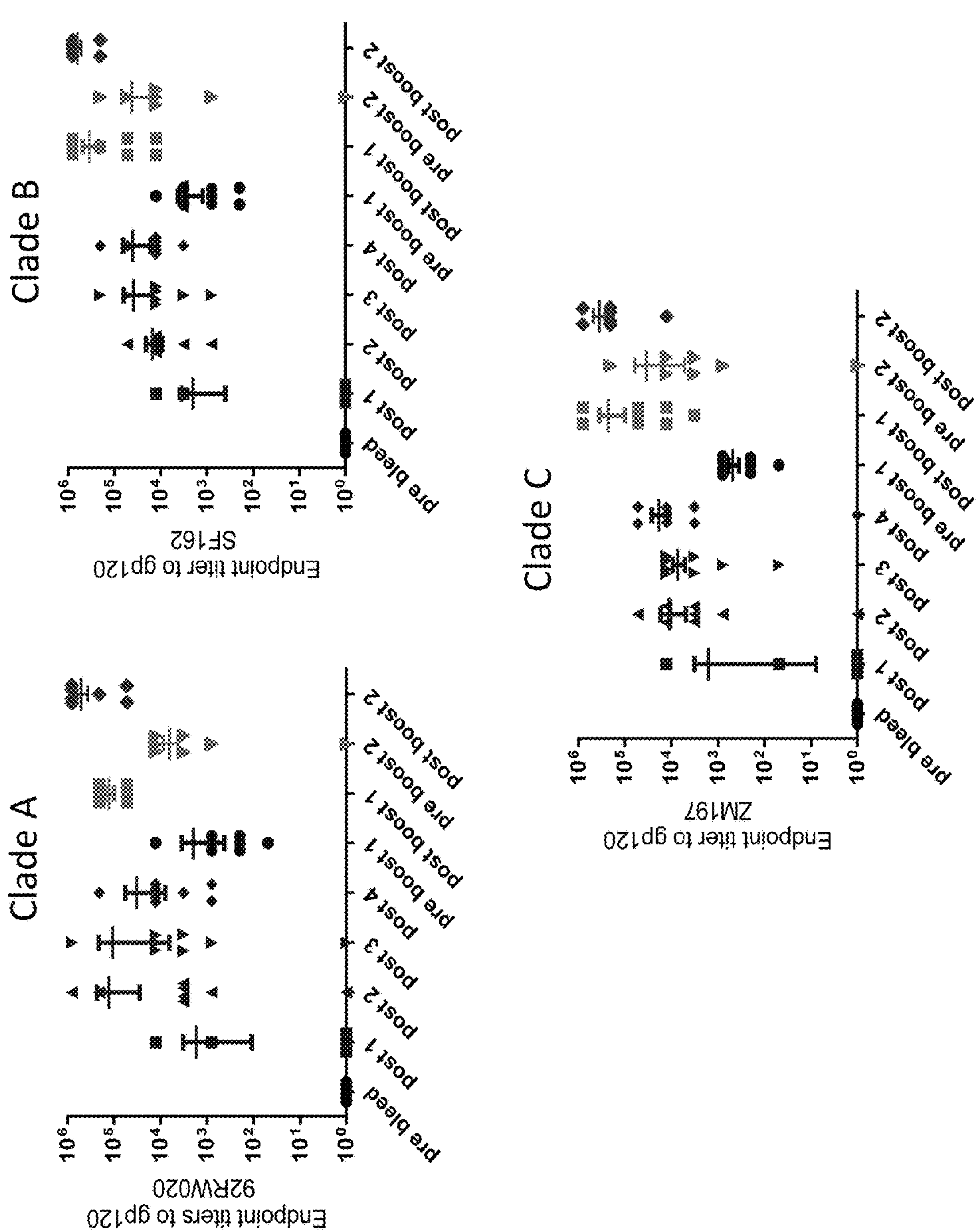
FIG. 10 is an image demonstrating that RhMs immunized with "cloud" immunizations develop broad cross-clade binding titers. Endpoint binding titers were determined against clade A (92RW020), clade B (SF162) and clade C (ZM197) primary gp120s. Individual titers are denoted in the shapes and geometric mean titers by the horizontal bar.
Figure 11:
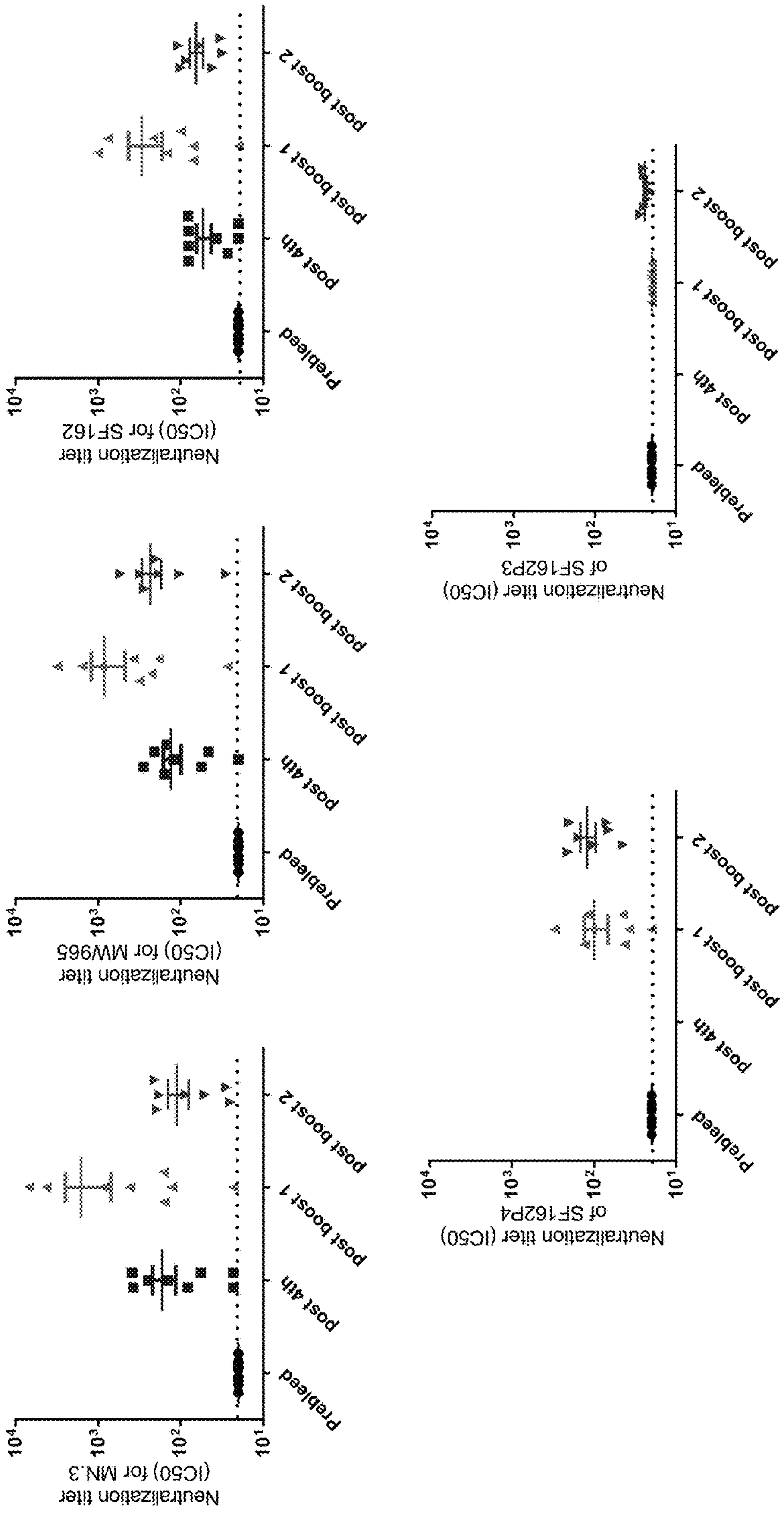
FIG. 11 is an image demonstrating that RhMs immunized with "cloud" immunizations develop neutralization titers which are expanded upon IM boost. Neutralization titers were determined after final ID immunization, post $1^{st}$ or $2^{nd}$ IM boost against tier 1 viruses as well as IMC for SF163P4 and SF162P3.

The primary envelope cloud immunization also induces potent humoral responses. After a single immunization, two out of eight RhMs seroconvert to clade A, B and C primary gp120 proteins. After the final ID immunization, all animals have strong endpoint binding titers against the primary envelopes averaging above $10^4$ (FIG. 10). These responses also contract down in the memory phase but remain high (average above $10^3$) six month post last ID immunization. Similar to cellular responses, after the IM boost, binding titers reach levels higher than after ID immunization with the average binding titer above $10^5$. These responses are also slightly boosted after a second IM immunization to levels reaching $10^6$ binding titers. In addition to binding titers, the vaccination regimen also induces functional antibodies. Using only DNA vaccination we are able to get cross clade neutralization titers against a diversity of tier 1 viruses (FIG. 11). After ID immunization, neutralization titers for MN.3, MW965 and SF162 average above or around $10^2$. After the first IM boost, levels are increased to above $10^3$ for MN.3 and MW965 and just below $10^3$ for SF162. Additionally after the first IM boost, neutralization titers are detected against infectious molecular clone (IMC) of SF162P4 virus. These average above $10^2$. After the second IM boost we do not see levels increase above those observed after the initial IM boost. In fact, for MN.3, MW965 and SF162, the levels were lower and usually averaged around the same titers as those seen after the ID immunizations. However, levels against SF162P4 IMC were maintained and importantly, there were limited but low neutralization titers induced against the tier 2 virus SF163P3. These data supports the use of primary transmitter founder envelopes deliver in small "cloud" immunizations for the induction of potent cellular and humoral responses.

The Mixed Clouds Induce Primarily V3 Binding Antibodies

Figure 12:
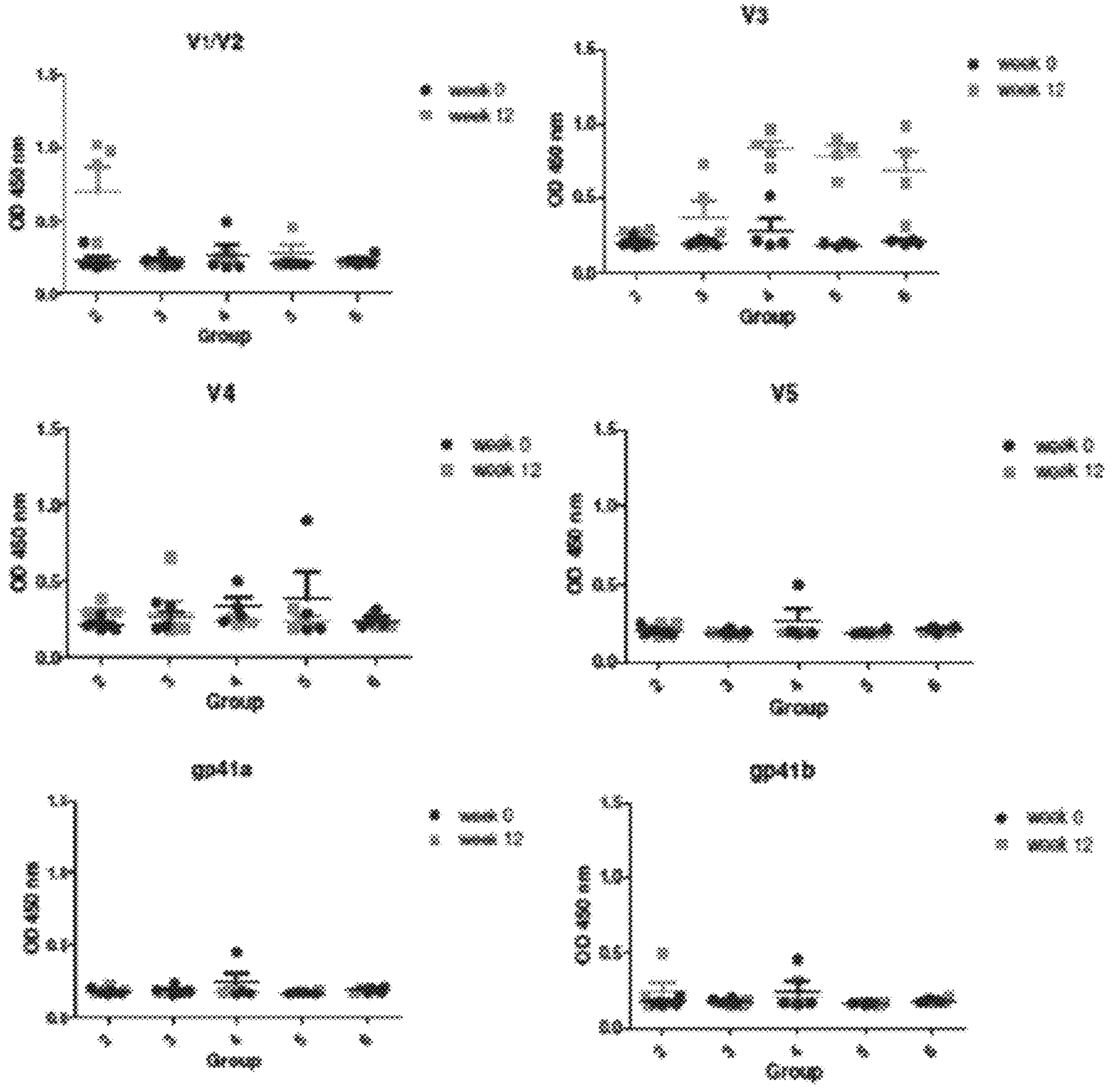
FIG. 12 displays graphs of binding titers. Mixing of plasmids together drives binding titers against peptides from the V3 region of gp160. Linear 15mer amino acid peptides overlapping by 11 amino acids representing the entire protein consensus sequence of HIV-1 clade C were used to create pools for the variable regions of gp120 as well as gp41. Serum from weeks 0 and 12 were used in a binding ELISA to determine the footprint of the antibodies. There is increased induction of binding antibodies to the V3 region of gp120 in groups 3, 4, 5, and 6 and increased binding to the V1/V2 region in group2.

In order to determine the binding epitope of sera antibodies, linear 15mer peptides will 11 amino acid overlap consisting of the entire consensus clade C gp160 (NIH AIDs Reagents and Reference program) were used to create pools of variable regions of gp120 as well as two pools for gp41. Binding ELISAs were performed using each pool and sera from week 0 and week 12 for the groups which induced binding titers (groups 2-6). All groups except for group 2 induced a high amount of binding to the V3 peptide pool (FIG. 12). Group 2 which consisted of the same DNA as group 3 but each plasmid was immunized to a separate site seemed to drive binding titers to the V1/V2 pool. Both the V1/V2 and the V3 have classes of broadly neutralizing antibodies associated with them (PG and the PGT family respectfully) (reference). However, this binding epitope analysis was not expansive as it did not cover any of the constant regions and relied on linear epitopes. Many potent broadly neutralizing antibodies, including the PG's and the CD4 bs antibodies rely on conformational or quaternary epitope binding. Thus additional test should be performed to determine the exact epitope the vaccination is able to induce.

Example 2—Extreme Polyvalency Induces Potent Cross-Clade Cellular and Humoral Responses in Rabbits and Non-Human Primates As described herein, over 40 different DNA plasmids have been developed which express consensus as well as primary HIV Envs. All of these optimized plasmids are able to induce both cellular and humoral responses in mice. Different combinations of Envs were tested in rabbits to further characterize the humoral responses and explore neutralization. Rabbits immunized with clusters of clade A transmitted founder (TF) gp160 DNA induced cross-clade binding titers with limited neutralization. Including TF Envs from different clades increased binding titers as well as neutralization breadth and potency. Formulating the gp160s to be administered to the same site induced faster seroconversion than delivering the Envs at separate sites. The most potent combination was moved forward into non-human primates, which were immunized with clusters of gp160 DNAs (14 different Envs in total) at weeks 0, 4, 8, 12 and boosted at weeks 48 and 85. The vaccine induced cross-clade cellular and humoral responses after two immunizations. These responses increased after each immunization and were maintained into memory. In addition to binding, the vaccine also induced tier 1A and 1B neutralization titers and antibody dependent cellular cytotoxicity against both homologous and heterologous targets. Boosting at week 48 and 85 further increased both responses.

It is shown herein that DNA plasmids encoding consensus and TF Envs are expressed and induce a potent immune response. It is observed herein for the first time that exposure of the immune system to multiple Envs at one time can dramatically change the immune phenotype by inducing broader breadth of responses which has significant implications for HIV vaccine development.

METHODS

Envelope Immunogens

Plasmids expressing codon and RNA optimized HIV Envelope glycoproteins (gp160) were made synthetically using OptimumGene® Codon optimization analysis (GenScript, Piscataway, NJ). Inserts were then cloned into the pVAX (Invitrogen, Carlsbad, CA) backbone using either BamHI/XhoI or BamHI/EcoRI cloning sites. Each insert was under the control of the cytomegalovirus immediate-early promoter. A description of each of the inserts can be found in FIG. 24.

Expression of Plasmids

Each plasmid was tested in vitro for proper expression. Briefly, HEK 293T cells (ATCC, Manassas, VA) were cultured in Dulbecco's Modified Eagle Medium (Thermo Fisher Scientific, Carlsbad, CA) supplemented with 10% fetal bovine serum (Atlas, Ft. Collins, CO) and 1% penicillin and streptomycin (Thermo Fisher Scientific). Twenty four hours before transfection, $7.5\times10^5$ cells were plated in 1.5 mls of media in a 6 well dish. Each plasmid was used in a separate transfection with pVax empty backbone serving as a negative control. Transfection was performed using NeoFectin transfection reagent (NeoScientific, Cambridge, MA) following manufactures protocol. Forty-eight hours after transfection, cells were collected and washed with PBS and lysed using Cell Signaling lysis buffer (Cell Signaling, Danvers, MA) modified with EDTA-free protease inhibitor (Roche, Basel, Switzerland). Bradford assay was used to quantify protein concentration of lysate following manufactures protocol (BioRad, Hercules, CA). Normalized lysate was then run on a NuPAGE® 12% Tris-Acetate gel and transferred to a PVDF membrane following manufactures protocol (Thermo Fisher Scientific). After 1 hour blocking with LI-COR Odyssey blocking buffer (LI-COR, Lincoln, Nebraska), membranes were probed overnight with a 1:1000 dilution of human 2G12 antibody (ImmuneTechnologies Corp, New York, NY) and 1:5000 dilution of mouse-anti human β-actin (Sigma Aldrich, St. Louis, MO) as a loading control. After washing with PBS-Tween, 1:10,000 dilution of secondary goat anti-human IRdye 680 and goat anti-mouse IRdye 800CW (LI-COR) antibodies were added in blocking buffer supplemented with 0.1% Tween and 0.01% SDS (Sigma Aldrich). Membranes were probed for 1 hour at room temperature followed by washing with PBS-Tween and PBS. Membranes were then scanned using LI-COR Odyssey CXL.

Immunization of Mice

To test for immunogenicity, 6-8 week old C57Bl/6 mice (Jackson Laboratories, Bar Harbor ME) were immunized with 25 μg of each plasmid followed by in vivo electroporation (EP) using the CELLECTA® 3P adaptive constant current electroporation device (Inovio Pharmaceuticals, Plymouth Meeting, PA) as previously described (Muthumani et al., 2013, PLoS One 8:e84234). Mice were immunized 3 times at 2 week intervals and sacrificed one week after final vaccination to assess vaccine induced immune responses.

Immunization of Guinea Pigs for Formulation Study

Female Hartley guinea pigs (300-350 grams) were immunized with 100 μg of DNA intradermal mantoux injection every 3 weeks with in vivo EP as described above. Six clade A plasmids were delivered to six separate sites or formulated together and spread across six different sites. Each guinea pig received the same total amount of DNA, volume of injection and sites of immunization. Blood was collected for analysis before every vaccination.

Immunization of Guinea Pigs for In Vivo Analysis

In order to differentiate each of the Envelopes, three tags were added via plasmid mutagenesis (Genscript): pQ168ENVe2-his, pQ23ENV17-flag, pDu151.2-cMyc. All tags were added to the C-terminus of the protein. Two female Hartley guinea pigs (300-350 grams) were injected with 16.5 μg of each plasmid (50 μg of total DNA) formulated together and injected ID using a mantoux injection. The area was then immediately electroporated using the ELGEN-SEP 4×4 array (3 pulses at 25V, pulse length 100 msec, pulse delay 200 msec). Guinea pigs were then euthanized 24 hours after treatment and the vaccinated skin was harvested. The skin biopsies were fixed by immersion in 4% paraformaldehyde (Sigma Aldrich) for 12 hr at 4° C. After washing with PBS, biopsies were immersed in 15% sucrose solution followed by immersion in 30% sucrose. The biopsies were then embedded in O.C.T compound (Fisher Scientific) and snap frozen. The skin was then sectioned in cryostat at a thickness of 15 μm, placed on a glass slide and stored at −80° C. Sections were then incubated with BSA-Histology buffer (0.5% (v/v) Triton X, 3% (w/v) BSA in 1×PBS) for 30 min at room temp. Primary antibodies were then added to each section and incubated for 2 hours at room temp. Primary antibodies include: Goat anti-FLAG (1:1000 QED Bioscience, San Diego, CA); mouse anti-HIS (1:200 Abcam, Cambridge, UK) and rabbit anti-myc (1:100, Abcam). After washing with PBS, the first round of secondary antibodies were added in BSA-Histology buffer. Following washing with PBS, sections were incubated with a second round of secondary antibodies. Round one included: donkey anti goat IgG—AF488 (1:200 Abcam) and donkey anti-rabbit IgG-AF55 (1:200 LifeTechnologies). The second round included goat anti-mouse-AF647 (1:200 Invitrogen). Sections were washed again and mounted with DAPI-Fluoromount (Fisher Scientific) and covered with a cover-slip. Sections were imaged with Olympus BX51 Fluorescent Microscope, QImaging Retiga3000 camera and QImaging software.

Immunization of Rabbits

Female New Zealand white rabbits (1900 grams) were immunized using 100 μg/plasmid of DNA intradermal every 3 weeks with in vivo EP as described above. All plasmids were formulated together and injected into multiple sites (3-6 depending on the number of plasmids). Each site received 100 μg of mixed DNA in a 100 μl mantoux injection. Blood was collected for analysis before every vaccination.

Immunization of Non-Human Primates

Four Indian rhesus macaques received six vaccinations: the first four were administered intradermally and the last two were administered intramuscularly. The first and second vaccination on weeks 0 and 6 were a combination of six clade A primary Envelopes (1.0 mgs each), formulated together and delivered to 6 separate sites. The third immunization delivered on week 12 was a combination of three clade B Envelopes (1.0 mgs each), formulated together and administered to three different sites. The four immunization delivered on week 18 was a combination of five clade B Envelopes (1.0 mgs each), formulated together and administered to five different sites. The fifth and six vaccination were given on weeks 44 and 81, composed of all 14 Envelopes (1.0 mgs each) formulated together and delivered to a single site. All DNA deliveries were followed by in vivo EP with the constant current CELLECTRA® device (Inovio Pharmaceuticals, Plymouth Meeting, Pa.) with 3 pulses at 0.5 A constant current, a 52 ms pulse length and 1s rest between pulses.

Blood Collection

Animals were bled 2 weeks following each immunization (weeks 2, 8, 14, 20, 46, 83) and at memory time points (weeks 32, 43, 68, 81). Blood (15 ml at each time point) was collected in EDTA tubes and peripheral blood mononuclear cells (PBMCs) were isolated using standard Ficoll-Hypaque procedure with Accuspin tubes (Sigma-Aldrich). An additional 10 ml was collected into clot tubes for serum collection.

Mouse IFN-Gamma Enzyme-Linked Immunospot Assay (ELISpot)

Ninety-six well filter plates (Millipore, Billerica, MA) were coated with anti-IFN-γ capture antibody (R&D, Minneapolis, MN) overnight at 4° C. Spleens were isolated from mice one week after final immunization. After processing the spleens as previously described (Muthumani et al., 2013, PLoS One 8:e84234), $2\times10^5$ cells were added to the blocked plates. Cells were stimulated with overlapping 15mer peptide pools for consensus clade A, B, or C gp160 (5 μg/ml per peptide). Media alone and concacavalin A (Sigma Aldrich) were used as negative and positive controls respectively. After 18 hrs of stimulation, the plates were washed and secondary detection antibody (R&D) was added for 24 hrs at 4° C. Plates were then washed and developed using the ELISpot Blue Color Module (Millipore) per the manufactures protocol. Plater were then scanned and counted using CTL-ImmunoSpot® S6 FluoroSpot plate reader (CTL, Shaker Heights, OH).

Mouse Serum Binding Using Enzyme Linked Immunosorbent Assay (ELISA)

Before sacrificing, serum from mice was collected to determine the vaccine induced humoral responses. Maxisorp 96 well plates (Thermo Fisher Scientific) were coated with 1 μg/ml of consensus clade A, B, or C gp120; consensus clade A, B, or C gp140; or HXBC2 gp41 (clade B) (Immune Technology Corp.) in PBS and stored at 4° C. overnight. After blocking with 10% fetal bovine serum (FBS) in PBS for 1 hour, mouse serum was diluted 1:50 in 1% FBS in PBST (0.1% Tween). After 1 hour at room temperature and washing, secondary goat anti-mouse HRP-labeled antibody (Santa Cruz Biotechnology, Dallas, TX) was used at a 1:5000 dilution. Plates were washed and developed for 5 minutes using SimgaFast OPD tablets (Sigma Aldrich) and stopped with 100 μl of 2N sulfuric acid (Sigma Aldrich). The OD450 nm was determined using the Promega GloMax plate reader (Promega, Madison, WI).

Endpoint Binding Titer ELISA

Maxisorp 96 well plates (Thermo Fisher Scientific) were coated with 1 μg/ml of 92RW020, SF162, or ZM197M (Immune Technology Corp) and incubated overnight at 4° C. Plates were blocked as described above for 1 hour at room temperature. Plates were then washed again and incubated with specific guinea pig, rabbit or NHP sera diluted with 1% FBS in 1×PBS+0.02% Tween-20 for 1 hour at room temperature. Dilutions started at 1:50 and then a four-fold dilution was performed. After washing, plates were incubated with dilutions of horseradish peroxidase-conjugated goat anti-guinea pig (1:2000) or donkey anti-rabbit (1:5000) IgG (Santa Cruz Biotech) or goat anti-NHP (1:5000) (Southern Biotech, Birmingham, AL) for 1 hour at room temperature. The plates were developed and read as described above. Endpoint titers were determined as previously reported (Frey et al 1998). Briefly, the upper prediction limit of Envelope specific IgG antibodies was calculated using the Student t distribution. The upper prediction limit was defined as the standard deviation multiplied by a factor based on the number of naïve controls and a 95% confidence interval. Endpoint titer was the lowest dilution that remained above the upper prediction limit.

Avidity Index ELISA

Plates were coated with 1 μg/ml of either 92RW020 (clade A), Sf162 (clade B) and ZM197 (clade C) gp120 (Immune Technology, New York, NY) in PBS. After blocking, guinea pig or NHP serum was diluted 1:100 or 1:500 (respectively) in 1% FBS in PBS-T. Each sample was run in quadruplicate where half of the wells were treated and half were untreated. After 1 hour incubation, plates were washed 5 times with PBS-T. Half of the wells for each sample were incubated with denaturing reagent, 8M urea, for 5 minutes while the others were incubated with PBS. Plates were washed and incubated with goat anti-guinea pig IgG HRP (1:2000) (Sana Cruz Biotech) or mouse anti-NHP IgG HRP (1:5000) (Southern Biotech, Birmingham, AL) in 1% FBS in PBS-T. Plates were then developed as described above and OD450 values were obtained. The avidity index was determined by dividing the OD450 values of the treated by the untreated and multiplying by 100.

Neutralization

Neutralization was determined using the previously described TZM-bl based assay (Seaman et al., 2010, J Virol 84:1439-52). The 50% inhibitory dose ($ID_{50}$) titer was determined as the serum dilution that caused a 50% reduction in the RLU compared to the level in the virus control after subtraction of the cell control background.

Rhesus IFN-Gamma ELISpot

To determine cellular responses, interferon-gamma (IFN-γ) ELISpots (MabTech, Stockholm Sweden) were performed following manufactures protocols. Isolated PBMCs were stimulated overnight in the presence of either specific peptide antigens (Consensus clade A and B Envelope peptides (NIH AIDS Research & Reagent Program, Germantown, MD), R10 (negative control), or anti-CD3 (positive control). All samples were run in triplicate. Spot-forming units were determined using the CTL-ImmunoSpot® S6 FluoroSpot plate reader.

Intracellular Staining of PBMCs

Intracellular staining of PBMCs was performed as previously described (Hutnick et al., 2012, Hum Gene Ther 23:943-50). Briefly, after isolation, PBMCs ($1\text{-}2\times10^6$) were stimulated with pools of either consensus clade A, B or C peptides for 6 hours in a 96 well U-bottom plate. Each peptide pool contained approximately 1 μg of each peptide. Media only (R10) and PMA (0.1 μg/ml) and ionomycin (0.5 μg/ml) (BD Bioscience, San Jose, CA) were used as negative and positive controls respectively. All stimulations were performed in the presence of Golgi stop/Golgi Golgi Plug™ (1:500 dilution BD Biosciences) and anti-CD107a (PE cy7 clone H4A3 BD Bioscience). After stimulation, cells were washed with PBS and stained with violet amine-reactive dye Live/Dead stain (Life Technologies, Carlsbad, CA) for 5 minutes followed by surface staining for 30 minutes at room temperature. Surface stain included CD4 (PECy5.5 clone S3.5 Invitrogen), CD8 (BV650 clone SK1 Biolegend, San Diego), CD95 (PE cy 5 clone DX2, Biolegend), CD28 (BV510 clone CD28.2 Biolegend) and dump channel antibodies CD14 (Pacific Blue clone M5E2 Biolegend) and CD16 (Pacific Blue clone 3G8 Biolegend). Cells were washed with PBS and fixed/permeabilized with BD Cytofix/Cytoperm (BD Biosciences) for 15 minutes at room temperature. Following washing with BD Perm/Wash buffer, cells were stained with intracellular antibodies for 1 hour at room temperature. Intracellular stain included CD3 (APC-Cy7, clone SP34-2 BD Bioscience), IL-2 (PE clonse Mq1-17H12, Biolegend), (APC, clone B27 Biolegend), and TNF-α (PE-Cy7 clone Mab11, Biolegend). Cells were analyzed using a modified BD LSR II (BD Biosciences) and analysis performed with FlowJo 9.2 (Tree Star, Ashland, OR).

Binding Antibody Multiplex Assay (SAMA)

To further determine binding to various gp120s, gp140s and V1/V2 scaffold proteins, a customized multiplex binding assay was used as previously described (Tomaras et al., 2008, J Virol 82:12449-63; Haynes et al., 2012, NEJM 366:1275-86). Serum from week 20 (post ID), week 46 (post IM 1) and week 83 (post IM 2) were tested at six 5-fold serial dilutions starting at 1:80. Area under the curve (AUC) was calculated using GraphPad Prism.

Antibody Dependent Cellular Cytotoxicity (ADCC)

ADCC activity against various Env coated target cells was measured using the ADCC-GranToxiLux (GTL) assay as previously described (Pollara et al., Cytometry A 79:603-12). Briefly, target cells were CEM.NKR$_{CCR5}$ cells (NIH AIDS Reagent Program, Division of AIDS, NIAID, NIH: CEM.NKR-CCR5) coated with recombinant HIV gp120 against WITO (B), JR-FL (B) and 92MG037.1 (A) or gp140 1086 (C). Effector cells were PBMC isolated from a HIV seronegative human donor heterozygous for 158F/V polymorphic variants of Fcγ receptor 3A. NHP serum was tested at baseline, week 20 (2 weeks post 4$^{th}$ ID immunization), week 46 (2 week post 1$^{st}$ IM boost), and week 83 (2 weeks post 2$^{nd}$ IM boost). Serum samples were tested using 4-fold serial dilutions ranging from 1:100 to 1:102,400. ADCC titers were calculated as the dilution at which responses were greater than or equal to 8% GzB expression.

Statistics

Statistical analysis was performed using GraphPad Prism (GraphPad Software, Inc. La Jolla, CA). Analysis among groups was performed using an independent T-test and a Mann-Whitney test depending on normalcy of data when two groups were being compared and an ANOVA when three groups were being compared. A p-value less than 0.05 was considered statistically significant.

RESULTS

Figure 13:
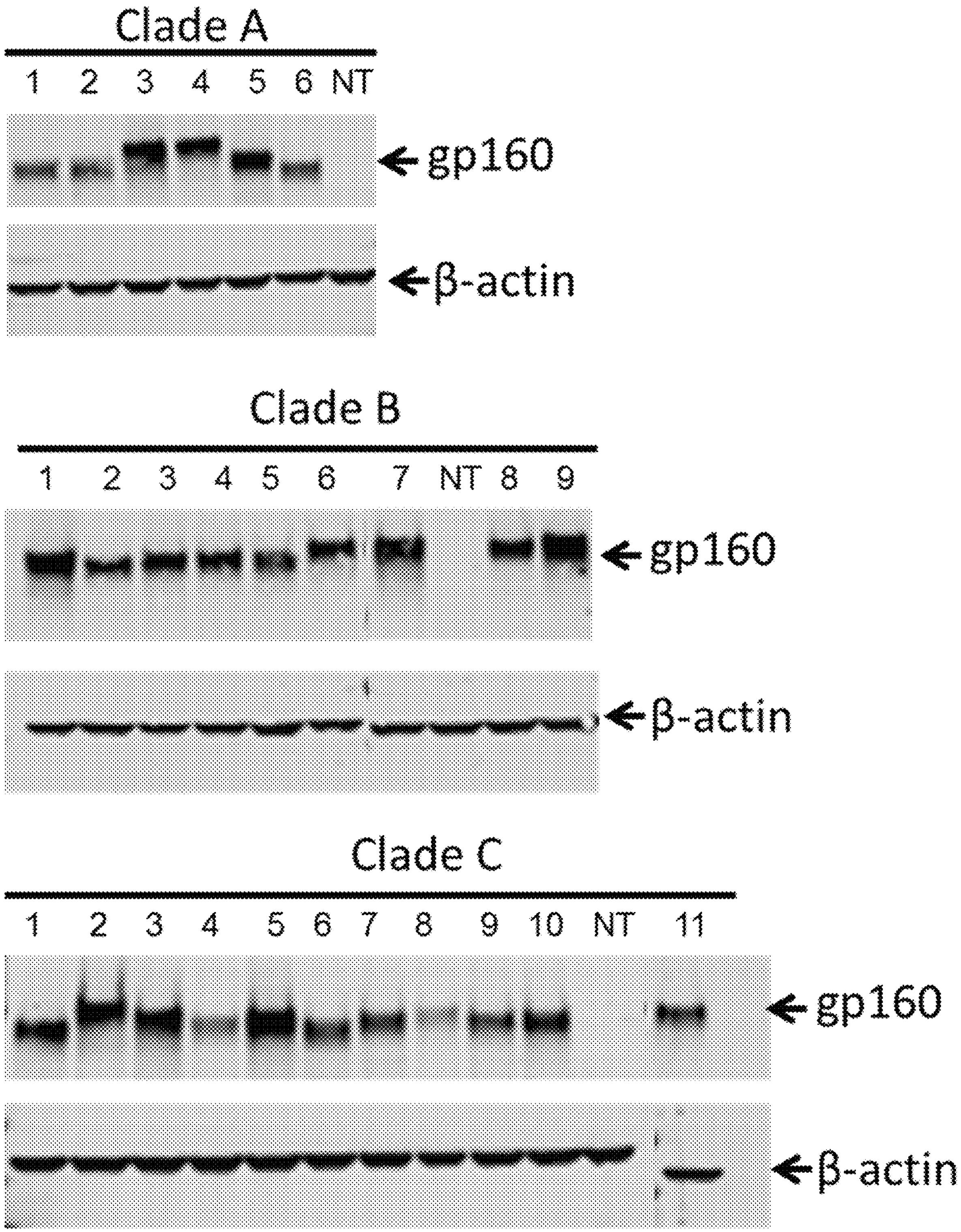
FIG. 13 depicts in vitro expression of primary HIV Env plasmids. 293T cells were transfected with each plasmid. Forty-eight hours later, cell lysate was harvested and western blot was performed to determine expression levels. All plasmid express Env detected by the neutralizing antibody 2G12 and the expected length.

Construction and Design of Primary Isolate HIV Envelopes and In Vitro Expression A panel of plasmids expressing RNA and codon optimized HIV gp160 primary Envelopes from clade A, B, and C were constructed using the pVAX backbone. All sequences were obtained from GenBank using the accession numbers listed in FIG. 24. Envelope sequences were isolated from patents that ranged in disease progress from acute/early transmitted isolates to Fiebig stage VI (Li et al., 2006, J Virol 89:11776-90; Li et al., 2006, J Virol 79:10108-25; Wilen et al., 2011, J Virol 85:8514-27). To confirm expression of each plasmid, western blot analysis was performed on transfected 293T lysate. All plasmids expressed and were detected by the neutralizing antibody 2G12 (FIG. 13).

Immunogenicity of Primary HIV Env Plasmids in Mice

Figures 14A, 14B, 14C, 14D:
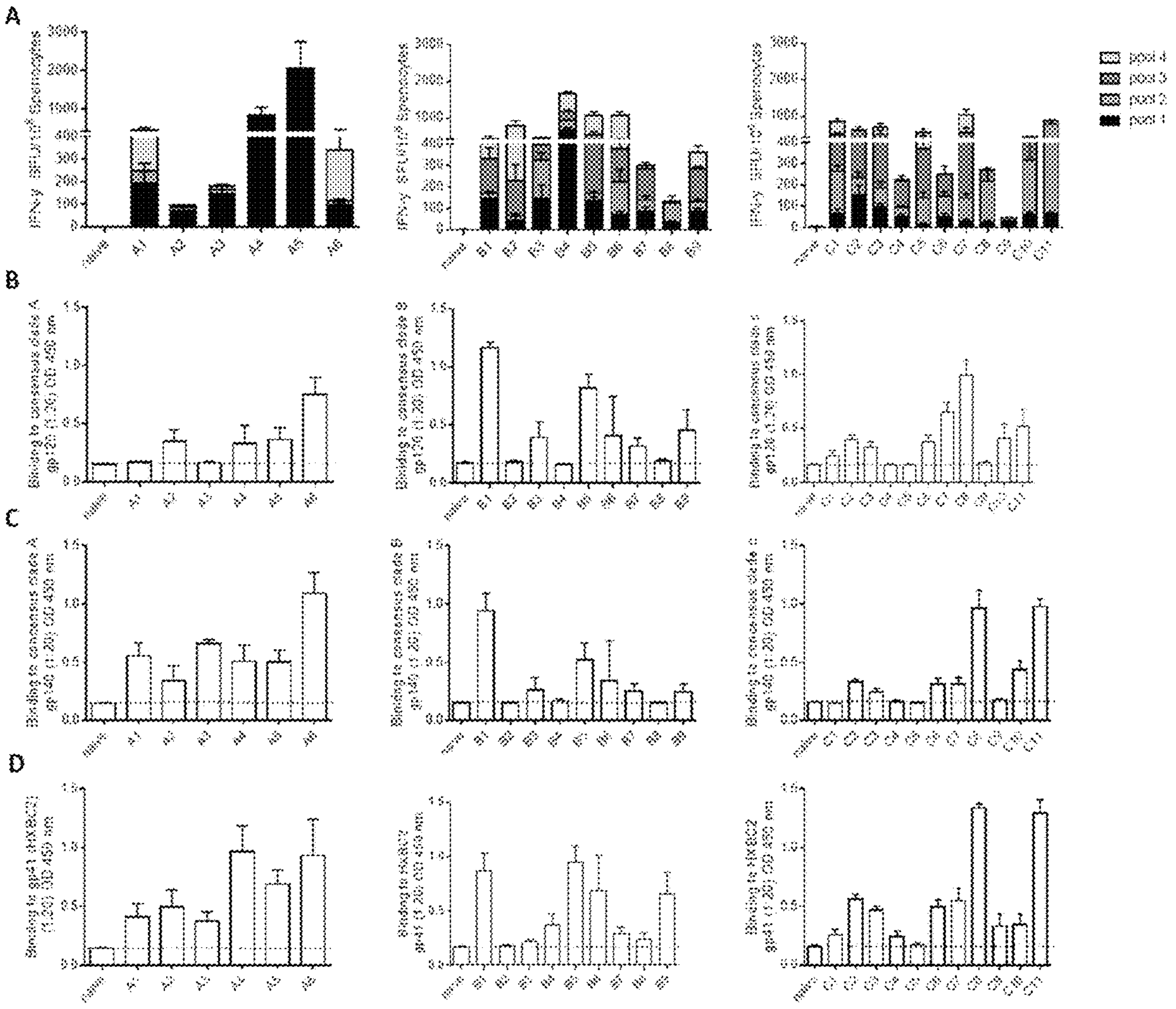
FIG. 14A through FIG. 14D, depicts experimental results demonstrating the immunogenicity of each plasmid in mice.

To ensure that each plasmid was immunogenic, C57Bl/6 mice were immunized with 25 μg of each plasmid 3 times at 2 week intervals. One week after final immunization, cellular and humoral responses were determined against consensus clade A, B and C. All plasmids induced either a cellular or humoral responses; however there was variation between different plasmids (FIG. 14). For example, the highest cellular response as assessed by IFN-γ spot forming units (SFU) is plasmid A5 (Q23ENV17) (over 2000 SFU) and the lowest is plasmid C9 (Du156.12) (<100 SFU but above background) (FIG. 14A). Additionally, the regions of the antigen which stimulate T cell responses differ across plasmids. Cellular responses induced by clade A Envs tend to be more reactive to the N-terminus peptides (pool 1) whereas responses to clade B and C Env are spread across the protein (FIG. 14A). Humoral responses induced by these plasmids were also determined using consensus clade A, B, and C gp120 and gp140 proteins as well as HXBC2 gp41 (FIG. 14B, FIG. 14C and FIG. 14D). Similar to the cellular responses, a wide range of binding reactivity across the plasmids was observed. Surprisingly, certain plasmids like B2 (REJO4541.67), B4 (TRJO4551.58), C1 (CAP45. 2.00.G3), and C5 (ZM233M.PB6) which induces strong cellular responses, do not induce any humoral responses against consensus proteins. While not being limited to any particular theory, this could potentially be due to the lack of consensus proteins expressing the binding epitope; the binding epitope induced by each plasmid is conformational; or a lack of overall humoral responses. In contrast, there are plasmids which induce both strong humoral and cellular responses like A6 (Q259d2.17), B1 (WITO4160.33), B5 (CAAN5342.A2), C7 (ZM214M.PL15), and C11 (Du172.17).

Formulation of Plasmids Affects the Strength of the Response

Figures 15A, 15B, 15C, 15D:
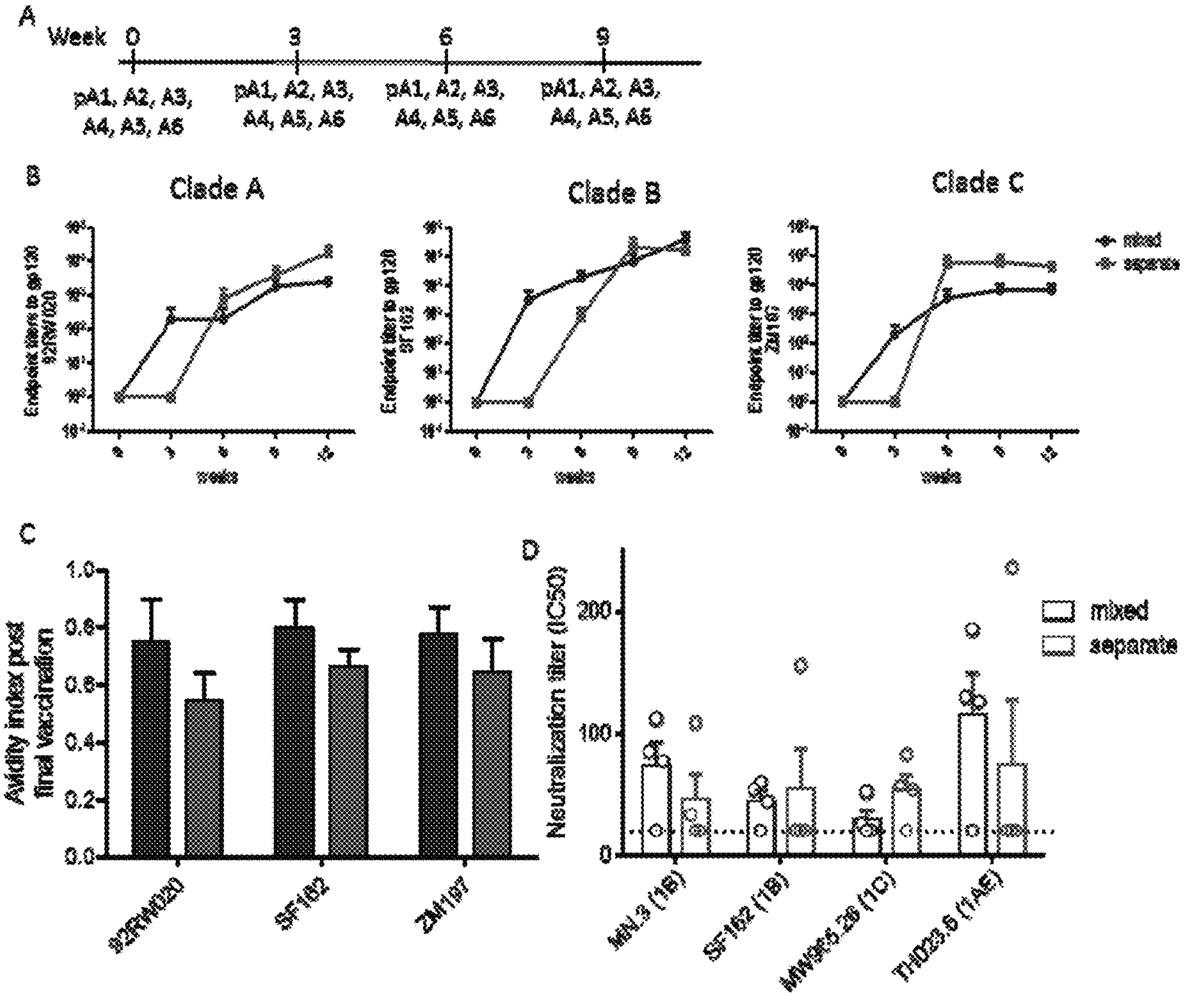
FIG. 15A through FIG. 15D, depicts experimental results demonstrating guinea pigs immunized with mixed Envelopes induce stronger and quick humoral responses compared to separate immunization.

It was next sought to determine if multiple plasmids expressing the clade A primary Envs could be formulated together and delivered to increase the breadth of antibody responses. However, questions arose as to if there would be antigen competition between the groups of Envelopes and thus, two vaccination regimens were performed: one where all of the plasmids were formulated together and another were each plasmid was given in a separate site. Guinea pigs were immunized four times with 100 μg of each plasmid ID followed by electroporation (FIG. 15A). The total amount of DNA for each immunization was the same across both groups (600 μg total–100 μg/plasmid) and the route and electroporation protocol were the same. The only difference was whether or not the plasmids were immunized separately or mixed together. Endpoint binding titers to the same primary gp120s were used to determine the induction of humoral responses. Though at the end of the vaccination (week 12) binding titers between the mixed vs separate are similar, the induction of humoral responses is quicker in the mixed group than in the separate group (FIG. 15B). Avidity of humoral responses was assessed at week 12 to determine if there was any difference between the two vaccination groups (FIG. 15C). The avidity index to 92RW020, SF162, and ZM197 were all slightly higher, though not significantly different, in the guinea pigs which received the mixed formulation. In addition, post final vaccination neutralization titers were slightly, though not significantly, higher in the mix vs separate group for three different tier 1 viruses (MN.3, SF162, and TH023.6) (FIG. 15D). This data suggest that mixing the Envelopes together does not dampen the humoral responses but instead, increases the initial seroconversion rate and could induce more superior functional antibody titers. Due to this and the ease mixed formulation provides for vaccine administration, all further studies were performed in this fashion.

Multiple Env Plasmids are Expressed in the Same Cells within the Skin

Figures 16A, 16B:
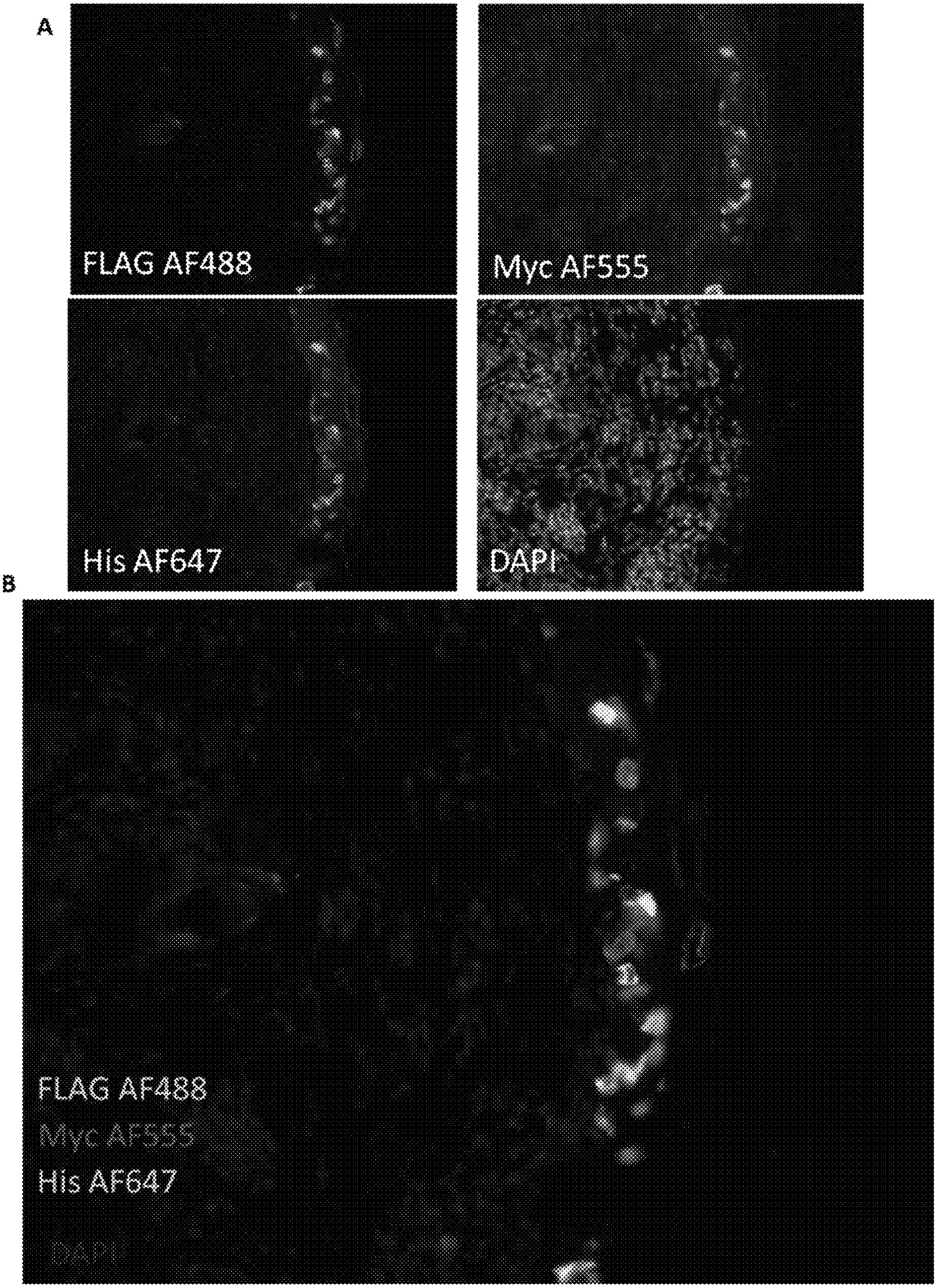
FIG. 16A and FIG. 16B, depicts experimental results demonstrating the expression of multiple constructs in skin. Guinea pigs were vaccinated intradermally with three constructs expressing a tagged HIV Env construct. After 24 hours, skin was biopsied and stained for expression of the tags.

In order to determine if multiple Envelopes were being expressed in the same cell, tags were added to three different plasmids to efficiently detect each Envelope. Three tags were added to the C-terminus of three existing constructs using plasmid mutagenesis. The three constructs were pQ168ENVe2-HIS, pQ23ENV17-FLAG, pDu151.2-MYC and all expressed in vitro (data not shown). Two guinea pigs were injected with 16.5 μg of each plasmid formulated together and delivered to the dermis followed by electroporation. Expression of all constructs can be detected after 24 hours after injection (FIG. 16A). Importantly, there is overlap of fluorescent signal in multiple cells (FIG. 16B). This suggests that multiple constructs are being expressed in a single cell.

Groups of 6 Env Plasmids Induce Strong Humoral Responses in Rabbits

Figures 17A, 17B, 17C, 17D:
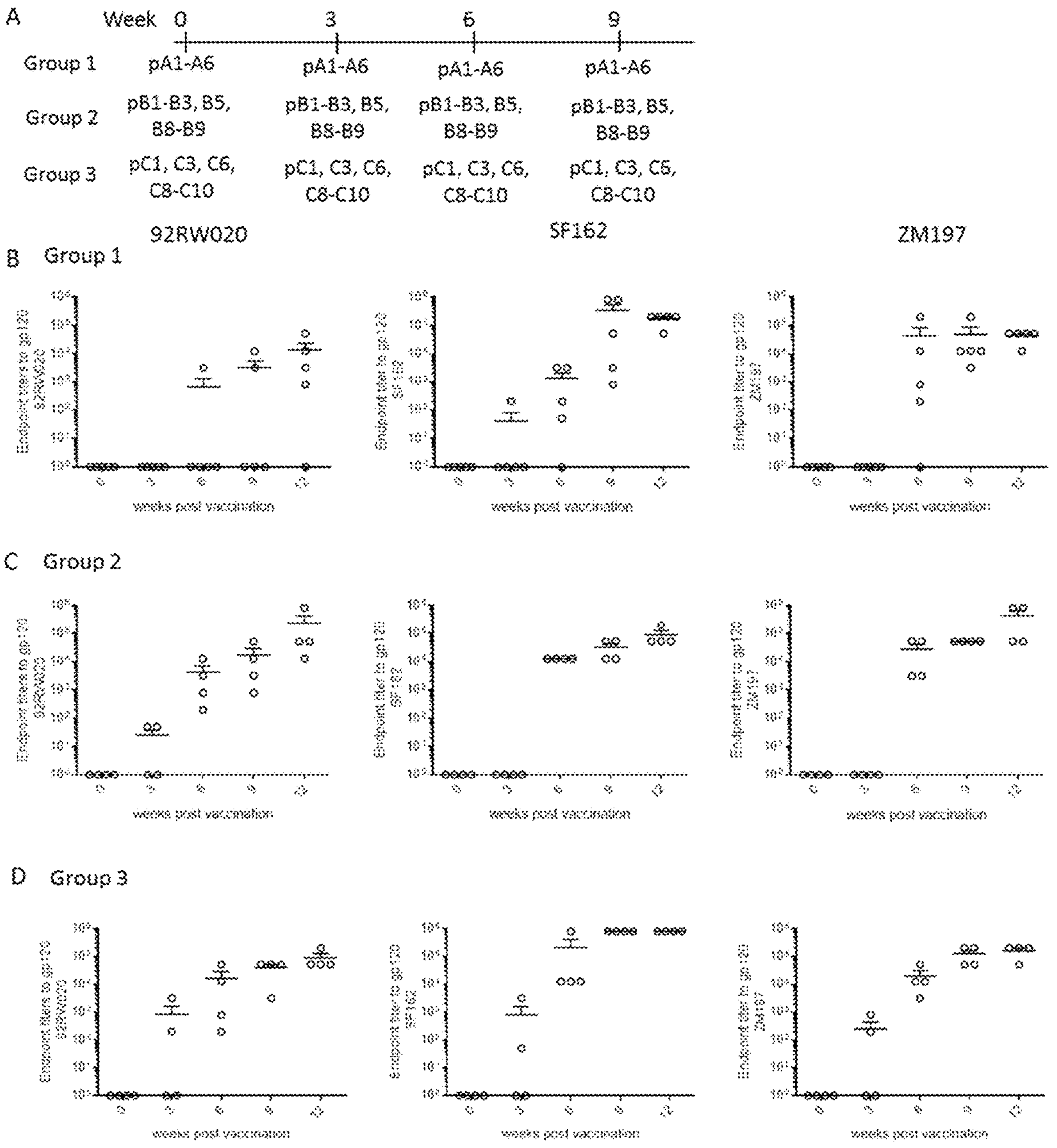
FIG. 17A through FIG. 17D, depicts experimental results demonstrating rabbits immunized with mixed clade A, B or C Envelopes are able to induce strong humoral responses.

To further investigate the use of small groups of primary Envelopes, groups of four rabbits were immunized with six plasmids expressing either clade A, clade B or clade C Envs (FIG. 17A). All plasmids (100 μg/plasmid) were formulated together and delivered to six sites ID followed by electroporation. Binding titers against clade A (92RW020), clade B (SF162) and clade C (ZM197) were assessed for each group of immunized rabbits over time (FIGS. 17B, 17C and 17D). After a single immunization, half of the animals immunized with clade C Envs seroconvert to clade A, B, and C gp120 proteins (FIG. 17D). By the second immunization, all animals immunized with clade B and C Envs seroconverted to all gp120s (FIGS. 17C and 17D). Humoral responses in the rabbits immunized with clade A Envs took slightly longer than with clade B and C combinations but eventually did induce strong binding titers to all 3 gp120s (FIG. 17B) Humoral responses are boosted by each immunization reaching peak titers 3 weeks after final immunizations. Even though the animals are immunized with only a single clade, all rabbits induce strong cross-clade binding titers. In fact, the clade C immunized rabbits had the highest binding titer responses to the clade B (SF162) gp120 protein. Overall, formulating multiple primary transmitter founder or acute Envelopes together in a single formulation induces strong cross-clade binding titers.

Increasing Diversity within Group Expands Antibody Responses

Figures 18A, 18B, 18C, 18D, 18E:
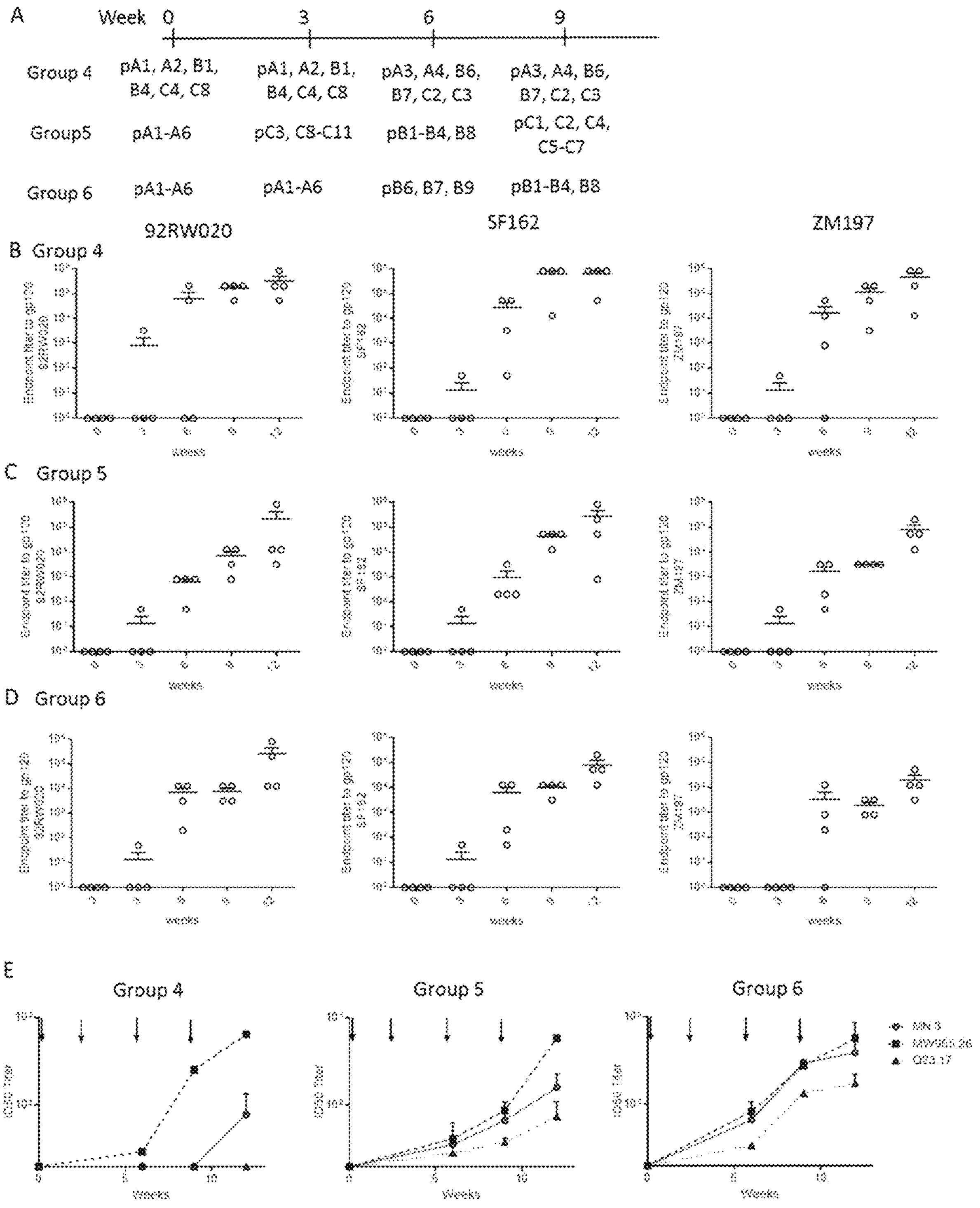
FIG. 18A depicts the experimental design. Rabbits were immunized with 3-6 Envelope plasmids formulated together and delivered intradermally followed by EP.
FIG. 18B depicts endpoint binding titers over time against 92RW020 (clade A), SF162 (clade B) and ZM197 (clade C) for group 4 immunized rabbits.
FIG. 18C depicts endpoint binding titers over time against 92RW020 (clade A), SF162 (clade B) and ZM197 (clade C) for group 5 immunized rabbits.
FIG. 18D depicts endpoint binding titers over time against 92RW020 (clade A), SF162 (clade B) and ZM197 (clade C) for group 6 immunized rabbits.
FIG. 18E depicts neutralization titers against tier 1 viruses across time for each immunization group.

To investigate whether the results seen in the single clade immunizations could be further expanded upon, two different groups of plasmids were used each containing two clade A, B, and C primary gp160 Envelopes. Four rabbits were immunized with combination 1 (pA1, A2, B1, B4, C4, C8) twice followed by combination 2 (pA3, A4, B6, B7, C2, C3) (FIG. 18A). The plasmids were all formulated together per different combination with 100 μg (600 μg total) of DNA construct used per immunization, delivered ID followed by electroporation. The mean diversity within the groups was 22.0% and 21.0% respectively. The mean diversity between the groups was 20.6%. Once again after two immunizations, there is potent induction of binding titers against primary clade A, B, and C gp120s (FIG. 18B). Neutralization titers were assessed over time against tier 1 viruses (MN.3, MW965.26 and Q23ENV17) (FIG. 18E). The highest neutralization titers were observed against MW965.26 on weeks 9 and 12. Limited responses were detected against MN.3 with no responses induced against Q23ENV17. The combination of plasmids expressing two clade A, B, and C gp160s does appear to induce potent binding titers but limited neutralization breadth.

Creating "Clouds" with Limited Diversity Expands the Neutralization Breadth of Sera It was next investigated if limiting the diversity within a "cloud" could enhance responses. Using the same six clade A plasmids (pA1-A6) as a priming dose, four rabbits were immunized with additional "clouds" or groups of plasmid which were more limited in diversity and stayed within clades (FIG. 18A). The intra-cloud diversity ranged from 12.4-16.4% and inter-cloud was consistently around 20%. Each immunization was between 500 μg-600 μg of total DNA (100 μg of each plasmid) mixed together and administered ID to five or six separate sites followed by electroporation. Using this limited intra-cloud diversity regimen did not disrupt the ability to induce potent cross-clade binding tiers against the three primary isolate gp120 (FIG. 18C). There is a consistent boosting of titers after every immunization with the highest binding titers obtained after the final immunization at week 12. Neutralization titers demonstrated stronger kinetics of induction and higher titers compared to group 4 (A, B, C mixed) (FIG. 18E). In comparison to group 4 (A, B, C mixed together), group 5 induced responses to MW965, MN.3 and Q23ENV17 after the second immunization and continued to increase after final immunization. The ability to induce this robust of a response by DNA alone has yet to be seen and could lend itself well to further expansion by boosting with a different platform.

Highest Induction of Robust Antibody Responses in Rabbits Primed Twice with the Same "Cloud"

The final group of rabbits looked to determine if these responses would increase by priming with the same group twice. This would allow for the immune system to potentially honing in on specific epitopes which would later be expanded by boosting with additional clouds. Rabbits were immunized twice with the clade A plasmids (pA1-A6) and boosted with two different groups of primarily clade B immunogens (FIG. 18A). The intra-cloud diversity ranged from 13.3-14.3% and the inter-cloud diversity between 14-17.6%. Thus this regimen has the lowest diversity between the clouds compared to the other two combinations. This low intra-cloud diversity did not limit the responses, as potent binding titers are induced in all animals after two immunizations (FIG. 18D). The highest and quickest induction of neutralization is seen for this group, with the most powerful response happening after the final immunization (FIG. 18E). In addition, sera from two rabbits were able to neutralize more isolates at higher IC50 concentrations than groups 4 and 5 (FIG. 25). This includes hard to neutralize tier 2 viruses where only one virus (Ce1176_A3) is not able to be neutralized. Thus, priming rabbits with two immunizations of same group of plasmids seems to focus the immune system in a way that allows for effective induction of broadly binding and neutralizing antibodies.

Figures 19A, 19B, 19C, 19D, 19E:
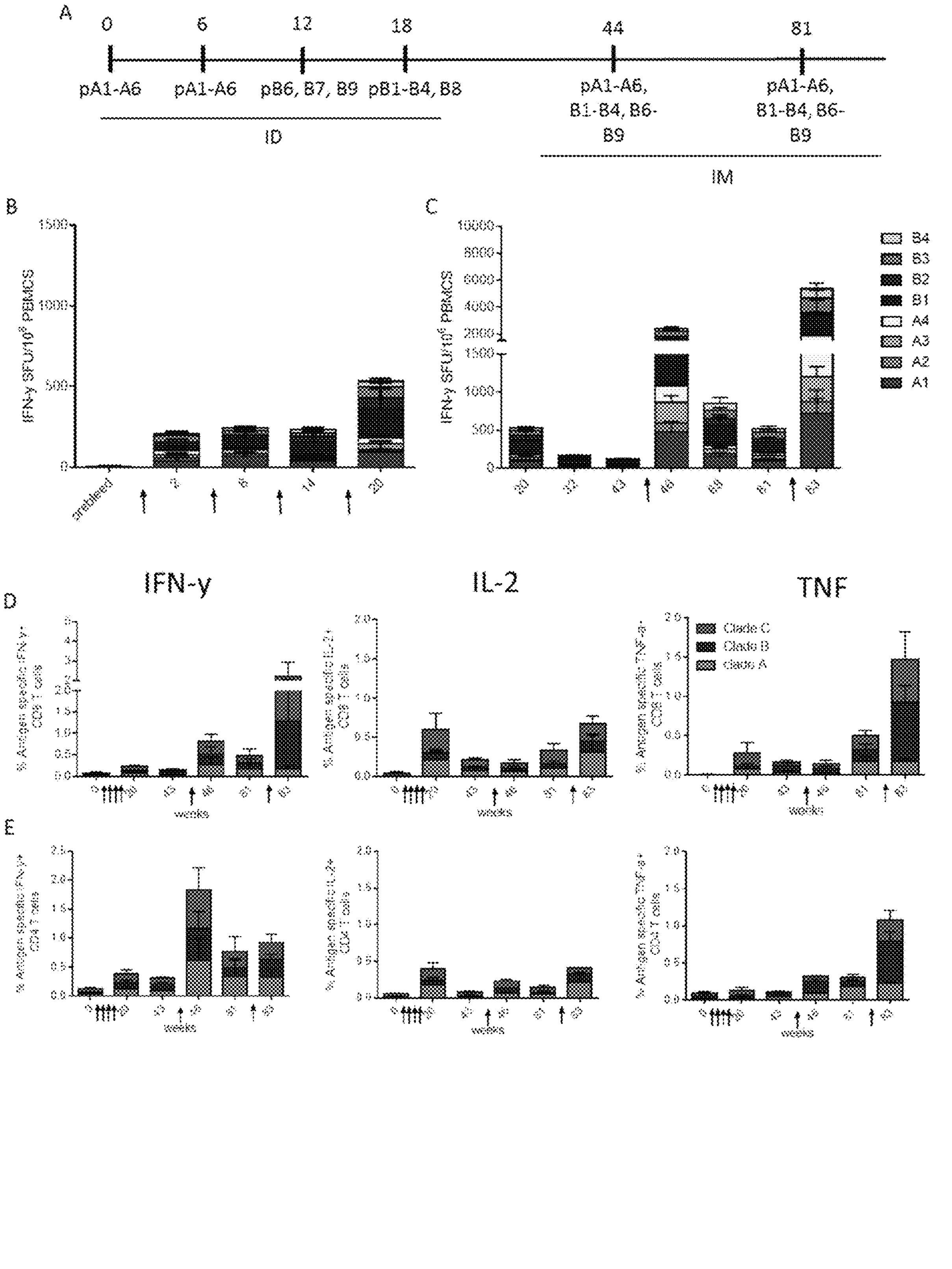
FIG. 19A through FIG. 19E, depicts experimental results demonstrating cellular responses induced by clouds of primary HIV Env plasmids in non-human primates.
Figure 20A:
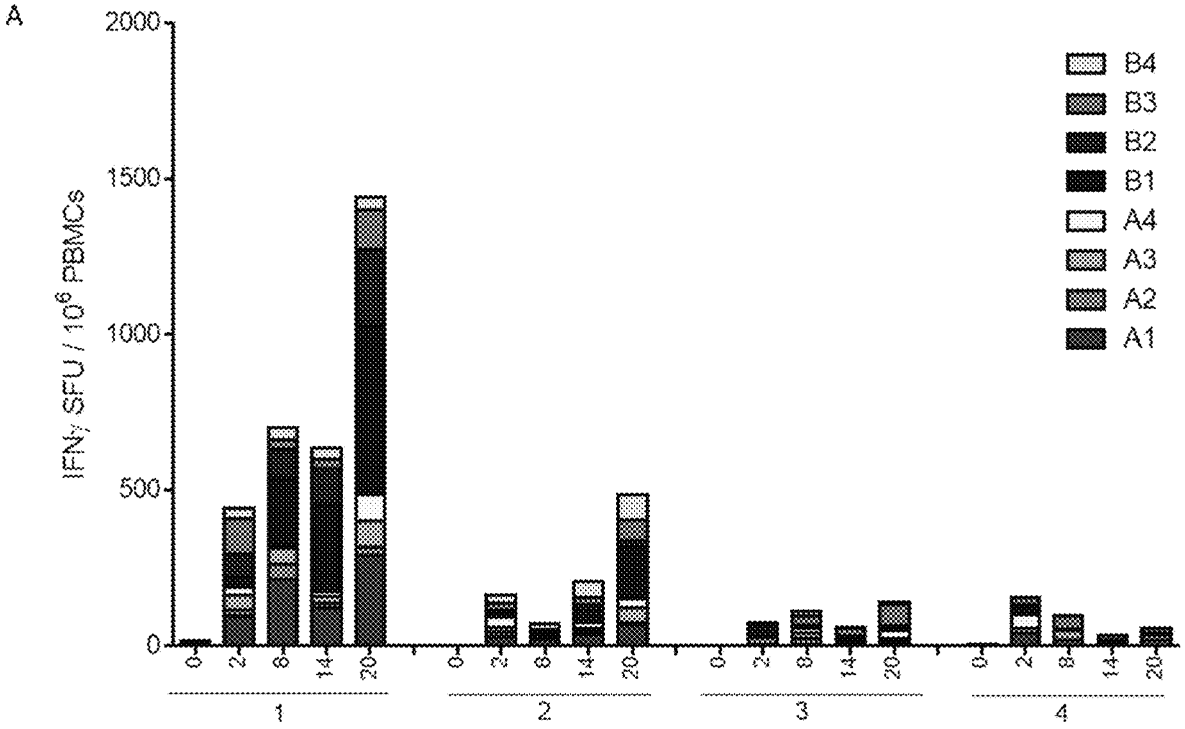
FIG. 20A and FIG. 20B, depicts experimental results demonstrating individual ELISpot responses over time.
Figure 20B:
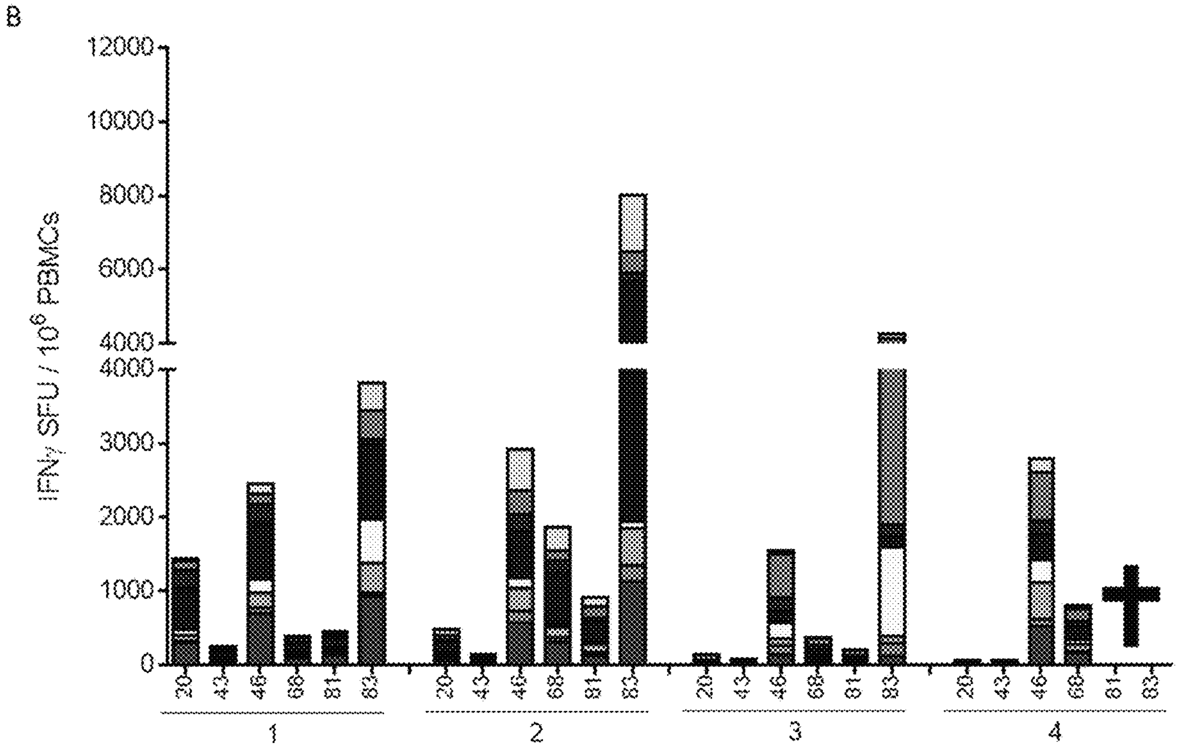

Non-Human Primates Immunized with "Clouds" of Primary Envelopes Induce Potent Cellular Responses To further characterize the vaccine induced responses produced by the most potent regimen, four rhesus macaques (RhMs) were immunized with a similar vaccine regimen (FIG. 19A). On weeks 0, 6, 12 and 18, the NHP received a mixture of different Envelopes (1 mg/plasmid) formulated together and delivered ID followed by electroporation. To further expand the vaccine induced responses, at weeks 44 and 81 post first vaccination, all animals received all of the Envelopes from vaccination 1-4 (1 mg/plasmid) delivered IM at a single site followed by electroporation. Cellular and humoral responses were followed two weeks after each vaccination. After only a single immunization, IFN-γ spot forming units (SFU) are detected against consensus clades A and B peptides (FIG. 19B). These responses are not boosted with the second or third immunization of the priming cloud but are expanded upon after the fourth immunization. After the final ID immunization, the average total IFN-γ SFU is around 500 SFU with even distribution of reactivity between clade A and B (range 100-1,500 SFU) (FIG. 20A). Though there is contraction into the memory phase (weeks 32 and 43), cellular responses can still be detected against consensus clade A and B almost 6 months (week 43) after final ID immunization (FIG. 19C). After the first IM boosting immunization at week 44, cellular responses expand greatly to levels over quadruple the amount seen after final ID immunization. Over eight months after IM immunization (week 81), cellular responses have contracted but remain around the levels seen after final ID immunization. Upon second IM boost, cellular responses again expand above those seen after the previous IM immunization with IFN-γ SFU averaging around 7000 (responses varying from 4000-10,000 SFU) (FIG. 20B). These responses are extremely high, especially since they are against unmatched peptides. In addition, since consensus peptides are used, this suggests that these small "clouds" of immunogens are able to induce potent cellular responses against conserved regions within the Envelope. This could be important for the induction of cytotoxic T cells as well as providing broad CD4 T cell help.

To further explore the cellular responses induced by the primary Envelope cloud immunization, intracellular cytokine staining was performed using consensus clade A, B and C peptides. CD8 T cell responses after ID immunization (week 20) primarily express IL-2 and TNF-α with limited IFN-γ production (FIG. 19D). Each IM immunization increased the percent of CD8 T cells expressing IFN-γ. An additional increase in TNF-α production is also seen after the final IM immunization (week 83). In contrast, the IL-2 production observed after final ID immunization is not boosted by either IM immunization and levels after final IM immunization are the same as after final ID immunization. CD4 T cell responses were also assessed against clade A, B and C peptides (FIG. 19E). The percent of CD4 T cells expressing IFN-γ and IL-2 is relatively the same after the ID immunization (week 20) with a lower percentage of CD4 T cells expressing TNF-α. Similar to CD8 T cells, the proportion of CD4 T cells secreting IL-2 remains relatively consistent across time with slight waning at each memory time point. However, after the first IM immunization, there is a sharp increase in CD4 T cells secreting IFN-γ. Similar boost is not observed after the second immunization. Expression of TNF-α remains consistent into memory after ID immunization, is boosted by the first and second IM immunization. Importantly, similar to ELISpots, potent cytokine secretion was observed after stimulation with cross-clade consensus peptides. Though these NHPs were only immunized with clade A and B primary Envs, cellular responses against consensus clade C peptides are detected at similar levels to clade B responses.

Binding and Functional Antibodies Induced Using Primary Env DNA Vaccination

Figures 21A, 21B, 21C, 21D:
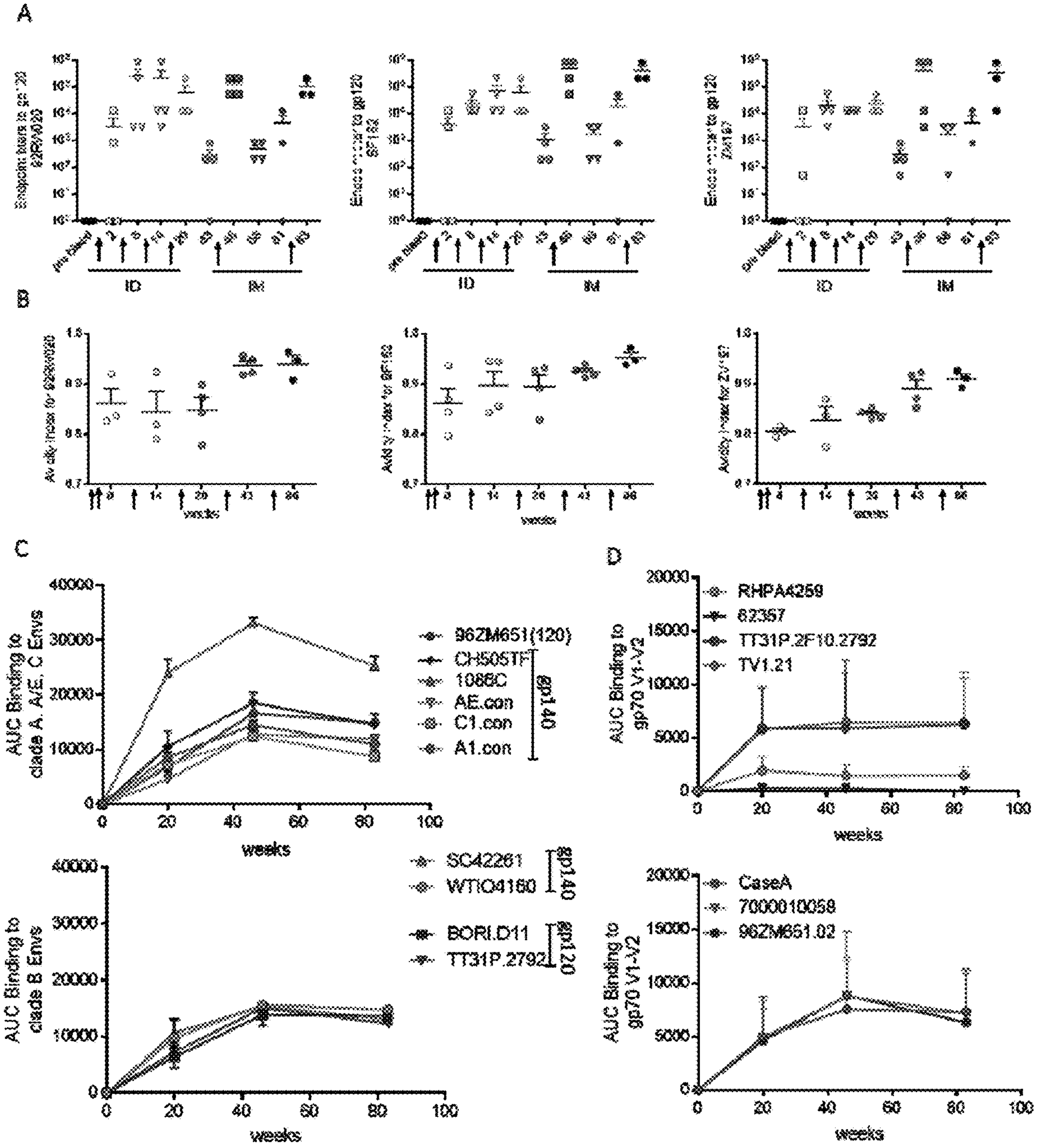
FIG. 21A through FIG. 21D, depicts experimental results demonstrating strong humoral binding responses induced by clouds of plasmids expressing primary HIV Envs.

The primary Envelope cloud immunization also induces potent humoral responses. After a single immunization, two out of eight RhMs seroconvert to clade A, B and C gp120 proteins (FIG. 21A). After the final ID immunization, all animals have strong endpoint binding titers against the primary Envelopes averaging above $10^4$. Similar to cellular responses, binding titers also contract down in the memory phase but remain high (average above $10^3$) six month post last ID immunization (week 43). Also similar to cellular responses, after the IM boost, binding titers reach levels higher than after ID immunization with the average binding titer above $10^5$. These responses are also slightly boosted after a second IM immunization to levels reaching $10^6$. Strong avidity indexes of around 0.8 are induced after the second ID immunization (FIG. 21B). However, subsequent ID immunization did not improve the avidity index. The first IM boost increased the avidity index across all three gp120 proteins with minimal to no increase in avidity after the second IM immunization. To further explore the binding capacity of the humoral responses induced, binding to consensus and primary gp120 and gp140s was determined using binding antibody multiplex assay (BAMA) (FIG. 21C). Strong binding titers against clade A, B, C and AE Envs were detected with the highest responses obtained after the first IM immunization. The strongest binding response was detected against the primary isolate gp140 Env 1086c, with almost 3 fold higher area under the curve (AUC) binding compared to other Envs. V1/V2 binding against multiple different gp70 scaffold was also assessed (FIG. 21D). Interestingly there were three binding patterns to V1/V2 scaffolds which emerged. The first is binding kinetics similar to that which was observed in the binding to the whole protein with induction by the final ID immunization, peak after second IM immunization and similar levels after the second IM immunization (FIG. 21D, bottom graph). The second pattern is induction of binding after ID immunization but no boosting after each IM immunization (FIG. 21D, top graph—TT31P and TV1.21). The final pattern is limited to no induction of binding (FIG. 21D, top graph—RHPA4259 and 62357). These differences in binding patters could help suggest a potential target epitope.

Figures 22A, 22B, 22C, 22D:
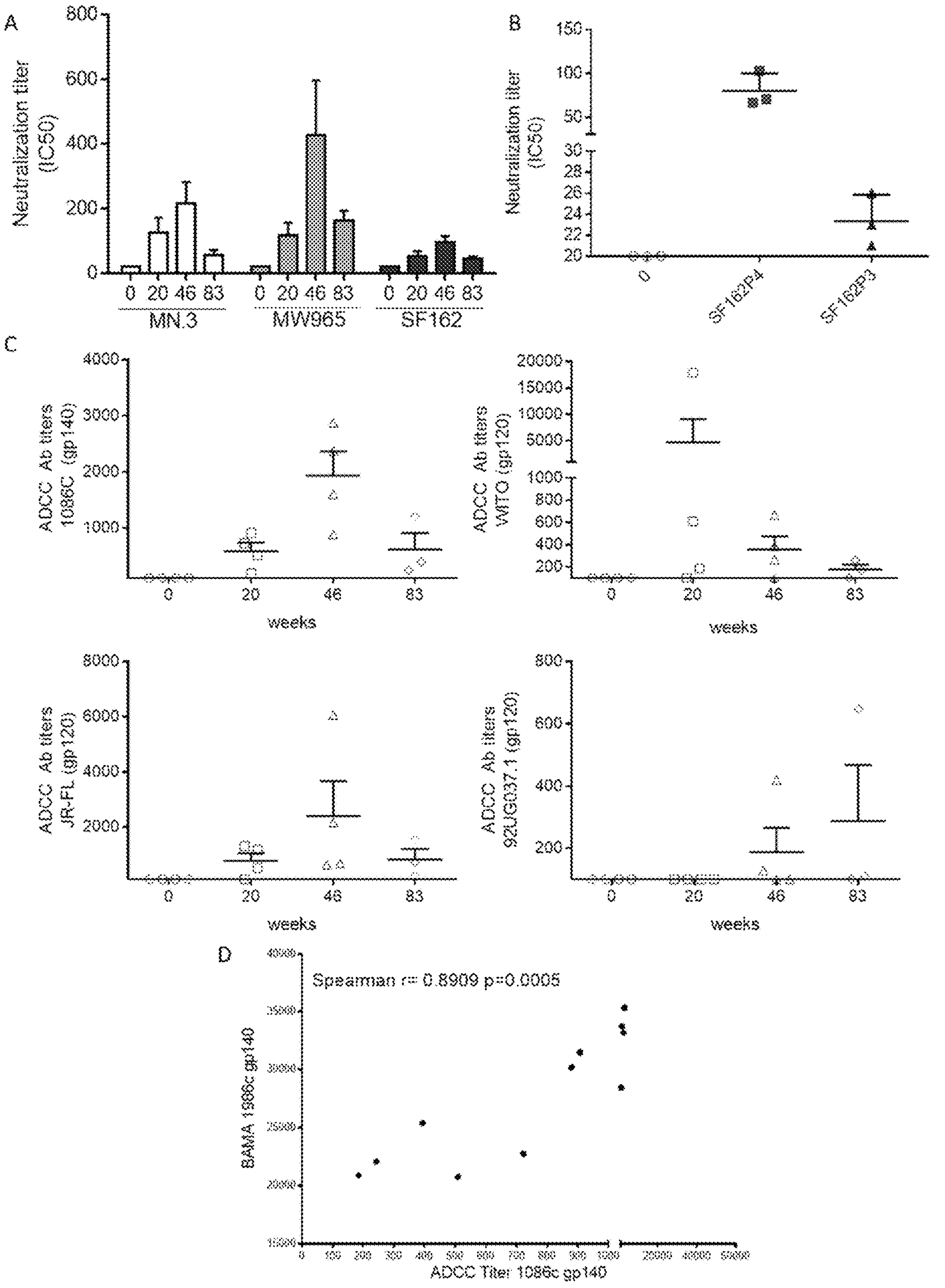
FIG. 22A through FIG. 22D, depicts experimental results demonstrating DNA immunization alone induced functional antibody titers. In order to further understand the vaccine induced humoral response induced by the cloud DNA vaccination, both neutralization titers as well as ADCC activity were assess over the time course of immunizations.
Figure 23:
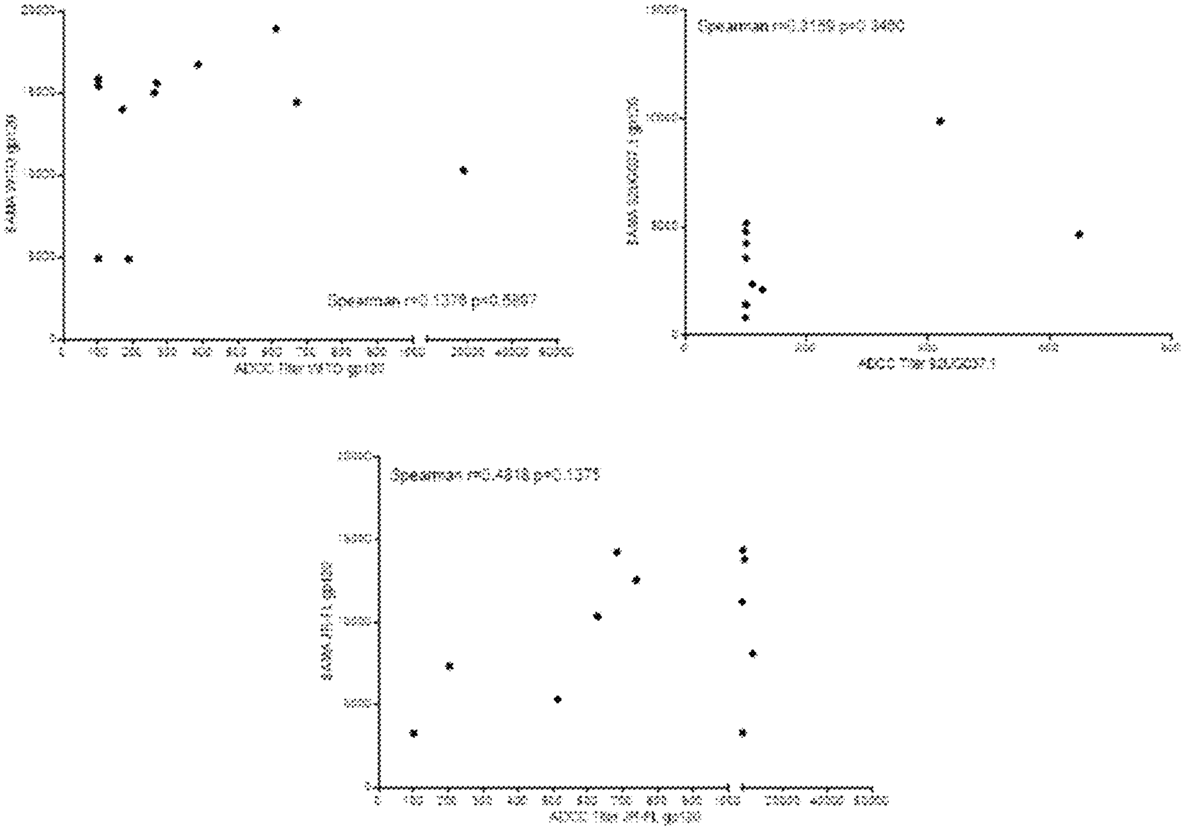
FIG. 23 depicts experimental results demonstrating no correlation between SAMA binding and ADCC titers for WITO, JR-FL and 93MG037.1. Contrary to the correlation observed with 1086c, there was no correlation between SAMA binding and ADCC titers for the other three gp120s which were assessed in both assays.

In addition to binding titers, the vaccination regimen also induces functional antibodies. Using only DNA vaccination cross clade neutralization titers against a diversity of tier 1 viruses is achieved (FIG. 22A). After ID immunization, neutralization titers for MN.3, MW965 and SF162 average above or around $10^2$. After the first IM boost, levels are increased to above $10^3$ for MN.3 and MW965 and just below $10^3$ for SF162. After the second IM boost levels increase are not seen above those observed after the initial IM boost. In fact, for MN.3, MW965 and SF162, the levels were lower and usually averaged around the same titers as those seen after the ID immunizations. However, levels against SF162P4 IMC were detected and importantly, there were limited but low neutralization titers induced against the tier 2 virus SF163P3 after final IM immunization (FIG. 22B). Since the role of antibodies with ADCC capabilities has been suggestive in protection against HIV infection (RV144 correlates analysis), ADCC activity was tested against targets coated with 1086c (gp140), WITO (gp120), JR-FL (gp120) and 92MG037.1 (gp120) (FIG. 22C). Similar to V1/V2 binding, three different patterns of ADCC induction emerge. The first displays similar kinetics to BAMA, V1/V2 binding pattern 1 and neutralization titers with peak titers induced post $1^{st}$ IM immunization which were not further boosted after the $2^{nd}$ IM (1086c and JR-FL). The second pattern is observed with WITO coated targets where the strongest response was observed after the ID immunizations. If the one outlier is removed from the analysis, these responses are maintained with the first IM immunization but slightly decline with the second. The third pattern is seen with 92MG037.1 where only 1 or 2 NHPs are able to induce low ADCC activity against the target cells. Differences between these three Env could again suggest differences in binding epitopes and induction of certain humoral responses after each immunization. Interestingly, the AUC determined by the binding antibody multiplex assay and ADCC titers against 1086c correlated (spearman r=0.8909 p=0.0005) (FIG. 22E). However, similar correlations were not found for WITO, JR-FL and 92MG037.1 (FIG. 23). These data supports the use of primary transmitter founder Envelopes deliver in small "cloud" immunizations for the induction of potent cellular and humoral responses.

DISCUSSION

An effective HIV vaccine will likely need to induce both cellular and humoral responses. Previously, DNA vaccines have been able to induce potent cellular responses but lacked humoral responses. Advances in plasmid optimizations, formulation and delivery have significantly increased DNA vaccines ability to induce humoral responses. Here, it is explored the ability to use combinations of full length gp160 Envs which were isolated during the early/acute phase of infection (Li et al., 2006, J Virol 89:11776-90; Li et al., 2006, J Virol 79:10108-25; Wilen et al., 2011, J Virol 85:8514-27). All inserts were immunogenic in mice, displaying a range of cellular and humoral responses. Interestingly, there was not a consistent pool of peptides which was dominated across all antigens. Instead for clades B and C inserts, cellular immune responses were detected across the entire antigen. Similar breadth of responses is observed using our consensus antigens (Yan et al., 2011, Vaccine 29:7173-81). In contrast, the majority of clade A Env inserts induced very strong responses against the N terminus (pool 1) and fewer responses across the rest of the protein. This could be due to the heterogous nature of the peptide used or a dominant epitope at the N terminus of the protein. Additionally, this dominance could be mouse specific as when a combination of these plasmids is administered into NHPs, responses to all 4 peptide pools is evident; however, pool 1 still dominates (FIG. 19 and FIG. 20).

The ability to induce protective responses against multiple serotypes is evident in the Influenza, Human Papillomavirus, and Pneumococcus vaccines (Ortqvist et al., 1998, Lancet 351:399-403; Harper et al., 2006, Lancet 367:1247-55; Paavoen et al., 2009, Lancet 374:301-14; Joura et al., 2015, NEJM 372:711-23; Osterholm et al., 2012, Lancet Infect Dis 12:36-44). Due to the breadth of HIV diversity is it likely that multiple antigens will need to be formulated into a single injection for ease of delivery. In terms of humoral responses, within this study, it is demonstrated that up to six plasmids can be combined together and lead to strong humoral responses than when delivered to individual sites. Using immunofluorescence and tagged constructs it is also shown that up to three constructs can be detected in the same cell. This leads to the possibility of heterotrimers, which have been previously show to induce stronger neutralization titers compared to homotrimers of Env proteins (Bowles et al., 2014, PLoS One 9:e114709; Sellhorn et al., 2012, J Virol 86:128-42). In theory, the diversity within these heterotrimers could focus the immune response on conserved epitopes. Importantly, it is within these conserved regions of HIV that broadly neutralizing antibodies targets (Kwong and Mascola, 2012, Immunity 37:412-5). However, these regions tend to be much less immunogenicity than the variable loops and thus are more difficult to target. It is important to follow up on whether or not DNA encoded gp160s can form in vivo heterotrimers and if so, how does the percent diversity between the Envs affect this ability.

In addition to exploring multiple different combinations of HIV Envs, different sites of delivery were also used. Advances in electroporation technology have allowed for multiple different tissues to be targeted included the traditional, intradermal and intramuscular (Sardesai and Weiner, 2011, Curr Opin Immunol 23:421-9). Within this study, NHP were vaccinated with four ID immunizations followed by two IM boost. These two sites have different cellular composition and thus could produce unique vaccine induced responses. A single ID immunization is able to induce strong cellular responses and seroconversion in 50% of the animals (FIG. 19A and FIG. 21A). Interestingly, even though cellular responses do not boost with the $2^{nd}$ and $3^{rd}$ ID immunization, continual improvement in humoral responses were observed. However, though binding titers improve over the ID immunizations, the avidity of these antibodies remains fairly consistent only increasing upon IM immunization (FIG. 21A and FIG. 21B). A sharp increase in cellular responses were observed after the first IM immunization, with both CD4 and CD8 T cells expressing IFN-γ. This boost in responses was also observed in both binding and functional antibody titers (FIG. 21 and FIG. 22). Unexpectedly, these functional antibody titers did not further increase after the second IM immunization but instead were at levels similar to after the ID immunizations. Following the second IM immunization, CD8 T cell dominate IFN-γ production with a decrease in CD4 T cell production compared to after the 1st IM immunization (FIGS. 19D and 19E). Here it is demonstrated for the first time that ID DNA immunization can be further expanded by IM immunization. The ability to understand how the different sites of immunization skews the immune response and how boosting can affect memory cell activation is imperative for DNA vaccine development.

Numerous different plasmids expressing consensus, chronic and acute/early Envs have been developed. It is demonstrated herein that guinea pigs and rabbits exposed to groups of immunogens are able to induce strong binding titers to heterologous Envs and different clouds of plasmids can influence the kinetics of tier 1 neutralization induction. Additionally, combinations of 14 different Env plasmids were able to induce strong cellular and humoral responses. Importantly, these humoral responses were functional after only DNA vaccination. Determining what combination of Envs produces the strongest and broadest responses is imperative for the HIV vaccine development field.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising two or more nucleic acid molecules encoding an HIV immunogen, wherein each nucleic acid molecule comprises a sequence independently selected from the group consisting of: a nucleic acid sequence encoding SEQ ID NO: 12; and a nucleic acid sequence encoding a sequence that is at least 96% homologous to SEQ ID NO: 12 across the length of SEQ ID NO:12; wherein the nucleic acid sequence is optionally linked to a nucleic acid sequence encoding an IgE signal peptide, wherein the HIV immunogen induces an immune response against HIV.

2. The composition of claim 1, wherein at least one nucleic acid molecule comprises a sequence encoding SEQ ID NO:12.

3. The composition of claim 1, wherein each nucleic acid molecule comprises a sequence independently selected from the group consisting of: a nucleic acid comprising SEQ ID NO: 11; and a nucleic acid comprising a sequence at least 96% homologous to SEQ ID NO: 11 across the length of SEQ ID NO:11.

4. The composition of claim 3, wherein at least one nucleic acid molecule comprises SEQ ID NO: 11.

5. The composition of claim 1, wherein the composition comprises 3 or more nucleic acid molecules.

6. The composition of claim 1, wherein the composition comprises 6 or more nucleic acid molecules.

7. The composition of claim 1, wherein the composition comprises 10 or more nucleic acid molecules.

8. The composition of claim 1, wherein the composition comprises 14 or more nucleic acid molecules.

9. The composition of claim 1, wherein the composition comprises two or more plasmids, wherein a first plasmid comprises a sequence encoding a sequence that is at least 96% homologous to SEQ ID NO:12 and one or more plasmids each comprise a sequence encoding a sequence that is at least 90% homologous to one of SEQ ID NOs: 2, 4, 6, 8, 10, 14, 16, 18, 20, 22, 24, 26, 28, 30, 32, 34, 36, 38, 40, 42, 44, 46, 52, 54, 56, 58, 60, and 62.

10. The composition of claim 1 formulated for delivery to a subject using electroporation.

11. A method of inducing an immune response in a subject in need thereof against HIV, the method comprising administering the composition of claim 1.

12. The method of claim 11, the method further comprising administering a second composition comprising one or more nucleic acid molecules comprising a sequence independently selected from SEQ ID NO: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, and 61, a variant thereof or a fragment thereof.

13. The method of claim 12, the method further comprising administering a third composition vaccine comprising one or more nucleic acid molecules comprising a sequence independently selected from SEQ ID NO: 1, 3, 5, 7, 9, 11, 13, 15, 17, 19, 21, 23, 25, 27, 29, 31, 33, 35, 37, 39, 41, 43, 45, 47, 49 51, 53, 55, 57, 59, and 61, a variant thereof or a fragment thereof.

14. The method of claim 11, wherein the first composition is administered intradermally.

15. The method of claim 12, wherein the second composition is administered intradermally.

16. The method of claim 13, wherein the third composition is administered intramuscularly.

17. The method of claim 11, wherein the first composition is administered twice.

18. The method of claim 12, wherein the second composition is administered twice.

19. The method of claim 13, wherein the third composition is administered twice.

20. A method of treating HIV infection in an individual comprising administering a therapeutic effective amount of the composition of claim 1 to an individual.

* * * * *

SEQUENCE LISTING

```
<160> NUMBER OF SEQ ID NOS: 62

<210> SEQ ID NO 1
<211> LENGTH: 2583
<212> TYPE: DNA
<213> ORGANISM: Artificial Sequence
```

<220> FEATURE:
<223> OTHER INFORMATION: pGX1025 - Env Clade A tier 2 Q769ENVd22 DNA
Sequence

<400> SEQUENCE: 1
atgagggcaa tgggcattca gagaaactgg cagaacctgt ggagatgggg cactatgatc 60
ctgggcatga tcctgatttg ttgtagcgcc gctgggaacc tgtgggtgac cgtctactat 120
ggagtgcccg tctggcggga cgctgaaacc acactgttct gcgcaagcga cgcaaaggcc 180
tacgatagag aggcccacaa cgtgtgggct actcatgcat gcgtgccaac cgatccaagc 240
ccacaggagg tgcctctggg caacgtcacc gaggagttca acatgtggaa gaacaatatg 300
gtggaacaga tgcacacaga catcatttct ctgtgggatc agagtctgca gccttgcgtg 360
aaactgacac cactgtgcgt cactctgaac tgttcaaata gcaacaatat tccatccgtg 420
tctaacatca ccgacgatat gaaggaggaa atcaaaaact gttccttcaa tatgactacc 480
gagctgaagg acaagaaaca gaacgtgtac tctctgtttt atcggctgga tgtggtcccc 540
ctggagacca aaacaaacca gaatagctcc cactcacgat accggctgat taactgcaat 600
acaagcgcca tcactcaggc atgtcctaag gtgtccttcg agcctattcc aatccattat 660
tgcgctccag caggcttcgc cattctgaag tgtaacgaca aagggtttaa tggaacaggc 720
ctgtgcaaga acgtgagcac cgtccagtgt acacatggca tcaaacctgt ggtcagcact 780
cagctgctgc tgaatgggtc cctggccgaa ggcaaagtga tggtgcggag cgagaacatc 840
acaaacaacg ctaagaacat catcatccag ttcaacaatt cagtgcagat taactgcaca 900
cggccaggaa acaatactag aaagagcatc cacctggggc ccggaaaagt gttttacgcc 960
accgacatta tcggcgatat cagaaaggct cattgtaacg tgaataggca gcagtggaac 1020
aaaactctgc aggacgtggc cactcagctg agaacccact tcagaaacag gaccatcatc 1080
tttaacaact ctctgggcgg ggatctggaa attacaactc atagtttcaa ctgcaggggc 1140
gagttctttt actgtaatac atctgggctg tttaacggaa tctggaatgg cacccaggaa 1200
cctaaccgca cagagagtaa tgacactatt accctgcagt gccgcatcaa gcagattatc 1260
aacatgtggc agcgagtggg acaggccatc tatgctcccc ctattcaggg cgaaatcagg 1320
tgtgagagta acattaccgg gctgatcctg acacgcgatg gaggcattat caattcaact 1380
gaggaaacct tcaggccagg aggaggcgac atgcgagata actggcgatc tgaactgtac 1440
aagtataaag tggtcaagat cgagccactg ggagtggcac caaccaaggc taaacggaga 1500
gtggtcgaac gagagaaacg ggccgtgggc ttcggggctt tctttctggg atttctgggc 1560
gcagccggga gtacaatggg agctgcatca atcacactga ctgtgcaggc caggcagctg 1620
ctgagcggca ttgtccagca gcagaacaat ctgctgcgcg caatcgaggc ccagcagcac 1680
ctgctgaagc tgaccgtgtg gggcatcaaa cagctgcagg caagggtgct ggcagtcgag 1740
cggtacctga aggaccagca gctgctggga atttggggct gcagcggcaa gttcatctgt 1800
accacaactg tgccctggaa ctctagttgg tccaataaga gtcagtcaga aatctgggac 1860
aacatgacat ggatgcagtg ggataaggag attaacaact acactcagat catctatgac 1920
ctgatcgagg aatcccagcg gcagcaggaa aagaacgagc aggacctgct ggcactggat 1980
aaatgggcca acctgtggaa ttggttcgat atctctaatt ggctgtggta cattaagatc 2040
tttattatga tcgtgggggg actgattggg ctgcggatcg ccttcgctgt gctgagcgtc 2100
atcaaccgcg tgcgacaggg atatagcccc ctgtcctttc agacccacac acccaatcct 2160
agagacctgg atagacctgg caggattgag gaagagggcg gggagcagga ccgggataga 2220

```
tcaatccgac tggtgagcgg gttcctggca ctggcctggg acgatctgag atccctgtgc   2280

ctgttctctt atcacaggct gcgcgacttc atcctggtgg ccgctaggac cgtcgaactg   2340

ctgggccata tcagcctgaa gggactgagg cgaggatggg agggcctgaa atacctggga   2400

aacctgctgt cttattgggg ccgcgaactg aagattagtg ccatcaatct gctggacact   2460

attgctatcg tggtcgcaga atggaccgat cgaattatcg agatcggcca gcggctgtgt   2520

agagccatta ttaacattcc aagacggatt cgccagggat ttgaaagagc actgctgtga   2580

taa                                                                 2583
```

<210> SEQ ID NO 2
<211> LENGTH: 859
<212> TYPE: PRT
<213> ORGANISM: Artificial Sequence
<220> FEATURE:
<223> OTHER INFORMATION: pGX1025 - Env Clade A tier 2 Q769ENVd22 Amino Acid Sequence

<400> SEQUENCE: 2

```
Met Arg Ala Met Gly Ile Gln Arg Asn Trp Gln Asn Leu Trp Arg Trp
1               5                   10                  15

Gly Thr Met Ile Leu Gly Met Ile Leu Ile Cys Cys Ser Ala Ala Gly
            20                  25                  30

Asn Leu Trp Val Thr Val Tyr Tyr Gly Val Pro Val Trp Arg Asp Ala
        35                  40                  45

Glu Thr Thr Leu Phe Cys Ala Ser Asp Ala Lys Ala Tyr Asp Arg Glu
    50                  55                  60

Ala His Asn Val Trp Ala Thr His Ala Cys Val Pro Thr Asp Pro Ser
65                  70                  75                  80

Pro Gln Glu Val Pro Leu Gly Asn Val Thr Glu Glu Phe Asn Met Trp
                85                  90                  95

Lys Asn Asn Met Val Glu Gln Met His Thr Asp Ile Ile Ser Leu Trp
            100                 105                 110

Asp Gln Ser Leu Gln Pro Cys Val Lys Leu Thr Pro Leu Cys Val Thr
        115                 120                 125

Leu Asn Cys Ser Asn Ser Asn Asn Ile Pro Ser Val Ser Asn Ile Thr
    130                 135                 140

Asp Asp Met Lys Glu Glu Ile Lys Asn Cys Ser Phe Asn Met Thr Thr
145                 150                 155                 160

Glu Leu Lys Asp Lys Lys Gln Asn Val Tyr Ser Leu Phe Tyr Arg Leu
                165                 170                 175

Asp Val Val Pro Leu Glu Thr Lys Thr Asn Gln Asn Ser Ser His Ser
            180                 185                 190

Arg Tyr Arg Leu Ile Asn Cys Asn Thr Ser Ala Ile Thr Gln Ala Cys
        195                 200                 205

Pro Lys Val Ser Phe Glu Pro Ile Pro Ile His Tyr Cys Ala Pro Ala
    210                 215                 220

Gly Phe Ala Ile Leu Lys Cys Asn Asp Lys Gly Phe Asn Gly Thr Gly
225                 230                 235                 240

Leu Cys Lys Asn Val Ser Thr Val Gln Cys Thr His Gly Ile Lys Pro
                245                 250                 255

Val Val Ser Thr Gln Leu Leu Leu Asn Gly Ser Leu Ala Glu Gly Lys
            260                 265                 270

Val Met Val Arg Ser Glu Asn Ile Thr Asn Asn Ala Lys Asn Ile Ile
        275                 280                 285
```

-continued

```
Ile Gln Phe Asn Asn Ser Val Gln Ile Asn Cys Thr Arg Pro Gly Asn
    290                 295                 300

Asn Thr Arg Lys Ser Ile His Leu Gly Pro Gly Lys Val Phe Tyr Ala
305                 310                 315                 320

Thr Asp Ile Ile Gly Asp Ile Arg Lys Ala His Cys Asn Val Asn Arg
                325                 330                 335

Gln Gln Trp Asn Lys Thr Leu Gln Asp Val Ala Thr Gln Leu Arg Thr
            340                 345                 350

His Phe Arg Asn Arg Thr Ile Ile Phe Asn Asn Ser Leu Gly Gly Asp
        355                 360                 365

Leu Glu Ile Thr Thr His Ser Phe Asn Cys Arg Gly Glu Phe Phe Tyr
    370                 375                 380

Cys Asn Thr Ser Gly Leu Phe Asn Gly Ile Trp Asn Gly Thr Gln Glu
385                 390                 395                 400

Pro Asn Arg Thr Glu Ser Asn Asp Thr Ile Thr Leu Gln Cys Arg Ile
                405                 410                 415

Lys Gln Ile Ile Asn Met Trp Gln Arg Val Gly Gln Ala Ile Tyr Ala
            420                 425                 430

Pro Pro Ile Gln Gly Glu Ile Arg Cys Glu Ser Asn Ile Thr Gly Leu
        435                 440                 445

Ile Leu Thr Arg Asp Gly Gly Ile Ile Asn Ser Thr Glu Glu Thr Phe
    450                 455                 460

Arg Pro Gly Gly Gly Asp Met Arg Asp Asn Trp Arg Ser Glu Leu Tyr
465                 470                 475                 480

Lys Tyr Lys Val Val Lys Ile Glu Pro Leu Gly Val Ala Pro Thr Lys
                485                 490                 495

Ala Lys Arg Arg Val Val Glu Arg Glu Lys Arg Ala Val Gly Phe Gly
            500                 505                 510

Ala Phe Phe Leu Gly Phe Leu Gly Ala Ala Gly Ser Thr Met Gly Ala
        515                 520                 525

Ala Ser Ile Thr Leu Thr Val Gln Ala Arg Gln Leu Leu Ser Gly Ile
    530                 535                 540

Val Gln Gln Gln Asn Asn Leu Leu Arg Ala Ile Glu Ala Gln Gln His
545                 550                 555                 560

Leu Leu Lys Leu Thr Val Trp Gly Ile Lys Gln Leu Gln Ala Arg Val
                565                 570                 575

Leu Ala Val Glu Arg Tyr Leu Lys Asp Gln Gln Leu Leu Gly Ile Trp
            580                 585                 590

Gly Cys Ser Gly Lys Phe Ile Cys Thr Thr Thr Val Pro Trp Asn Ser
        595                 600                 605

Ser Trp Ser Asn Lys Ser Gln Ser Glu Ile Trp Asp Asn Met Thr Trp
    610                 615                 620

Met Gln Trp Asp Lys Glu Ile Asn Asn Tyr Thr Gln Ile Ile Tyr Asp
625                 630                 635                 640

Leu Ile Glu Glu Ser Gln Arg Gln Gln Glu Lys Asn Glu Gln Asp Leu
                645                 650                 655

Leu Ala Leu Asp Lys Trp Ala Asn Leu Trp Asn Trp Phe Asp Ile Ser
            660                 665                 670

Asn Trp Leu Trp Tyr Ile Lys Ile Phe Ile Met Ile Val Gly Gly Leu
        675                 680                 685

Ile Gly Leu Arg Ile Ala Phe Ala Val Leu Ser Val Ile Asn Arg Val
    690                 695                 700
```

-continued

```
Arg Gln Gly Tyr Ser Pro Leu Ser Phe Gln Thr His Thr Pro Asn Pro
705                 710                 715                 720

Arg Asp Leu Asp Arg Pro Gly Arg Ile Glu Glu Glu Gly Gly Glu Gln
                725                 730                 735

Asp Arg Asp Arg Ser Ile Arg Leu Val Ser Gly Phe Leu Ala Leu Ala
            740                 745                 750

Trp Asp Asp Leu Arg Ser Leu Cys Leu Phe Ser Tyr His Arg Leu Arg
        755                 760                 765

Asp Phe Ile Leu Val Ala Ala Arg Thr Val Glu Leu Leu Gly His Ile
    770                 775                 780

Ser Leu Lys Gly Leu Arg Arg Gly Trp Glu Gly Leu Lys Tyr Leu Gly
785                 790                 795                 800

Asn Leu Leu Ser Tyr Trp Gly Arg Glu Leu Lys Ile Ser Ala Ile Asn
                805                 810                 815

Leu Leu Asp Thr Ile Ala Ile Val Val Ala Glu Trp Thr Asp Arg Ile
            820                 825                 830

Ile Glu Ile Gly Gln Arg Leu Cys Arg Ala Ile Ile Asn Ile Pro Arg
        835                 840                 845

Arg Ile Arg Gln Gly Phe Glu Arg Ala Leu Leu
    850                 855


<210> SEQ ID NO 3
<211> LENGTH: 2517
<212> TYPE: DNA
<213> ORGANISM: Artificial Sequence
<220> FEATURE:
<223> OTHER INFORMATION: pGX1026 - Env Clade A tier 2 Q168ENVe2 DNA
      Sequence

<400> SEQUENCE: 3

atgaaggtgc gaggaatcaa aaggaatctg tggaaatggg ggacaatgct gctgggaatg      60

ctgatgacat atagcgtggc tgaacagctg tgggtgactg tctactatgg cgtgccagtc     120

tggaaggacg ctgaaaccac actgttctgc gcaagtgatg ccaaggctta ctcaaccgag     180

aaacacaata tttgggctac tcatgcatgc gtgcccaccg acccaaaccc ccaggaaatc     240

cacctggaga atgtgaccga ggagttcaac atgtggaaaa acaatatggt cgagcagatg     300

catacagaca tcatttcact gtgggatcag agcctgcgac catgcgtgaa gctgacccct     360

ctgtgcgtca ctctgaattg taccaacgtg aacaacaaca ctaccaatgt caacaacaac     420

acagggtggg acgaggaaag aaagaactgt tctttcaaca tcacaactga gctgagggat     480

aagcgccaga aagtgtacag tctgttttat aagctggacg tggtccagat cgataacagc     540

tcctaccggc tgatcaattg caacacatct gccattactc aggcttgtcc taaagtgacc     600

ttcgaaccta tcccaattca ctattgcgca ccagccggct tcgccatcct gaagtgtaaa     660

gatgagaagt ttaatgggac aggaccctgc aaaaacgtgt ctaccgtcca gtgtacacat     720

ggaattaagc ctgtggtctc aactcagctg ctgctgaatg gcagcctggc tgaaaaagaa     780

gtgatgatcc ggagcgaaaa tttcactaac aatgccaaga acattctggt gcagtttaag     840

gagccagtca aaatcaactg caccagaccc gacaacaata ccagaacaag catcaggatt     900

ggccccgggc aggcctttta cgctacaggc atcattgggg atattaggca ggcatattgt     960

actgtgaatg gctccgagtg gaacaaggcc ctgcagaaag tggtcgaaca gctgcgctct    1020

agtttcgaga ataagacaat catcttcgcc aactcaagcg gcggggacct ggaaatcacc    1080

acacacagtt tcaattgcgg aggcgagttc ttttactgta acacttccgg gctgtttgat    1140
```

-continued

```
tctacttgga atgacaccga tagcaggcag gagaacggaa ctatcaccct gccttgcaga   1200

attaagcaga tcattaatat gtggcagagg accggccagg caatctatgc accacctatc   1260

cagggagcaa ttcgatgcgt gagcaacatc acaggactga ttctgacccg ggacggggga   1320

aacaataaca gcaccaatga aacattcaga ccaggcgggg gagacatgcg cgataactgg   1380

cgaagcgaac tgtacaagta taaagtggtc aagatcgagc ctctgggcgt ggcaccaacc   1440

aaagcccgga gaagggtggt cggacgagag aagcgagcag tgggaattgg cgctgtcttc   1500

ctgggatttc tgggagcagc tgggagcaca atgggagcag cctccatcac actgactgtg   1560

caggccaggc agctgctgtc tgggattgtc cagcagcaga gtaacctgct gaaagctatc   1620

gaagcacagc agcatctgct gcgcctgacc gtgtggggca tcaagcagct gcaggctagg   1680

gtgctggcag tcgagcggta cctgaaagac cagcagctgc tgggaatctg ggctgctcc   1740

gggaagctga tttgtactac caatgtgccc tggaactcct cttggtctaa caagagtcag   1800

tcagaaatct gggagaacat gacatggctg cagtgggaaa aggagattag caattacacc   1860

cagatcatct acacactgat cgaggaatcc cagaatcagc aggagaagaa cgagcaggac   1920

ctgctggcac tggataagtg ggcctccctg tggaactggt tcgatatctc taagtggctg   1980

tggtacatca ggatcttcat catgattgtg ggcgggctga tcggactgcg catcgtgttc   2040

gccgtcctga gcgtggtcaa ccgggtgaga cagggctata gccctctgtc ctttcagacc   2100

ctgctgccag cacctcgggg gccagacaga cccgatggaa ttgaggaaga gggaggagag   2160

cagggaaggg gacgcagtcg acagctggtg aatggcttct caacactgat ctgggacgat   2220

ctgcggaacc tgtgcctgtt ttcctatcac cggctgagag acctgatcct gattgctgca   2280

agaattgtgg aactgctggg acgccgagga tgggaggcta tcaaatacct gtggaacctg   2340

ctgcagtatt ggattcagga gctgaagaat tctgccatta gtctgctgaa cacaactgct   2400

atcgcagtgg ccgaaggcac cgatcgagcc atcgagatca ttcagcgggc tattaccgcc   2460

gtcctgaaca ttcctacccg cattagacag ggatttgaac gcgctctgct gtgataa      2517
```

<210> SEQ ID NO 4
<211> LENGTH: 837
<212> TYPE: PRT
<213> ORGANISM: Artificial Sequence
<220> FEATURE:
<223> OTHER INFORMATION: pGX1026 - Env Clade A tier 2 Q168ENVe2 DNA
Sequence

<400> SEQUENCE: 4

```
Met Lys Val Arg Gly Ile Lys Arg Asn Leu Trp Lys Trp Gly Thr Met
1               5                   10                  15

Leu Leu Gly Met Leu Met Thr Tyr Ser Val Ala Glu Gln Leu Trp Val
            20                  25                  30

Thr Val Tyr Tyr Gly Val Pro Val Trp Lys Asp Ala Glu Thr Thr Leu
        35                  40                  45

Phe Cys Ala Ser Asp Ala Lys Ala Tyr Ser Thr Glu Lys His Asn Ile
    50                  55                  60

Trp Ala Thr His Ala Cys Val Pro Thr Asp Pro Asn Pro Gln Glu Ile
65                  70                  75                  80

His Leu Glu Asn Val Thr Glu Glu Phe Asn Met Trp Lys Asn Asn Met
                85                  90                  95

Val Glu Gln Met His Thr Asp Ile Ile Ser Leu Trp Asp Gln Ser Leu
            100                 105                 110

Arg Pro Cys Val Lys Leu Thr Pro Leu Cys Val Thr Leu Asn Cys Thr
```

-continued

```
        115                 120                 125

Asn Val Asn Asn Asn Thr Thr Asn Val Asn Asn Asn Thr Gly Trp Asp
    130                 135                 140

Glu Glu Arg Lys Asn Cys Ser Phe Asn Ile Thr Thr Glu Leu Arg Asp
145                 150                 155                 160

Lys Arg Gln Lys Val Tyr Ser Leu Phe Tyr Lys Leu Asp Val Val Gln
                165                 170                 175

Ile Asp Asn Ser Ser Tyr Arg Leu Ile Asn Cys Asn Thr Ser Ala Ile
            180                 185                 190

Thr Gln Ala Cys Pro Lys Val Thr Phe Glu Pro Ile Pro Ile His Tyr
        195                 200                 205

Cys Ala Pro Ala Gly Phe Ala Ile Leu Lys Cys Lys Asp Glu Lys Phe
    210                 215                 220

Asn Gly Thr Gly Pro Cys Lys Asn Val Ser Thr Val Gln Cys Thr His
225                 230                 235                 240

Gly Ile Lys Pro Val Val Ser Thr Gln Leu Leu Leu Asn Gly Ser Leu
                245                 250                 255

Ala Glu Lys Glu Val Met Ile Arg Ser Glu Asn Phe Thr Asn Asn Ala
            260                 265                 270

Lys Asn Ile Leu Val Gln Phe Lys Glu Pro Val Lys Ile Asn Cys Thr
        275                 280                 285

Arg Pro Asp Asn Asn Thr Arg Thr Ser Ile Arg Ile Gly Pro Gly Gln
    290                 295                 300

Ala Phe Tyr Ala Thr Gly Ile Ile Gly Asp Ile Arg Gln Ala Tyr Cys
305                 310                 315                 320

Thr Val Asn Gly Ser Glu Trp Asn Lys Ala Leu Gln Lys Val Val Glu
                325                 330                 335

Gln Leu Arg Ser Ser Phe Glu Asn Lys Thr Ile Ile Phe Ala Asn Ser
            340                 345                 350

Ser Gly Gly Asp Leu Glu Ile Thr Thr His Ser Phe Asn Cys Gly Gly
        355                 360                 365

Glu Phe Phe Tyr Cys Asn Thr Ser Gly Leu Phe Asp Ser Thr Trp Asn
    370                 375                 380

Asp Thr Asp Ser Arg Gln Glu Asn Gly Thr Ile Thr Leu Pro Cys Arg
385                 390                 395                 400

Ile Lys Gln Ile Ile Asn Met Trp Gln Arg Thr Gly Gln Ala Ile Tyr
                405                 410                 415

Ala Pro Pro Ile Gln Gly Ala Ile Arg Cys Val Ser Asn Ile Thr Gly
            420                 425                 430

Leu Ile Leu Thr Arg Asp Gly Gly Asn Asn Asn Ser Thr Asn Glu Thr
        435                 440                 445

Phe Arg Pro Gly Gly Gly Asp Met Arg Asp Asn Trp Arg Ser Glu Leu
    450                 455                 460

Tyr Lys Tyr Lys Val Val Lys Ile Glu Pro Leu Gly Val Ala Pro Thr
465                 470                 475                 480

Lys Ala Arg Arg Arg Val Val Gly Arg Glu Lys Arg Ala Val Gly Ile
                485                 490                 495

Gly Ala Val Phe Leu Gly Phe Leu Gly Ala Ala Gly Ser Thr Met Gly
            500                 505                 510

Ala Ala Ser Ile Thr Leu Thr Val Gln Ala Arg Gln Leu Leu Ser Gly
        515                 520                 525

Ile Val Gln Gln Gln Ser Asn Leu Leu Lys Ala Ile Glu Ala Gln Gln
    530                 535                 540
```

```
His Leu Leu Arg Leu Thr Val Trp Gly Ile Lys Gln Leu Gln Ala Arg
545                 550                 555                 560

Val Leu Ala Val Glu Arg Tyr Leu Lys Asp Gln Gln Leu Leu Gly Ile
                565                 570                 575

Trp Gly Cys Ser Gly Lys Leu Ile Cys Thr Thr Asn Val Pro Trp Asn
            580                 585                 590

Ser Ser Trp Ser Asn Lys Ser Gln Ser Glu Ile Trp Glu Asn Met Thr
        595                 600                 605

Trp Leu Gln Trp Glu Lys Glu Ile Ser Asn Tyr Thr Gln Ile Ile Tyr
    610                 615                 620

Thr Leu Ile Glu Glu Ser Gln Asn Gln Gln Glu Lys Asn Glu Gln Asp
625                 630                 635                 640

Leu Leu Ala Leu Asp Lys Trp Ala Ser Leu Trp Asn Trp Phe Asp Ile
                645                 650                 655

Ser Lys Trp Leu Trp Tyr Ile Arg Ile Phe Ile Met Ile Val Gly Gly
            660                 665                 670

Leu Ile Gly Leu Arg Ile Val Phe Ala Val Leu Ser Val Val Asn Arg
        675                 680                 685

Val Arg Gln Gly Tyr Ser Pro Leu Ser Phe Gln Thr Leu Leu Pro Ala
    690                 695                 700

Pro Arg Gly Pro Asp Arg Pro Asp Gly Ile Glu Glu Glu Gly Gly Glu
705                 710                 715                 720

Gln Gly Arg Gly Arg Ser Arg Gln Leu Val Asn Gly Phe Ser Thr Leu
                725                 730                 735

Ile Trp Asp Asp Leu Arg Asn Leu Cys Leu Phe Ser Tyr His Arg Leu
            740                 745                 750

Arg Asp Leu Ile Leu Ile Ala Ala Arg Ile Val Glu Leu Leu Gly Arg
        755                 760                 765

Arg Gly Trp Glu Ala Ile Lys Tyr Leu Trp Asn Leu Leu Gln Tyr Trp
    770                 775                 780

Ile Gln Glu Leu Lys Asn Ser Ala Ile Ser Leu Leu Asn Thr Thr Ala
785                 790                 795                 800

Ile Ala Val Ala Glu Gly Thr Asp Arg Ala Ile Glu Ile Ile Gln Arg
                805                 810                 815

Ala Ile Thr Ala Val Leu Asn Ile Pro Thr Arg Ile Arg Gln Gly Phe
            820                 825                 830

Glu Arg Ala Leu Leu
        835
```

<210> SEQ ID NO 5
<211> LENGTH: 2562
<212> TYPE: DNA
<213> ORGANISM: Artificial Sequence
<220> FEATURE:
<223> OTHER INFORMATION: pGX1027 - Env Clade A tier 2 Q842ENVd12 DNA Sequence

<400> SEQUENCE: 5

```
atgagagcga tggggataca gatgaattgt caaaacttgt ggaggtgggg gactatgatc     60

ttggggatga taatattctg tagtgctgta gacaacttgt gggttactgt ctactatggg    120

gtacctgtgt ggaaagaggc agaaaccacc ttattttgtg catcagatgc taaagcatat    180

gagacagaaa aacataatgt ctgggctaca catgcctgtg tacccacaga ccccaaccca    240

caagaaatac atttggaaaa tgtgacagaa gagtttaaca tgtggaaaaa taacatggta    300
```

-continued

```
gagcagatgc atacagatat aatcagtcta tgggaccaaa gcctaaagcc atgtgtaaag    360
ttaacccctc tctgtgttac tttagattgt aacaatgtca ccaataatgg caccagtgac    420
atgagagaag aaataaaaaa ctgctctttc aatatgacca cagaactaag ggataagaga    480
cagaaagtat attcactttt ttataaactt gatatagtac aaattaatga agatcagggt    540
aatagtagta acaataagta tagattaata acttgtaata cctcagccat tacacaagca    600
tgcccaaagg taacctttga gccaattccc atacattatt gtgctccagc tggttttgcg    660
atcctaaagt gtaaggatga ggagttcaat ggaatagggc catgcaagaa tgtcagcaca    720
gtccaatgca cacatggaat caagccagta gtatcaactc aactactgtt aaatggcagt    780
ctagcagaaa aagaggtaaa aattagatgt gaaaatatca caaacaatgc taaaactata    840
atagtacaac ttgtcaatcc tgtgaaaatt aattgtacca gacctaacaa caatacaaga    900
aaaagtatac atataggacc aggacaagca ttctatgcaa caggtgacat aataggggat    960
ataagacaag cacattgtaa tgtcaacagg acagaatgga acaacacttt gcaccaggta   1020
gtcgaacaat taagaaaaca ctttaacaaa acaataaact ttgctaactc cacaggaggg   1080
gatctagaaa taacaacaca tagttttaat tgtggaggag aatttttcta ttgcaataca   1140
acaaacctgt ttaatagcac ttggaatcac actgccagca tgaatagcac agagtcaaat   1200
gacactataa ttctcccatg cagaataaaa caaattataa atatgtggca gagagtagga   1260
caagcaatgt atgcccctcc cattcgagga gtaataaggt gtgaatcaaa cattacagga   1320
ctaatattaa caagagatgg tgggaatact aacagtacaa gggaaacctt cagacctgga   1380
ggtggagata tgagggacaa ttggagaagt gaattataca agtataaagt agtaaaaatt   1440
gaaccactag gagtagcacc caccaaggca aagagaagag tggtggagag agaaaaaaga   1500
gcagttggaa taggagctgt cttcattggg ttcttaggag cagcgggaag cactatgggc   1560
gcggcgtcaa taacgctgac ggtacaggcc agacaattat tgtctggcat agtgcaacag   1620
caaagcaatt tgctgagggc tatagaggct caacagcatc tgttgaaact cacggtctgg   1680
ggcattaaac agctccaggc aagagtcctg gctgtggaaa gatacctaaa ggatcaacag   1740
ctcctaggaa tttggggctg ctctggaaaa ctcatctgca ccactagtgt gccctggaat   1800
tctagttgga gtaataaatc ccagaatgag atatgggaca acatgacctg gctgcaatgg   1860
gataaagaaa ttagcaatta cacacagata atatatgatc tacttgaaga atcgcagaac   1920
cagcaggaaa agaatgaaca agacttattg gcattggaca agtgggcaaa tctgtggaat   1980
tggtttgaca tatcaaactg gctgtggtat ataaaaatat ttataatgat agtaggaggt   2040
ttaataggat taagaatagt ttttgctgtg ctttctgtaa taaatagagt taggcaggga   2100
tactcacctt tgtcgttcca gacccatacc ccaaacccaa ggggtctcga caggcccgaa   2160
agaatcgaag aagaaggtgg agagcaagac aaaaacagat cgattcgatt agtgagcgga   2220
ttcttagcac ttgcctggga cgatctacgg agcctgtgcc tcttcagcta ccaccgattg   2280
agagacttca tcttgattgt agcgaggact gtggaacttc tgggacacag cagtctcaag   2340
ggctgagac tggggtggga aggcctcaag tatctgggga atcttctatc atattggggt   2400
cgggaactaa ggattagtgc tactaatttg cttgatacca tagcaatagt aatagctggg   2460
tggacagata gggttataga aataggacag agactttgta gagcttttct caacatacct   2520
agaagaatca gacagggctt cgaaagggct ttgctatgat aa                      2562
```

<210> SEQ ID NO 6
<211> LENGTH: 852

```
<212> TYPE: PRT
<213> ORGANISM: Artificial Sequence
<220> FEATURE:
<223> OTHER INFORMATION: pGX1027 - Env Clade A tier 2 Q842ENVd12 Amino
      Acid Sequence

<400> SEQUENCE: 6

Met Arg Ala Met Gly Ile Gln Met Asn Cys Gln Asn Leu Trp Arg Trp
1               5                   10                  15

Gly Thr Met Ile Leu Gly Met Ile Ile Phe Cys Ser Ala Val Asp Asn
            20                  25                  30

Leu Trp Val Thr Val Tyr Tyr Gly Val Pro Val Trp Lys Glu Ala Glu
        35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Asp Cys Asn Asn Val Thr Asn Asn Gly Thr Ser Asp Met Arg Glu Glu
    130                 135                 140

Ile Lys Asn Cys Ser Phe Asn Met Thr Thr Glu Leu Arg Asp Lys Arg
145                 150                 155                 160

Gln Lys Val Tyr Ser Leu Phe Tyr Lys Leu Asp Ile Val Gln Ile Asn
                165                 170                 175

Glu Asp Gln Gly Asn Ser Ser Asn Asn Lys Tyr Arg Leu Ile Thr Cys
            180                 185                 190

Asn Thr Ser Ala Ile Thr Gln Ala Cys Pro Lys Val Thr Phe Glu Pro
        195                 200                 205

Ile Pro Ile His Tyr Cys Ala Pro Ala Gly Phe Ala Ile Leu Lys Cys
    210                 215                 220

Lys Asp Glu Glu Phe Asn Gly Ile Gly Pro Cys Lys Asn Val Ser Thr
225                 230                 235                 240

Val Gln Cys Thr His Gly Ile Lys Pro Val Val Ser Thr Gln Leu Leu
                245                 250                 255

Leu Asn Gly Ser Leu Ala Glu Lys Glu Val Lys Ile Arg Cys Glu Asn
            260                 265                 270

Ile Thr Asn Asn Ala Lys Thr Ile Ile Val Gln Leu Val Asn Pro Val
        275                 280                 285

Lys Ile Asn Cys Thr Arg Pro Asn Asn Asn Thr Arg Lys Ser Ile His
    290                 295                 300

Ile Gly Pro Gly Gln Ala Phe Tyr Ala Thr Gly Asp Ile Ile Gly Asp
305                 310                 315                 320

Ile Arg Gln Ala His Cys Asn Val Asn Arg Thr Glu Trp Asn Asn Thr
                325                 330                 335

Leu His Gln Val Val Glu Gln Leu Arg Lys His Phe Asn Lys Thr Ile
            340                 345                 350

Asn Phe Ala Asn Ser Thr Gly Gly Asp Leu Glu Ile Thr Thr His Ser
        355                 360                 365

Phe Asn Cys Gly Gly Glu Phe Phe Tyr Cys Asn Thr Thr Asn Leu Phe
    370                 375                 380
```

-continued

```
Asn Ser Thr Trp Asn His Thr Ala Ser Met Asn Ser Thr Glu Ser Asn
385                 390                 395                 400

Asp Thr Ile Ile Leu Pro Cys Arg Ile Lys Gln Ile Ile Asn Met Trp
                405                 410                 415

Gln Arg Val Gly Gln Ala Met Tyr Ala Pro Pro Ile Arg Gly Val Ile
            420                 425                 430

Arg Cys Glu Ser Asn Ile Thr Gly Leu Ile Leu Thr Arg Asp Gly Gly
        435                 440                 445

Asn Thr Asn Ser Thr Arg Glu Thr Phe Arg Pro Gly Gly Gly Asp Met
    450                 455                 460

Arg Asp Asn Trp Arg Ser Glu Leu Tyr Lys Tyr Lys Val Val Lys Ile
465                 470                 475                 480

Glu Pro Leu Gly Val Ala Pro Thr Lys Ala Lys Arg Arg Val Val Glu
                485                 490                 495

Arg Glu Lys Arg Ala Val Gly Ile Gly Ala Val Phe Ile Gly Phe Leu
            500                 505                 510

Gly Ala Ala Gly Ser Thr Met Gly Ala Ala Ser Ile Thr Leu Thr Val
        515                 520                 525

Gln Ala Arg Gln Leu Leu Ser Gly Ile Val Gln Gln Gln Ser Asn Leu
    530                 535                 540

Leu Arg Ala Ile Glu Ala Gln Gln His Leu Leu Lys Leu Thr Val Trp
545                 550                 555                 560

Gly Ile Lys Gln Leu Gln Ala Arg Val Leu Ala Val Glu Arg Tyr Leu
                565                 570                 575

Lys Asp Gln Gln Leu Leu Gly Ile Trp Gly Cys Ser Gly Lys Leu Ile
            580                 585                 590

Cys Thr Thr Ser Val Pro Trp Asn Ser Ser Trp Ser Asn Lys Ser Gln
        595                 600                 605

Asn Glu Ile Trp Asp Asn Met Thr Trp Leu Gln Trp Asp Lys Glu Ile
    610                 615                 620

Ser Asn Tyr Thr Gln Ile Ile Tyr Asp Leu Leu Glu Glu Ser Gln Asn
625                 630                 635                 640

Gln Gln Glu Lys Asn Glu Gln Asp Leu Leu Ala Leu Asp Lys Trp Ala
                645                 650                 655

Asn Leu Trp Asn Trp Phe Asp Ile Ser Asn Trp Leu Trp Tyr Ile Lys
            660                 665                 670

Ile Phe Ile Met Ile Val Gly Gly Leu Ile Gly Leu Arg Ile Val Phe
        675                 680                 685

Ala Val Leu Ser Val Ile Asn Arg Val Arg Gln Gly Tyr Ser Pro Leu
    690                 695                 700

Ser Phe Gln Thr His Thr Pro Asn Pro Arg Gly Leu Asp Arg Pro Glu
705                 710                 715                 720

Arg Ile Glu Glu Glu Gly Gly Glu Gln Asp Lys Asn Arg Ser Ile Arg
                725                 730                 735

Leu Val Ser Gly Phe Leu Ala Leu Ala Trp Asp Asp Leu Arg Ser Leu
            740                 745                 750

Cys Leu Phe Ser Tyr His Arg Leu Arg Asp Phe Ile Leu Ile Val Ala
        755                 760                 765

Arg Thr Val Glu Leu Leu Gly His Ser Ser Leu Lys Gly Leu Arg Leu
    770                 775                 780

Gly Trp Glu Gly Leu Lys Tyr Leu Gly Asn Leu Leu Ser Tyr Trp Gly
785                 790                 795                 800
```

```
Arg Glu Leu Arg Ile Ser Ala Thr Asn Leu Leu Asp Thr Ile Ala Ile
                805                 810                 815

Val Ile Ala Gly Trp Thr Asp Arg Val Ile Glu Ile Gly Gln Arg Leu
            820                 825                 830

Cys Arg Ala Phe Leu Asn Ile Pro Arg Arg Ile Arg Gln Gly Phe Glu
        835                 840                 845

Arg Ala Leu Leu
    850


<210> SEQ ID NO 7
<211> LENGTH: 2601
<212> TYPE: DNA
<213> ORGANISM: Artificial Sequence
<220> FEATURE:
<223> OTHER INFORMATION: pGX1028 - Env Clade A tier 2 Q461ENVe2 DNA
      Sequence

<400> SEQUENCE: 7

atgagagtga tggggattca gaggaactat cagcacctgt ggagatgggg gacaatgctg     60

ctgggaatgc tgatgacctg tagcgtcaca ggacagtggg tgactgtcta ctatggcgtg    120

cccgtctgga aggacgcaga gaccacactg ttctgcgcct ctgatgctaa ggcatacgag    180

acagaaaaac acaacgtgtg ggctacacat gcatgcgtgc ctactgaccc aaaccccag    240

gagatcaggc tggaaaatgt gaccgaggac ttcaacatgt ggaagaatag catggtggaa    300

cagatgaatg aggacatcat ttctctgtgg gatcagagtc tgaagccatg cgtgaaactg    360

acccctctgt gcgtgaccct gaactgtacc gactggacaa acaatgctac atcaactaat    420

cagactaccc ccgcaactag cgaggaaacc ggcgtgaaga actgttcctt caatattaca    480

actgagctga gggacaagaa acagaaggtg tactccctgt tttataaact ggatgtggtc    540

cagatctctg aaaacaatag ctccaactct agtaatttca cccagtaccg cctgattaac    600

tgcaatacat cagccatcac tcaggcttgt cccaaggtga gctttgagcc tatcccaatt    660

cactattgcg cccctgctgg cttcgccatt ctgaaatgta acgatagcgt gttcaacggc    720

accgggccat gcaagaacgt gtcaaccgtc cagtgtacac atggcatcaa acccgtggtc    780

tcaacacagc tgatgctgaa tgggagcctg gcagaacgca aagtgatgat tcgaagcgag    840

aacatcacta acaatgccaa gaatatcatt gtgcagttca ccaaacctgt caacattaca    900

tgcatcaggc caggcaacaa tacccgaaaa tccgtgcgga tcggaccagg ccaggccttt    960

tacgctactg gcgacattac cggggatatc cgaaacgctc actgcgtggt caatcggact   1020

gagtggaaca ataccctgca gaaggtggtc gaacagctgc gcgagtactt ccccaacaaa   1080

acaatcatct tcaccaattc aagcggcggg gacatcgaaa ttaccacaca tagcttcaat   1140

tgcggaggcg agttctttta ttgtaacacc tcaaagctgt ttaatagccg gtgggagaac   1200

aatgggactg ccaacatgct gaaaaatgat accggcagca acgaaactac cctgattctg   1260

aggtgccgca tcaagcagat cattaatatg tggcagagag tgggccaggc aatgtatgcc   1320

cctcccattc agggcgtgat caactgtacc tctaatatta caggactgat cctgacaaga   1380

gacgggggag gcgaaaacga taccgagaca ttcaggcctg gggaggcgga catgagagat   1440

aattggagga gcgaactgta caagtataaa gtggtcaagc tggagccact gggagtggca   1500

cctaccatgg ccaagcggag agtggtcgag cgggaaaaaa gagcagtggg aatggcagct   1560

gtcttcctgg ggtttctggg aactgctggc agcaccatgg gagcagcatc cctgactctg   1620

accgtgcagg cacgacagct gctgtctggc attgtccagc agcagagtaa cctgctgaag   1680
```

```
gctatcgagg cacagcagca cctgctgaga ctgaccgtgt ggggcatcaa acagctgcag   1740

gctcgggtgc tggcagtcga gagatacctg aaggaccagc agctgctggg gatttgggga   1800

tgctccggca aactgatctg tacaacttct gtgccctgga actcctcttg gagtaataag   1860

acccagcagg aaatctggaa caataccaca tggctgcagt gggacaaaga gattagcaac   1920

tacacaggca ctatctatcg gctgctggag gaatcccaga accagcagga gaagaatgaa   1980

caggacctgc tggccctgga taaatgggct aacctgtgga attggttcga tatctctaag   2040

tggctgtggt acatcaaaat cttcatcatg gtggtcgggg gactgattgg gctgagaatc   2100

gtgttcgcca tcattagtgt ggtcaaccga gtgcggcagg gatatagccc tctgtccttt   2160

cagatcccca cacctaatcc agaaggactg gacaggccag gacgaattga ggaaggcggg   2220

ggagagcagg atagaaccag gtccatccgc ctggtgtctg gcttcctggc actggcctgg   2280

gacgatctgc gaagtctgtg cctgttctca tatcaccgcc tgcgagactt tattctgatc   2340

gtggccagga ccgtcgaact gctggggcat agttcactga agggactgcg cctggggtgg   2400

gagggactga aatacctggg caacctgctg tcttattggg ggcaggaact gaagaacagt   2460

gctacaaatc tgctggacac taccgctatt gcagtggccg gctggactga tagggccatt   2520

gagatcgtgc agcgcatcgt cagagccatt ctgcatattc cacgccgcat tagacaggga   2580

tttgaacgcg cactgctgta a                                             2601
```

<210> SEQ ID NO 8
<211> LENGTH: 866
<212> TYPE: PRT
<213> ORGANISM: Artificial Sequence
<220> FEATURE:
<223> OTHER INFORMATION: pGX1028 - Env Clade A tier 2 Q461ENVe2 Amino Acid Sequence

<400> SEQUENCE: 8

```
Met Arg Val Met Gly Ile Gln Arg Asn Tyr Gln His Leu Trp Arg Trp
1               5                   10                  15

Gly Thr Met Leu Leu Gly Met Leu Met Thr Cys Ser Val Thr Gly Gln
            20                  25                  30

Trp Val Thr Val Tyr Tyr Gly Val Pro Val Trp Lys Asp Ala Glu Thr
        35                  40                  45

Thr Leu Phe Cys Ala Ser Asp Ala Lys Ala Tyr Glu Thr Glu Lys His
    50                  55                  60

Asn Val Trp Ala Thr His Ala Cys Val Pro Thr Asp Pro Asn Pro Gln
65                  70                  75                  80

Glu Ile Arg Leu Glu Asn Val Thr Glu Asp Phe Asn Met Trp Lys Asn
                85                  90                  95

Ser Met Val Glu Gln Met Asn Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Thr Asp Trp Thr Asn Asn Ala Thr Ser Thr Asn Gln Thr Thr Pro
    130                 135                 140

Ala Thr Ser Glu Glu Thr Gly Val Lys Asn Cys Ser Phe Asn Ile Thr
145                 150                 155                 160

Thr Glu Leu Arg Asp Lys Lys Gln Lys Val Tyr Ser Leu Phe Tyr Lys
                165                 170                 175

Leu Asp Val Val Gln Ile Ser Glu Asn Asn Ser Ser Asn Ser Ser Asn
            180                 185                 190
```

-continued

```
Phe Thr Gln Tyr Arg Leu Ile Asn Cys Asn Thr Ser Ala Ile Thr Gln
        195                 200                 205

Ala Cys Pro Lys Val Ser Phe Glu Pro Ile Pro Ile His Tyr Cys Ala
    210                 215                 220

Pro Ala Gly Phe Ala Ile Leu Lys Cys Asn Asp Ser Val Phe Asn Gly
225                 230                 235                 240

Thr Gly Pro Cys Lys Asn Val Ser Thr Val Gln Cys Thr His Gly Ile
                245                 250                 255

Lys Pro Val Val Ser Thr Gln Leu Met Leu Asn Gly Ser Leu Ala Glu
            260                 265                 270

Arg Lys Val Met Ile Arg Ser Glu Asn Ile Thr Asn Asn Ala Lys Asn
        275                 280                 285

Ile Ile Val Gln Phe Thr Lys Pro Val Asn Ile Thr Cys Ile Arg Pro
    290                 295                 300

Gly Asn Asn Thr Arg Lys Ser Val Arg Ile Gly Pro Gly Gln Ala Phe
305                 310                 315                 320

Tyr Ala Thr Gly Asp Ile Thr Gly Asp Ile Arg Asn Ala His Cys Val
                325                 330                 335

Val Asn Arg Thr Glu Trp Asn Asn Thr Leu Gln Lys Val Val Glu Gln
            340                 345                 350

Leu Arg Glu Tyr Phe Pro Asn Lys Thr Ile Ile Phe Thr Asn Ser Ser
        355                 360                 365

Gly Gly Asp Ile Glu Ile Thr Thr His Ser Phe Asn Cys Gly Gly Glu
    370                 375                 380

Phe Phe Tyr Cys Asn Thr Ser Lys Leu Phe Asn Ser Arg Trp Glu Asn
385                 390                 395                 400

Asn Gly Thr Ala Asn Met Leu Lys Asn Asp Thr Gly Ser Asn Glu Thr
                405                 410                 415

Thr Leu Ile Leu Arg Cys Arg Ile Lys Gln Ile Ile Asn Met Trp Gln
            420                 425                 430

Arg Val Gly Gln Ala Met Tyr Ala Pro Pro Ile Gln Gly Val Ile Asn
        435                 440                 445

Cys Thr Ser Asn Ile Thr Gly Leu Ile Leu Thr Arg Asp Gly Gly Gly
    450                 455                 460

Glu Asn Asp Thr Glu Thr Phe Arg Pro Gly Gly Gly Asp Met Arg Asp
465                 470                 475                 480

Asn Trp Arg Ser Glu Leu Tyr Lys Tyr Lys Val Val Lys Leu Glu Pro
                485                 490                 495

Leu Gly Val Ala Pro Thr Met Ala Lys Arg Arg Val Val Glu Arg Glu
            500                 505                 510

Lys Arg Ala Val Gly Met Ala Ala Val Phe Leu Gly Phe Leu Gly Thr
        515                 520                 525

Ala Gly Ser Thr Met Gly Ala Ala Ser Leu Thr Leu Thr Val Gln Ala
    530                 535                 540

Arg Gln Leu Leu Ser Gly Ile Val Gln Gln Gln Ser Asn Leu Leu Lys
545                 550                 555                 560

Ala Ile Glu Ala Gln Gln His Leu Leu Arg Leu Thr Val Trp Gly Ile
                565                 570                 575

Lys Gln Leu Gln Ala Arg Val Leu Ala Val Glu Arg Tyr Leu Lys Asp
            580                 585                 590

Gln Gln Leu Leu Gly Ile Trp Gly Cys Ser Gly Lys Leu Ile Cys Thr
        595                 600                 605

Thr Ser Val Pro Trp Asn Ser Ser Trp Ser Asn Lys Thr Gln Gln Glu
```

```
    610                 615                 620

Ile Trp Asn Asn Thr Thr Trp Leu Gln Trp Asp Lys Glu Ile Ser Asn
625                 630                 635                 640

Tyr Thr Gly Thr Ile Tyr Arg Leu Leu Glu Glu Ser Gln Asn Gln Gln
                645                 650                 655

Glu Lys Asn Glu Gln Asp Leu Leu Ala Leu Asp Lys Trp Ala Asn Leu
            660                 665                 670

Trp Asn Trp Phe Asp Ile Ser Lys Trp Leu Trp Tyr Ile Lys Ile Phe
        675                 680                 685

Ile Met Val Val Gly Gly Leu Ile Gly Leu Arg Ile Val Phe Ala Ile
    690                 695                 700

Ile Ser Val Val Asn Arg Val Arg Gln Gly Tyr Ser Pro Leu Ser Phe
705                 710                 715                 720

Gln Ile Pro Thr Pro Asn Pro Glu Gly Leu Asp Arg Pro Gly Arg Ile
                725                 730                 735

Glu Glu Gly Gly Gly Glu Gln Asp Arg Thr Arg Ser Ile Arg Leu Val
            740                 745                 750

Ser Gly Phe Leu Ala Leu Ala Trp Asp Asp Leu Arg Ser Leu Cys Leu
        755                 760                 765

Phe Ser Tyr His Arg Leu Arg Asp Phe Ile Leu Ile Val Ala Arg Thr
    770                 775                 780

Val Glu Leu Leu Gly His Ser Ser Leu Lys Gly Leu Arg Leu Gly Trp
785                 790                 795                 800

Glu Gly Leu Lys Tyr Leu Gly Asn Leu Leu Ser Tyr Trp Gly Gln Glu
                805                 810                 815

Leu Lys Asn Ser Ala Thr Asn Leu Leu Asp Thr Thr Ala Ile Ala Val
            820                 825                 830

Ala Gly Trp Thr Asp Arg Ala Ile Glu Ile Val Gln Arg Ile Val Arg
        835                 840                 845

Ala Ile Leu His Ile Pro Arg Arg Ile Arg Gln Gly Phe Glu Arg Ala
    850                 855                 860

Leu Leu
865
```

<210> SEQ ID NO 9
<211> LENGTH: 2532
<212> TYPE: DNA
<213> ORGANISM: Artificial Sequence
<220> FEATURE:
<223> OTHER INFORMATION: pGX1039 - Env Clade A tier 2 Q259d2.17 DNA
Sequence

<400> SEQUENCE: 9

```
atgaactcac agaactcact gcgatggggc attactatcc tgggcatgat tattatttgc      60

tctgctgctg aaaacctgtg ggtcaccgtg tactatgggg tgcctgtctg gaaagacgcc     120

gagaccacac tgttctgcgc ttctaatgcc aaggcttacg gaaccgaagt cgagaacatc     180

tgggcaaccc acgcctgcgt gccaacagat ccaaatcccc aggaaattaa tctggagaac     240

gtcactgagg agttcaacat gtggaagaac aatatggtgg aacagatgca taccgacatc     300

attagcctgt gggatcaggg cctgaaacct tgcgtgaagc tgactccact gtgcgtcacc     360

ctggactgtt ataatgtgac taagtcagac aaaatcacca aggatatgca ggaggaaatc     420

aaaaactgta gcttcaacat cactaccgag ctgcgcgata agaaacagaa ggtgcacagc     480

ctgttttacc gactggacgt ggtccccatg ggcgggaaaa acgatagtca gtataggctg     540
```

-continued

```
atcaattgca acacttcagc aattacccag gcctgtccca aggtgacatt cgagcctatc    600
ccaattcact actgcgcacc tgccggcttc gccatcctga aatgtaatga caaggaattt    660
tctggcactg ggccatgcaa gaacgtgagc tccgtccagt gtacccatgg aatcaggccc    720
gtggtctcca cacagctgct gctgaacggc tctctggccg aggaaaaggt gcggatcaga    780
agcgaggata tcacaaacaa cggcaaaaac atcatcgtgc agctgaagac tccagtcaac    840
atcagctgca cacgccccaa caataacact agaaagtccg tgaggattgg acccggccag    900
gctttttatg caaccgacga tatcattggg aatatccgac aggcctactg tacagtcaac    960
cggactcagt gggactatac cctgcaggag gtggctaatc agctgagaat ctacttcaac   1020
aaaacaatca tcttcaacaa ctctgccgga ggcgacctgg aaattacaac tcacagtttc   1080
aattgcgggg gagagttctt ttattgtgat acctcagggc tgtttaatag cacttggacc   1140
tggaacgaca ccgtgagctg gcaaggaagt gataatatca ccctgcagtg cagaattaag   1200
cagatcatta acatgtggca gagggccgga caggctatct acgcaccccc tatccagggc   1260
gtgattaggt gtgacagcaa catcacaggg ctgattctga ctcgcgatgg cggaaataac   1320
tctagtccca atgagatctt ccggcctgga ggcggggaca tgcgagataa ctggcgatcc   1380
gaactgtaca agtataaagt ggtcaagatc gagccactgg gcgtggctcc cacaagagca   1440
aaacggagag tggtcgaacg ggagaagaga gcagtgggga tcggagccgt cttcattggc   1500
tttctgggag cagctggatc taccatggga gcagccagta tcacactgac tgctcaggca   1560
aggaagctgc tgtcagggat cgtccagcag cagagcaacc tgctgcgcgc cattgaggct   1620
cagcagcatc tgctgaaact gaccgtgtgg ggcatcaagc agctgcaggc ccgggtgctg   1680
gctgtcgaaa gatacctgaa agaccagcag ctgctgggaa tctggggatg ctccggaaag   1740
ctgatttgta ccacaaatgt gccctggaac tcaagctggt ctaataagag tcagtcagaa   1800
atctgggaga acatgacctg gctgcagtgg gacaaagaaa ttaataacta cacacagctg   1860
atctattccc tgattgagaa gtctcagact cagcaggaaa tcaatgagca ggacctgctg   1920
gctctggata aatgggcaaa tctgtggaac tggttcgata tttccaactg gctgtggtac   1980
atccggatct tcatcatgat tgtcggaggc ctgatcggac tgagaatcgt gttcgccgtc   2040
ctgagtatca ttaaccgagt gcggcaggga cacagccctc tgtcctttca gacccataca   2100
ccaagccctc gggaactgga caggcctgga cgaatcgagg aagagggcgg cgagccagat   2160
agaggcagga gtattaggct ggtgtcaggg ttcctggccc tggcttggga cgatctgcgc   2220
agcctgtgcc tgttctccta tcaccgcctg cgagacttta tcagcattgc tgcacggaca   2280
gtggaactgc tgggacattc ctctctgaaa ggcctgagac tgggctggga ggggctgaag   2340
tacctgggga atctgctggt gtattgggga cgagaactgc ggctgtccgc catcaacctg   2400
ctggatacca tcgcaattgc caccgctgac tggacagata gagtgatcga gctgggccag   2460
cgcctgtgcc gagctattct gcatattccc aggaggattc gccagggatt tgagagagca   2520
ctgctgtgat aa                                                       2532
```

<210> SEQ ID NO 10
<211> LENGTH: 842
<212> TYPE: PRT
<213> ORGANISM: Artificial Sequence
<220> FEATURE:
<223> OTHER INFORMATION: pGX1039 -  Env Clade A tier 2 Q259d2.17 Amino
      Acid Sequence

<400> SEQUENCE: 10

-continued

```
Met Asn Ser Gln Asn Ser Leu Arg Trp Gly Ile Thr Ile Leu Gly Met
1               5                   10                  15

Ile Ile Ile Cys Ser Ala Ala Glu Asn Leu Trp Val Thr Val Tyr Tyr
            20                  25                  30

Gly Val Pro Val Trp Lys Asp Ala Glu Thr Thr Leu Phe Cys Ala Ser
        35                  40                  45

Asn Ala Lys Ala Tyr Gly Thr Glu Val Glu Asn Ile Trp Ala Thr His
    50                  55                  60

Ala Cys Val Pro Thr Asp Pro Asn Pro Gln Glu Ile Asn Leu Glu Asn
65                  70                  75                  80

Val Thr Glu Glu Phe Asn Met Trp Lys Asn Asn Met Val Glu Gln Met
                85                  90                  95

His Thr Asp Ile Ile Ser Leu Trp Asp Gln Gly Leu Lys Pro Cys Val
            100                 105                 110

Lys Leu Thr Pro Leu Cys Val Thr Leu Asp Cys Tyr Asn Val Thr Lys
        115                 120                 125

Ser Asp Lys Ile Thr Lys Asp Met Gln Glu Glu Ile Lys Asn Cys Ser
    130                 135                 140

Phe Asn Ile Thr Thr Glu Leu Arg Asp Lys Lys Gln Lys Val His Ser
145                 150                 155                 160

Leu Phe Tyr Arg Leu Asp Val Val Pro Met Gly Gly Lys Asn Asp Ser
                165                 170                 175

Gln Tyr Arg Leu Ile Asn Cys Asn Thr Ser Ala Ile Thr Gln Ala Cys
            180                 185                 190

Pro Lys Val Thr Phe Glu Pro Ile Pro Ile His Tyr Cys Ala Pro Ala
        195                 200                 205

Gly Phe Ala Ile Leu Lys Cys Asn Asp Lys Glu Phe Ser Gly Thr Gly
    210                 215                 220

Pro Cys Lys Asn Val Ser Ser Val Gln Cys Thr His Gly Ile Arg Pro
225                 230                 235                 240

Val Val Ser Thr Gln Leu Leu Leu Asn Gly Ser Leu Ala Glu Glu Lys
                245                 250                 255

Val Arg Ile Arg Ser Glu Asp Ile Thr Asn Asn Gly Lys Asn Ile Ile
            260                 265                 270

Val Gln Leu Lys Thr Pro Val Asn Ile Ser Cys Thr Arg Pro Asn Asn
        275                 280                 285

Asn Thr Arg Lys Ser Val Arg Ile Gly Pro Gly Gln Ala Phe Tyr Ala
    290                 295                 300

Thr Asp Asp Ile Ile Gly Asn Ile Arg Gln Ala Tyr Cys Thr Val Asn
305                 310                 315                 320

Arg Thr Gln Trp Asp Tyr Thr Leu Gln Glu Val Ala Asn Gln Leu Arg
                325                 330                 335

Ile Tyr Phe Asn Lys Thr Ile Ile Phe Asn Asn Ser Ala Gly Gly Asp
            340                 345                 350

Leu Glu Ile Thr Thr His Ser Phe Asn Cys Gly Gly Glu Phe Phe Tyr
        355                 360                 365

Cys Asp Thr Ser Gly Leu Phe Asn Ser Thr Trp Thr Trp Asn Asp Thr
    370                 375                 380

Val Ser Trp Gln Gly Ser Asp Asn Ile Thr Leu Gln Cys Arg Ile Lys
385                 390                 395                 400

Gln Ile Ile Asn Met Trp Gln Arg Ala Gly Gln Ala Ile Tyr Ala Pro
                405                 410                 415

Pro Ile Gln Gly Val Ile Arg Cys Asp Ser Asn Ile Thr Gly Leu Ile
```

```
            420                 425                 430

Leu Thr Arg Asp Gly Gly Asn Asn Ser Ser Pro Asn Glu Ile Phe Arg
        435                 440                 445

Pro Gly Gly Gly Asp Met Arg Asp Asn Trp Arg Ser Glu Leu Tyr Lys
    450                 455                 460

Tyr Lys Val Val Lys Ile Glu Pro Leu Gly Val Ala Pro Thr Arg Ala
465                 470                 475                 480

Lys Arg Arg Val Val Glu Arg Glu Lys Arg Ala Val Gly Ile Gly Ala
                485                 490                 495

Val Phe Ile Gly Phe Leu Gly Ala Ala Gly Ser Thr Met Gly Ala Ala
            500                 505                 510

Ser Ile Thr Leu Thr Ala Gln Ala Arg Lys Leu Leu Ser Gly Ile Val
        515                 520                 525

Gln Gln Gln Ser Asn Leu Leu Arg Ala Ile Glu Ala Gln Gln His Leu
    530                 535                 540

Leu Lys Leu Thr Val Trp Gly Ile Lys Gln Leu Gln Ala Arg Val Leu
545                 550                 555                 560

Ala Val Glu Arg Tyr Leu Lys Asp Gln Gln Leu Leu Gly Ile Trp Gly
                565                 570                 575

Cys Ser Gly Lys Leu Ile Cys Thr Thr Asn Val Pro Trp Asn Ser Ser
            580                 585                 590

Trp Ser Asn Lys Ser Gln Ser Glu Ile Trp Glu Asn Met Thr Trp Leu
        595                 600                 605

Gln Trp Asp Lys Glu Ile Asn Asn Tyr Thr Gln Leu Ile Tyr Ser Leu
    610                 615                 620

Ile Glu Lys Ser Gln Thr Gln Gln Glu Ile Asn Glu Gln Asp Leu Leu
625                 630                 635                 640

Ala Leu Asp Lys Trp Ala Asn Leu Trp Asn Trp Phe Asp Ile Ser Asn
                645                 650                 655

Trp Leu Trp Tyr Ile Arg Ile Phe Ile Met Ile Val Gly Gly Leu Ile
            660                 665                 670

Gly Leu Arg Ile Val Phe Ala Val Leu Ser Ile Ile Asn Arg Val Arg
        675                 680                 685

Gln Gly His Ser Pro Leu Ser Phe Gln Thr His Thr Pro Ser Pro Arg
    690                 695                 700

Glu Leu Asp Arg Pro Gly Arg Ile Glu Glu Glu Gly Gly Glu Pro Asp
705                 710                 715                 720

Arg Gly Arg Ser Ile Arg Leu Val Ser Gly Phe Leu Ala Leu Ala Trp
                725                 730                 735

Asp Asp Leu Arg Ser Leu Cys Leu Phe Ser Tyr His Arg Leu Arg Asp
            740                 745                 750

Phe Ile Ser Ile Ala Ala Arg Thr Val Glu Leu Leu Gly His Ser Ser
        755                 760                 765

Leu Lys Gly Leu Arg Leu Gly Trp Glu Gly Leu Lys Tyr Leu Gly Asn
    770                 775                 780

Leu Leu Val Tyr Trp Gly Arg Glu Leu Arg Leu Ser Ala Ile Asn Leu
785                 790                 795                 800

Leu Asp Thr Ile Ala Ile Ala Thr Ala Asp Trp Thr Asp Arg Val Ile
                805                 810                 815

Glu Leu Gly Gln Arg Leu Cys Arg Ala Ile Leu His Ile Pro Arg Arg
            820                 825                 830

Ile Arg Gln Gly Phe Glu Arg Ala Leu Leu
        835                 840
```

<210> SEQ ID NO 11
<211> LENGTH: 2553
<212> TYPE: DNA
<213> ORGANISM: Artificial Sequence
<220> FEATURE:
<223> OTHER INFORMATION: pGX1030 - Env Clade B tier 2 WITO4160.33 DNA
Sequence

<400> SEQUENCE: 11
atgaaagtga tgggaacaaa gaagaactac cagcacctgt ggagatgggg gattatgctg 60
ctgggaatgc tgatgatgtc aagcgcagcc gagcagctgt gggtgaccgt ctactatggg 120
gtgccagtct ggagagaagc aaacaccaca ctgttctgcg ccagcgacgc taaagcatac 180
gatacagagg tgcacaatgt ctgggcaacc catgcctgcg tgcccacaga cccaaacccc 240
caggaggtgg tcatgggcaa tgtgaccgaa gacttcaaca tgtggaagaa caatatggtg 300
gagcagatgc acgaagacat catttccctg tgggatcagt ctctgaagcc ctgcgtcaaa 360
ctgacacctc tgtgcgtgac tctgcattgt acaaacgtca ctatcagctc caccaatggc 420
agcacagcta acgtgactat gagggaggaa atgaagaatt gttccttcaa cactaccaca 480
gtgattcgcg acaagatcca gaaagagtac gcactgtttt ataaactgga tattgtgcca 540
atcgaaggca agaacactaa taccgggtac agactgatta actgcaatac cagtgtgatc 600
acacaggcct gtcctaaggt gtcattcgag cctattccaa tccactattg cgccccagct 660
ggcttcgcta ttctgaagtg taacaacaag accttcaacg ggaaaggacc ctgcaggaac 720
gtgagcactg tccagtgtac ccatgggatc aagcctgtgg tctccaccca gctgctgctg 780
aacggatctc tggccgagga agacatcatt atccgctccg agaatttcac aaacaacggg 840
aaaaacatca tcgtccagct gaaggaacca gtgaaaatca attgcactcg gcccggaaac 900
aatacccgga gaagtattaa catcggccct gggcgcgctt tttacgcaac cggggccatt 960
atcggagata ttcgaaaggc ccactgtaat atcagcacag agcagtggaa caatacactg 1020
actcagatcg tggacaaact gcgcgaacag ttcggaaata agactatcat ctttaaccag 1080
tctagtggcg gcgaccccga ggtggtcatg catacattca actgcggagg cgaattcttt 1140
tactgtaata gcacacagct gttcaactcc acttggttta acaatggcac ctcaacatgg 1200
aatagcaccg ccgacaacat cacactgcca tgccggatca agcaggtcat caacatgtgg 1260
caggaggtcg ggaaggctat gtatgcaccc cctattcgcg gacagatcga ctgttcaagc 1320
aacattactg gactgatcct gacccgggat ggaggcagca attcctctca gaacgagacc 1380
tttagacccg gcgggggaaa tatgaaagat aactggaggt ctgagctgta caagtataaa 1440
gtggtcaaga ttgaacctct gggcatcgca ccaacaagag ccaaaaggcg agtggtccag 1500
cgagagaagc gagcagtgac tctgggagct gtcttcctgg gatttctggg agcagctggg 1560
tctaccatgg gagcagccag tctgactctg accgtgcagg cccgactgct gctgtcaggc 1620
attgtgcagc agcagagcaa tctgctgagg gccatcgagg ctcagcagca catgctgcag 1680
ctgaccgtgt ggggcatcaa gcagctgcag gctagggtgc tggcaatcga acgctacctg 1740
aaagaccagc agctgctggg aatttggggc tgctctggga agctgatctg tactaccaca 1800
gtgccctgga atacaagttg gtcaaacaag agttacgact atatttggaa caatatgact 1860
tggatgcagt gggagaggga aatcgataac tacacaggct tcatctacac tctgatcgag 1920
gaatcacaga atcagcagga gaaaaacgag ctggaactgc tggaactgga taagtgggcc 1980
agcctgtgga actggttcaa tatcaccaac tggctgtggt acattaagct gtttatcatg 2040

```
attatcggcg ggctggtggg actgagaatc gtgtgcgctg tcctgtctat cgtgaataga   2100

gtcaggcagg gctatagccc tctgtccttt cagactaggc tgcccaaccc tcggggacca   2160

gacagacccg aggaaaccga gggagaagga ggagagcgag accgagatcg gtccgctcga   2220

ctggtgaatg gcttcctggc aattatctgg gacgatctga gaagtctgtg cctgttttca   2280

tatcatagac tgagggatct gctgctgatt gtggcccggg tggtcgagat cctgggacga   2340

cggggctggg aaatcctgaa gtactggtgg aacctgctga aatattggag ccaggagctg   2400

aagaattctg cagtgagtct gctgaacgtc accgcaatcg ccgtggctga gggcacagac   2460

cgagtgattg aaatcgtcca gcgggccgtg agagccattc tgcatattcc cacccgcatt   2520

cgccagggat ttgaacgcgc actgctgtga taa                                2553
```

```
<210> SEQ ID NO 12
<211> LENGTH: 849
<212> TYPE: PRT
<213> ORGANISM: Artificial Sequence
<220> FEATURE:
<223> OTHER INFORMATION: pGX1030 - Env Clade B tier 2 WITO4160.33  Amino
      Acid Sequence

<400> SEQUENCE: 12

Met Lys Val Met Gly Thr Lys Lys Asn Tyr Gln His Leu Trp Arg Trp
1               5                   10                  15

Gly Ile Met Leu Leu Gly Met Leu Met Met Ser Ser Ala Ala Glu Gln
            20                  25                  30

Leu Trp Val Thr Val Tyr Tyr Gly Val Pro Val Trp Arg Glu Ala Asn
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Met Gly Asn Val Thr Glu Asp Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

His Cys Thr Asn Val Thr Ile Ser Ser Thr Asn Gly Ser Thr Ala Asn
    130                 135                 140

Val Thr Met Arg Glu Glu Met Lys Asn Cys Ser Phe Asn Thr Thr Thr
145                 150                 155                 160

Val Ile Arg Asp Lys Ile Gln Lys Glu Tyr Ala Leu Phe Tyr Lys Leu
                165                 170                 175

Asp Ile Val Pro Ile Glu Gly Lys Asn Thr Asn Thr Gly Tyr Arg Leu
            180                 185                 190

Ile Asn Cys Asn Thr Ser Val Ile Thr Gln Ala Cys Pro Lys Val Ser
        195                 200                 205

Phe Glu Pro Ile Pro Ile His Tyr Cys Ala Pro Ala Gly Phe Ala Ile
    210                 215                 220

Leu Lys Cys Asn Asn Lys Thr Phe Asn Gly Lys Gly Pro Cys Arg Asn
225                 230                 235                 240

Val Ser Thr Val Gln Cys Thr His Gly Ile Lys Pro Val Val Ser Thr
                245                 250                 255

Gln Leu Leu Leu Asn Gly Ser Leu Ala Glu Glu Asp Ile Ile Ile Arg
```

-continued

```
            260                 265                 270

Ser Glu Asn Phe Thr Asn Asn Gly Lys Asn Ile Ile Val Gln Leu Lys
        275                 280                 285

Glu Pro Val Lys Ile Asn Cys Thr Arg Pro Gly Asn Asn Thr Arg Arg
    290                 295                 300

Ser Ile Asn Ile Gly Pro Gly Arg Ala Phe Tyr Ala Thr Gly Ala Ile
305                 310                 315                 320

Ile Gly Asp Ile Arg Lys Ala His Cys Asn Ile Ser Thr Glu Gln Trp
                325                 330                 335

Asn Asn Thr Leu Thr Gln Ile Val Asp Lys Leu Arg Glu Gln Phe Gly
            340                 345                 350

Asn Lys Thr Ile Ile Phe Asn Gln Ser Ser Gly Gly Asp Pro Glu Val
        355                 360                 365

Val Met His Thr Phe Asn Cys Gly Gly Glu Phe Phe Tyr Cys Asn Ser
    370                 375                 380

Thr Gln Leu Phe Asn Ser Thr Trp Phe Asn Asn Gly Thr Ser Thr Trp
385                 390                 395                 400

Asn Ser Thr Ala Asp Asn Ile Thr Leu Pro Cys Arg Ile Lys Gln Val
                405                 410                 415

Ile Asn Met Trp Gln Glu Val Gly Lys Ala Met Tyr Ala Pro Pro Ile
            420                 425                 430

Arg Gly Gln Ile Asp Cys Ser Ser Asn Ile Thr Gly Leu Ile Leu Thr
        435                 440                 445

Arg Asp Gly Gly Ser Asn Ser Ser Gln Asn Glu Thr Phe Arg Pro Gly
    450                 455                 460

Gly Gly Asn Met Lys Asp Asn Trp Arg Ser Glu Leu Tyr Lys Tyr Lys
465                 470                 475                 480

Val Val Lys Ile Glu Pro Leu Gly Ile Ala Pro Thr Arg Ala Lys Arg
                485                 490                 495

Arg Val Val Gln Arg Glu Lys Arg Ala Val Thr Leu Gly Ala Val Phe
            500                 505                 510

Leu Gly Phe Leu Gly Ala Ala Gly Ser Thr Met Gly Ala Ala Ser Leu
        515                 520                 525

Thr Leu Thr Val Gln Ala Arg Leu Leu Leu Ser Gly Ile Val Gln Gln
    530                 535                 540

Gln Ser Asn Leu Leu Arg Ala Ile Glu Ala Gln Gln His Met Leu Gln
545                 550                 555                 560

Leu Thr Val Trp Gly Ile Lys Gln Leu Gln Ala Arg Val Leu Ala Ile
                565                 570                 575

Glu Arg Tyr Leu Lys Asp Gln Gln Leu Leu Gly Ile Trp Gly Cys Ser
            580                 585                 590

Gly Lys Leu Ile Cys Thr Thr Thr Val Pro Trp Asn Thr Ser Trp Ser
        595                 600                 605

Asn Lys Ser Tyr Asp Tyr Ile Trp Asn Asn Met Thr Trp Met Gln Trp
    610                 615                 620

Glu Arg Glu Ile Asp Asn Tyr Thr Gly Phe Ile Tyr Thr Leu Ile Glu
625                 630                 635                 640

Glu Ser Gln Asn Gln Gln Glu Lys Asn Glu Leu Glu Leu Leu Glu Leu
                645                 650                 655

Asp Lys Trp Ala Ser Leu Trp Asn Trp Phe Asn Ile Thr Asn Trp Leu
            660                 665                 670

Trp Tyr Ile Lys Leu Phe Ile Met Ile Ile Gly Gly Leu Val Gly Leu
        675                 680                 685
```

Arg Ile Val Cys Ala Val Leu Ser Ile Val Asn Arg Val Arg Gln Gly
    690                 695                 700

Tyr Ser Pro Leu Ser Phe Gln Thr Arg Leu Pro Asn Pro Arg Gly Pro
705                 710                 715                 720

Asp Arg Pro Glu Glu Thr Glu Gly Glu Gly Gly Glu Arg Asp Arg Asp
                725                 730                 735

Arg Ser Ala Arg Leu Val Asn Gly Phe Leu Ala Ile Ile Trp Asp Asp
            740                 745                 750

Leu Arg Ser Leu Cys Leu Phe Ser Tyr His Arg Leu Arg Asp Leu Leu
        755                 760                 765

Leu Ile Val Ala Arg Val Val Glu Ile Leu Gly Arg Arg Gly Trp Glu
    770                 775                 780

Ile Leu Lys Tyr Trp Trp Asn Leu Leu Lys Tyr Trp Ser Gln Glu Leu
785                 790                 795                 800

Lys Asn Ser Ala Val Ser Leu Leu Asn Val Thr Ala Ile Ala Val Ala
                805                 810                 815

Glu Gly Thr Asp Arg Val Ile Glu Ile Val Gln Arg Ala Val Arg Ala
            820                 825                 830

Ile Leu His Ile Pro Thr Arg Ile Arg Gln Gly Phe Glu Arg Ala Leu
        835                 840                 845

Leu

<210> SEQ ID NO 13
<211> LENGTH: 2577
<212> TYPE: DNA
<213> ORGANISM: Artificial Sequence
<220> FEATURE:
<223> OTHER INFORMATION: pGX1033 - Env Clade B tier 3 TRJO4551.58 DNA
      Sequence

<400> SEQUENCE: 13
atgcgcgtga tggggattag gaaaaactac cagcacctgt ggagatgggg cactatgggg 60
atgatgctgc tggggattct gatgatttgc aacgccacag aaaaactgtg ggtgactgtc 120
tactatggcg tgccagtctg gaaggaggct accacaactc tgttctgcgc aagcgatgcc 180
aaagcttacg agacagaagt gcacaatgtc tgggcaaccc atgcctgcgt gcccacagat 240
ccaaaccccc aggagctggt gctggaaaat gtcactgagt attttgacat gtggaagaac 300
aatatggtgg aacagatgca cgaggacatc atttccctgt gggatcagtc tctgaaaccc 360
tgcgtgaagc tgactcctct gtgcgtcacc ctgaactgta ccgactggac aaatggcact 420
gattggaaca ccacaaactc taacaacact accatcagta aggaggaaac tattgagggc 480
ggggaaatga agaactgtag cttcaatatc acaactgcca ccggggacaa gaaaaaggaa 540
agggcattct tttacaagct ggacgtggcc cccatcgata actcaaatac cagctatcgc 600
ctgatctctt gcaacaccag tgtgattaca caggcatgtc ccaaaatcag ctttgagcct 660
atcccaattc actactgcgc acctgccggc ttcgctatcc tgaagtgtaa cgataagaag 720
tttaatggaa ctggcagttg caccaacgtg tcaacagtcc agtgtactca tggaattcgg 780
cctgtggtct ccacccagct gctgctgaat ggctctctgg ctgaggaaga ggtggtcatc 840
agatcaaaaa acttcagcga caatgcaaag atcattatcg tgcagctgaa cgagtctgtc 900
ccaatcaatt gcactcgacc ccacaacaat acccggaaaa gtatccatat tgggccagga 960
cgagcttggt acgcaaccgg ggacattatc ggagatatta gaaaggccta ttgtaacatc 1020
tccgaggcta aatggaacaa tacactgaag cagatcactg aaaaactgaa ggagcagttc 1080

```
aacaagacta ttatcgtgtt taatcagcca agcggaggcg atcccgaagt gaccatgcac   1140

tccttcaact gcgggggaga gttcttttac tgtaacacca gtaagctgtt taacgggacc   1200

tggaattcaa caaagagggc caacaataca gagggaatta tcattctgca gtgcagaatc   1260

aaacagatca ttaacaggtg gcaggaagtg ggaaaggcca tgtatgctcc ccctatcgag   1320

ggccagatta agtgtagctc caatatcacc gggctgctgc tgacaaggga tggcgggaaa   1380

accgccaaca ataccacaga gttctttcgc cccggaggcg ggaacatgaa agacaattgg   1440

aggagcgaac tgtacaaata taaggtggtc cgcatcgagc ctctgggagt ggctccaaca   1500

aaagcaaagc ggagagtggt ccagcgcgag aagcgagcaa tcggcattgg ggccgtgttc   1560

ctgggatttc tgggagcagc tgggtcaacc atgggagcag ccagcatcac actgactgtg   1620

caggcccgga aactgctgtc cggcattgtg cagcagcaga acaatctgct gagagcaatc   1680

gaagcccagc agcacctgct gcagctgacc gtgtggggca tcaagcagct gcaggcccgg   1740

gtgctggctg tcgagcggta cctgagagac cagcagctgc tgggaatttg gggctgctct   1800

gggaagctga tctgtactac cgccgtgccc tggaactcta gttggtccaa caagtctctg   1860

gatacaattt ggaacaatat gacttggatg cagtgggaga aggaaatcga caactacact   1920

ggcctgatct ataccctgat tgaagagtca cagattcagc aggagaaaaa tgaactggac   1980

ctgctgaagc tggatcagtg ggccagcctg tggaactggt tcgatatcac aaattggctg   2040

tggtacatca agatcttcat catgattgtg ggaggactgg tcggactgcg aatcgtgttc   2100

gctgtcctgt ccatcgtgaa ccgagtccgg cagggctata gtcctctgtc atttcagacc   2160

catctgccaa attctagggg gccagaccga cctggaggaa tcgaagagga aggcggggag   2220

agggacaacg gcagaagtag gcctctggtg gatgggttcc tggccatcat ttgggtcgac   2280

ctgcgcagcc tgtgcctgtt ttcctatcac catctgcggg gcctgctgct gatcgctgca   2340

agaattgtgg aactgctggg aaggcgcgga tgggaggccc tgaagtactg gtggaacctg   2400

ctgcagtatt gggggcagga gctgagaaac agcgccgtga gcctgctgaa tgctaccgca   2460

attgccgtgg ctgaaggaac agaccgcatc attgaggtgg tccagcgaat cggccgagcc   2520

attctgaaca tcccccgacg cattagacag ggagccgaaa gagcactgca gtgataa      2577
```

<210> SEQ ID NO 14
<211> LENGTH: 857
<212> TYPE: PRT
<213> ORGANISM: Artificial Sequence
<220> FEATURE:
<223> OTHER INFORMATION: pGX1033 - Env Clade B tier 3 TRJO4551.58 Amino Acid Sequence

<400> SEQUENCE: 14

```
Met Arg Val Met Gly Ile Arg Lys Asn Tyr Gln His Leu Trp Arg Trp
1               5                   10                  15

Gly Thr Met Gly Met Met Leu Leu Gly Ile Leu Met Ile Cys Asn Ala
            20                  25                  30

Thr Glu Lys Leu Trp Val Thr Val Tyr Tyr Gly Val Pro Val Trp Lys
        35                  40                  45

Glu Ala Thr Thr Thr Leu Phe Cys Ala Ser Asp Ala Lys Ala Tyr Glu
    50                  55                  60

Thr Glu Val His Asn Val Trp Ala Thr His Ala Cys Val Pro Thr Asp
65                  70                  75                  80

Pro Asn Pro Gln Glu Leu Val Leu Glu Asn Val Thr Glu Tyr Phe Asp
                85                  90                  95
```

```
Met Trp Lys Asn Asn Met Val Glu Gln Met His Glu Asp Ile Ile Ser
            100                 105                 110

Leu Trp Asp Gln Ser Leu Lys Pro Cys Val Lys Leu Thr Pro Leu Cys
        115                 120                 125

Val Thr Leu Asn Cys Thr Asp Trp Thr Asn Gly Thr Asp Trp Asn Thr
    130                 135                 140

Thr Asn Ser Asn Asn Thr Thr Ile Ser Lys Glu Glu Thr Ile Glu Gly
145                 150                 155                 160

Gly Glu Met Lys Asn Cys Ser Phe Asn Ile Thr Thr Ala Thr Gly Asp
                165                 170                 175

Lys Lys Lys Glu Arg Ala Phe Phe Tyr Lys Leu Asp Val Ala Pro Ile
            180                 185                 190

Asp Asn Ser Asn Thr Ser Tyr Arg Leu Ile Ser Cys Asn Thr Ser Val
        195                 200                 205

Ile Thr Gln Ala Cys Pro Lys Ile Ser Phe Glu Pro Ile Pro Ile His
    210                 215                 220

Tyr Cys Ala Pro Ala Gly Phe Ala Ile Leu Lys Cys Asn Asp Lys Lys
225                 230                 235                 240

Phe Asn Gly Thr Gly Ser Cys Thr Asn Val Ser Thr Val Gln Cys Thr
                245                 250                 255

His Gly Ile Arg Pro Val Val Ser Thr Gln Leu Leu Leu Asn Gly Ser
            260                 265                 270

Leu Ala Glu Glu Glu Val Val Ile Arg Ser Lys Asn Phe Ser Asp Asn
        275                 280                 285

Ala Lys Ile Ile Ile Val Gln Leu Asn Glu Ser Val Pro Ile Asn Cys
    290                 295                 300

Thr Arg Pro His Asn Asn Thr Arg Lys Ser Ile His Ile Gly Pro Gly
305                 310                 315                 320

Arg Ala Trp Tyr Ala Thr Gly Asp Ile Ile Gly Asp Ile Arg Lys Ala
                325                 330                 335

Tyr Cys Asn Ile Ser Glu Ala Lys Trp Asn Asn Thr Leu Lys Gln Ile
            340                 345                 350

Thr Glu Lys Leu Lys Glu Gln Phe Asn Lys Thr Ile Ile Val Phe Asn
        355                 360                 365

Gln Pro Ser Gly Gly Asp Pro Glu Val Thr Met His Ser Phe Asn Cys
    370                 375                 380

Gly Gly Glu Phe Phe Tyr Cys Asn Thr Ser Lys Leu Phe Asn Gly Thr
385                 390                 395                 400

Trp Asn Ser Thr Lys Arg Ala Asn Asn Thr Glu Gly Ile Ile Ile Leu
                405                 410                 415

Gln Cys Arg Ile Lys Gln Ile Ile Asn Arg Trp Gln Glu Val Gly Lys
            420                 425                 430

Ala Met Tyr Ala Pro Pro Ile Glu Gly Gln Ile Lys Cys Ser Ser Asn
        435                 440                 445

Ile Thr Gly Leu Leu Leu Thr Arg Asp Gly Gly Lys Thr Ala Asn Asn
    450                 455                 460

Thr Thr Glu Phe Phe Arg Pro Gly Gly Gly Asn Met Lys Asp Asn Trp
465                 470                 475                 480

Arg Ser Glu Leu Tyr Lys Tyr Lys Val Val Arg Ile Glu Pro Leu Gly
                485                 490                 495

Val Ala Pro Thr Lys Ala Lys Arg Arg Val Val Gln Arg Glu Lys Arg
            500                 505                 510
```

```
Ala Ile Gly Ile Gly Ala Val Phe Leu Gly Phe Leu Gly Ala Ala Gly
        515                 520                 525

Ser Thr Met Gly Ala Ala Ser Ile Thr Leu Thr Val Gln Ala Arg Lys
    530                 535                 540

Leu Leu Ser Gly Ile Val Gln Gln Gln Asn Asn Leu Leu Arg Ala Ile
545                 550                 555                 560

Glu Ala Gln Gln His Leu Leu Gln Leu Thr Val Trp Gly Ile Lys Gln
                565                 570                 575

Leu Gln Ala Arg Val Leu Ala Val Glu Arg Tyr Leu Arg Asp Gln Gln
            580                 585                 590

Leu Leu Gly Ile Trp Gly Cys Ser Gly Lys Leu Ile Cys Thr Thr Ala
        595                 600                 605

Val Pro Trp Asn Ser Ser Trp Ser Asn Lys Ser Leu Asp Thr Ile Trp
    610                 615                 620

Asn Asn Met Thr Trp Met Gln Trp Glu Lys Glu Ile Asp Asn Tyr Thr
625                 630                 635                 640

Gly Leu Ile Tyr Thr Leu Ile Glu Glu Ser Gln Ile Gln Gln Glu Lys
                645                 650                 655

Asn Glu Leu Asp Leu Leu Lys Leu Asp Gln Trp Ala Ser Leu Trp Asn
            660                 665                 670

Trp Phe Asp Ile Thr Asn Trp Leu Trp Tyr Ile Lys Ile Phe Ile Met
        675                 680                 685

Ile Val Gly Gly Leu Val Gly Leu Arg Ile Val Phe Ala Val Leu Ser
    690                 695                 700

Ile Val Asn Arg Val Arg Gln Gly Tyr Ser Pro Leu Ser Phe Gln Thr
705                 710                 715                 720

His Leu Pro Asn Ser Arg Gly Pro Asp Arg Pro Gly Gly Ile Glu Glu
                725                 730                 735

Glu Gly Gly Glu Arg Asp Asn Gly Arg Ser Arg Pro Leu Val Asp Gly
            740                 745                 750

Phe Leu Ala Ile Ile Trp Val Asp Leu Arg Ser Leu Cys Leu Phe Ser
        755                 760                 765

Tyr His His Leu Arg Gly Leu Leu Leu Ile Ala Ala Arg Ile Val Glu
    770                 775                 780

Leu Leu Gly Arg Arg Gly Trp Glu Ala Leu Lys Tyr Trp Trp Asn Leu
785                 790                 795                 800

Leu Gln Tyr Trp Gly Gln Glu Leu Arg Asn Ser Ala Val Ser Leu Leu
                805                 810                 815

Asn Ala Thr Ala Ile Ala Val Ala Glu Gly Thr Asp Arg Ile Ile Glu
            820                 825                 830

Val Val Gln Arg Ile Gly Arg Ala Ile Leu Asn Ile Pro Arg Arg Ile
        835                 840                 845

Arg Gln Gly Ala Glu Arg Ala Leu Gln
    850                 855
```

<210> SEQ ID NO 15
<211> LENGTH: 2604
<212> TYPE: DNA
<213> ORGANISM: Artificial Sequence
<220> FEATURE:
<223> OTHER INFORMATION: pGX1037 - Env Clade B tier 3 PVO.4 DNA Sequence

<400> SEQUENCE: 15

```
atgagggtca cagggattag aaaaaactac cagcactctt ggagatgggg aatgatgctg      60

ctgggaatgc tgatgatttg ttctgccgag gaaaagctgt gggtgacagt ctactatggc     120
```

```
gtgcctgtct ggaaagaagc aaccacaact ctgttctgcg cctccgacgc taaggcatac    180
aatactgagg tgcacaacgt ctgggctact catgcatgcg tgccaaccga tccaaatccc    240
caggaagtgg ggctggaaaa cgtcaccgag aactttaata tgtggaagaa caatatggtg    300
gaacagatgc acgaggacat catttcactg tgggatcaga gcctgaagcc ctgcgtgaaa    360
ctgacacctc tgtgcgtcac tctgaactgt agcgacctgc ggaacgccac aaataccaca    420
aaccctactg tgagctccag agtcattaag aaagaaatga tgggcgaggt gaaaaattgc    480
tccttcaacg tcactaccga catccgggat agaatgcaga aggtgtacgc cctgttttat    540
aggccagacg tggtccccat ccaggatcat accatcgaaa acaacaacac aatcgagaac    600
aacacaactt accgcctgat ctcttgcaat acaagtgtga ttactcaggc ttgtcccaaa    660
atcagcttcg agcctatccc aattcactat tgcacacctg ccggcttcgc tattctgaag    720
tgtaacgata agaagttcaa cggctctggg ccatgcacca acgtgagtac agtccagtgt    780
actcatggca tcaggcccgt ggtctcaacc cagctgctgc tgaatgggag ccgagccgag    840
gaagaagtga tcattcggag cgaaaacttc accaataacg ctaagacaat cattgtgcag    900
ctgaacaaga ctgtcgagat caactgcacc cgccctaata acaatacacg aaagtcaatc    960
agcattggac caggcagggc cttctacgcc accggagaca tcattggcga tattagacag   1020
gctcactgta atctgtccag ggcagaatgg aacaagactc tgaaatatat ctctaccaag   1080
ctgcgcgagc agttcgggaa caagaccatc atcttcaacg gatctagtgg cggggacccc   1140
gaaatcgtga cacatagctt caactgcgga ggcgagttct tttactgtaa taccacaaag   1200
ctgtttaaca gtacctggga tgccaacggg aattgcacag gatgtgacga atcagatggc   1260
aacaatacaa tcactctgcc ttgcagaatc aagcagattg tgaatatgtg gcaggaggtc   1320
ggcaaagcta tgtatgcacc ccctatcaag gggctgatca agtgtacctc taacatcaca   1380
ggactgctgc tgacaaggga cgggggagcc aacaatacta atgagacctt ccgcccagga   1440
ggaggagaca tgcgagataa ctggcggagt gaactgtaca agtataaagt ggtccagatc   1500
gagcctctgg gaattgcacc aacccgggcc cggagaaggg tggtccagag ggagaagcga   1560
gcagtgggga ctctgggagc tatgttcctg ggctttctgg gggccgctgg aagtaccatg   1620
ggagcagcct cagtgaccct gacagtccag gccagacagc tgctgtccgg cattgtgcag   1680
cagcagaaca atctgctgaa agccatcgaa gctcagcagc acatgctgca gctgacagtg   1740
tggggcatta agcagctgca ggctcgggtg ctggcaatcg agagatacct gaaagatcag   1800
cagctgctgg gcatttgggg gtgcagcgga aagctgatct gtactaccgc cgtgccatgg   1860
aatacctcct ggtctaataa gtccttcaac aaaatctggg acaacatgac atggatggaa   1920
tgggagaggg aaattgataa ttacactggc ctgatctata acctgctgga agagtctcag   1980
aatcagcagg agaagaacga acaggacctg ctggctctgg ataaatggga gagcctgtgg   2040
aattggttct ccattaccaa gtggctgtgg tacatcaaaa tcttcatcat gattgtggga   2100
ggactgatcg gactgcgaat cgtgttcgca gtcctgtcta tcgtgaacag ggtccgccag   2160
ggatatagtc cactgtcatt tcagactcac ctgcccacca gtagaggacc agacaggcct   2220
gagggaatcg gaggagaggg aggagaacga gaccgagata gatcaggccc cctggtggac   2280
gggtttctgg ccatcatttg ggtggatctg cgctccctgt tcctgttttc ttatcatcga   2340
ctgacagatc tgctgctgat cctgactcgg attgtggaac tgctgggccg ccgaggatgg   2400
gaggcactga agtactggtg gaacctgctg cagtattgga gccaggagct gagaaatagc   2460
```

-continued

```
gccgtgtccc tgctgaacgc cactgctatc gcagtggccg aaggcaccga caggatcatt   2520

gaggtggtcc agcgcacctt ccgcgccatt attcatattc caagacgcat tagacaggga   2580

ctggagagac tgctgctgtg ataa                                          2604


<210> SEQ ID NO 16
<211> LENGTH: 866
<212> TYPE: PRT
<213> ORGANISM: Artificial Sequence
<220> FEATURE:
<223> OTHER INFORMATION: pGX1037 - Env Clade B tier 3 PVO.4 Amino Acid
      Sequence

<400> SEQUENCE: 16

Met Arg Val Thr Gly Ile Arg Lys Asn Tyr Gln His Ser Trp Arg Trp
1               5                   10                  15

Gly Met Met Leu Leu Gly Met Leu Met Ile Cys Ser Ala Glu Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asn Thr Glu Val
    50                  55                  60

His Asn Val Trp Ala Thr His Ala Cys Val Pro Thr Asp Pro Asn Pro
65                  70                  75                  80

Gln Glu Val Gly Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Ser Asp Leu Arg Asn Ala Thr Asn Thr Thr Asn Pro Thr Val
    130                 135                 140

Ser Ser Arg Val Ile Lys Lys Glu Met Met Gly Glu Val Lys Asn Cys
145                 150                 155                 160

Ser Phe Asn Val Thr Thr Asp Ile Arg Asp Arg Met Gln Lys Val Tyr
                165                 170                 175

Ala Leu Phe Tyr Arg Pro Asp Val Val Pro Ile Gln Asp His Thr Ile
            180                 185                 190

Glu Asn Asn Asn Thr Ile Glu Asn Asn Thr Thr Tyr Arg Leu Ile Ser
        195                 200                 205

Cys Asn Thr Ser Val Ile Thr Gln Ala Cys Pro Lys Ile Ser Phe Glu
    210                 215                 220

Pro Ile Pro Ile His Tyr Cys Thr Pro Ala Gly Phe Ala Ile Leu Lys
225                 230                 235                 240

Cys Asn Asp Lys Lys Phe Asn Gly Ser Gly Pro Cys Thr Asn Val Ser
                245                 250                 255

Thr Val Gln Cys Thr His Gly Ile Arg Pro Val Val Ser Thr Gln Leu
            260                 265                 270

Leu Leu Asn Gly Ser Arg Ala Glu Glu Glu Val Ile Ile Arg Ser Glu
        275                 280                 285

Asn Phe Thr Asn Asn Ala Lys Thr Ile Ile Val Gln Leu Asn Lys Thr
    290                 295                 300

Val Glu Ile Asn Cys Thr Arg Pro Asn Asn Asn Thr Arg Lys Ser Ile
305                 310                 315                 320

Ser Ile Gly Pro Gly Arg Ala Phe Tyr Ala Thr Gly Asp Ile Ile Gly
                325                 330                 335
```

-continued

```
Asp Ile Arg Gln Ala His Cys Asn Leu Ser Arg Ala Glu Trp Asn Lys
            340                 345                 350

Thr Leu Lys Tyr Ile Ser Thr Lys Leu Arg Glu Gln Phe Gly Asn Lys
        355                 360                 365

Thr Ile Ile Phe Asn Gly Ser Ser Gly Gly Asp Pro Glu Ile Val Thr
    370                 375                 380

His Ser Phe Asn Cys Gly Gly Glu Phe Phe Tyr Cys Asn Thr Thr Lys
385                 390                 395                 400

Leu Phe Asn Ser Thr Trp Asp Ala Asn Gly Asn Cys Thr Gly Cys Asp
                405                 410                 415

Glu Ser Asp Gly Asn Asn Thr Ile Thr Leu Pro Cys Arg Ile Lys Gln
            420                 425                 430

Ile Val Asn Met Trp Gln Glu Val Gly Lys Ala Met Tyr Ala Pro Pro
        435                 440                 445

Ile Lys Gly Leu Ile Lys Cys Thr Ser Asn Ile Thr Gly Leu Leu Leu
    450                 455                 460

Thr Arg Asp Gly Gly Ala Asn Asn Thr Asn Glu Thr Phe Arg Pro Gly
465                 470                 475                 480

Gly Gly Asp Met Arg Asp Asn Trp Arg Ser Glu Leu Tyr Lys Tyr Lys
                485                 490                 495

Val Val Gln Ile Glu Pro Leu Gly Ile Ala Pro Thr Arg Ala Arg Arg
            500                 505                 510

Arg Val Val Gln Arg Glu Lys Arg Ala Val Gly Thr Leu Gly Ala Met
        515                 520                 525

Phe Leu Gly Phe Leu Gly Ala Ala Gly Ser Thr Met Gly Ala Ala Ser
    530                 535                 540

Val Thr Leu Thr Val Gln Ala Arg Gln Leu Leu Ser Gly Ile Val Gln
545                 550                 555                 560

Gln Gln Asn Asn Leu Leu Lys Ala Ile Glu Ala Gln Gln His Met Leu
                565                 570                 575

Gln Leu Thr Val Trp Gly Ile Lys Gln Leu Gln Ala Arg Val Leu Ala
            580                 585                 590

Ile Glu Arg Tyr Leu Lys Asp Gln Gln Leu Leu Gly Ile Trp Gly Cys
        595                 600                 605

Ser Gly Lys Leu Ile Cys Thr Thr Ala Val Pro Trp Asn Thr Ser Trp
    610                 615                 620

Ser Asn Lys Ser Phe Asn Lys Ile Trp Asp Asn Met Thr Trp Met Glu
625                 630                 635                 640

Trp Glu Arg Glu Ile Asp Asn Tyr Thr Gly Leu Ile Tyr Asn Leu Leu
                645                 650                 655

Glu Glu Ser Gln Asn Gln Gln Glu Lys Asn Glu Gln Asp Leu Leu Ala
            660                 665                 670

Leu Asp Lys Trp Glu Ser Leu Trp Asn Trp Phe Ser Ile Thr Lys Trp
        675                 680                 685

Leu Trp Tyr Ile Lys Ile Phe Ile Met Ile Val Gly Gly Leu Ile Gly
    690                 695                 700

Leu Arg Ile Val Phe Ala Val Leu Ser Ile Val Asn Arg Val Arg Gln
705                 710                 715                 720

Gly Tyr Ser Pro Leu Ser Phe Gln Thr His Leu Pro Thr Ser Arg Gly
                725                 730                 735

Pro Asp Arg Pro Glu Gly Ile Gly Gly Glu Gly Gly Glu Arg Asp Arg
            740                 745                 750
```

```
Asp Arg Ser Gly Pro Leu Val Asp Gly Phe Leu Ala Ile Ile Trp Val
        755                 760                 765

Asp Leu Arg Ser Leu Phe Leu Phe Ser Tyr His Arg Leu Thr Asp Leu
    770                 775                 780

Leu Leu Ile Leu Thr Arg Ile Val Glu Leu Leu Gly Arg Arg Gly Trp
785                 790                 795                 800

Glu Ala Leu Lys Tyr Trp Trp Asn Leu Leu Gln Tyr Trp Ser Gln Glu
                805                 810                 815

Leu Arg Asn Ser Ala Val Ser Leu Leu Asn Ala Thr Ala Ile Ala Val
            820                 825                 830

Ala Glu Gly Thr Asp Arg Ile Ile Glu Val Val Gln Arg Thr Phe Arg
        835                 840                 845

Ala Ile Ile His Ile Pro Arg Arg Ile Arg Gln Gly Leu Glu Arg Leu
    850                 855                 860

Leu Leu
865


<210> SEQ ID NO 17
<211> LENGTH: 2598
<212> TYPE: DNA
<213> ORGANISM: Artificial Sequence
<220> FEATURE:
<223> OTHER INFORMATION: pGX1038 - Env Clade B tier 2 TRO.11 DNA
      Sequence

<400> SEQUENCE: 17

atgagggcaa aagggattag gaagaactgt cagcacctgt ggatttgggg aacaatgctg      60

ctgggaatgc tgatgatcta ctctgcagcc gagcaggggc agctgtgggt gactgtctac     120

tatggagtgc ctgtctggaa ggacgcctct accacactgt tttgcgctag tgacgctaaa     180

gcatacgata ccgaagtgca caatgtctgg gcaacccatg cctgcgtgcc aacagatcca     240

aatccccagg aggtggtcct gggcaacgtg acagaaaact tcaatatgtg gaagaacaac     300

atggtggacc agatgcacga ggatatcatt tcactgtggg accagagcct gaagccatgc     360

gtgaaactga cccccctgtg cgtcaccctg aattgtacag ataacatcac caacacaaat     420

actaacagct ccaagaactc tagtacacat agctataaca attccctgga aggagagatg     480

aaaaattgta gctttaacat cactgcaggc attcgggaca aggtgaagaa agagtacgcc     540

ctgttctata aactggatgt ggtccctatc gaggaagaca aggataccaa caagactacc     600

tacagactga ggtcttgcaa cactagtgtg attacccagg cctgtcccaa ggtcacattt     660

gagcctatcc caattcacta ttgcgcccct gctggcttcg ctatcctgaa atgtaatgac     720

aagaagttca acggaacagg cccatgcact aacgtgtcca ccgtccagtg tacacatggg     780

atcaggcccg tggtctcaac acagctgctg ctgaatggaa gcctggccga ggaagaggtg     840

gtcattcgct ctgagaactt tacaaacaac gctaagacta tcatcgtgca gctgaatgaa     900

tccatcgcaa ttaactgcac tcgccctaac aataacaccc ggagatctat ccacattggg     960

ccaggacgag ctttctacgc aaccggggac atcattggag atatccgaca ggcccattgt    1020

aatattagtc ggaccgagtg gaactcaaca ctgcggcaga tcgtgacaaa gctgagagaa    1080

cagctgggcg acccaaacaa gactatcatt ttcaaccagt caagcggcgg ggatacagag    1140

atcactatgc acagttttaa ttgcggaggc gaattctttt actgtaacac aactaagctg    1200

ttcaattcaa cctggaacgg caataacacc acagagagcg attccactgg ggaaaatatc    1260

accctgccct gcaggattaa gcagatcatt aacctgtggc aggaagtggg aaaggccatg    1320
```

-continued

```
tatgctcccc ctatcaaagg ccagattagc tgttcctcta acatcacagg actgctgctg   1380

actcgcgacg gaggaaataa caatagttca gggcctgaaa cattcagacc aggcggggga   1440

aatatgaagg ataactggag gagcgagctg tacaagtaca aagtgatcaa aatcgaaccc   1500

ctgggcgtgg ctcctaccag ggcaaagagg cgcgtggtcc agcgagagaa acgggctgtg   1560

ggcactctgg gggcaatgtt cctgggattt ctgggagcag ctgggagcac catgggagca   1620

gcatccgtga ccctgacagt ccaggccagg ctgctgctgt ccgggatcgt gcagcagcag   1680

aacaatctgc tgcgcgcaat tgaggcccag cagcacatgc tgcagctgac cgtgtggggc   1740

atcaagcagc tgcaggcccg ggtgctggct gtcgaaagat acctgaggga ccagcagctg   1800

ctgggaatct ggggctgcag cgggaagctg atttgtacta ccaatgtgcc ctggaacgct   1860

tcttggagta acaagtccct gaacaatatc tgggagaaca tgacctggat ggaatgggag   1920

agagaaatcg acaactacac agatctgatc tatattctgc tggagaagtc tcagatccag   1980

caggagaaga acgagcagga actgctggaa ctggactcat gggccagcct gtggaactgg   2040

ttcgatatta gtaagtggct gtggtacatc aaaatcttca tcatgattgt gggaggactg   2100

gtcggactgc gaatcgtgtt tgcagtcctg agcattgcca accgcgtgcg acagggctat   2160

tccccccctgt ctttccagac tagactgcca acccctcgcg gcccagaccg accagagggg   2220

atcgagaagg aaggaggagg acgagacaga gatggcagcc ggcctctggt gcacggactg   2280

ctggccctga tctgggacga tctgagatcc ctgtgcctgt tctcttatca taggctgcgc   2340

gatctgctgc tgattgtgac tagaaccgtc gagctgctgg gacgacgggg atgggaactg   2400

ctgaagtact ggtggaacct gctgcagtat tggtctcagg agctgaaaaa tagtgcagtg   2460

tcactgctga acacaactgc aatcgccgtg gctgagggca ccgacagggt cattgaagtg   2520

gtccagcgcg cctttagagc cattctgcat attcccgccc gcattagaca gggactggag   2580

agagcactgc tgtgataa                                                2598
```

<210> SEQ ID NO 18
<211> LENGTH: 864
<212> TYPE: PRT
<213> ORGANISM: Artificial Sequence
<220> FEATURE:
<223> OTHER INFORMATION: pGX1038 - Env Clade B tier 2 TRO.11 Amino Acid Sequence

<400> SEQUENCE: 18

```
Met Arg Ala Lys Gly Ile Arg Lys Asn Cys Gln His Leu Trp Ile Trp
1               5                   10                  15

Gly Thr Met Leu Leu Gly Met Leu Met Ile Tyr Ser Ala Ala Glu Gln
            20                  25                  30

Gly Gln Leu Trp Val Thr Val Tyr Tyr Gly Val Pro Val Trp Lys Asp
        35                  40                  45

Ala Ser Thr Thr Leu Phe Cys Ala Ser Asp Ala Lys Ala Tyr Asp Thr
    50                  55                  60

Glu Val His Asn Val Trp Ala Thr His Ala Cys Val Pro Thr Asp Pro
65                  70                  75                  80

Asn Pro Gln Glu Val Val Leu Gly Asn Val Thr Glu Asn Phe Asn Met
                85                  90                  95

Trp Lys Asn Asn Met Val Asp Gln Met His Glu Asp Ile Ile Ser Leu
            100                 105                 110

Trp Asp Gln Ser Leu Lys Pro Cys Val Lys Leu Thr Pro Leu Cys Val
        115                 120                 125
```

```
Thr Leu Asn Cys Thr Asp Asn Ile Thr Asn Thr Asn Thr Asn Ser Ser
    130                 135                 140

Lys Asn Ser Ser Thr His Ser Tyr Asn Asn Ser Leu Glu Gly Glu Met
145                 150                 155                 160

Lys Asn Cys Ser Phe Asn Ile Thr Ala Gly Ile Arg Asp Lys Val Lys
                165                 170                 175

Lys Glu Tyr Ala Leu Phe Tyr Lys Leu Asp Val Val Pro Ile Glu Glu
            180                 185                 190

Asp Lys Asp Thr Asn Lys Thr Thr Tyr Arg Leu Arg Ser Cys Asn Thr
        195                 200                 205

Ser Val Ile Thr Gln Ala Cys Pro Lys Val Thr Phe Glu Pro Ile Pro
    210                 215                 220

Ile His Tyr Cys Ala Pro Ala Gly Phe Ala Ile Leu Lys Cys Asn Asp
225                 230                 235                 240

Lys Lys Phe Asn Gly Thr Gly Pro Cys Thr Asn Val Ser Thr Val Gln
                245                 250                 255

Cys Thr His Gly Ile Arg Pro Val Val Ser Thr Gln Leu Leu Leu Asn
            260                 265                 270

Gly Ser Leu Ala Glu Glu Glu Val Val Ile Arg Ser Glu Asn Phe Thr
        275                 280                 285

Asn Asn Ala Lys Thr Ile Ile Val Gln Leu Asn Glu Ser Ile Ala Ile
    290                 295                 300

Asn Cys Thr Arg Pro Asn Asn Asn Thr Arg Arg Ser Ile His Ile Gly
305                 310                 315                 320

Pro Gly Arg Ala Phe Tyr Ala Thr Gly Asp Ile Ile Gly Asp Ile Arg
                325                 330                 335

Gln Ala His Cys Asn Ile Ser Arg Thr Glu Trp Asn Ser Thr Leu Arg
            340                 345                 350

Gln Ile Val Thr Lys Leu Arg Glu Gln Leu Gly Asp Pro Asn Lys Thr
        355                 360                 365

Ile Ile Phe Asn Gln Ser Ser Gly Gly Asp Thr Glu Ile Thr Met His
    370                 375                 380

Ser Phe Asn Cys Gly Gly Glu Phe Phe Tyr Cys Asn Thr Thr Lys Leu
385                 390                 395                 400

Phe Asn Ser Thr Trp Asn Gly Asn Asn Thr Thr Glu Ser Asp Ser Thr
                405                 410                 415

Gly Glu Asn Ile Thr Leu Pro Cys Arg Ile Lys Gln Ile Ile Asn Leu
            420                 425                 430

Trp Gln Glu Val Gly Lys Ala Met Tyr Ala Pro Pro Ile Lys Gly Gln
        435                 440                 445

Ile Ser Cys Ser Ser Asn Ile Thr Gly Leu Leu Leu Thr Arg Asp Gly
    450                 455                 460

Gly Asn Asn Asn Ser Ser Gly Pro Glu Thr Phe Arg Pro Gly Gly Gly
465                 470                 475                 480

Asn Met Lys Asp Asn Trp Arg Ser Glu Leu Tyr Lys Tyr Lys Val Ile
                485                 490                 495

Lys Ile Glu Pro Leu Gly Val Ala Pro Thr Arg Ala Lys Arg Arg Val
            500                 505                 510

Val Gln Arg Glu Lys Arg Ala Val Gly Thr Leu Gly Ala Met Phe Leu
        515                 520                 525

Gly Phe Leu Gly Ala Ala Gly Ser Thr Met Gly Ala Ala Ser Val Thr
    530                 535                 540

Leu Thr Val Gln Ala Arg Leu Leu Leu Ser Gly Ile Val Gln Gln Gln
```

545 550 555 560

Asn Asn Leu Leu Arg Ala Ile Glu Ala Gln Gln His Met Leu Gln Leu
565 570 575

Thr Val Trp Gly Ile Lys Gln Leu Gln Ala Arg Val Leu Ala Val Glu
580 585 590

Arg Tyr Leu Arg Asp Gln Gln Leu Leu Gly Ile Trp Gly Cys Ser Gly
595 600 605

Lys Leu Ile Cys Thr Thr Asn Val Pro Trp Asn Ala Ser Trp Ser Asn
610 615 620

Lys Ser Leu Asn Asn Ile Trp Glu Asn Met Thr Trp Met Glu Trp Glu
625 630 635 640

Arg Glu Ile Asp Asn Tyr Thr Asp Leu Ile Tyr Ile Leu Leu Glu Lys
645 650 655

Ser Gln Ile Gln Gln Glu Lys Asn Glu Gln Glu Leu Leu Glu Leu Asp
660 665 670

Ser Trp Ala Ser Leu Trp Asn Trp Phe Asp Ile Ser Lys Trp Leu Trp
675 680 685

Tyr Ile Lys Ile Phe Ile Met Ile Val Gly Gly Leu Val Gly Leu Arg
690 695 700

Ile Val Phe Ala Val Leu Ser Ile Ala Asn Arg Val Arg Gln Gly Tyr
705 710 715 720

Ser Pro Leu Ser Phe Gln Thr Arg Leu Pro Thr Pro Arg Gly Pro Asp
725 730 735

Arg Pro Glu Gly Ile Glu Lys Glu Gly Gly Gly Arg Asp Arg Asp Gly
740 745 750

Ser Arg Pro Leu Val His Gly Leu Leu Ala Leu Ile Trp Asp Asp Leu
755 760 765

Arg Ser Leu Cys Leu Phe Ser Tyr His Arg Leu Arg Asp Leu Leu Leu
770 775 780

Ile Val Thr Arg Thr Val Glu Leu Leu Gly Arg Arg Gly Trp Glu Leu
785 790 795 800

Leu Lys Tyr Trp Trp Asn Leu Leu Gln Tyr Trp Ser Gln Glu Leu Lys
805 810 815

Asn Ser Ala Val Ser Leu Leu Asn Thr Thr Ala Ile Ala Val Ala Glu
820 825 830

Gly Thr Asp Arg Val Ile Glu Val Val Gln Arg Ala Phe Arg Ala Ile
835 840 845

Leu His Ile Pro Ala Arg Ile Arg Gln Gly Leu Glu Arg Ala Leu Leu
850 855 860

<210> SEQ ID NO 19
<211> LENGTH: 2571
<212> TYPE: DNA
<213> ORGANISM: Artificial Sequence
<220> FEATURE:
<223> OTHER INFORMATION: pGX1031 - Env Clade B tier 2 REJO4541.67 DNA Sequence

<400> SEQUENCE: 19
atgaaagtga aggggattag gagaaactat cagcacctgt ggagatgggg gattatgctg 60
ctggggattc tgatgatttg ttccgcaact gaaaagctgt gggtgaccgt ctactatggc 120
gtgccagtct ggaaagaggc caccacaact ctgttctgcg ctagcgacgc taaggcatac 180
gatcaggaaa tccacaacat ttgggccaca catgcttgcg tgcccactga cccaaacccc 240
caggaggtgg aactgaagaa tgtcaccgag aacttcaaca tgtggaaaag caatatggtg 300

-continued

```
gaacagatgc acgaggacat cattagtctg tgggatcagt cactgaagcc atgcgtgaaa    360
ctgacacccc tgtgcgtcac cctgaagtgt acagacctga acgtgactaa tagcaactcc    420
actgatcatt caaccaatag ctccctggaa gctaagggcg agatcaagaa ctgcagcttc    480
aatatcacca caactccccg ggacaagatt cagaaagagt acgccatctt ttataagcag    540
gacgtggtcc ctatcaaaaa cgataacatc agctacagac tgatctcctg caacacatct    600
gtgatcactc aggcctgtcc aaaggtcacc ttcgagccta ttccaatcca ctattgcgcc    660
cccgctggct tcgctatcct gaagtgtaac gataaagggt ttaatgggac cggaccttgc    720
acaaacgtgt ccactgtcca gtgtacccat ggaatcaggc cagcaattag cactcagctg    780
ctgctgaatg gctccctggc cgaggacaag gtggtcattc gctctgagaa cttcacagat    840
aatgccaaga tcattatcgt gcacctgaac gaaaccgtca aaatcaattg cacacgcccc    900
aacaacaaca ctcgaaagag tatccatatc gctcctggca gagccttcta cgccactggc    960
gagattatcg ggacattag gaaggcatat tgtaccatca acgagagcga atggaataac   1020
accctgcaga agattgtggt cacactgagg gaacagttcc gcaacaaaac catcgtgttt   1080
aatcagtcta gtggcggcga ccccgaagtg acaatgcaca ctttcaattg cggaggcgag   1140
ttcttttact gtaacacagc ccagctgttt aattcaagct gggacaccaa tacaaacgga   1200
aatgatacac agggcccttc cgagaataac actattatcc tgccatgcag gattaagcag   1260
attatcaaca tgtggcagcg cgtgggaaaa gctatctatg cacccccctat ctccggccag   1320
attcgatgtc tgtctaacat cacagggctg attctgactc gggacggggg aaattcctct   1380
ctgagttcac ctgagatctt taggccaggc gggggagaca tgcgagataa ttggcggtct   1440
gaactgtaca agtataaagt ggtccagatt gagccactgg gaatcgcacc tacccgcgcc   1500
aagcggagag ctgtgcagag agagaaaagg gctgtcggca tcggggcact gttcctgggc   1560
tttctggggg ccgctggatc tacaatgggc gcagccagtg tgactctgac cgtccaggca   1620
cgacagctgc tgagtgggat tgtgcagcag cagtcaaacc tgctgcgagc catcgaagct   1680
cagcagcacc tgctgcagct gaccgtgtgg gggatcaagc agctgcaggc aagggtgctg   1740
gccatggagt cttacctgaa agaccagcag ctgctgggca tttgggggtg cagtggaaag   1800
ctgatctgta ccacaactgt gccttggaac acctcttgga gtaacaagag cctggatcag   1860
atttggaata acatgacatg gcgcgagtgg gaaaaggaga tcgacaacta caccgatctg   1920
atctatacac tgattgaaaa gtcccagaac cagcaggaga aaaatgaaca ggagctgctg   1980
gagctggaca aatgggcctc tctgtggaac tggttcgata ttaccaattg gctgtggtac   2040
attaagatct ttattatggt ggtcggcggg ctggtgggcc tgagaatcgt gttcgcagtc   2100
ctgtccatta tcaaccgagt gcggcagggg tattcacctc tgagctttca gacccacctg   2160
ccagcaccta gaggaccaga caggcccgaa ggaatcggag aggaaggagg agagcgagac   2220
tccgatcgct ctgggcgaag tgtggacgga ttcctgccac tgatctgggt ggatctgcgg   2280
agcctgttcc tgttttccta tcatagactg actgatctgc tgctgatcgt gaccagaatt   2340
gtcgaactgc tgggcaggcg cggatgggga atcctgaaat actggtggtc actgctgcag   2400
tattggagcc aggagctgaa gaactcagcc gtgagcctgc tgaatgcaac cgccattgct   2460
gtggcagaac ggacagatag aattatcgag atcgtgcaga gggtcttccg cgcactgctg   2520
catattccaa gacgcattcg acagggattt gagagagcac tgctgtgata a            2571
```

<210> SEQ ID NO 20

```
<211> LENGTH: 855
<212> TYPE: PRT
<213> ORGANISM: Artificial Sequence
<220> FEATURE:
<223> OTHER INFORMATION: pGX1031 - Env Clade B tier 2 REJO4541.67  Amino
      Acid Sequence

<400> SEQUENCE: 20

Met Lys Val Lys Gly Ile Arg Arg Asn Tyr Gln His Leu Trp Arg Trp
1               5                   10                  15

Gly Ile Met Leu Leu Gly Ile Leu Met Ile Cys Ser Ala Thr Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Gln Glu Ile
    50                  55                  60

His Asn Ile Trp Ala Thr His Ala Cys Val Pro Thr Asp Pro Asn Pro
65                  70                  75                  80

Gln Glu Val Glu Leu Lys Asn Val Thr Glu Asn Phe Asn Met Trp Lys
                85                  90                  95

Ser Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Lys Cys Thr Asp Leu Asn Val Thr Asn Ser Asn Ser Thr Asp His Ser
    130                 135                 140

Thr Asn Ser Ser Leu Glu Ala Lys Gly Glu Ile Lys Asn Cys Ser Phe
145                 150                 155                 160

Asn Ile Thr Thr Thr Pro Arg Asp Lys Ile Gln Lys Glu Tyr Ala Ile
                165                 170                 175

Phe Tyr Lys Gln Asp Val Val Pro Ile Lys Asn Asp Asn Ile Ser Tyr
            180                 185                 190

Arg Leu Ile Ser Cys Asn Thr Ser Val Ile Thr Gln Ala Cys Pro Lys
        195                 200                 205

Val Thr Phe Glu Pro Ile Pro Ile His Tyr Cys Ala Pro Ala Gly Phe
    210                 215                 220

Ala Ile Leu Lys Cys Asn Asp Lys Gly Phe Asn Gly Thr Gly Pro Cys
225                 230                 235                 240

Thr Asn Val Ser Thr Val Gln Cys Thr His Gly Ile Arg Pro Ala Ile
                245                 250                 255

Ser Thr Gln Leu Leu Leu Asn Gly Ser Leu Ala Glu Asp Lys Val Val
            260                 265                 270

Ile Arg Ser Glu Asn Phe Thr Asp Asn Ala Lys Ile Ile Ile Val His
        275                 280                 285

Leu Asn Glu Thr Val Lys Ile Asn Cys Thr Arg Pro Asn Asn Asn Thr
    290                 295                 300

Arg Lys Ser Ile His Ile Ala Pro Gly Arg Ala Phe Tyr Ala Thr Gly
305                 310                 315                 320

Glu Ile Ile Gly Asp Ile Arg Lys Ala Tyr Cys Thr Ile Asn Glu Ser
                325                 330                 335

Glu Trp Asn Asn Thr Leu Gln Lys Ile Val Val Thr Leu Arg Glu Gln
            340                 345                 350

Phe Arg Asn Lys Thr Ile Val Phe Asn Gln Ser Ser Gly Gly Asp Pro
        355                 360                 365

Glu Val Thr Met His Thr Phe Asn Cys Gly Gly Glu Phe Phe Tyr Cys
```

```
    370                 375                 380

Asn Thr Ala Gln Leu Phe Asn Ser Ser Trp Asp Thr Asn Thr Asn Gly
385                 390                 395                 400

Asn Asp Thr Gln Gly Pro Ser Glu Asn Asn Thr Ile Ile Leu Pro Cys
                405                 410                 415

Arg Ile Lys Gln Ile Ile Asn Met Trp Gln Arg Val Gly Lys Ala Ile
            420                 425                 430

Tyr Ala Pro Pro Ile Ser Gly Gln Ile Arg Cys Leu Ser Asn Ile Thr
        435                 440                 445

Gly Leu Ile Leu Thr Arg Asp Gly Gly Asn Ser Ser Leu Ser Ser Pro
    450                 455                 460

Glu Ile Phe Arg Pro Gly Gly Gly Asp Met Arg Asp Asn Trp Arg Ser
465                 470                 475                 480

Glu Leu Tyr Lys Tyr Lys Val Val Gln Ile Glu Pro Leu Gly Ile Ala
                485                 490                 495

Pro Thr Arg Ala Lys Arg Arg Ala Val Gln Arg Glu Lys Arg Ala Val
            500                 505                 510

Gly Ile Gly Ala Leu Phe Leu Gly Phe Leu Gly Ala Ala Gly Ser Thr
        515                 520                 525

Met Gly Ala Ala Ser Val Thr Leu Thr Val Gln Ala Arg Gln Leu Leu
    530                 535                 540

Ser Gly Ile Val Gln Gln Gln Ser Asn Leu Leu Arg Ala Ile Glu Ala
545                 550                 555                 560

Gln Gln His Leu Leu Gln Leu Thr Val Trp Gly Ile Lys Gln Leu Gln
                565                 570                 575

Ala Arg Val Leu Ala Met Glu Ser Tyr Leu Lys Asp Gln Gln Leu Leu
            580                 585                 590

Gly Ile Trp Gly Cys Ser Gly Lys Leu Ile Cys Thr Thr Thr Val Pro
        595                 600                 605

Trp Asn Thr Ser Trp Ser Asn Lys Ser Leu Asp Gln Ile Trp Asn Asn
    610                 615                 620

Met Thr Trp Arg Glu Trp Glu Lys Glu Ile Asp Asn Tyr Thr Asp Leu
625                 630                 635                 640

Ile Tyr Thr Leu Ile Glu Lys Ser Gln Asn Gln Gln Glu Lys Asn Glu
                645                 650                 655

Gln Glu Leu Leu Glu Leu Asp Lys Trp Ala Ser Leu Trp Asn Trp Phe
            660                 665                 670

Asp Ile Thr Asn Trp Leu Trp Tyr Ile Lys Ile Phe Ile Met Val Val
        675                 680                 685

Gly Gly Leu Val Gly Leu Arg Ile Val Phe Ala Val Leu Ser Ile Ile
    690                 695                 700

Asn Arg Val Arg Gln Gly Tyr Ser Pro Leu Ser Phe Gln Thr His Leu
705                 710                 715                 720

Pro Ala Pro Arg Gly Pro Asp Arg Pro Glu Gly Ile Gly Glu Glu Gly
                725                 730                 735

Gly Glu Arg Asp Ser Asp Arg Ser Gly Arg Ser Val Asp Gly Phe Leu
            740                 745                 750

Pro Leu Ile Trp Val Asp Leu Arg Ser Leu Phe Leu Phe Ser Tyr His
        755                 760                 765

Arg Leu Thr Asp Leu Leu Leu Ile Val Thr Arg Ile Val Glu Leu Leu
    770                 775                 780

Gly Arg Arg Gly Trp Gly Ile Leu Lys Tyr Trp Trp Ser Leu Leu Gln
785                 790                 795                 800
```

```
Tyr Trp Ser Gln Glu Leu Lys Asn Ser Ala Val Ser Leu Leu Asn Ala
                805                 810                 815

Thr Ala Ile Ala Val Ala Glu Arg Thr Asp Arg Ile Ile Glu Ile Val
            820                 825                 830

Gln Arg Val Phe Arg Ala Leu Leu His Ile Pro Arg Arg Ile Arg Gln
        835                 840                 845

Gly Phe Glu Arg Ala Leu Leu
    850                 855


<210> SEQ ID NO 21
<211> LENGTH: 2568
<212> TYPE: DNA
<213> ORGANISM: Artificial Sequence
<220> FEATURE:
<223> OTHER INFORMATION: pGX1032 - Env Clade B tier 2 RHPA4259.7 DNA
      Sequence

<400> SEQUENCE: 21

atgagagtga tggggattag gaaaaactac cagcacctgt ggaaatgggg gactatgctg      60

ctgtggctgc tgatgatctg ttctgcagcc gatcagctgt gggtgaccgt ctactatggc     120

gtgccagtct ggaaggaagc aaacaccaca ctgttctgcg ccagcgacgc taaagcatac     180

gatacagagg cccacaatgt ctgggcaaca catgcctgcg tgcccactga cccaaacccc     240

caggaggtgg tcctggaaaa tgtgacagag aacttcaaca tgtggaagaa ccacatggtg     300

gaacagatgc atgaggacat catttctctg tgggatcaga gtctgaagcc ctgcgtcaaa     360

ctgactcctc tgtgcgtgac cctgaactgt acagacctgg tcaattctaa cattacccgc     420

gtggataaca ctaccgagaa ggaaatgaag aactgttcat tcaacgtcac cagcggcatc     480

cgggacaagg tgcagaaaga gtacgccctg ctgtataaac tggatatcgt gcagattgac     540

aatgataaca cctcccacag ggacaacaca tcttaccgcc tgatctcttg caatactagt     600

gtgattaccc aggcctgtcc taagatcagc ttcgagccta tcccaattca tttctgcgcc     660

ccagctggct ttgctatcct gaaatgtaat gacaagaagt tcaacggaac aggcccctgc     720

actaacgtca gtaccgtgca gtgtacacac gggattagac ctgtggtctc tacacagctg     780

ctgctgaacg gaagtctggc cgaggaagag gtggtcatca ggagcgaaaa tttcactaac     840

aatgtcaaga acatcattgt gcagctgaac gagtcagtgc agatcaattg cactcgacac     900

aacaataaca cccggaagag catcaatatt gggcccggaa gagcttttta tgcaaccggg     960

aaaatcattg gagatattcg gcaggcccat tgtaacatct ctagagaaaa gtggcagaat    1020

accctgaaac agatcgtgaa gaaactgagg gagcagttca agaacaaaac aattgcattt    1080

gccccaagct ccggagggga ccccgaaatc gtgatgcata gcttcaattg caacggggag    1140

ttcttttact gtaacacaac taagctgttt acatcaactt ggaatagcac ttggaactcc    1200

acctggaata acacagaagg atcaaacagc acagtgatca ctctgccttg ccgaattcgg    1260

cagatcatta atatgtggca ggaagtgggg aaggccatgt atgctccccc tatccaggga    1320

cagatcaagt gttctagtaa cattactgga ctgctgctga cccgagacgg aggagtggat    1380

accacaaagg agacattcag gccaggggga ggcaatatga aagataactg gaggtccgaa    1440

ctgtacaagt ataaagtggt ccgcatcgag cctctgggag tggctccaac taaggcaaaa    1500

cggagagtgg tccagcgcga gaagcgagca gtgggcattg ggccatgtt cctgggattt    1560

ctgggagcag ctgggagtac catgggagca gcctcaatca ccctgacagt ccaggccaga    1620

ctgctgctga gcgggattgt gcagcagcag tccaacctgc tgagggcaat cgaagcccag    1680
```

-continued

```
cagcacctgc tgcagctgac cgtgtggggc atcaagcagc tgcaggccag agtcctggct   1740
gtggagaggt acctgaagga tcagcagctg ctgggaattt ggggctgctc cgggaaactg   1800
atctgtacta ccgctgtgcc ctggaatgca tcctggtcta acaaatctca ggacacaatc   1860
tgggggaata tgacttggat gcagtgggag agagaaattg acaactacac agatctgatc   1920
tataatctgc tggaagagag ccagaatcag caggagaaga acgagcagga actgctggcc   1980
ctggacaaat gggctagtct gtggtcatgg ttcagcatta cccactggct gtggtacatc   2040
aagatgttta tcatgattgt cgggggactg gtgggactgc gcattgtctt tgccgtgctg   2100
tccatcgtca acagagtgag gcagggctat tcccctctgt ctttccagac ccgatttcca   2160
gctcctcggg gaccagatag acccgaaggc attgaagagg aaggaggaga gcgagaccga   2220
gatcggagtg gccgctcagc cgacgggttc ctggtgctgg tctgggtgga tctgcggaac   2280
ctgtgcctgt ttagctatca tagactgagg gacctgctgc tgatcgtcac tcgaaccgtg   2340
gaactgctgg gaaggcgcgg atgggaggct ctgaagtact ggtggaatct gctgcagtat   2400
tggtcccagg agctgaagaa aagcgcagtg tccctgctgg acgctatcgc aattgccgtg   2460
gctgaaggca ccgatcgcat cattgagctg ctgcagcgaa tcttccgagc ctttctgcat   2520
attcccacac gcattcgcca gggactggag agagcactgc agtgataa                2568
```

<210> SEQ ID NO 22
<211> LENGTH: 854
<212> TYPE: PRT
<213> ORGANISM: Artificial Sequence
<220> FEATURE:
<223> OTHER INFORMATION: pGX1032 - Env Clade B tier 2 RHPA4259.7 Amino Acid Sequence

<400> SEQUENCE: 22

```
Met Arg Val Met Gly Ile Arg Lys Asn Tyr Gln His Leu Trp Lys Trp
1               5                   10                  15

Gly Thr Met Leu Leu Trp Leu Leu Met Ile Cys Ser Ala Ala Asp Gln
            20                  25                  30

Leu Trp Val Thr Val Tyr Tyr Gly Val Pro Val Trp Lys Glu Ala Asn
        35                  40                  45

Thr Thr Leu Phe Cys Ala Ser Asp Ala Lys Ala Tyr Asp Thr Glu Ala
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn His Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Val Asn Ser Asn Ile Thr Arg Val Asp Asn Thr
    130                 135                 140

Thr Glu Lys Glu Met Lys Asn Cys Ser Phe Asn Val Thr Ser Gly Ile
145                 150                 155                 160

Arg Asp Lys Val Gln Lys Glu Tyr Ala Leu Leu Tyr Lys Leu Asp Ile
                165                 170                 175

Val Gln Ile Asp Asn Asp Asn Thr Ser His Arg Asp Asn Thr Ser Tyr
            180                 185                 190

Arg Leu Ile Ser Cys Asn Thr Ser Val Ile Thr Gln Ala Cys Pro Lys
```

-continued

```
        195                 200                 205

Ile Ser Phe Glu Pro Ile Pro Ile His Phe Cys Ala Pro Ala Gly Phe
    210                 215                 220

Ala Ile Leu Lys Cys Asn Asp Lys Lys Phe Asn Gly Thr Gly Pro Cys
225                 230                 235                 240

Thr Asn Val Ser Thr Val Gln Cys Thr His Gly Ile Arg Pro Val Val
                245                 250                 255

Ser Thr Gln Leu Leu Leu Asn Gly Ser Leu Ala Glu Glu Glu Val Val
            260                 265                 270

Ile Arg Ser Glu Asn Phe Thr Asn Asn Val Lys Asn Ile Ile Val Gln
        275                 280                 285

Leu Asn Glu Ser Val Gln Ile Asn Cys Thr Arg His Asn Asn Asn Thr
    290                 295                 300

Arg Lys Ser Ile Asn Ile Gly Pro Gly Arg Ala Phe Tyr Ala Thr Gly
305                 310                 315                 320

Lys Ile Ile Gly Asp Ile Arg Gln Ala His Cys Asn Ile Ser Arg Glu
                325                 330                 335

Lys Trp Gln Asn Thr Leu Lys Gln Ile Val Lys Lys Leu Arg Glu Gln
            340                 345                 350

Phe Lys Asn Lys Thr Ile Ala Phe Ala Pro Ser Ser Gly Gly Asp Pro
        355                 360                 365

Glu Ile Val Met His Ser Phe Asn Cys Asn Gly Glu Phe Phe Tyr Cys
    370                 375                 380

Asn Thr Thr Lys Leu Phe Thr Ser Thr Trp Asn Ser Thr Trp Asn Ser
385                 390                 395                 400

Thr Trp Asn Asn Thr Glu Gly Ser Asn Ser Thr Val Ile Thr Leu Pro
                405                 410                 415

Cys Arg Ile Arg Gln Ile Ile Asn Met Trp Gln Glu Val Gly Lys Ala
            420                 425                 430

Met Tyr Ala Pro Pro Ile Gln Gly Gln Ile Lys Cys Ser Ser Asn Ile
        435                 440                 445

Thr Gly Leu Leu Leu Thr Arg Asp Gly Gly Val Asp Thr Thr Lys Glu
    450                 455                 460

Thr Phe Arg Pro Gly Gly Gly Asn Met Lys Asp Asn Trp Arg Ser Glu
465                 470                 475                 480

Leu Tyr Lys Tyr Lys Val Val Arg Ile Glu Pro Leu Gly Val Ala Pro
                485                 490                 495

Thr Lys Ala Lys Arg Arg Val Val Gln Arg Glu Lys Arg Ala Val Gly
            500                 505                 510

Ile Gly Ala Met Phe Leu Gly Phe Leu Gly Ala Ala Gly Ser Thr Met
        515                 520                 525

Gly Ala Ala Ser Ile Thr Leu Thr Val Gln Ala Arg Leu Leu Leu Ser
    530                 535                 540

Gly Ile Val Gln Gln Gln Ser Asn Leu Leu Arg Ala Ile Glu Ala Gln
545                 550                 555                 560

Gln His Leu Leu Gln Leu Thr Val Trp Gly Ile Lys Gln Leu Gln Ala
                565                 570                 575

Arg Val Leu Ala Val Glu Arg Tyr Leu Lys Asp Gln Gln Leu Leu Gly
            580                 585                 590

Ile Trp Gly Cys Ser Gly Lys Leu Ile Cys Thr Thr Ala Val Pro Trp
        595                 600                 605

Asn Ala Ser Trp Ser Asn Lys Ser Gln Asp Thr Ile Trp Gly Asn Met
    610                 615                 620
```

```
Thr Trp Met Gln Trp Glu Arg Glu Ile Asp Asn Tyr Thr Asp Leu Ile
625                 630                 635                 640

Tyr Asn Leu Leu Glu Glu Ser Gln Asn Gln Gln Glu Lys Asn Glu Gln
                645                 650                 655

Glu Leu Leu Ala Leu Asp Lys Trp Ala Ser Leu Trp Ser Trp Phe Ser
            660                 665                 670

Ile Thr His Trp Leu Trp Tyr Ile Lys Met Phe Ile Met Ile Val Gly
        675                 680                 685

Gly Leu Val Gly Leu Arg Ile Val Phe Ala Val Leu Ser Ile Val Asn
    690                 695                 700

Arg Val Arg Gln Gly Tyr Ser Pro Leu Ser Phe Gln Thr Arg Phe Pro
705                 710                 715                 720

Ala Pro Arg Gly Pro Asp Arg Pro Glu Gly Ile Glu Glu Glu Gly Gly
                725                 730                 735

Glu Arg Asp Arg Asp Arg Ser Gly Arg Ser Ala Asp Gly Phe Leu Val
            740                 745                 750

Leu Val Trp Val Asp Leu Arg Asn Leu Cys Leu Phe Ser Tyr His Arg
        755                 760                 765

Leu Arg Asp Leu Leu Leu Ile Val Thr Arg Thr Val Glu Leu Leu Gly
    770                 775                 780

Arg Arg Gly Trp Glu Ala Leu Lys Tyr Trp Trp Asn Leu Leu Gln Tyr
785                 790                 795                 800

Trp Ser Gln Glu Leu Lys Lys Ser Ala Val Ser Leu Leu Asp Ala Ile
                805                 810                 815

Ala Ile Ala Val Ala Glu Gly Thr Asp Arg Ile Ile Glu Leu Leu Gln
            820                 825                 830

Arg Ile Phe Arg Ala Phe Leu His Ile Pro Thr Arg Ile Arg Gln Gly
        835                 840                 845

Leu Glu Arg Ala Leu Gln
    850
```

<210> SEQ ID NO 23
<211> LENGTH: 2568
<212> TYPE: DNA
<213> ORGANISM: Artificial Sequence
<220> FEATURE:
<223> OTHER INFORMATION: pGX1040 - Env Clade C tier 2 Du123.6 DNA Sequence

<400> SEQUENCE: 23

```
atgagagtca agggcattca gcgcaactgg cctcagtggt ggatttgggg cattctggga     60

ttctggatga ttattatctg tagagtcgtg ggcaacctgt gggtgacagt ctactatggg    120

gtgccagtct ggactgaggc aaagaccaca ctgttctgcg ccagcgacgc aaaagcctac    180

gagagagaag tgcacaatgt ctgggcaact catgcctgtg tgcccaccga tccaaatccc    240

caggaaatcg tgctgggcaa cgtcaccgag aattttaaca tgtggaagaa cgacatggtg    300

gatcagatgc acgaagacat catttctatc tgggatcaga gtctgaagcc ttgcgtgaaa    360

ctgactccac tgtgcgtcac tctgaattgt accgacgtga aggtcaatgc caccagcaac    420

gggactacca catacaacaa ttccattgat tctatgaacg gagaaatcaa gaactgtagc    480

ttcaacatca ctaccgagat ccgcgacaag aaacagaaag tgtacgccct gttttatcga    540

ccagatgtgg tcccccctgaa tgagaacagc tcctcttata ttctgatcaa ttgcaacaca    600

tccacaacta cccaggcttg tcctaaggtg tctttcgacc ctattccaat ccactactgc    660
```

-continued

```
gctccagcag gctatgccat cctgaagtgt aacaacaaga ccttcaacgg gactggaccc    720
tgccacaacg tgtccaccgt ccagtgtaca catggcatca agcctgtggt ctctacccag    780
ctgctgctga atgggagtct ggccgaggaa gagatcatta tccggtctga gaatctgacc    840
aacaatgcta agacaattat cgtgcatctg aacgagagca ttgaaatcgt ctgcacaaga    900
ccaaacaata acactcgaaa atccattcgg atcggccccg ggcagactgt gtacgctacc    960
aacgacatta tcggggatat tcggcaggca cactgtaata tcagcaagac aaaatggaac   1020
acaactctgg agaaggtgaa agaaaagctg aaagagcatt tcccctcaaa ggccatcact   1080
tttcagcctc acagcggcgg ggacctggaa gtgaccacac attctttcaa ttgcagaggc   1140
gagttctttt actgtgatac taccaagctg tttaatgaga gtaatctgaa cacaactaac   1200
accacaactc tgaccctgcc ctgccggatc aagcagatcg tgaacatgtg gcagggagtc   1260
ggccgcgcta tgtatgcacc ccctgtggag ggaaatatta cctgtaacag ttcaatcaca   1320
ggcctgctgc tggtgaggga cggaggcaat acatcaaaca gcactcccga aattttcaga   1380
cctgggggag gcaatatgaa ggataactgg aggtccgaac tgtacaagta taaagtggtc   1440
gagatcaaac cactgggcgt ggcacccaca aaggccaaac ggagagtggt cgagcgggaa   1500
aagagagccg tggggattgg agctgtcctg ttcggctttc tgggagcagc tggcagcacc   1560
atgggagcag cctctatcac tctgaccgtg caggcacgac agctgctgag cggcattgtc   1620
cagcagcagt ccaacctgct gagagccatc gaggctcagc agcacatgct gcagctgacc   1680
gtgtggggca ttaagcagct gcaggcccgg gtgctggcaa tcgaacggta cctgaaggac   1740
cagcagctgc tgggactgtg gggatgctct ggaaaactga tttgtcctac cacagtgcca   1800
tggaatagct cctggagtaa caagtcacag actgacatct gggataatat gacctggatg   1860
cagtgggacc gcgagattag taactacaca ggcactatct ataaactgct ggaagagtca   1920
cagaatcagc aggagaagaa cgaaaaagac ctgctggccc tggatagttg gaagaatctg   1980
tggtcatggt tcgatatcac caactggctg tggtacatca agatctttat tatgatcgtg   2040
gggggactga ttgggctgag gattatcttc ggagtgctga gcatcgtgaa gcgagtccgg   2100
cagggatata gccctctgtc ctttcagacc ctgacaccca atcctcgcgg actggacagg   2160
ctgggccgca ttgaagagga aggcggggag caggacaaag atcgaagcat ccgactggtg   2220
aacggcttcc tggcactggc ttgggacgat ctgaggtcac tgtgcctgtt cagctatcat   2280
agactgaggg attttatcct ggtggctgca cgcgcagtcg aactgctggg gagatctagt   2340
ctgaggggac tgcagcgagg atgggaggcc ctgaagtacc tgggaaatct ggtgcagtat   2400
ggaggcctgg aactgaaaag gcgcgctatc tccctgttcg acaccattgc aatcgccgtg   2460
gctgaaggca cagatagaat tctggaggtc atcctgagaa ttatcagggc cattcgcaac   2520
atccccaccc gcatccgaca ggggtttgag gccgctctgc tgtgataa                2568
```

```
<210> SEQ ID NO 24
<211> LENGTH: 854
<212> TYPE: PRT
<213> ORGANISM: Artificial Sequence
<220> FEATURE:
<223> OTHER INFORMATION: pGX1040 - Env Clade C tier 2 Du123.6  Amino
      Acid Sequence

<400> SEQUENCE: 24

Met Arg Val Lys Gly Ile Gln Arg Asn Trp Pro Gln Trp Trp Ile Trp
1               5                   10                  15

Gly Ile Leu Gly Phe Trp Met Ile Ile Ile Cys Arg Val Val Gly Asn
```

```
            20                  25                  30

Leu Trp Val Thr Val Tyr Tyr Gly Val Pro Val Trp Thr Glu Ala Lys
        35                  40                  45

Thr Thr Leu Phe Cys Ala Ser Asp Ala Lys Ala Tyr Glu Arg Glu Val
    50                  55                  60

His Asn Val Trp Ala Thr His Ala Cys Val Pro Thr Asp Pro Asn Pro
65                  70                  75                  80

Gln Glu Ile Val Leu Gly Asn Val Thr Glu Asn Phe Asn Met Trp Lys
                85                  90                  95

Asn Asp Met Val Asp Gln Met His Glu Asp Ile Ile Ser Ile Trp Asp
            100                 105                 110

Gln Ser Leu Lys Pro Cys Val Lys Leu Thr Pro Leu Cys Val Thr Leu
        115                 120                 125

Asn Cys Thr Asp Val Lys Val Asn Ala Thr Ser Asn Gly Thr Thr Thr
    130                 135                 140

Tyr Asn Asn Ser Ile Asp Ser Met Asn Gly Glu Ile Lys Asn Cys Ser
145                 150                 155                 160

Phe Asn Ile Thr Thr Glu Ile Arg Asp Lys Lys Gln Lys Val Tyr Ala
                165                 170                 175

Leu Phe Tyr Arg Pro Asp Val Val Pro Leu Asn Glu Asn Ser Ser Ser
            180                 185                 190

Tyr Ile Leu Ile Asn Cys Asn Thr Ser Thr Thr Thr Gln Ala Cys Pro
        195                 200                 205

Lys Val Ser Phe Asp Pro Ile Pro Ile His Tyr Cys Ala Pro Ala Gly
    210                 215                 220

Tyr Ala Ile Leu Lys Cys Asn Asn Lys Thr Phe Asn Gly Thr Gly Pro
225                 230                 235                 240

Cys His Asn Val Ser Thr Val Gln Cys Thr His Gly Ile Lys Pro Val
                245                 250                 255

Val Ser Thr Gln Leu Leu Leu Asn Gly Ser Leu Ala Glu Glu Glu Ile
            260                 265                 270

Ile Ile Arg Ser Glu Asn Leu Thr Asn Asn Ala Lys Thr Ile Ile Val
        275                 280                 285

His Leu Asn Glu Ser Ile Glu Ile Val Cys Thr Arg Pro Asn Asn Asn
    290                 295                 300

Thr Arg Lys Ser Ile Arg Ile Gly Pro Gly Gln Thr Val Tyr Ala Thr
305                 310                 315                 320

Asn Asp Ile Ile Gly Asp Ile Arg Gln Ala His Cys Asn Ile Ser Lys
                325                 330                 335

Thr Lys Trp Asn Thr Thr Leu Glu Lys Val Lys Glu Lys Leu Lys Glu
            340                 345                 350

His Phe Pro Ser Lys Ala Ile Thr Phe Gln Pro His Ser Gly Gly Asp
        355                 360                 365

Leu Glu Val Thr Thr His Ser Phe Asn Cys Arg Gly Glu Phe Phe Tyr
    370                 375                 380

Cys Asp Thr Thr Lys Leu Phe Asn Glu Ser Asn Leu Asn Thr Thr Asn
385                 390                 395                 400

Thr Thr Thr Leu Thr Leu Pro Cys Arg Ile Lys Gln Ile Val Asn Met
                405                 410                 415

Trp Gln Gly Val Gly Arg Ala Met Tyr Ala Pro Pro Val Glu Gly Asn
            420                 425                 430

Ile Thr Cys Asn Ser Ser Ile Thr Gly Leu Leu Leu Val Arg Asp Gly
        435                 440                 445
```

```
Gly Asn Thr Ser Asn Ser Thr Pro Glu Ile Phe Arg Pro Gly Gly Gly
    450                 455                 460

Asn Met Lys Asp Asn Trp Arg Ser Glu Leu Tyr Lys Tyr Lys Val Val
465                 470                 475                 480

Glu Ile Lys Pro Leu Gly Val Ala Pro Thr Lys Ala Lys Arg Arg Val
                485                 490                 495

Val Glu Arg Glu Lys Arg Ala Val Gly Ile Gly Ala Val Leu Phe Gly
            500                 505                 510

Phe Leu Gly Ala Ala Gly Ser Thr Met Gly Ala Ala Ser Ile Thr Leu
        515                 520                 525

Thr Val Gln Ala Arg Gln Leu Leu Ser Gly Ile Val Gln Gln Gln Ser
    530                 535                 540

Asn Leu Leu Arg Ala Ile Glu Ala Gln Gln His Met Leu Gln Leu Thr
545                 550                 555                 560

Val Trp Gly Ile Lys Gln Leu Gln Ala Arg Val Leu Ala Ile Glu Arg
                565                 570                 575

Tyr Leu Lys Asp Gln Gln Leu Leu Gly Leu Trp Gly Cys Ser Gly Lys
            580                 585                 590

Leu Ile Cys Pro Thr Thr Val Pro Trp Asn Ser Ser Trp Ser Asn Lys
        595                 600                 605

Ser Gln Thr Asp Ile Trp Asp Asn Met Thr Trp Met Gln Trp Asp Arg
    610                 615                 620

Glu Ile Ser Asn Tyr Thr Gly Thr Ile Tyr Lys Leu Leu Glu Glu Ser
625                 630                 635                 640

Gln Asn Gln Gln Glu Lys Asn Glu Lys Asp Leu Leu Ala Leu Asp Ser
                645                 650                 655

Trp Lys Asn Leu Trp Ser Trp Phe Asp Ile Thr Asn Trp Leu Trp Tyr
            660                 665                 670

Ile Lys Ile Phe Ile Met Ile Val Gly Gly Leu Ile Gly Leu Arg Ile
        675                 680                 685

Ile Phe Gly Val Leu Ser Ile Val Lys Arg Val Arg Gln Gly Tyr Ser
    690                 695                 700

Pro Leu Ser Phe Gln Thr Leu Thr Pro Asn Pro Arg Gly Leu Asp Arg
705                 710                 715                 720

Leu Gly Arg Ile Glu Glu Glu Gly Gly Glu Gln Asp Lys Asp Arg Ser
                725                 730                 735

Ile Arg Leu Val Asn Gly Phe Leu Ala Leu Ala Trp Asp Asp Leu Arg
            740                 745                 750

Ser Leu Cys Leu Phe Ser Tyr His Arg Leu Arg Asp Phe Ile Leu Val
        755                 760                 765

Ala Ala Arg Ala Val Glu Leu Leu Gly Arg Ser Ser Leu Arg Gly Leu
    770                 775                 780

Gln Arg Gly Trp Glu Ala Leu Lys Tyr Leu Gly Asn Leu Val Gln Tyr
785                 790                 795                 800

Gly Gly Leu Glu Leu Lys Arg Arg Ala Ile Ser Leu Phe Asp Thr Ile
                805                 810                 815

Ala Ile Ala Val Ala Glu Gly Thr Asp Arg Ile Leu Glu Val Ile Leu
            820                 825                 830

Arg Ile Ile Arg Ala Ile Arg Asn Ile Pro Thr Arg Ile Arg Gln Gly
        835                 840                 845

Phe Glu Ala Ala Leu Leu
    850
```

<210> SEQ ID NO 25
<211> LENGTH: 2532
<212> TYPE: DNA
<213> ORGANISM: Artificial Sequence
<220> FEATURE:
<223> OTHER INFORMATION: pGX1021 - Env Clade C tier 2 ZM53M.PB12 DNA
Sequence

<400> SEQUENCE: 25
atgcgagtcc gggagattcc tcgaaactat cagcagtggt ggatttgggg gattctgggc 60
ttctggatgc tgatgatttg tagcgtggtg gggaatctgt gggtgaccgt ctactatgga 120
gtgcccgtct ggagggaggc taagaccaca ctgttctgcg caagcgacgc taaagcatac 180
gaacgcgagg tgcacaatgt ctgggcaact catgcctgcg tgcctaccga tccaaatccc 240
caggaaatgg tgctggagaa cgtcacagaa aactttaata tgtggaagaa cgacatggtg 300
gatcagatgc aggaggacat catttcactg tgggatcaga gcctgaaacc atgcgtgaag 360
ctgactcccc tgtgcgtcac cctgaactgt agtaagctga acaatgcaac cgacggagag 420
atgaaaaatt gttcattcaa cgccactacc gaactgaggg ataagaaaaa gcaggtgtac 480
gccctgtttt ataagctgga catcgtccct ctggatggcc ggaacaatag ctccgagtat 540
agactgatta actgcaatac ctctacaatc actcaggcat gtccaaaagt gagtttcgac 600
cctattccaa tccactactg cgcccccgct ggctatgcca tcctgaaatg taacaataag 660
acttttaatg ggaccggacc ttgccacaac gtgtctacag tccagtgtac tcatggcatt 720
aagccagtga tcagcactca gctgctgctg aacgggtcca ccgctgagga agacatcatt 780
atcaggagtg agaatctgac aaacaatgca aagactatta tcgtgcatct gaacgaaagc 840
attgaaatcg agtgcacacg ccccggcaac aatactagga aatccattcg catcggccct 900
gggcaggctt tctttgcaac aactaatatt atcggggata tccggcaggc ctactgtatt 960
atcaacaagg ctaattggac caacacactg cacagagtgt caaaaaagct ggaggaacat 1020
ttcccaaaca aaacaattaa ctttaattct agttcaggcg gggacctgga gatcaccaca 1080
cacagcttca attgcggagg cgaattcttt tactgtaaca ccagctccct gtttaatggc 1140
acctacaacg acacagatat ctacaattcc acagatatta tcctgctgtg cagaatcaag 1200
cagattatca acatgtggca ggaagtgggc agggccatgt atgctccccc tattgaaggg 1260
aatatcacct gttctagtaa catcaccgga ctgctgctga cacgcgacgg gggactgacc 1320
aatgaatcta aggagacatt ccgacccggc gggggagaca tgcgagataa ctggcggagt 1380
gagctgtaca aatataaggt ggtcgaaatt aagcccctgg gcatcgctcc tactaaagca 1440
aagcggagag tggtcgaacg cgagaaacga gcagtgggac tgggcgccat gttcctgggg 1500
tttctgggag ccgctggcag taccatggga gcagcctcaa tcactctgac cgtgcaggca 1560
cgacagctgc tgagcggcat tgtccagcag cagaacaatc tgctgagagc aatcgaggcc 1620
cagcagcata tgctgcagct gaccgtgtgg ggcattaagc agctgcaggc ccgcgtcctg 1680
gctatcgagc gatacctgaa ggaccagcag ctgctgggac tgtggggatg ctccggcaaa 1740
ctggtgtgca ctaccgccgt cccctggaat tcaagctgga gtaacaagtc acaggaggac 1800
atttggaaca atacaacttg gatgcagtgg gataaagaag tgtccaacta cacaaaaact 1860
atctataagc tgctggagaa atctcagaat cagcaggagg aaaacgaaaa ggacctgctg 1920
gccctggatt catggaacaa tctgtggaat tggttcgata tcagcaactg gctgtggtac 1980
atcaagatct ttattatgat cgtgggcggg ctgattgggc tgcggattat cttcgccgtg 2040

```
ctgagcatcg tgaatagggt ccgccaggga tatagccctc tgtcctttca gaccctgaca   2100

cagaacccaa gaggcctgga ccggctgggg agaatcgagg aagagggagg cgagcaggac   2160

cgagatcggt ccgtgaggct ggtcaacggg ttcctggctc tgttttggga cgatctgcgc   2220

tccctgtgcc tgttctctta ccacagactg agggacttca tcctgatcgc aaccagggtg   2280

gtcgagctgc tgggccgctc ctctctgaag ggctgcaga gaggatggga agccctgaga   2340

tacctgggat ctagggtgca gtattggggc ctggagctga aaaagtctgc tattagtctg   2400

ttcgacacaa ttgcaatcgc cgtggctgag ggcactgatc gaattatcga actgatccag   2460

cggtcctgga gagctattcg gaacatccca agaagaatcc gccagggctt tgagaccgca   2520

ctgctgtgat aa                                                       2532
```

<210> SEQ ID NO 26
<211> LENGTH: 842
<212> TYPE: PRT
<213> ORGANISM: Artificial Sequence
<220> FEATURE:
<223> OTHER INFORMATION: pGX1021 - Env Clade C tier 2 ZM53M.PB12 Amino Acid Sequence

<400> SEQUENCE: 26

```
Met Arg Val Arg Glu Ile Pro Arg Asn Tyr Gln Gln Trp Trp Ile Trp
1               5                   10                  15

Gly Ile Leu Gly Phe Trp Met Leu Met Ile Cys Ser Val Val Gly Asn
            20                  25                  30

Leu Trp Val Thr Val Tyr Tyr Gly Val Pro Val Trp Arg Glu Ala Lys
        35                  40                  45

Thr Thr Leu Phe Cys Ala Ser Asp Ala Lys Ala Tyr Glu Arg Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met Gln Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Ser Lys Leu Asn Asn Ala Thr Asp Gly Glu Met Lys Asn Cys
    130                 135                 140

Ser Phe Asn Ala Thr Thr Glu Leu Arg Asp Lys Lys Lys Gln Val Tyr
145                 150                 155                 160

Ala Leu Phe Tyr Lys Leu Asp Ile Val Pro Leu Asp Gly Arg Asn Asn
                165                 170                 175

Ser Ser Glu Tyr Arg Leu Ile Asn Cys Asn Thr Ser Thr Ile Thr Gln
            180                 185                 190

Ala Cys Pro Lys Val Ser Phe Asp Pro Ile Pro Ile His Tyr Cys Ala
        195                 200                 205

Pro Ala Gly Tyr Ala Ile Leu Lys Cys Asn Asn Lys Thr Phe Asn Gly
    210                 215                 220

Thr Gly Pro Cys His Asn Val Ser Thr Val Gln Cys Thr His Gly Ile
225                 230                 235                 240

Lys Pro Val Ile Ser Thr Gln Leu Leu Leu Asn Gly Ser Thr Ala Glu
                245                 250                 255

Glu Asp Ile Ile Ile Arg Ser Glu Asn Leu Thr Asn Asn Ala Lys Thr
            260                 265                 270
```

-continued

```
Ile Ile Val His Leu Asn Glu Ser Ile Glu Ile Glu Cys Thr Arg Pro
        275                 280                 285

Gly Asn Asn Thr Arg Lys Ser Ile Arg Ile Gly Pro Gly Gln Ala Phe
    290                 295                 300

Phe Ala Thr Thr Asn Ile Ile Gly Asp Ile Arg Gln Ala Tyr Cys Ile
305                 310                 315                 320

Ile Asn Lys Ala Asn Trp Thr Asn Thr Leu His Arg Val Ser Lys Lys
                325                 330                 335

Leu Glu Glu His Phe Pro Asn Lys Thr Ile Asn Phe Asn Ser Ser Ser
            340                 345                 350

Gly Gly Asp Leu Glu Ile Thr Thr His Ser Phe Asn Cys Gly Gly Glu
        355                 360                 365

Phe Phe Tyr Cys Asn Thr Ser Ser Leu Phe Asn Gly Thr Tyr Asn Asp
    370                 375                 380

Thr Asp Ile Tyr Asn Ser Thr Asp Ile Ile Leu Leu Cys Arg Ile Lys
385                 390                 395                 400

Gln Ile Ile Asn Met Trp Gln Glu Val Gly Arg Ala Met Tyr Ala Pro
                405                 410                 415

Pro Ile Glu Gly Asn Ile Thr Cys Ser Ser Asn Ile Thr Gly Leu Leu
            420                 425                 430

Leu Thr Arg Asp Gly Gly Leu Thr Asn Glu Ser Lys Glu Thr Phe Arg
        435                 440                 445

Pro Gly Gly Gly Asp Met Arg Asp Asn Trp Arg Ser Glu Leu Tyr Lys
    450                 455                 460

Tyr Lys Val Val Glu Ile Lys Pro Leu Gly Ile Ala Pro Thr Lys Ala
465                 470                 475                 480

Lys Arg Arg Val Val Glu Arg Glu Lys Arg Ala Val Gly Leu Gly Ala
                485                 490                 495

Met Phe Leu Gly Phe Leu Gly Ala Ala Gly Ser Thr Met Gly Ala Ala
            500                 505                 510

Ser Ile Thr Leu Thr Val Gln Ala Arg Gln Leu Leu Ser Gly Ile Val
        515                 520                 525

Gln Gln Gln Asn Asn Leu Leu Arg Ala Ile Glu Ala Gln Gln His Met
    530                 535                 540

Leu Gln Leu Thr Val Trp Gly Ile Lys Gln Leu Gln Ala Arg Val Leu
545                 550                 555                 560

Ala Ile Glu Arg Tyr Leu Lys Asp Gln Gln Leu Leu Gly Leu Trp Gly
                565                 570                 575

Cys Ser Gly Lys Leu Val Cys Thr Thr Ala Val Pro Trp Asn Ser Ser
            580                 585                 590

Trp Ser Asn Lys Ser Gln Glu Asp Ile Trp Asn Asn Thr Thr Trp Met
        595                 600                 605

Gln Trp Asp Lys Glu Val Ser Asn Tyr Thr Lys Thr Ile Tyr Lys Leu
    610                 615                 620

Leu Glu Lys Ser Gln Asn Gln Gln Glu Glu Asn Glu Lys Asp Leu Leu
625                 630                 635                 640

Ala Leu Asp Ser Trp Asn Asn Leu Trp Asn Trp Phe Asp Ile Ser Asn
                645                 650                 655

Trp Leu Trp Tyr Ile Lys Ile Phe Ile Met Ile Val Gly Gly Leu Ile
            660                 665                 670

Gly Leu Arg Ile Ile Phe Ala Val Leu Ser Ile Val Asn Arg Val Arg
        675                 680                 685
```

```
Gln Gly Tyr Ser Pro Leu Ser Phe Gln Thr Leu Thr Gln Asn Pro Arg
    690                 695                 700

Gly Leu Asp Arg Leu Gly Arg Ile Glu Glu Glu Gly Gly Glu Gln Asp
705                 710                 715                 720

Arg Asp Arg Ser Val Arg Leu Val Asn Gly Phe Leu Ala Leu Phe Trp
                725                 730                 735

Asp Asp Leu Arg Ser Leu Cys Leu Phe Ser Tyr His Arg Leu Arg Asp
            740                 745                 750

Phe Ile Leu Ile Ala Thr Arg Val Val Glu Leu Leu Gly Arg Ser Ser
        755                 760                 765

Leu Lys Gly Leu Gln Arg Gly Trp Glu Ala Leu Arg Tyr Leu Gly Ser
    770                 775                 780

Arg Val Gln Tyr Trp Gly Leu Glu Leu Lys Lys Ser Ala Ile Ser Leu
785                 790                 795                 800

Phe Asp Thr Ile Ala Ile Ala Val Ala Glu Gly Thr Asp Arg Ile Ile
                805                 810                 815

Glu Leu Ile Gln Arg Ser Trp Arg Ala Ile Arg Asn Ile Pro Arg Arg
            820                 825                 830

Ile Arg Gln Gly Phe Glu Thr Ala Leu Leu
        835                 840


<210> SEQ ID NO 27
<211> LENGTH: 2580
<212> TYPE: DNA
<213> ORGANISM: Artificial Sequence
<220> FEATURE:
<223> OTHER INFORMATION: pGX1020 - Env Clade C tier 2 Du422.1 DNA
      Sequence

<400> SEQUENCE: 27

atgcgagtcc gggggattcc tcgaaactgg cctcagtggt ggatctgggg gattctggga     60

ttctggatga ttatcatctg tagggtcgtg ggaaacctgg atctgtgggt gacagtctac    120

tatggcgtgc ctgtctggaa agaagctaag accacactgt tctgcgcaag cgacgcaaaa    180

gcctacgata aggaggtgca caatgtctgg gcaacacatg cctgcgtgcc aactgaccca    240

aatccccagg aaatcgtgct ggagaacgtc accgaaaact tcaacatgtg gaagaacgac    300

atggtggatc agatgcacga ggacatcatt tcactgtggg atcagagcct gaaaccctgc    360

gtgaagctga cacctctgtg cgtcactctg aactgtaaaa atgtgaacat ctccgctaat    420

gcaaacgcca ccgctacact gaatagctcc atgaacggcg agattaagaa ttgttctttc    480

aacactacca cagaactgag agacaagaaa cagaaagtgt acgccctgtt ttataagcca    540

gatgtggtcc ccctgaatgg cggggagcac aacgaaacag ggagtatat cctgattaat    600

tgcaactcta gtactatcac ccaggcatgt cccaaggtgt ccttcgatcc tatcccaatt    660

cattactgcg cacctgccgg atatgccatt ctgaaatgta acaataagac ttttaatggg    720

accggaccat gcaacaatgt gagcacagtc cagtgtactc acggcatcaa gcccgtggtc    780

tccacccagc tgctgctgaa cgggtctctg gccgaggaag agatcattgt gagatccgaa    840

aatctgacca acaacatcaa aacaatcatt gtgcatctga acaaaagcgt cgagattaag    900

tgcaccaggc caaacaataa cacacgaaag tccgtgcgaa tcggaccagg acagaccttc    960

tacgcaacag gggagatcat tggagacatc agggaagctc actgtaatat tagccgcgag   1020

acttggaact ccaccctgat ccaggtgaag gagaaactgc gcgaacacta taacaagacc   1080

attaagttcg agccctcaag cggaggcgac ctggaagtga ctacccatag ttttaactgc   1140
```

```
cggggcgagt tcttttactg tgatacaact aagctgttca atgaaaccaa gctgtttaac   1200

gagagcgaat atgtggacaa caagacaatc attctgcctt gcagaatcaa gcagatcatt   1260

aacatgtggc aggaagtggg aagggctatg tacgcacccc ctatcgaagg caacatcact   1320

tgtaagtcta acatcactgg gctgctgctg acctgggatg gggagagaa cagtaccgaa   1380

ggcgtgttca gacccggcgg gggaaatatg aaagacaact ggaggtcaga gctgtacaag   1440

tataaagtgg tcgaaatcaa gcctctgggg gtggccccaa ccaagagcaa aaggaaggtg   1500

gtcggaaggg agaagcgagc agtgggactg ggagccgtcc tgctggggtt tctgggagcc   1560

gctggctcta caatgggagc agccagtatc acactgactg tccaggctcg ccagctgctg   1620

tcaggcatcg tgcagcagca gagcaatctg ctgcgggcca ttgaggctca gcagcacctg   1680

ctgcagctga ctgtctgggg catcaaacag ctgcagaccc gcgtgctggc cattgagcga   1740

tacctgaaag atcagcagct gctggggctg tggggatgct ctggcaagct gatctgtgct   1800

acagcagtgc cctggaattc ctcttggagc aacaagtccc tgggcgacat ttgggataac   1860

atgacttgga tgcagtggga ccgcgagatc agtaattata ccaacacaat tttccgactg   1920

ctggaagatt cacagaatca gcaggagaag aacgagaagg acctgctggc tctggatagc   1980

tggaaaaatc tgtggaactg gttcgacatc actaattggc tgtggtacat caagatcttc   2040

atcatgattg tcggcgggct gatcggcctg agaatcattt tcggagtgct ggccattgtg   2100

aaacgggtca gacagggcta ttctcctctg agttttcaga ccctgatccc caaccctagg   2160

ggaccagatc gactgggccg gattgaagag gaaggaggcg agcaggacaa ggatagatcc   2220

atcaggctgg tgtctggctt cctggccctg gcttgggacg atctgcgcag tctgtgcctg   2280

ttctcatacc atcagctgcg agactttatc ctgaccgctg cacgggccgc tgagctgctg   2340

gggcggagtt cactgagagg cctgcagagg gggtgggaag tcctgaaata cctgggcaat   2400

ctggtgcagt attgggggct ggagctgaag cggtctgcca tcaacctgtt tgacacaatc   2460

gcaattgccg tcgctgaggg cactgatcgg atcattgaag tgatccagag aatttgccga   2520

gctattcgct acattcctac ccgcattcgc cagggatttg aagccgctct gctgtgataa   2580
```

<210> SEQ ID NO 28
<211> LENGTH: 858
<212> TYPE: PRT
<213> ORGANISM: Artificial Sequence
<220> FEATURE:
<223> OTHER INFORMATION: pGX1020 - Env Clade C tier 2 Du422.1 Amino Acid Sequence

<400> SEQUENCE: 28

```
Met Arg Val Arg Gly Ile Pro Arg Asn Trp Pro Gln Trp Trp Ile Trp
1               5                   10                  15

Gly Ile Leu Gly Phe Trp Met Ile Ile Ile Cys Arg Val Val Gly Asn
            20                  25                  30

Leu Asp Leu Trp Val Thr Val Tyr Tyr Gly Val Pro Val Trp Lys Glu
        35                  40                  45

Ala Lys Thr Thr Leu Phe Cys Ala Ser Asp Ala Lys Ala Tyr Asp Lys
    50                  55                  60

Glu Val His Asn Val Trp Ala Thr His Ala Cys Val Pro Thr Asp Pro
65                  70                  75                  80

Asn Pro Gln Glu Ile Val Leu Glu Asn Val Thr Glu Asn Phe Asn Met
                85                  90                  95

Trp Lys Asn Asp Met Val Asp Gln Met His Glu Asp Ile Ile Ser Leu
            100                 105                 110
```

-continued

```
Trp Asp Gln Ser Leu Lys Pro Cys Val Lys Leu Thr Pro Leu Cys Val
        115                 120                 125

Thr Leu Asn Cys Lys Asn Val Asn Ile Ser Ala Asn Ala Asn Ala Thr
    130                 135                 140

Ala Thr Leu Asn Ser Ser Met Asn Gly Glu Ile Lys Asn Cys Ser Phe
145                 150                 155                 160

Asn Thr Thr Thr Glu Leu Arg Asp Lys Lys Gln Lys Val Tyr Ala Leu
                165                 170                 175

Phe Tyr Lys Pro Asp Val Val Pro Leu Asn Gly Gly Glu His Asn Glu
            180                 185                 190

Thr Gly Glu Tyr Ile Leu Ile Asn Cys Asn Ser Ser Thr Ile Thr Gln
        195                 200                 205

Ala Cys Pro Lys Val Ser Phe Asp Pro Ile Pro Ile His Tyr Cys Ala
    210                 215                 220

Pro Ala Gly Tyr Ala Ile Leu Lys Cys Asn Asn Lys Thr Phe Asn Gly
225                 230                 235                 240

Thr Gly Pro Cys Asn Asn Val Ser Thr Val Gln Cys Thr His Gly Ile
                245                 250                 255

Lys Pro Val Val Ser Thr Gln Leu Leu Leu Asn Gly Ser Leu Ala Glu
            260                 265                 270

Glu Glu Ile Ile Val Arg Ser Glu Asn Leu Thr Asn Asn Ile Lys Thr
        275                 280                 285

Ile Ile Val His Leu Asn Lys Ser Val Glu Ile Lys Cys Thr Arg Pro
    290                 295                 300

Asn Asn Asn Thr Arg Lys Ser Val Arg Ile Gly Pro Gly Gln Thr Phe
305                 310                 315                 320

Tyr Ala Thr Gly Glu Ile Ile Gly Asp Ile Arg Glu Ala His Cys Asn
                325                 330                 335

Ile Ser Arg Glu Thr Trp Asn Ser Thr Leu Ile Gln Val Lys Glu Lys
            340                 345                 350

Leu Arg Glu His Tyr Asn Lys Thr Ile Lys Phe Glu Pro Ser Ser Gly
        355                 360                 365

Gly Asp Leu Glu Val Thr Thr His Ser Phe Asn Cys Arg Gly Glu Phe
    370                 375                 380

Phe Tyr Cys Asp Thr Thr Lys Leu Phe Asn Glu Thr Lys Leu Phe Asn
385                 390                 395                 400

Glu Ser Glu Tyr Val Asp Asn Lys Thr Ile Ile Leu Pro Cys Arg Ile
                405                 410                 415

Lys Gln Ile Ile Asn Met Trp Gln Glu Val Gly Arg Ala Met Tyr Ala
            420                 425                 430

Pro Pro Ile Glu Gly Asn Ile Thr Cys Lys Ser Asn Ile Thr Gly Leu
        435                 440                 445

Leu Leu Thr Trp Asp Gly Gly Glu Asn Ser Thr Glu Gly Val Phe Arg
    450                 455                 460

Pro Gly Gly Gly Asn Met Lys Asp Asn Trp Arg Ser Glu Leu Tyr Lys
465                 470                 475                 480

Tyr Lys Val Val Glu Ile Lys Pro Leu Gly Val Ala Pro Thr Lys Ser
                485                 490                 495

Lys Arg Lys Val Val Gly Arg Glu Lys Arg Ala Val Gly Leu Gly Ala
            500                 505                 510

Val Leu Leu Gly Phe Leu Gly Ala Ala Gly Ser Thr Met Gly Ala Ala
        515                 520                 525
```

```
Ser Ile Thr Leu Thr Val Gln Ala Arg Gln Leu Leu Ser Gly Ile Val
    530                 535                 540

Gln Gln Gln Ser Asn Leu Leu Arg Ala Ile Glu Ala Gln Gln His Leu
545                 550                 555                 560

Leu Gln Leu Thr Val Trp Gly Ile Lys Gln Leu Gln Thr Arg Val Leu
                565                 570                 575

Ala Ile Glu Arg Tyr Leu Lys Asp Gln Gln Leu Leu Gly Leu Trp Gly
            580                 585                 590

Cys Ser Gly Lys Leu Ile Cys Ala Thr Ala Val Pro Trp Asn Ser Ser
        595                 600                 605

Trp Ser Asn Lys Ser Leu Gly Asp Ile Trp Asp Asn Met Thr Trp Met
    610                 615                 620

Gln Trp Asp Arg Glu Ile Ser Asn Tyr Thr Asn Thr Ile Phe Arg Leu
625                 630                 635                 640

Leu Glu Asp Ser Gln Asn Gln Gln Glu Lys Asn Glu Lys Asp Leu Leu
                645                 650                 655

Ala Leu Asp Ser Trp Lys Asn Leu Trp Asn Trp Phe Asp Ile Thr Asn
            660                 665                 670

Trp Leu Trp Tyr Ile Lys Ile Phe Ile Met Ile Val Gly Gly Leu Ile
        675                 680                 685

Gly Leu Arg Ile Ile Phe Gly Val Leu Ala Ile Val Lys Arg Val Arg
    690                 695                 700

Gln Gly Tyr Ser Pro Leu Ser Phe Gln Thr Leu Ile Pro Asn Pro Arg
705                 710                 715                 720

Gly Pro Asp Arg Leu Gly Arg Ile Glu Glu Glu Gly Gly Glu Gln Asp
                725                 730                 735

Lys Asp Arg Ser Ile Arg Leu Val Ser Gly Phe Leu Ala Leu Ala Trp
            740                 745                 750

Asp Asp Leu Arg Ser Leu Cys Leu Phe Ser Tyr His Gln Leu Arg Asp
        755                 760                 765

Phe Ile Leu Thr Ala Ala Arg Ala Ala Glu Leu Leu Gly Arg Ser Ser
    770                 775                 780

Leu Arg Gly Leu Gln Arg Gly Trp Glu Val Leu Lys Tyr Leu Gly Asn
785                 790                 795                 800

Leu Val Gln Tyr Trp Gly Leu Glu Leu Lys Arg Ser Ala Ile Asn Leu
                805                 810                 815

Phe Asp Thr Ile Ala Ile Ala Val Ala Glu Gly Thr Asp Arg Ile Ile
            820                 825                 830

Glu Val Ile Gln Arg Ile Cys Arg Ala Ile Arg Tyr Ile Pro Thr Arg
        835                 840                 845

Ile Arg Gln Gly Phe Glu Ala Ala Leu Leu
    850                 855
```

<210> SEQ ID NO 29
<211> LENGTH: 2601
<212> TYPE: DNA
<213> ORGANISM: Artificial Sequence
<220> FEATURE:
<223> OTHER INFORMATION: pGX1019 - Env Clade C tier 2 Cap210.2.00.E8 DNA Sequence

<400> SEQUENCE: 29

```
atgagggtca tgggcattca gcgcaactgg cagcagtggg gcatctgggg cattctgggc      60

ttctggctgc tgatgatttg ttcagggatg ggaaacctgt gggtgacagt ctactatggc     120

gtgcctgtct ggaaggaggc caaaaccaca ctgttttgcg ctagcgacgc aaagggctac     180
```

-continued

```
gatactgaag tgcacaacgt ctgggccact catgcttgcg tgccaaccga ccccaatcct    240
caggagatcg tgctggaaaa cgtcaccgag aacttcaata tgtggaaaaa tgacatggtg    300
gatcagatgc accaggacat catttcactg tgggatcaga gcctgaagcc ctgcgtgaaa    360
ctgacccctc tgtgcgtcac actgaattgt tccgacgcca cttacaacaa tggcaccaac    420
tctactgata ccatgaagat ctgtagtttc aatgctacta ccgaactgcg ggacaagaaa    480
aagaaagagt acgcactgtt ttatagactg gatatcgtgc ctctgaagaa cgagtcagaa    540
agccagaatt tcagtgagta tatcctgatt aactgcaata catcaactat cgcccaggct    600
tgtcccaaag tgagctttga tccaatcccc attcactact gcgcacctgc cggctatgct    660
attctgaagt gtaacaacaa gaccttcaac ggcaccgggc catgcaacaa cgtgagcaca    720
gtccagtgta ctcatgggat caagcccgtg gtctcaacac agctgctgct gaacggaagc    780
ctggccgagg aagaggtggt catccggtct gaaaacatca gtaataatgt gaagaccatc    840
attgtccacc tgaacgagag tgtgaatatt acatgcatca ggcctggcaa caatactcgg    900
agatcaatcc gcattggacc aggccaggcc ttctacgcca tgggcgacat cattgggaac    960
atcagagagg cacattgcaa tattagcgaa aaggcctgga acgagactct gaagaaagtc   1020
gtggagaaac tggtgaaata cttccccaac aaaaccatcg aatttgctcc ccctgtgggc   1080
ggggatctgg agattacaac tcacagcttc aattgcggag gcgagttctt ttattgtaac   1140
accacaaagc tgtttaactc cacacataat tccaccgact ctacagtgaa tagtactgat   1200
tcaaccgccg agacaggcaa ctctaccaac acaaatatca ccctgccctg ccgaattcgg   1260
cagatcatta atatgtggca ggaagtgggg agggctatgt atgcaccacc ctccaaggga   1320
aacattacct gtatctctaa tattacagga ctgctgctga ctcgcgacgg gggagaaaac   1380
aaaaccgaga acaatgatac agagatcttc cgacctggcg gggagacat gaaggataat   1440
tggagaagcg aactgtacaa gtataaagtg gtcgagatca agcctctggg cgtggcacct   1500
acaagagcca agaggcgcgt ggtcgagagg gaaaaacgcg ctgtggggat cggagcagtc   1560
ttcctgggct ttctgggagc agctggaagt accatgggag cagcctcaat tactctgacc   1620
gtgcaggcac gacagctgct gagcgggatc gtccagcagc agtccaacct gctgagagcc   1680
attgaggctc agcagcacat gctgcagctg accgtgtggg ggatcaagca gctgcagaca   1740
agagtcctgg ccattgagag gtacctgaag gaccagcagc tgctgggaat ctggggatgc   1800
agcggaaaac tgatttgtac taccaacgtg ccatggaata gctcctggag caataagtcc   1860
tatggcgaca tctgggataa catgacctgg atgcagtggg acagggaaat caacaactac   1920
acaaacacta tctaccgcct gctggaggat tcccagaacc agcaggagaa gaatgaacag   1980
gacctgctgg ccctggataa atggcagtct ctgtggagtt ggttctcaat ctctagttgg   2040
ctgtggtaca tcaagatctt catcatggtg gtcggcgggc tgatcggact gaggatcatt   2100
ttcgctgtgc tgtccattgt gaacagagtc aggcagggct atagcccact gtccctgcag   2160
accctgcctc caaatccccg agaactggac cggctgggag gcatcgaaga ggaagggggga   2220
gagcaggatc gaggccgatc cgtgaggctg gtctctgggt tcctgccact ggcatgggac   2280
gatctgcgct ctctgtgcct gttttgttac catcggctga gagacctgct gctgatcaca   2340
actcgcgccg tggaactgct ggctcgaagt atcctgaagg gactgcagcg gggctgggag   2400
attctgaaat acctggggtc cctggtgcag tattggggac aggaactgaa gaaatctgcc   2460
atcaacctgc tggacaccac agctattgca gtggccgaag ctgcagatag aatcctggag   2520
```

```
ctgctgcaga gaatttggag agggatttgt aatgtgccta cccgcatccg acagggcttt   2580

gaagccgctc tgcagtgata a                                             2601


<210> SEQ ID NO 30
<211> LENGTH: 865
<212> TYPE: PRT
<213> ORGANISM: Artificial Sequence
<220> FEATURE:
<223> OTHER INFORMATION: pGX1019 - Env Clade C tier 2 Cap210.2.00.E8
      Amino Acid Sequence

<400> SEQUENCE: 30

Met Arg Val Met Gly Ile Gln Arg Asn Trp Gln Gln Trp Gly Ile Trp
1               5                   10                  15

Gly Ile Leu Gly Phe Trp Leu Leu Met Ile Cys Ser Gly Met Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Gly Tyr Asp Thr Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Gln Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Ser Asp Ala Thr Tyr Asn Asn Gly Thr Asn Ser Thr Asp Thr
    130                 135                 140

Met Lys Ile Cys Ser Phe Asn Ala Thr Thr Glu Leu Arg Asp Lys Lys
145                 150                 155                 160

Lys Lys Glu Tyr Ala Leu Phe Tyr Arg Leu Asp Ile Val Pro Leu Lys
                165                 170                 175

Asn Glu Ser Glu Ser Gln Asn Phe Ser Glu Tyr Ile Leu Ile Asn Cys
            180                 185                 190

Asn Thr Ser Thr Ile Ala Gln Ala Cys Pro Lys Val Ser Phe Asp Pro
        195                 200                 205

Ile Pro Ile His Tyr Cys Ala Pro Ala Gly Tyr Ala Ile Leu Lys Cys
    210                 215                 220

Asn Asn Lys Thr Phe Asn Gly Thr Gly Pro Cys Asn Asn Val Ser Thr
225                 230                 235                 240

Val Gln Cys Thr His Gly Ile Lys Pro Val Val Ser Thr Gln Leu Leu
                245                 250                 255

Leu Asn Gly Ser Leu Ala Glu Glu Glu Val Val Ile Arg Ser Glu Asn
            260                 265                 270

Ile Ser Asn Asn Val Lys Thr Ile Ile Val His Leu Asn Glu Ser Val
        275                 280                 285

Asn Ile Thr Cys Ile Arg Pro Gly Asn Asn Thr Arg Arg Ser Ile Arg
    290                 295                 300

Ile Gly Pro Gly Gln Ala Phe Tyr Ala Met Gly Asp Ile Ile Gly Asn
305                 310                 315                 320

Ile Arg Glu Ala His Cys Asn Ile Ser Glu Lys Ala Trp Asn Glu Thr
                325                 330                 335

Leu Lys Lys Val Val Glu Lys Leu Val Lys Tyr Phe Pro Asn Lys Thr
```

-continued

```
            340                 345                 350

Ile Glu Phe Ala Pro Pro Val Gly Gly Asp Leu Glu Ile Thr Thr His
        355                 360                 365

Ser Phe Asn Cys Gly Gly Glu Phe Phe Tyr Cys Asn Thr Thr Lys Leu
    370                 375                 380

Phe Asn Ser Thr His Asn Ser Thr Asp Ser Thr Val Asn Ser Thr Asp
385                 390                 395                 400

Ser Thr Ala Glu Thr Gly Asn Ser Thr Asn Thr Asn Ile Thr Leu Pro
                405                 410                 415

Cys Arg Ile Arg Gln Ile Ile Asn Met Trp Gln Glu Val Gly Arg Ala
            420                 425                 430

Met Tyr Ala Pro Pro Ser Lys Gly Asn Ile Thr Cys Ile Ser Asn Ile
        435                 440                 445

Thr Gly Leu Leu Leu Thr Arg Asp Gly Gly Glu Asn Lys Thr Glu Asn
    450                 455                 460

Asn Asp Thr Glu Ile Phe Arg Pro Gly Gly Gly Asp Met Lys Asp Asn
465                 470                 475                 480

Trp Arg Ser Glu Leu Tyr Lys Tyr Lys Val Val Glu Ile Lys Pro Leu
                485                 490                 495

Gly Val Ala Pro Thr Arg Ala Lys Arg Arg Val Val Glu Arg Glu Lys
            500                 505                 510

Arg Ala Val Gly Ile Gly Ala Val Phe Leu Gly Phe Leu Gly Ala Ala
        515                 520                 525

Gly Ser Thr Met Gly Ala Ala Ser Ile Thr Leu Thr Val Gln Ala Arg
    530                 535                 540

Gln Leu Leu Ser Gly Ile Val Gln Gln Gln Ser Asn Leu Leu Arg Ala
545                 550                 555                 560

Ile Glu Ala Gln Gln His Met Leu Gln Leu Thr Val Trp Gly Ile Lys
                565                 570                 575

Gln Leu Gln Thr Arg Val Leu Ala Ile Glu Arg Tyr Leu Lys Asp Gln
            580                 585                 590

Gln Leu Leu Gly Ile Trp Gly Cys Ser Gly Lys Leu Ile Cys Thr Thr
        595                 600                 605

Asn Val Pro Trp Asn Ser Ser Trp Ser Asn Lys Ser Tyr Gly Asp Ile
    610                 615                 620

Trp Asp Asn Met Thr Trp Met Gln Trp Asp Arg Glu Ile Asn Asn Tyr
625                 630                 635                 640

Thr Asn Thr Ile Tyr Arg Leu Leu Glu Asp Ser Gln Asn Gln Gln Glu
                645                 650                 655

Lys Asn Glu Gln Asp Leu Leu Ala Leu Asp Lys Trp Gln Ser Leu Trp
            660                 665                 670

Ser Trp Phe Ser Ile Ser Ser Trp Leu Trp Tyr Ile Lys Ile Phe Ile
        675                 680                 685

Met Val Val Gly Gly Leu Ile Gly Leu Arg Ile Ile Phe Ala Val Leu
    690                 695                 700

Ser Ile Val Asn Arg Val Arg Gln Gly Tyr Ser Pro Leu Ser Leu Gln
705                 710                 715                 720

Thr Leu Pro Pro Asn Pro Arg Glu Leu Asp Arg Leu Gly Gly Ile Glu
                725                 730                 735

Glu Glu Gly Gly Glu Gln Asp Arg Gly Arg Ser Val Arg Leu Val Ser
            740                 745                 750

Gly Phe Leu Pro Leu Ala Trp Asp Asp Leu Arg Ser Leu Cys Leu Phe
        755                 760                 765
```

Cys Tyr His Arg Leu Arg Asp Leu Leu Leu Ile Thr Thr Arg Ala Val
770 775 780

Glu Leu Leu Ala Arg Ser Ile Leu Lys Gly Leu Gln Arg Gly Trp Glu
785 790 795 800

Ile Leu Lys Tyr Leu Gly Ser Leu Val Gln Tyr Trp Gly Gln Glu Leu
805 810 815

Lys Lys Ser Ala Ile Asn Leu Leu Asp Thr Thr Ala Ile Ala Val Ala
820 825 830

Glu Ala Ala Asp Arg Ile Leu Glu Leu Leu Gln Arg Ile Trp Arg Gly
835 840 845

Ile Cys Asn Val Pro Thr Arg Ile Arg Gln Gly Phe Glu Ala Ala Leu
850 855 860

Gln
865

<210> SEQ ID NO 31
<211> LENGTH: 2532
<212> TYPE: DNA
<213> ORGANISM: Artificial Sequence
<220> FEATURE:
<223> OTHER INFORMATION: pGX1041 - Env Clade C tier 2 Du151.2 DNA Sequence

<400> SEQUENCE: 31
atgcgcgtgc gggagattct gcgaaactat cagcagtggt ggatttgggg gactctggga 60
ttctggatgc tgatgatttg taatgtggtg ggaaacctgt gggtgaccgt ctactatggc 120
gtgcccgtct ggaaagaggc caagaccaca ctgttttgcg cttctgacgc caaagcttac 180
gataaggaag tgcacaatgt ctgggctaca catgcatgtg tgcctactga ccctaatcca 240
caggagatcg tgctggaaaa cgtcacagag aatttcaaca tgtggaagaa cgacatggtg 300
gatcagatgc acgaggacat catttcactg tgggatcaga gcctgaaacc atgcgtgaag 360
ctgacccccc tgtgcgtcac actgaattgt actaacgcac ccgcctacaa caatagtatg 420
catggcgaaa tgaaaaattg tagcttcaac actaccacag agatcagaga caggaaacag 480
aaggcttacg cactgttcta taagcctgat gtggtcccac tgaatcggag agaggaaaac 540
aatgggaccg gagagtatat tctgatcaat tgcaacagct ccacaatcac tcaggcctgt 600
ccaaaggtga catttgatcc cattcctatc cactactgcg cccccgctgg ctatgctatt 660
ctgaaatgta acaataagac cttcaacggc acagggcctt gcaacaatgt cagtactgtc 720
cagtgtaccc atgggatcaa tccagtggtc tccacccagc tgctgctgaa cggatctctg 780
gccgaggaag agatcattat ccggagcgag aatctgacca acaacatcaa aacaatcatc 840
gtgcacctga acaagtcagt ggaaattgtc tgcacccgcc ctaacaataa cacaaggcgc 900
agcattcgaa tcggaccagg ccagacattc tacgcaactg gcgaaattat cgggaatatc 960
agggaggccc attgtaacat tagcaagtct agttggacct ccacactgga gcaggtgaag 1020
aaaaagctga aagaacacta caataagaca atcgagttca acccacctag cggaggggac 1080
ctggaagtga ctacccattc ctttaattgc agaggcgagt tcttttattg taacacaact 1140
aagctgttca gcaataacag tgattcaaat aacgagacta tcaccctgcc atgcaaaatt 1200
aagcagatta tcaacatgtg gcagaaagtg gggcgggcca tgtatgctcc acccatcgag 1260
ggaaatatta cctgtaaatc caacatcact ggcctgctgc tgaccagaga cggaggcaag 1320
aataccacaa acgagatttt taggcccggg ggaggcaata tgaaagataa ctggcgctcc 1380
gaactgtaca aatataaggt ggtcgagatc gaaccactgg gagtggcacc tactaaatct 1440
aagcgacggg tggtcgagcg agaaaagcga gctgtgggac tgggagcagt cctgctgggc 1500
ttcctgggag cagctggatc taccatggga gcagccagta tcacactgac tgtgcaggcc 1560
aggcagctgc tgtcagggat cgtccagcag cagagcaacc tgctgcgcgc aattgaggcc 1620
cagcagcaca tgctgcagct gactgtgtgg ggcatcaagc agctgcagac cagagtcctg 1680
gcaattgaaa ggtacctgaa agaccagcag ctgctgggac tgtggggatg cagcggaaag 1740
attatctgta ctaccgccgt gccttggaat tcaagctgga gcaacaagtc ccaggaggac 1800
atctgggata atatgacatg gatgcagtgg gaccgggaaa tctctaacta caccggcaca 1860
atctacagac tgctggagga tagtcagaat cagcaggaga aaaacgaaaa ggacctgctg 1920
gccctggatt cttggaaaaa tctgtggaac tggttcaata tcaccaactg gctgtggtac 1980
attaagatct ttattatgat cgtgggggga ctgatcggcc tgaggattat ctttggggtg 2040
ctggccattg tgaaacgcgt ccgacagggc tattctcccc tgagtttcca gactctgacc 2100
ccaagcccca gaggccctga cagactggga aggatcgaag aggaaggcgg ggagcaggat 2160
aagaatcgct ccattcgact ggtgtctggg ttcctggcac tggcctggga cgatctgcgg 2220
agtctgtgcc tgttttcata ccaccggctg agagacctga tcctggtggt caccagagct 2280
gtggaactgc tgggacgctc ctctctgcga ggactgcagc gaggatggga ggcactgaag 2340
tacctgggca acctggtgca gtatggaggc ctggaactga aaaggtccgc tatcaagctg 2400
tttgacacaa ttgctatcgc agtggccgaa gggactgatc gcatcctgga ggtcatccag 2460
cggatttgca gagccattag gcatattccc atcaggattc gccagggatt cgaggctgca 2520
ctgctgtgat aa 2532

<210> SEQ ID NO 32
<211> LENGTH: 842
<212> TYPE: PRT
<213> ORGANISM: Artificial Sequence
<220> FEATURE:
<223> OTHER INFORMATION: pGX1041 - Env Clade C tier 2 Du151.2 Amino Acid Sequence

<400> SEQUENCE: 32

Met Arg Val Arg Glu Ile Leu Arg Asn Tyr Gln Gln Trp Trp Ile Trp
1               5                   10                  15

Gly Thr Leu Gly Phe Trp Met Leu Met Ile Cys Asn Val Val Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Asp Lys Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Ala Pro Ala Tyr Asn Asn Ser Met His Gly Glu Met
    130                 135                 140

Lys Asn Cys Ser Phe Asn Thr Thr Thr Glu Ile Arg Asp Arg Lys Gln

```
145                 150                 155                 160

Lys Ala Tyr Ala Leu Phe Tyr Lys Pro Asp Val Val Pro Leu Asn Arg
                165                 170                 175

Arg Glu Glu Asn Asn Gly Thr Gly Glu Tyr Ile Leu Ile Asn Cys Asn
            180                 185                 190

Ser Ser Thr Ile Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Asn Pro Val Val Ser Thr Gln Leu Leu Leu
                245                 250                 255

Asn Gly Ser Leu Ala Glu Glu Glu Ile Ile Ile Arg Ser Glu Asn Leu
            260                 265                 270

Thr Asn Asn Ile Lys Thr Ile Ile Val His Leu Asn Lys Ser Val Glu
        275                 280                 285

Ile Val Cys Thr Arg Pro Asn Asn Asn Thr Arg Arg Ser Ile Arg Ile
    290                 295                 300

Gly Pro Gly Gln Thr Phe Tyr Ala Thr Gly Glu Ile Ile Gly Asn Ile
305                 310                 315                 320

Arg Glu Ala His Cys Asn Ile Ser Lys Ser Ser Trp Thr Ser Thr Leu
                325                 330                 335

Glu Gln Val Lys Lys Lys Leu Lys Glu His Tyr Asn Lys Thr Ile Glu
            340                 345                 350

Phe Asn Pro Pro Ser Gly Gly Asp Leu Glu Val Thr Thr His Ser Phe
        355                 360                 365

Asn Cys Arg Gly Glu Phe Phe Tyr Cys Asn Thr Thr Lys Leu Phe Ser
    370                 375                 380

Asn Asn Ser Asp Ser Asn Asn Glu Thr Ile Thr Leu Pro Cys Lys Ile
385                 390                 395                 400

Lys Gln Ile Ile Asn Met Trp Gln Lys Val Gly Arg Ala Met Tyr Ala
                405                 410                 415

Pro Pro Ile Glu Gly Asn Ile Thr Cys Lys Ser Asn Ile Thr Gly Leu
            420                 425                 430

Leu Leu Thr Arg Asp Gly Gly Lys Asn Thr Thr Asn Glu Ile Phe Arg
        435                 440                 445

Pro Gly Gly Gly Asn Met Lys Asp Asn Trp Arg Ser Glu Leu Tyr Lys
    450                 455                 460

Tyr Lys Val Val Glu Ile Glu Pro Leu Gly Val Ala Pro Thr Lys Ser
465                 470                 475                 480

Lys Arg Arg Val Val Glu Arg Glu Lys Arg Ala Val Gly Leu Gly Ala
                485                 490                 495

Val Leu Leu Gly Phe Leu Gly Ala Ala Gly Ser Thr Met Gly Ala Ala
            500                 505                 510

Ser Ile Thr Leu Thr Val Gln Ala Arg Gln Leu Leu Ser Gly Ile Val
        515                 520                 525

Gln Gln Gln Ser Asn Leu Leu Arg Ala Ile Glu Ala Gln Gln His Met
    530                 535                 540

Leu Gln Leu Thr Val Trp Gly Ile Lys Gln Leu Gln Thr Arg Val Leu
545                 550                 555                 560

Ala Ile Glu Arg Tyr Leu Lys Asp Gln Gln Leu Leu Gly Leu Trp Gly
                565                 570                 575
```

```
Cys Ser Gly Lys Ile Ile Cys Thr Thr Ala Val Pro Trp Asn Ser Ser
            580                 585                 590

Trp Ser Asn Lys Ser Gln Glu Asp Ile Trp Asp Asn Met Thr Trp Met
        595                 600                 605

Gln Trp Asp Arg Glu Ile Ser Asn Tyr Thr Gly Thr Ile Tyr Arg Leu
    610                 615                 620

Leu Glu Asp Ser Gln Asn Gln Gln Glu Lys Asn Glu Lys Asp Leu Leu
625                 630                 635                 640

Ala Leu Asp Ser Trp Lys Asn Leu Trp Asn Trp Phe Asn Ile Thr Asn
                645                 650                 655

Trp Leu Trp Tyr Ile Lys Ile Phe Ile Met Ile Val Gly Gly Leu Ile
            660                 665                 670

Gly Leu Arg Ile Ile Phe Gly Val Leu Ala Ile Val Lys Arg Val Arg
        675                 680                 685

Gln Gly Tyr Ser Pro Leu Ser Phe Gln Thr Leu Thr Pro Ser Pro Arg
    690                 695                 700

Gly Pro Asp Arg Leu Gly Arg Ile Glu Glu Glu Gly Gly Glu Gln Asp
705                 710                 715                 720

Lys Asn Arg Ser Ile Arg Leu Val Ser Gly Phe Leu Ala Leu Ala Trp
                725                 730                 735

Asp Asp Leu Arg Ser Leu Cys Leu Phe Ser Tyr His Arg Leu Arg Asp
            740                 745                 750

Leu Ile Leu Val Val Thr Arg Ala Val Glu Leu Leu Gly Arg Ser Ser
        755                 760                 765

Leu Arg Gly Leu Gln Arg Gly Trp Glu Ala Leu Lys Tyr Leu Gly Asn
    770                 775                 780

Leu Val Gln Tyr Gly Gly Leu Glu Leu Lys Arg Ser Ala Ile Lys Leu
785                 790                 795                 800

Phe Asp Thr Ile Ala Ile Ala Val Ala Glu Gly Thr Asp Arg Ile Leu
                805                 810                 815

Glu Val Ile Gln Arg Ile Cys Arg Ala Ile Arg His Ile Pro Ile Arg
            820                 825                 830

Ile Arg Gln Gly Phe Glu Ala Ala Leu Leu
        835                 840
```

<210> SEQ ID NO 33
<211> LENGTH: 2577
<212> TYPE: DNA
<213> ORGANISM: Artificial Sequence
<220> FEATURE:
<223> OTHER INFORMATION: pGX1042 - Env Clade C tier 2 Du156.12 DNA
      Sequence

<400> SEQUENCE: 33

```
atgagagtgc ggggcattcc tcgcaactgg cctcagtggt ggacctgggg cattctggga      60

ttctggatga ttattatgtg caaagtggcc gggaacagtt gggtgactgt ctactatgga     120

gtgcccgtct ggaccgaagc taagaccaca ctgttctgcg catctgacgc caaagcttac     180

gagaaggaag tgcacaatgt ctgggcaacc catgcctgtg tgcctacaga tcctaatcca     240

caggagatct tcctgaaaaa cgtgaccgaa aattttaaca tgtggaagaa cgacatggtc     300

gatcagatgc acgaggacat cattagcctg tgggatcagt ccctgaaacc ctgcgtgaag     360

ctgacccctc tgtgcgtgac actgaattgt gtcacttaca acaatagcat gaacagctcc     420

gctacctata acaattctat gaacggcgag atcaaaaatt gtagtttcaa cactaccaca     480
```

-continued

```
gaactgcgag acaagaaaca gaaggtgtac gccctgtttt ataggacaga tgtggtccct    540
ctgaacaaca acaacaacaa ctcagagtac atcctgatca attgcaacac tagcaccatt    600
acacaggctt gtcctaaagt gtccttcgac cccattccta tccactactg cgcaccagcc    660
ggctatgcca tcctgaagtg tacagataag aagttcaacg gcactgggtc ttgcaacaat    720
gtcagtactg tccagtgtac ccatgggatc aaaccagtgg tcagcaccca gctgctgctg    780
aacggcagcc tggcagagga agagatcatt atcaaatccg agaatctgac cgacaacatt    840
aagacaatta tcgtgcagct gaatcagtcc attggcatca actgcactag accaaacaat    900
aacacccgga agtctgtgag aatcggaccc ggccagacat tctatgccac tggggacatt    960
atcggagata ttcgccaggc tcactgtaac atctctcgaa atcagtggaa cgagaccctg   1020
gaacaggtga agaaaaagct gggagagcac ttccataacc agacaaaaat taagttcgag   1080
ccccccttctg gcggggatct ggaaatcact acccatagtt tcaactgcag aggcgaattc   1140
ttttactgta ataccgcaga cctgtttacc aacgccacaa aactggtgaa tgataccgag   1200
aacaaggccg tcattacaat cccatgccgc atcaagcaga ttatcaatat gtggcagggg   1260
gtgggacggg ctatgtatgc accacccatt gagggcaaca tcacatgtaa tagcaacatc   1320
actggactgc tgctgaccag ggacggagga ggaaatgtga cagagattaa ccgaactgaa   1380
atctttcggc ccggaggcgg gaatatgaaa gataattgga gaaacgagct gtacaaatat   1440
aaggtggtcg aaatcaagcc tctgggagtg gcaccaactg gcgccaaaag gaaggtggtc   1500
aaaagagaga agagggcagt gggactggga gctgtcctgt tcgggtttct gggagcagct   1560
ggctccacaa tgggagcagc ctctatcact ctgaccgctc aggcaagaca gctgctgagt   1620
gggattgtgc agcagcagtc aaacctgctg agggccatcg aagctcagca gcacatgctg   1680
cagctgaccg tgtggggcat taagcagctg caggctagag tcctggcaat cgagaggtac   1740
ctgaaagacc agcagctgct gggactgtgg ggatgctccg gcaagctgat ttgtacaact   1800
aatgtgccct ggaactctag ttggtccaac aagtctcaga ccgatatctg gaataacacc   1860
acatggatgc agtgggagag ggaaatttca aactacacag acactatcta tcgcctgctg   1920
gaggatagcc agaatcagca ggaagagaac gaaaaggacc tgctggccct ggatcgctgg   1980
cagaatctgt ggaactggtt cgacatcacc aattggctgt ggtacatcaa gatctttatt   2040
atgatcgtgg gaggcctgat tggcctgcgc attatcttcg ggtcctgag catcgtgaag   2100
cgagtccggg aaggctatag tcctctgtca tttcagaccc tgacaccaac tcccagaggc   2160
ctggaccgcc tgggacgaat tgaagaggaa gggggagagc aggacaagga tcggagcatc   2220
agactggtga acgggttcct ggccctggct tgggacgatc tgaggtcact gtgcctgttc   2280
agctaccatc agctgcggga ttttattctg atcgctgcaa gagctgtgga gctgctggga   2340
aggtcaagcc tgcgaggcct gcagaaaggg tgggaagcac tgaagtacct gggaaatctg   2400
attcagtatt ggggcctgga gctgaagcgg agagccatca acctgctgga cattagcgca   2460
atcgccgtgg ctgagggaac agaccgcatt atcgatattg tcctgaggac tggccgcgca   2520
attcgaaaca tcccaaggcg catccggcag ggatttggag caaccctgct gtgataa      2577
```

<210> SEQ ID NO 34
<211> LENGTH: 857
<212> TYPE: PRT
<213> ORGANISM: Artificial Sequence
<220> FEATURE:
<223> OTHER INFORMATION: pGX1042 - Env Clade C tier 2 Du156.12 Amino
      Acid Sequence

<400> SEQUENCE: 34

Met Arg Val Arg Gly Ile Pro Arg Asn Trp Pro Gln Trp Trp Thr Trp
1 5 10 15

Gly Ile Leu Gly Phe Trp Met Ile Ile Met Cys Lys Val Ala Gly Asn
20 25 30

Ser Trp Val Thr Val Tyr Tyr Gly Val Pro Val Trp Thr Glu Ala Lys
35 40 45

Thr Thr Leu Phe Cys Ala Ser Asp Ala Lys Ala Tyr Glu Lys Glu Val
50 55 60

His Asn Val Trp Ala Thr His Ala Cys Val Pro Thr Asp Pro Asn Pro
65 70 75 80

Gln Glu Ile Phe Leu Lys Asn Val Thr Glu Asn Phe Asn Met Trp Lys
85 90 95

Asn Asp Met Val Asp Gln Met His Glu Asp Ile Ile Ser Leu Trp Asp
100 105 110

Gln Ser Leu Lys Pro Cys Val Lys Leu Thr Pro Leu Cys Val Thr Leu
115 120 125

Asn Cys Val Thr Tyr Asn Asn Ser Met Asn Ser Ser Ala Thr Tyr Asn
130 135 140

Asn Ser Met Asn Gly Glu Ile Lys Asn Cys Ser Phe Asn Thr Thr Thr
145 150 155 160

Glu Leu Arg Asp Lys Lys Gln Lys Val Tyr Ala Leu Phe Tyr Arg Thr
165 170 175

Asp Val Val Pro Leu Asn Asn Asn Asn Asn Asn Ser Glu Tyr Ile Leu
180 185 190

Ile Asn Cys Asn Thr Ser Thr Ile Thr Gln Ala Cys Pro Lys Val Ser
195 200 205

Phe Asp Pro Ile Pro Ile His Tyr Cys Ala Pro Ala Gly Tyr Ala Ile
210 215 220

Leu Lys Cys Thr Asp Lys Lys Phe Asn Gly Thr Gly Ser Cys Asn Asn
225 230 235 240

Val Ser Thr Val Gln Cys Thr His Gly Ile Lys Pro Val Val Ser Thr
245 250 255

Gln Leu Leu Leu Asn Gly Ser Leu Ala Glu Glu Glu Ile Ile Ile Lys
260 265 270

Ser Glu Asn Leu Thr Asp Asn Ile Lys Thr Ile Ile Val Gln Leu Asn
275 280 285

Gln Ser Ile Gly Ile Asn Cys Thr Arg Pro Asn Asn Asn Thr Arg Lys
290 295 300

Ser Val Arg Ile Gly Pro Gly Gln Thr Phe Tyr Ala Thr Gly Asp Ile
305 310 315 320

Ile Gly Asp Ile Arg Gln Ala His Cys Asn Ile Ser Arg Asn Gln Trp
325 330 335

Asn Glu Thr Leu Glu Gln Val Lys Lys Lys Leu Gly Glu His Phe His
340 345 350

Asn Gln Thr Lys Ile Lys Phe Glu Pro Pro Ser Gly Gly Asp Leu Glu
355 360 365

Ile Thr Thr His Ser Phe Asn Cys Arg Gly Glu Phe Phe Tyr Cys Asn
370 375 380

Thr Ala Asp Leu Phe Thr Asn Ala Thr Lys Leu Val Asn Asp Thr Glu
385 390 395 400

Asn Lys Ala Val Ile Thr Ile Pro Cys Arg Ile Lys Gln Ile Ile Asn
405 410 415

```
Met Trp Gln Gly Val Gly Arg Ala Met Tyr Ala Pro Pro Ile Glu Gly
            420                 425                 430

Asn Ile Thr Cys Asn Ser Asn Ile Thr Gly Leu Leu Leu Thr Arg Asp
        435                 440                 445

Gly Gly Gly Asn Val Thr Glu Ile Asn Arg Thr Glu Ile Phe Arg Pro
    450                 455                 460

Gly Gly Gly Asn Met Lys Asp Asn Trp Arg Asn Glu Leu Tyr Lys Tyr
465                 470                 475                 480

Lys Val Val Glu Ile Lys Pro Leu Gly Val Ala Pro Thr Gly Ala Lys
                485                 490                 495

Arg Lys Val Val Lys Arg Glu Lys Arg Ala Val Gly Leu Gly Ala Val
            500                 505                 510

Leu Phe Gly Phe Leu Gly Ala Ala Gly Ser Thr Met Gly Ala Ala Ser
        515                 520                 525

Ile Thr Leu Thr Ala Gln Ala Arg Gln Leu Leu Ser Gly Ile Val Gln
    530                 535                 540

Gln Gln Ser Asn Leu Leu Arg Ala Ile Glu Ala Gln Gln His Met Leu
545                 550                 555                 560

Gln Leu Thr Val Trp Gly Ile Lys Gln Leu Gln Ala Arg Val Leu Ala
                565                 570                 575

Ile Glu Arg Tyr Leu Lys Asp Gln Gln Leu Leu Gly Leu Trp Gly Cys
            580                 585                 590

Ser Gly Lys Leu Ile Cys Thr Thr Asn Val Pro Trp Asn Ser Ser Trp
        595                 600                 605

Ser Asn Lys Ser Gln Thr Asp Ile Trp Asn Asn Thr Thr Trp Met Gln
    610                 615                 620

Trp Glu Arg Glu Ile Ser Asn Tyr Thr Asp Thr Ile Tyr Arg Leu Leu
625                 630                 635                 640

Glu Asp Ser Gln Asn Gln Gln Glu Glu Asn Glu Lys Asp Leu Leu Ala
                645                 650                 655

Leu Asp Arg Trp Gln Asn Leu Trp Asn Trp Phe Asp Ile Thr Asn Trp
            660                 665                 670

Leu Trp Tyr Ile Lys Ile Phe Ile Met Ile Val Gly Gly Leu Ile Gly
        675                 680                 685

Leu Arg Ile Ile Phe Gly Val Leu Ser Ile Val Lys Arg Val Arg Glu
    690                 695                 700

Gly Tyr Ser Pro Leu Ser Phe Gln Thr Leu Thr Pro Thr Pro Arg Gly
705                 710                 715                 720

Leu Asp Arg Leu Gly Arg Ile Glu Glu Glu Gly Gly Glu Gln Asp Lys
                725                 730                 735

Asp Arg Ser Ile Arg Leu Val Asn Gly Phe Leu Ala Leu Ala Trp Asp
            740                 745                 750

Asp Leu Arg Ser Leu Cys Leu Phe Ser Tyr His Gln Leu Arg Asp Phe
        755                 760                 765

Ile Leu Ile Ala Ala Arg Ala Val Glu Leu Leu Gly Arg Ser Ser Leu
    770                 775                 780

Arg Gly Leu Gln Lys Gly Trp Glu Ala Leu Lys Tyr Leu Gly Asn Leu
785                 790                 795                 800

Ile Gln Tyr Trp Gly Leu Glu Leu Lys Arg Arg Ala Ile Asn Leu Leu
                805                 810                 815

Asp Ile Ser Ala Ile Ala Val Ala Glu Gly Thr Asp Arg Ile Ile Asp
            820                 825                 830
```

```
Ile Val Leu Arg Thr Gly Arg Ala Ile Arg Asn Ile Pro Arg Arg Ile
        835                 840                 845

Arg Gln Gly Phe Gly Ala Thr Leu Leu
    850                 855


<210> SEQ ID NO 35
<211> LENGTH: 2586
<212> TYPE: DNA
<213> ORGANISM: Artificial Sequence
<220> FEATURE:
<223> OTHER INFORMATION: pGX1043 - Env Clade C tier 2 Du172.17 DNA
      Sequence

<400> SEQUENCE: 35

atgagagtga tggggattct gaggtcctat cagcagtggt ggatctgggg gattctggga     60

ttctggatgc tgatgatttg taatgtctgg ggcaacctgt gggtgaccgt ctactatggg    120

gtgcctgtct ggaaggaggc caaaaccaca ctgttctgcg cttccgacgc caaggctcat    180

aaagaggaag tccataacat ctgggcaaca cacgcctgtg tgccaactga tccaaacccc    240

caggagattg tgctgaagaa tgtcaccgaa aacttcaaca tgtggaagaa cgacatggtg    300

gatcagatgc atgaggacat catttctctg tgggatcaga gtctgaagcc ttgcgtgaaa    360

ctgacaccac tgtgcgtcac tctgaactgt tctgacgtga agatcaaagg cacaaatgcc    420

acttacaaca acgctaccta caacaacaac aacacaatca gtgacatgaa gaactgttca    480

ttcaatacta ccacagagat caccgataag aaaaagaaag aatacgcact gttttataag    540

ctggacgtgg tcgccctgga tggaaaagag accaacagca caaatagctc cgaataccgg    600

ctgatcaact gcaatactag tgcagtcacc caggcctgtc ccaaggtgtc attcgatcct    660

atcccaattc actactgcgc acctgccggc tatgccatcc tgaagtgtaa caacaagacc    720

ttcaacggga ctggaccatg caacaatgtg agcaccgtcc agtgtacaca tgggatcaag    780

cccgtggtct ccacccagct gctgctgaac ggatctctgg ctgaggaaga ggtggtcatt    840

aggttcgaga atctgacaaa caatgccaag atcattatcg tgcacctgaa cgagtccgtc    900

gaaatcaatt gcactcgccc aagcaacaat accagaaaat ccgtgaggat tggccccggg    960

cagactttct ttgctaccgg cgacattatc ggggatatca gacaggcaca ttgtaacatt   1020

tctaggaaga aatggaacac taccctgcag cgggtgaagg agaaactgaa ggaaaaattc   1080

cccaacaaga ctatccagtt tgccccttct agtggcgggg acctggagat tacaactcac   1140

agcttcaatt gcagaggcga attcttttac tgttatacat ccgatctgtt taacagcaca   1200

tacatgtcca acaatactgg aggcgctaat atcaccctgc agtgccggat taagcagatt   1260

atcagaatgt ggcagggagt gggccaggct atgtatgcac cccctatcgc cggaaacatt   1320

acctgtaaat ccaatatcac cggactgctg ctgacacgcg acggaggaaa ggagaaaaac   1380

gatactgaaa cctttcgacc aggaggagga gacatgcgag ataattggcg atctgagctg   1440

tacaagtata aagtggtcga aatcaagcca ctgggcattg ctcccgacaa ggcaaaacgg   1500

agagtggtcg agcgggaaaa aagagcagtg gggatcggag ccgtcttcct gggctttctg   1560

ggagcagctg gatctaccat gggagcagcc agtatgacac tgactgtgca ggccaggcag   1620

ctgctgtcag ggatcgtgca gcagcagagc aacctgctgc gcgccattga ggctcagcag   1680

catatgctgc agctgacagt gtgggggatc aagcagctgc agactagggt gctggccatt   1740

gaacgctacc tgaaggacca gcagctgctg ggcatctggg ggtgctctgg aaaactgatt   1800

tgtaccacag ctgtgccttg gaacgcatcc tggtctaata agagttatga agagatctgg   1860
```

```
ggcaacatga cctggatgca gtgggatagg gagatcaaca attacaccaa tacaatctac   1920

tcactgctgg aagagagcca gaaccagcag gagaagaatg aaaaagacct gctggctctg   1980

gatagttggg agtcactgtg gagctggttc aacatcacaa attggctgtg gtacatcagg   2040

atcttcatca tcattgtggg cgggctgatc ggactgcgca tcattttcgc cgtgctgtca   2100

attgtgaacc gagtccggca gggctattcc cctctgtctt ttcagactct gacccccagc   2160

cctagagagc cagacaggct ggggcgcatc gaagaggaag gaggcgaaca ggatagagcc   2220

aggagcgtgc ggctggtcaa tggattcctg gctctggcat gggaggacct gagatccctg   2280

tgcctgtttt cttaccaccg cctgcgagat ctgatcctga ttgctgcacg agccgctgca   2340

ctgctgggac ggtcaagcct gtggggactg cagaagggct gggaggccct gaaatacctg   2400

gggagtctgg tgcagtattg gggactggaa ctgaagaaaa gtgccatctc actgttcgac   2460

gccatcgcta ttactgtggc tgagggcacc gatcggatca ttaacatcgt gcagcgaatt   2520

agccgggcat tctacaatat ccccaggcgc attagacagg ggtttgaagc caccctgcag   2580

tgataa                                                              2586
```

<210> SEQ ID NO 36
<211> LENGTH: 860
<212> TYPE: PRT
<213> ORGANISM: Artificial Sequence
<220> FEATURE:
<223> OTHER INFORMATION: pGX1043 - Env Clade C tier 2 Du172.17 Amino Acid Sequence

<400> SEQUENCE: 36

```
Met Arg Val Met Gly Ile Leu Arg Ser Tyr Gln Gln Trp Trp Ile Trp
1               5                   10                  15

Gly Ile Leu Gly Phe Trp Met Leu Met Ile Cys Asn Val Trp Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala His Lys Glu Glu Val
    50                  55                  60

His Asn Ile Trp Ala Thr His Ala Cys Val Pro Thr Asp Pro Asn Pro
65                  70                  75                  80

Gln Glu Ile Val Leu Lys Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Ser Asp Val Lys Ile Lys Gly Thr Asn Ala Thr Tyr Asn Asn
    130                 135                 140

Ala Thr Tyr Asn Asn Asn Asn Thr Ile Ser Asp Met Lys Asn Cys Ser
145                 150                 155                 160

Phe Asn Thr Thr Thr Glu Ile Thr Asp Lys Lys Lys Lys Glu Tyr Ala
                165                 170                 175

Leu Phe Tyr Lys Leu Asp Val Val Ala Leu Asp Gly Lys Glu Thr Asn
            180                 185                 190

Ser Thr Asn Ser Ser Glu Tyr Arg Leu Ile Asn Cys Asn Thr Ser Ala
        195                 200                 205

Val Thr Gln Ala Cys Pro Lys Val Ser Phe Asp Pro Ile Pro Ile His
    210                 215                 220
```

-continued

```
Tyr Cys Ala Pro Ala Gly Tyr Ala Ile Leu Lys Cys Asn Asn Lys Thr
225                 230                 235                 240

Phe Asn Gly Thr Gly Pro Cys Asn Asn Val Ser Thr Val Gln Cys Thr
                245                 250                 255

His Gly Ile Lys Pro Val Val Ser Thr Gln Leu Leu Leu Asn Gly Ser
            260                 265                 270

Leu Ala Glu Glu Glu Val Val Ile Arg Phe Glu Asn Leu Thr Asn Asn
        275                 280                 285

Ala Lys Ile Ile Ile Val His Leu Asn Glu Ser Val Glu Ile Asn Cys
    290                 295                 300

Thr Arg Pro Ser Asn Asn Thr Arg Lys Ser Val Arg Ile Gly Pro Gly
305                 310                 315                 320

Gln Thr Phe Phe Ala Thr Gly Asp Ile Ile Gly Asp Ile Arg Gln Ala
                325                 330                 335

His Cys Asn Ile Ser Arg Lys Lys Trp Asn Thr Thr Leu Gln Arg Val
            340                 345                 350

Lys Glu Lys Leu Lys Glu Lys Phe Pro Asn Lys Thr Ile Gln Phe Ala
        355                 360                 365

Pro Ser Ser Gly Gly Asp Leu Glu Ile Thr Thr His Ser Phe Asn Cys
    370                 375                 380

Arg Gly Glu Phe Phe Tyr Cys Tyr Thr Ser Asp Leu Phe Asn Ser Thr
385                 390                 395                 400

Tyr Met Ser Asn Asn Thr Gly Gly Ala Asn Ile Thr Leu Gln Cys Arg
                405                 410                 415

Ile Lys Gln Ile Ile Arg Met Trp Gln Gly Val Gly Gln Ala Met Tyr
            420                 425                 430

Ala Pro Pro Ile Ala Gly Asn Ile Thr Cys Lys Ser Asn Ile Thr Gly
        435                 440                 445

Leu Leu Leu Thr Arg Asp Gly Gly Lys Glu Lys Asn Asp Thr Glu Thr
    450                 455                 460

Phe Arg Pro Gly Gly Gly Asp Met Arg Asp Asn Trp Arg Ser Glu Leu
465                 470                 475                 480

Tyr Lys Tyr Lys Val Val Glu Ile Lys Pro Leu Gly Ile Ala Pro Asp
                485                 490                 495

Lys Ala Lys Arg Arg Val Val Glu Arg Glu Lys Arg Ala Val Gly Ile
            500                 505                 510

Gly Ala Val Phe Leu Gly Phe Leu Gly Ala Ala Gly Ser Thr Met Gly
        515                 520                 525

Ala Ala Ser Met Thr Leu Thr Val Gln Ala Arg Gln Leu Leu Ser Gly
    530                 535                 540

Ile Val Gln Gln Gln Ser Asn Leu Leu Arg Ala Ile Glu Ala Gln Gln
545                 550                 555                 560

His Met Leu Gln Leu Thr Val Trp Gly Ile Lys Gln Leu Gln Thr Arg
                565                 570                 575

Val Leu Ala Ile Glu Arg Tyr Leu Lys Asp Gln Gln Leu Leu Gly Ile
            580                 585                 590

Trp Gly Cys Ser Gly Lys Leu Ile Cys Thr Thr Ala Val Pro Trp Asn
        595                 600                 605

Ala Ser Trp Ser Asn Lys Ser Tyr Glu Glu Ile Trp Gly Asn Met Thr
    610                 615                 620

Trp Met Gln Trp Asp Arg Glu Ile Asn Asn Tyr Thr Asn Thr Ile Tyr
625                 630                 635                 640

Ser Leu Leu Glu Glu Ser Gln Asn Gln Gln Glu Lys Asn Glu Lys Asp
```

```
                645                 650                 655

Leu Leu Ala Leu Asp Ser Trp Glu Ser Leu Trp Ser Trp Phe Asn Ile
            660                 665                 670

Thr Asn Trp Leu Trp Tyr Ile Arg Ile Phe Ile Ile Ile Val Gly Gly
        675                 680                 685

Leu Ile Gly Leu Arg Ile Ile Phe Ala Val Leu Ser Ile Val Asn Arg
    690                 695                 700

Val Arg Gln Gly Tyr Ser Pro Leu Ser Phe Gln Thr Leu Thr Pro Ser
705                 710                 715                 720

Pro Arg Glu Pro Asp Arg Leu Gly Arg Ile Glu Glu Glu Gly Gly Glu
                725                 730                 735

Gln Asp Arg Ala Arg Ser Val Arg Leu Val Asn Gly Phe Leu Ala Leu
            740                 745                 750

Ala Trp Glu Asp Leu Arg Ser Leu Cys Leu Phe Ser Tyr His Arg Leu
        755                 760                 765

Arg Asp Leu Ile Leu Ile Ala Ala Arg Ala Ala Ala Leu Leu Gly Arg
    770                 775                 780

Ser Ser Leu Trp Gly Leu Gln Lys Gly Trp Glu Ala Leu Lys Tyr Leu
785                 790                 795                 800

Gly Ser Leu Val Gln Tyr Trp Gly Leu Glu Leu Lys Lys Ser Ala Ile
                805                 810                 815

Ser Leu Phe Asp Ala Ile Ala Ile Thr Val Ala Glu Gly Thr Asp Arg
            820                 825                 830

Ile Ile Asn Ile Val Gln Arg Ile Ser Arg Ala Phe Tyr Asn Ile Pro
        835                 840                 845

Arg Arg Ile Arg Gln Gly Phe Glu Ala Thr Leu Gln
    850                 855                 860
```

<210> SEQ ID NO 37
<211> LENGTH: 2538
<212> TYPE: DNA
<213> ORGANISM: Artificial Sequence
<220> FEATURE:
<223> OTHER INFORMATION: pGX1018 - Env Clade C tier 2 Cap45.2.00.G3 DNA Sequence

<400> SEQUENCE: 37

```
atgcgcgtca gggggattct gcgaaactgg cctcagtggt ggatctggtc tattctgggc     60

ttctggatgc tgattatctg tagggtcatg ggaaacctgt gggtgactgt ctactatggc    120

gtgcctgtct ggaaagaggc taaggcaacc ctgttctgcg caagcgacgc ccgggcttac    180

gaaaaagagg tgcacaacgt ctgggcaacc catgcctgcg tgccaacaga tcctaaccca    240

caggaaatct atctgggaaa tgtgacagag aacttcaaca tgtggaagaa tgacatggtg    300

gatcagatgc acgaggacat catttcactg tgggatcaga gcctgaaacc atgcgtgaag    360

ctgacacccc tgtgcgtcac tctgagatgt actaacgcca ccatcaatgg ctcactgacc    420

gaggaagtga agaactgtag cttcaatatt accacagagc tgcgcgacaa gaaacagaaa    480

gcatacgccc tgttttatcg acctgatgtg gtcccactga ataagaactc cccctctggc    540

aacagctccg agtacattct gatcaattgc aacacttcca ccatcacaca ggcctgtccc    600

aaggtgtctt tcgaccccat tcctatccac tactgcgctc ctgcagggta tgctatcctg    660

aaatgtaaca acaagacctt caacgggact ggaccatgca acaacgtgag caccgtccag    720

tgtacacatg gcatcaaacc cgtggtctct acccagctgc tgctgaatgg gagtctggcc    780

gaggaagata tcattatcaa gtctgagaac ctgaccaaca atatcaaaac aattatcgtg    840
```

```
cacctgaata agtctgtgga aattgtctgc cggagaccta acaataacac acggaagagt    900

attagaatcg gcccagggca ggctttctat gcaactaacg acattatcgg cgatatcagg    960

caggcccatt gtaacattaa taactccact tggaatcgca ccctggaaca gatcaagaaa   1020

aagctgcgag agcacttcct gaatcggacc attgaatttg agccccctag tggcggggac   1080

ctggaagtga ctacccattc attcaactgc ggaggcgagt tcttttactg taacacaact   1140

aggctgttta aatggtctag taatgtgact aacgatacta ttaccatccc ctgccggatc   1200

aagcagttca ttaacatgtg gcagggagcc ggcagagcta tgtatgcacc acccatcgag   1260

gggaacatta cctgtaattc aagcatcact ggactgctgc tgacccgcga cggggggaaaa  1320

acagaccgaa acgatactga gatttttcgg cctggcgggg gaaacatgaa ggataactgg   1380

agaaacgaac tgtacaagta caaggtggtc gagatcaagc cactgggagt ggctcctacc   1440

gaggcaaggc gccgagtggt cgaacgagag aagcgagcag tgggaatcgg agctgtcctg   1500

ctgggcttcc tgggagcagc tggaagtaca atgggagcag cctcaatcac actgactgtg   1560

caggccaggc agctgctgag cggcatcgtc cagcagcagt ccaatctgct gcgcgccatt   1620

gaggctcagc agcacatgct gcagctgaca gtgtggggca tcaaacagct gcagactaga   1680

gtgctggcca ttgaaaggta cctgaaagac cagcagctgc tgggactgtg gggatgctct   1740

ggaaagctga tctgtaccac aaacgtgcca tggaattcct cttggagtaa caagtcacag   1800

actgacattt gggataatat gacctggatt cagtgggatc gggaaatcag caactactcc   1860

aacacaatct ataaactgct ggaggggagc cagaaccagc aggaacagaa tgagaaggac   1920

ctgctggccc tggatagctg gaataacctg tggaattggt tcaacatcac caattggctg   1980

tggtacatca agatctttat tatgatcatc ggcggactga tcgggctgag gattatcctg   2040

ggagtgctga gcattgtgaa gcgggtcaga cagggctatt ctcctctgag tttccagacc   2100

ctgacaccaa acccccgcgg actggataga ctgggcagga tcgaggaaga gggaggcgag   2160

caggacaagg atcgcagcat tcgactggtg aatgggtttc tggccctggc ttgggaagac   2220

ctgcggtccc tgtgcctgtt ctcttaccat aggctgcgcg acttcatcct gattgcagtg   2280

agagccgtcg aactgctggg aagttcaagc ctgaggggac tgcagcgagg atgggaggca   2340

ctgaagtacc tgggcagcct gctgcagtat tgggggctgg aactgaaaaa gtccgctatc   2400

aacctgctgg acaccgtggc aattgccgtc gctgaaggca cagatagaat tatcgagctg   2460

atccagagga tttgtcgcgc tatccgcaat atcccccgcc gcatccgcca gggctttgaa   2520

gccgctctgc tgtgataa                                                 2538
```

<210> SEQ ID NO 38
<211> LENGTH: 844
<212> TYPE: PRT
<213> ORGANISM: Artificial Sequence
<220> FEATURE:
<223> OTHER INFORMATION: pGX1018 - Env Clade C tier 2 Cap45.2.00.G3
      Amino Acid Sequence

<400> SEQUENCE: 38

```
Met Arg Val Arg Gly Ile Leu Arg Asn Trp Pro Gln Trp Trp Ile Trp
1               5                   10                  15

Ser Ile Leu Gly Phe Trp Met Leu Ile Ile Cys Arg Val Met Gly Asn
            20                  25                  30

Leu Trp Val Thr Val Tyr Tyr Gly Val Pro Val Trp Lys Glu Ala Lys
        35                  40                  45
```

-continued

```
Ala Thr Leu Phe Cys Ala Ser Asp Ala Arg Ala Tyr Glu Lys Glu Val
    50                  55                  60

His Asn Val Trp Ala Thr His Ala Cys Val Pro Thr Asp Pro Asn Pro
65                  70                  75                  80

Gln Glu Ile Tyr Leu Gly Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Arg Cys Thr Asn Ala Thr Ile Asn Gly Ser Leu Thr Glu Glu Val Lys
    130                 135                 140

Asn Cys Ser Phe Asn Ile Thr Thr Glu Leu Arg Asp Lys Lys Gln Lys
145                 150                 155                 160

Ala Tyr Ala Leu Phe Tyr Arg Pro Asp Val Val Pro Leu Asn Lys Asn
                165                 170                 175

Ser Pro Ser Gly Asn Ser Ser Glu Tyr Ile Leu Ile Asn Cys Asn Thr
            180                 185                 190

Ser Thr Ile Thr Gln Ala Cys Pro Lys Val Ser Phe Asp Pro Ile Pro
        195                 200                 205

Ile His Tyr Cys Ala Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Asp Ile Ile Ile Lys Ser Glu Asn Leu Thr
            260                 265                 270

Asn Asn Ile Lys Thr Ile Ile Val His Leu Asn Lys Ser Val Glu Ile
        275                 280                 285

Val Cys Arg Arg Pro Asn Asn Asn Thr Arg Lys Ser Ile Arg Ile Gly
    290                 295                 300

Pro Gly Gln Ala Phe Tyr Ala Thr Asn Asp Ile Ile Gly Asp Ile Arg
305                 310                 315                 320

Gln Ala His Cys Asn Ile Asn Asn Ser Thr Trp Asn Arg Thr Leu Glu
                325                 330                 335

Gln Ile Lys Lys Lys Leu Arg Glu His Phe Leu Asn Arg Thr Ile Glu
            340                 345                 350

Phe Glu Pro Pro Ser Gly Gly Asp Leu Glu Val Thr Thr His Ser Phe
        355                 360                 365

Asn Cys Gly Gly Glu Phe Phe Tyr Cys Asn Thr Thr Arg Leu Phe Lys
    370                 375                 380

Trp Ser Ser Asn Val Thr Asn Asp Thr Ile Thr Ile Pro Cys Arg Ile
385                 390                 395                 400

Lys Gln Phe Ile Asn Met Trp Gln Gly Ala Gly Arg Ala Met Tyr Ala
                405                 410                 415

Pro Pro Ile Glu Gly Asn Ile Thr Cys Asn Ser Ser Ile Thr Gly Leu
            420                 425                 430

Leu Leu Thr Arg Asp Gly Gly Lys Thr Asp Arg Asn Asp Thr Glu Ile
        435                 440                 445

Phe Arg Pro Gly Gly Gly Asn Met Lys Asp Asn Trp Arg Asn Glu Leu
    450                 455                 460

Tyr Lys Tyr Lys Val Val Glu Ile Lys Pro Leu Gly Val Ala Pro Thr
```

```
465                 470                 475                 480

Glu Ala Arg Arg Arg Val Val Glu Arg Glu Lys Arg Ala Val Gly Ile
                485                 490                 495

Gly Ala Val Leu Leu Gly Phe Leu Gly Ala Ala Gly Ser Thr Met Gly
            500                 505                 510

Ala Ala Ser Ile Thr Leu Thr Val Gln Ala Arg Gln Leu Leu Ser Gly
        515                 520                 525

Ile Val Gln Gln Gln Ser Asn Leu Leu Arg Ala Ile Glu Ala Gln Gln
    530                 535                 540

His Met Leu Gln Leu Thr Val Trp Gly Ile Lys Gln Leu Gln Thr Arg
545                 550                 555                 560

Val Leu Ala Ile Glu Arg Tyr Leu Lys Asp Gln Gln Leu Leu Gly Leu
                565                 570                 575

Trp Gly Cys Ser Gly Lys Leu Ile Cys Thr Thr Asn Val Pro Trp Asn
            580                 585                 590

Ser Ser Trp Ser Asn Lys Ser Gln Thr Asp Ile Trp Asp Asn Met Thr
        595                 600                 605

Trp Ile Gln Trp Asp Arg Glu Ile Ser Asn Tyr Ser Asn Thr Ile Tyr
    610                 615                 620

Lys Leu Leu Glu Gly Ser Gln Asn Gln Gln Glu Gln Asn Glu Lys Asp
625                 630                 635                 640

Leu Leu Ala Leu Asp Ser Trp Asn Asn Leu Trp Asn Trp Phe Asn Ile
                645                 650                 655

Thr Asn Trp Leu Trp Tyr Ile Lys Ile Phe Ile Met Ile Ile Gly Gly
            660                 665                 670

Leu Ile Gly Leu Arg Ile Ile Leu Gly Val Leu Ser Ile Val Lys Arg
        675                 680                 685

Val Arg Gln Gly Tyr Ser Pro Leu Ser Phe Gln Thr Leu Thr Pro Asn
    690                 695                 700

Pro Arg Gly Leu Asp Arg Leu Gly Arg Ile Glu Glu Glu Gly Gly Glu
705                 710                 715                 720

Gln Asp Lys Asp Arg Ser Ile Arg Leu Val Asn Gly Phe Leu Ala Leu
                725                 730                 735

Ala Trp Glu Asp Leu Arg Ser Leu Cys Leu Phe Ser Tyr His Arg Leu
            740                 745                 750

Arg Asp Phe Ile Leu Ile Ala Val Arg Ala Val Glu Leu Leu Gly Ser
        755                 760                 765

Ser Ser Leu Arg Gly Leu Gln Arg Gly Trp Glu Ala Leu Lys Tyr Leu
    770                 775                 780

Gly Ser Leu Leu Gln Tyr Trp Gly Leu Glu Leu Lys Lys Ser Ala Ile
785                 790                 795                 800

Asn Leu Leu Asp Thr Val Ala Ile Ala Val Ala Glu Gly Thr Asp Arg
                805                 810                 815

Ile Ile Glu Leu Ile Gln Arg Ile Cys Arg Ala Ile Arg Asn Ile Pro
            820                 825                 830

Arg Arg Ile Arg Gln Gly Phe Glu Ala Ala Leu Leu
        835                 840
```

<210> SEQ ID NO 39
<211> LENGTH: 2511
<212> TYPE: DNA
<213> ORGANISM: Artificial Sequence
<220> FEATURE:
<223> OTHER INFORMATION: pGX1022 - Env Clade C tier 2 ZM233M.PB6 DNA
Sequence

<400> SEQUENCE: 39
atgcgcgtgc gggggattat gaggaactgg cagcagtggt ggatctgggg aagtctggga 60
ttctggatgc tgattatctg taacgtgatg ggtccctgt gggtgacagt ctactatgga 120
gtgcctgtct ggagggaggc caagaccaca ctgttctgcg ctagcgatgc taaagcatac 180
gagactgaag cccactccgt gtgggcaaca catgcctgcg tgccaactga cccaaatccc 240
caggagatgg tgctggaaaa cgtcacagag aacttcaaca tgtggaagaa cgacatggtg 300
gatcagatgc acgaggacgt gatctctatt tgggatcaga gtctgaagcc ttgcgtgaaa 360
ctgaccccac tgtgcgtcac actggattgt agcacataca acaacactca taacatcagc 420
aaggaaatga agatctgttc cttcaacatg actaccgagc tgagggataa gaaacgcaaa 480
gtgaatgtcc tgttttacaa actggacctg gtgcccctga ccaatagctc caacacaact 540
aattatcggc tgatcagctg caacacctcc acaattactc aggcttgtcc caaggtgagt 600
ttcgatccta tcccaattca ctactgcgcc cctgctggct atgcaatcct gaagtgtaac 660
aacaagacct tcaacgggac aggaccatgc aacaacgtga gcactgtcca gtgtacccat 720
ggcatcaagc ccgtggtctc aactcagctg ctgctgaacg ggagcctggc cgaggaagag 780
atcattatca ggttcgaaaa cctgaccgac aatgtgaaga ttatcattgt ccagctgaac 840
gagacaatca atattacctg cacacgccca aacaataaca ctcgaaaatc catccggatt 900
ggccccgggc agtcttttta cgccacaggc gaaatcgtgg ggaacattag agaggctcac 960
tgtaatatct ctgcatccaa gtggaacaaa accctggaaa gagtgaggac aaagctgaaa 1020
gagcacttcc ccaataagac catcgagttt gaaccttcta gtggcgggga cctggaaatt 1080
accacacatt ccttcaattg cggaggcgag ttcttttact gtaacacctc aggactgttt 1140
aacagcgcca tcaatggcac tctgacctct aatgtgacac tgccctgccg gattaagcag 1200
atcattaaca tgtggcagga agtgggcaga gctatgtatg cacccccctat cgctgggaac 1260
attacctgta aatccaatat cactggactg ctgctgacca gggatggggg agaaaactca 1320
agctccacta ccgagacatt ccgacctact ggcggggaca tgaagaataa ctggagaagc 1380
gaactgtaca agtataaagt ggtcgagatc aaaccactgg gcattgcacc caccgaggca 1440
aagcgaagag tggtcgagcg agaaaaaaga gcagtgggaa tcggcgccgt cttcctgggg 1500
tttctgggag ccgctggcag tacaatgggg gcagcctcaa tgacactgac tgtgcaggcc 1560
cgccagctgc tgtctggaat cgtgcagcag cagagtaacc tgctgaaggc cattgaagct 1620
cagcagcaca tgctgcagct gaccgtgtgg ggcatcaaac agctgcaggc tcgcgtgctg 1680
gcaattgagc gatacctgaa ggatcagcag ctgctggggc tgtggggatg ctcaggcaaa 1740
ctgatctgta caactaacgt gccatggaat gcctcatgga gcaacaagag caaaaaatgac 1800
atttgggata atatgacatg gatgcagtgg gacagggaaa tctctaacca taccgataca 1860
atctaccgcc tgctggagga cagtcagaac cagcaggaga agaatgaaaa agacctgctg 1920
gccctggata gttggaagaa cctgtggaat tggttctcaa tcaccaagtg gctgtggtac 1980
atcaaaatct tcatcatgat tgtgggaggc ctgatcggcc tgcggatcat tttcgctgtg 2040
ctgtccattg tgaatcgcgt ccgacaggga tattcccctc tgtcttttca gactctgacc 2100
cccaacccta gaggcccaga taggctgggc ggcatcgaag aggaaggcgg ggagcaggac 2160
aagaacaaaa gcaggcgcct ggtgactggc ttcctgcctg tggtctggga cgatctgaga 2220
tccctgtgcc tgttctctta ccacctgctg agggacttta tcctgattgt ggcacgaacc 2280

```
gtcgaactgc tggggcgacg gggatgggag gccctgaagt acctgggagg cctggtgcag   2340

tattggggcc tggagctgaa gaaaagtact atctcactgc tggataccat cgccattgtg   2400

gtcgctgaag ggaccgaccg gatcattgag gtgctgcaga gaatcggccg agccatctac   2460

aatatcccaa gacgcattcg ccagggattt gagaccgctc tgctgtgata a            2511


<210> SEQ ID NO 40
<211> LENGTH: 835
<212> TYPE: PRT
<213> ORGANISM: Artificial Sequence
<220> FEATURE:
<223> OTHER INFORMATION: pGX1022 - Env Clade C tier 2 ZM233M.PB6 Amino
      Acid Sequence

<400> SEQUENCE: 40

Met Arg Val Arg Gly Ile Met Arg Asn Trp Gln Gln Trp Trp Ile Trp
1               5                   10                  15

Gly Ser Leu Gly Phe Trp Met Leu Ile Ile Cys Asn Val Met Gly Ser
            20                  25                  30

Leu Trp Val Thr Val Tyr Tyr Gly Val Pro Val Trp Arg Glu Ala Lys
        35                  40                  45

Thr Thr Leu Phe Cys Ala Ser Asp Ala Lys Ala Tyr Glu Thr Glu Ala
    50                  55                  60

His Ser Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Val Ile Ser Ile Trp Asp
            100                 105                 110

Gln Ser Leu Lys Pro Cys Val Lys Leu Thr Pro Leu Cys Val Thr Leu
        115                 120                 125

Asp Cys Ser Thr Tyr Asn Asn Thr His Asn Ile Ser Lys Glu Met Lys
    130                 135                 140

Ile Cys Ser Phe Asn Met Thr Thr Glu Leu Arg Asp Lys Lys Arg Lys
145                 150                 155                 160

Val Asn Val Leu Phe Tyr Lys Leu Asp Leu Val Pro Leu Thr Asn Ser
                165                 170                 175

Ser Asn Thr Thr Asn Tyr Arg Leu Ile Ser Cys Asn Thr Ser Thr Ile
            180                 185                 190

Thr Gln Ala Cys Pro Lys Val Ser Phe Asp Pro Ile Pro Ile His Tyr
        195                 200                 205

Cys Ala Pro Ala Gly Tyr Ala Ile Leu Lys Cys Asn Asn Lys Thr Phe
    210                 215                 220

Asn Gly Thr Gly Pro Cys Asn Asn Val Ser Thr Val Gln Cys Thr His
225                 230                 235                 240

Gly Ile Lys Pro Val Val Ser Thr Gln Leu Leu Leu Asn Gly Ser Leu
                245                 250                 255

Ala Glu Glu Glu Ile Ile Ile Arg Phe Glu Asn Leu Thr Asp Asn Val
            260                 265                 270

Lys Ile Ile Ile Val Gln Leu Asn Glu Thr Ile Asn Ile Thr Cys Thr
        275                 280                 285

Arg Pro Asn Asn Asn Thr Arg Lys Ser Ile Arg Ile Gly Pro Gly Gln
    290                 295                 300

Ser Phe Tyr Ala Thr Gly Glu Ile Val Gly Asn Ile Arg Glu Ala His
305                 310                 315                 320
```

-continued

```
Cys Asn Ile Ser Ala Ser Lys Trp Asn Lys Thr Leu Glu Arg Val Arg
                325                 330                 335

Thr Lys Leu Lys Glu His Phe Pro Asn Lys Thr Ile Glu Phe Glu Pro
            340                 345                 350

Ser Ser Gly Gly Asp Leu Glu Ile Thr Thr His Ser Phe Asn Cys Gly
        355                 360                 365

Gly Glu Phe Phe Tyr Cys Asn Thr Ser Gly Leu Phe Asn Ser Ala Ile
    370                 375                 380

Asn Gly Thr Leu Thr Ser Asn Val Thr Leu Pro Cys Arg Ile Lys Gln
385                 390                 395                 400

Ile Ile Asn Met Trp Gln Glu Val Gly Arg Ala Met Tyr Ala Pro Pro
                405                 410                 415

Ile Ala Gly Asn Ile Thr Cys Lys Ser Asn Ile Thr Gly Leu Leu Leu
            420                 425                 430

Thr Arg Asp Gly Gly Glu Asn Ser Ser Ser Thr Thr Glu Thr Phe Arg
        435                 440                 445

Pro Thr Gly Gly Asp Met Lys Asn Asn Trp Arg Ser Glu Leu Tyr Lys
    450                 455                 460

Tyr Lys Val Val Glu Ile Lys Pro Leu Gly Ile Ala Pro Thr Glu Ala
465                 470                 475                 480

Lys Arg Arg Val Val Glu Arg Glu Lys Arg Ala Val Gly Ile Gly Ala
                485                 490                 495

Val Phe Leu Gly Phe Leu Gly Ala Ala Gly Ser Thr Met Gly Ala Ala
            500                 505                 510

Ser Met Thr Leu Thr Val Gln Ala Arg Gln Leu Leu Ser Gly Ile Val
        515                 520                 525

Gln Gln Gln Ser Asn Leu Leu Lys Ala Ile Glu Ala Gln Gln His Met
    530                 535                 540

Leu Gln Leu Thr Val Trp Gly Ile Lys Gln Leu Gln Ala Arg Val Leu
545                 550                 555                 560

Ala Ile Glu Arg Tyr Leu Lys Asp Gln Gln Leu Leu Gly Leu Trp Gly
                565                 570                 575

Cys Ser Gly Lys Leu Ile Cys Thr Thr Asn Val Pro Trp Asn Ala Ser
            580                 585                 590

Trp Ser Asn Lys Ser Lys Asn Asp Ile Trp Asp Asn Met Thr Trp Met
        595                 600                 605

Gln Trp Asp Arg Glu Ile Ser Asn His Thr Asp Thr Ile Tyr Arg Leu
    610                 615                 620

Leu Glu Asp Ser Gln Asn Gln Gln Glu Lys Asn Glu Lys Asp Leu Leu
625                 630                 635                 640

Ala Leu Asp Ser Trp Lys Asn Leu Trp Asn Trp Phe Ser Ile Thr Lys
                645                 650                 655

Trp Leu Trp Tyr Ile Lys Ile Phe Ile Met Ile Val Gly Gly Leu Ile
            660                 665                 670

Gly Leu Arg Ile Ile Phe Ala Val Leu Ser Ile Val Asn Arg Val Arg
        675                 680                 685

Gln Gly Tyr Ser Pro Leu Ser Phe Gln Thr Leu Thr Pro Asn Pro Arg
    690                 695                 700

Gly Pro Asp Arg Leu Gly Gly Ile Glu Glu Glu Gly Gly Glu Gln Asp
705                 710                 715                 720

Lys Asn Lys Ser Arg Arg Leu Val Thr Gly Phe Leu Pro Val Val Trp
                725                 730                 735

Asp Asp Leu Arg Ser Leu Cys Leu Phe Ser Tyr His Leu Leu Arg Asp
```

-continued

```
            740                 745                 750

Phe Ile Leu Ile Val Ala Arg Thr Val Glu Leu Leu Gly Arg Arg Gly
        755                 760                 765

Trp Glu Ala Leu Lys Tyr Leu Gly Gly Leu Val Gln Tyr Trp Gly Leu
    770                 775                 780

Glu Leu Lys Lys Ser Thr Ile Ser Leu Leu Asp Thr Ile Ala Ile Val
785                 790                 795                 800

Val Ala Glu Gly Thr Asp Arg Ile Ile Glu Val Leu Gln Arg Ile Gly
                805                 810                 815

Arg Ala Ile Tyr Asn Ile Pro Arg Arg Ile Arg Gln Gly Phe Glu Thr
            820                 825                 830

Ala Leu Leu
        835


<210> SEQ ID NO 41
<211> LENGTH: 2565
<212> TYPE: DNA
<213> ORGANISM: Artificial Sequence
<220> FEATURE:
<223> OTHER INFORMATION: pGX1023 - Env Clade C tier 2 ZM249M.PL1 DNA
      Sequence

<400> SEQUENCE: 41

atgagagtga tggggattct gaggaactgt cagccctggt ggatctggag tattctggga      60

ttctggatgc tgatgaactg tagcggcaac ctgtgggtga ccgtctacta tggcgtgcct     120

gtctggaggg aggccaagac cacactgttc tgcgctagcg acgccaaggc ttacgaaaaa     180

gaggtgcaca acgtgtgggt cacccatgcc tgcgtgccaa cagatccaaa cccccaggaa     240

atgaatctgg agaacgtgac agaaaacttc aacatgtgga aaaacgacat ggtggatcag     300

atgcacgagg acatcattag cctgtgggat cagtccctga agccttgcgt gaaactgaca     360

ccactgtgcg tcactctgaa ctgtaacaat gtgaatgtca cacataactc aacttacaac     420

aataccgaag gggagcagat caagaattgt agcttcaaca ttactaccga gctgcgggac     480

aagaaacaga aggtgtacgc cctgttttat aaactggaca tcctgcccct gaatggaaac     540

aatgatagca acgaatatag actgatcaat tgcaacacaa gcgccattac tcaggcatgt     600

cccaaagtgt ccttcgatcc tatcccaatt cactactgcg cacctgccgg ctatgctatc     660

ctgaagtgta acaacaagac cttcaacgga aagggcccat gcaacaacgt gagcaccgtc     720

cagtgtacac atggcatcaa gcccgtggtc tccacccagc tgctgctgaa cggctctctg     780

gccgaaaagg agatcattat caggagtgag aacatcacag acaacgtgaa gatcatcatc     840

gtccacctga atgaatccgt ggagattaac tgcactcgcc caaacaataa caccaggaag     900

tctatccgca ttgggcccgg acagactttc tacgcaaccg gggagatcat tggaaagatc     960

cgggaagccc attgtaatat ttccaaggag aaatggaaca aaaccctgct gcgagtggct    1020

aagaaactgc gggaacactt ccccggaaag gcaatcaaat ttgagcctag ctccggcggg    1080

gacctggaaa ttacaactca tagcttcaat tgcagaggcg agttctttta ctgtaccaca    1140

tctaagctgt ttaacagtac atacaacccc aacgatactg agtctaatag taataacagc    1200

aacgaaacac tgactctgac ctgcaagatc aaacagatca ttaatatgtg gcagggagtg    1260

ggacgagcaa tgtatgctcc ccctatcgag gggtcaatta cctgtaacag cacaatcact    1320

ggactgctgc tgaccagaga cggaggcagc aagaataaca cagaggaaat cttccggcct    1380

gggggaggca atatgaaaga taactggcgc tccgagctgt acaagtataa agtggtcgaa    1440
```

-continued

```
atcaagccac tgggagtggc accaactgag gctaagcgaa gagtggtcga acgcgagaaa   1500

cgagctgtgg gactgggcgc agtcttcctg ggtttctgg  gagcagctgg ctccacaatg   1560

ggagcagcct ctatcaccct gacagtgcag gccaggcagc tgctgtctgg aatcgtccag   1620

cagcagaata acctgctgcg cgcaattgag gcccagcagc acatgctgca gctgaccgtg   1680

tggggcatca agcagctgca ggcaagagtc ctggccattg aaaggtacct gaaggaccag   1740

cagctgctgg ggatctgggg atgcagtggc aaactgattt gtactacctc agtgccctgg   1800

aatacatcat ggagcaacaa gagtaaagcc gagatctggg acaacatgac ttggatgcag   1860

tgggataagg aaatctcaaa ttacactcag accatctaca acctgctgga ggaatcccag   1920

tctcagcagg aaaagaatga gaaagacctg ctggagctgg attcttggaa taacctgtgg   1980

aactggttcg acatcagtaa gtggctgtgg tacatcaaaa tcttcatcat gattgtgggc   2040

ggcctgatcg gcctgaggat cattttcgcc gtgctgtcca ttgtgaatag ggtccgccag   2100

gggtatagtc ctctgtcatt tcagatcctg accccaaacc ctcgcggacc agatcgactg   2160

ggcagaattg aggaagaggg cggggagcag gaccgagatc ggtctgtgcg actggccaat   2220

gggttcctgg ctctggcatg ggaagacctg agaaacctgt gcctgttctt ttaccacaga   2280

ctgagggatt tcatcctgat tgctgcacgc acagtggagc tgctgcgaca gatcagcttt   2340

aagggcctgc agcgggggtg ggaagctctg aaatacctgg gcagtctggt gcagtattgg   2400

tcacaggaac tgaaggagag cgccatcaat ctgctgaaca ctatcgccat tgctgtggca   2460

gagggcaccg atcggatcat tgaagtggtc cagagagggt ttcgcgccat cctgaatgtc   2520

cccacccgca tccgccaggg cctggagaga gcactgctgt gataa                   2565
```

<210> SEQ ID NO 42
<211> LENGTH: 853
<212> TYPE: PRT
<213> ORGANISM: Artificial Sequence
<220> FEATURE:
<223> OTHER INFORMATION: pGX1023 - Env Clade C tier 2 ZM249M.PL1 Amino
      Acid Sequence

<400> SEQUENCE: 42

```
Met Arg Val Met Gly Ile Leu Arg Asn Cys Gln Pro Trp Trp Ile Trp
1               5                   10                  15

Ser Ile Leu Gly Phe Trp Met Leu Met Asn Cys Ser Gly Asn Leu Trp
            20                  25                  30

Val Thr Val Tyr Tyr Gly Val Pro Val Trp Arg Glu Ala Lys Thr Thr
        35                  40                  45

Leu Phe Cys Ala Ser Asp Ala Lys Ala Tyr Glu Lys Glu Val His Asn
    50                  55                  60

Val Trp Val Thr His Ala Cys Val Pro Thr Asp Pro Asn Pro Gln Glu
65                  70                  75                  80

Met Asn Leu Glu Asn Val Thr Glu Asn Phe Asn Met Trp Lys Asn Asp
                85                  90                  95

Met Val Asp Gln Met His Glu Asp Ile Ile Ser Leu Trp Asp Gln Ser
            100                 105                 110

Leu Lys Pro Cys Val Lys Leu Thr Pro Leu Cys Val Thr Leu Asn Cys
        115                 120                 125

Asn Asn Val Asn Val Thr His Asn Ser Thr Tyr Asn Asn Thr Glu Gly
    130                 135                 140

Glu Gln Ile Lys Asn Cys Ser Phe Asn Ile Thr Thr Glu Leu Arg Asp
145                 150                 155                 160
```

-continued

```
Lys Lys Gln Lys Val Tyr Ala Leu Phe Tyr Lys Leu Asp Ile Leu Pro
                165                 170                 175

Leu Asn Gly Asn Asn Asp Ser Asn Glu Tyr Arg Leu Ile Asn Cys Asn
            180                 185                 190

Thr Ser Ala Ile Thr Gln Ala Cys Pro Lys Val Ser Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Lys Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Lys Glu Ile Ile Ile Arg Ser Glu Asn Ile
            260                 265                 270

Thr Asp Asn Val Lys Ile Ile Ile Val His Leu Asn Glu Ser Val Glu
        275                 280                 285

Ile Asn Cys Thr Arg Pro Asn Asn Asn Thr Arg Lys Ser Ile Arg Ile
    290                 295                 300

Gly Pro Gly Gln Thr Phe Tyr Ala Thr Gly Glu Ile Ile Gly Lys Ile
305                 310                 315                 320

Arg Glu Ala His Cys Asn Ile Ser Lys Glu Lys Trp Asn Lys Thr Leu
                325                 330                 335

Leu Arg Val Ala Lys Lys Leu Arg Glu His Phe Pro Gly Lys Ala Ile
            340                 345                 350

Lys Phe Glu Pro Ser Ser Gly Gly Asp Leu Glu Ile Thr Thr His Ser
        355                 360                 365

Phe Asn Cys Arg Gly Glu Phe Phe Tyr Cys Thr Thr Ser Lys Leu Phe
    370                 375                 380

Asn Ser Thr Tyr Asn Pro Asn Asp Thr Glu Ser Asn Ser Asn Asn Ser
385                 390                 395                 400

Asn Glu Thr Leu Thr Leu Thr Cys Lys Ile Lys Gln Ile Ile Asn Met
                405                 410                 415

Trp Gln Gly Val Gly Arg Ala Met Tyr Ala Pro Pro Ile Glu Gly Ser
            420                 425                 430

Ile Thr Cys Asn Ser Thr Ile Thr Gly Leu Leu Leu Thr Arg Asp Gly
        435                 440                 445

Gly Ser Lys Asn Asn Thr Glu Glu Ile Phe Arg Pro Gly Gly Gly Asn
    450                 455                 460

Met Lys Asp Asn Trp Arg Ser Glu Leu Tyr Lys Tyr Lys Val Val Glu
465                 470                 475                 480

Ile Lys Pro Leu Gly Val Ala Pro Thr Glu Ala Lys Arg Arg Val Val
                485                 490                 495

Glu Arg Glu Lys Arg Ala Val Gly Leu Gly Ala Val Phe Leu Gly Phe
            500                 505                 510

Leu Gly Ala Ala Gly Ser Thr Met Gly Ala Ala Ser Ile Thr Leu Thr
        515                 520                 525

Val Gln Ala Arg Gln Leu Leu Ser Gly Ile Val Gln Gln Gln Asn Asn
    530                 535                 540

Leu Leu Arg Ala Ile Glu Ala Gln Gln His Met Leu Gln Leu Thr Val
545                 550                 555                 560

Trp Gly Ile Lys Gln Leu Gln Ala Arg Val Leu Ala Ile Glu Arg Tyr
                565                 570                 575

Leu Lys Asp Gln Gln Leu Leu Gly Ile Trp Gly Cys Ser Gly Lys Leu
```

```
            580                 585                 590

Ile Cys Thr Thr Ser Val Pro Trp Asn Thr Ser Trp Ser Asn Lys Ser
        595                 600                 605

Lys Ala Glu Ile Trp Asp Asn Met Thr Trp Met Gln Trp Asp Lys Glu
    610                 615                 620

Ile Ser Asn Tyr Thr Gln Thr Ile Tyr Asn Leu Leu Glu Glu Ser Gln
625                 630                 635                 640

Ser Gln Gln Glu Lys Asn Glu Lys Asp Leu Leu Glu Leu Asp Ser Trp
                645                 650                 655

Asn Asn Leu Trp Asn Trp Phe Asp Ile Ser Lys Trp Leu Trp Tyr Ile
            660                 665                 670

Lys Ile Phe Ile Met Ile Val Gly Gly Leu Ile Gly Leu Arg Ile Ile
        675                 680                 685

Phe Ala Val Leu Ser Ile Val Asn Arg Val Arg Gln Gly Tyr Ser Pro
    690                 695                 700

Leu Ser Phe Gln Ile Leu Thr Pro Asn Pro Arg Gly Pro Asp Arg Leu
705                 710                 715                 720

Gly Arg Ile Glu Glu Glu Gly Gly Glu Gln Asp Arg Asp Arg Ser Val
                725                 730                 735

Arg Leu Ala Asn Gly Phe Leu Ala Leu Ala Trp Glu Asp Leu Arg Asn
            740                 745                 750

Leu Cys Leu Phe Phe Tyr His Arg Leu Arg Asp Phe Ile Leu Ile Ala
        755                 760                 765

Ala Arg Thr Val Glu Leu Leu Arg Gln Ile Ser Phe Lys Gly Leu Gln
    770                 775                 780

Arg Gly Trp Glu Ala Leu Lys Tyr Leu Gly Ser Leu Val Gln Tyr Trp
785                 790                 795                 800

Ser Gln Glu Leu Lys Glu Ser Ala Ile Asn Leu Leu Asn Thr Ile Ala
                805                 810                 815

Ile Ala Val Ala Glu Gly Thr Asp Arg Ile Ile Glu Val Val Gln Arg
            820                 825                 830

Gly Phe Arg Ala Ile Leu Asn Val Pro Thr Arg Ile Arg Gln Gly Leu
        835                 840                 845

Glu Arg Ala Leu Leu
    850


<210> SEQ ID NO 43
<211> LENGTH: 2571
<212> TYPE: DNA
<213> ORGANISM: Artificial Sequence
<220> FEATURE:
<223> OTHER INFORMATION: pGX1024 - Env Clade C tier 2 ZM214M.PL15 DNA
      Sequence

<400> SEQUENCE: 43

atgcgcgtga gggggatgct gcgaaactgt cagcagtggt ggatctgggg gattctgggc      60

ttttggatgc tgatgatttg taacggggtg ggcaacctgt gggtgacagt ctactatggg     120

gtgcccgtct ggagggaggc aaagaccaca ctgttttgcg cctccgacgc caaggcttac     180

gaaaaagagg tgcacaatgt ctgggccacc catgcttgcg tgcctacaga tccaaacccc     240

caggaactgg tgctggagaa tgtcaccgaa aacttcaata tgtggaagaa cgacatggtg     300

aatcagatgc acgaggacat cattagtctg tgggatcagt cactgaagcc ttgcgtgaaa     360

ctgaccccac tgtgcgtcac actgaactgt agtaacgtga acatcaacga aacatcaatc     420

gatttcaacg tcactagcaa tatctccatg aaggaggaaa tgaagaactg tagctttaag     480
```

-continued

```
gtgaactccg agctgaggga caaaaatcgg agagaacatg ccctgttcta taagctggat    540
atcgtgcagc tgaacgacga gggcaatgat tcatacagct atcgcctgat taattgcaac    600
acctctacaa tcaagcaggc ttgtccaaaa gtgagttttg agcctatccc aattcactac    660
tgcgcacccg ccggctatgc aatcctgaag tgtaacaatg aaacattcaa cggcagcggc    720
ccttgcaaca acgtgagcac cgtccagtgt acacatggaa tcaaaccagt ggtcagcact    780
cagctgctgc tgaacggctc cctggccgaa aaggagatca tgattaggtc cgagaatctg    840
actaacaatg ctaaaaccat cattgtgcag ctgactgaag cagtcaacat tacctgcatg    900
cgacccggca acaataccag gcgcagtgtg cggatcggac ctggacagac tttttacgcc    960
accggggaga tcattggaga cattcggcag gctcactgta atatcagcaa ggataaatgg   1020
aaccagatcc tgcagaatgt gagagccaag ctgggcgagc acttccatga caagaccatc   1080
aagtttgagc caagctccgg cggggatctg gaaatcacta cccattcttt caactgcgga   1140
ggcgaattct tttactgtaa cacaactaat ctgttttccc gcacttatac caatggctcc   1200
aattctaacg tgaatattac ctctgccaca atcactctgc cctgccgcat taagcagatc   1260
attaacatgt ggcaggaagt gggacgagca atgtatgccc ctcccatcgc tggcaacatc   1320
acttgtatta gcaatatcac aggactgctg ctgactcggg acgggggaaa cggaaatgac   1380
accaacgata ccgagacatt cagacctgcc ggcggggaca tgagagataa ttggaggagc   1440
gagctgtaca agtataaagt ggtcgaaatt aagccactgg gcatcgcccc caccaaggct   1500
aaacgacgag tggtcggaag ggagaaacga gcagtgggca ttggggctgt cttcctggga   1560
tttctgggag cagctgggtc aacaatggga gcagccagca tcactctgac cgtccaggca   1620
aggcagctgc tgagcggaat tgtgcagcag cagaacaatc tgctgcgcgc tatcgaggca   1680
cagcagcacc tgctgcagct gaccgtctgg ggcattaagc agctgcaggc acgcgtgctg   1740
gccatcgaac gatacctgaa ggatcagcag ctgctgggac tgtggggctg ctcagggaaa   1800
ctgatctgta ccacaactgt cagctggaac tctagttggt ctaacaagag tgtggacgat   1860
atttggcaga acatgacctg gatgcagtgg gacagagaga tcaacaatta cacagaaatc   1920
atctacaggc tgctggaggt gagccagaac cagcaggaaa agaatgagga agacctgctg   1980
gccctggaca aatgggataa cctgtggaat tggttcgata tctccaagtg gctgtggtac   2040
atcaaaatct tcatcatgat tgtcggaggc ctgattggcc tgcggatcat ttttgctgtg   2100
ctgtctatcg tgaaccgcgt ccgacagggg tattcacccc tgagcttcca gacactgact   2160
cccaatccta gagagctgga ccgactggga cggattgagg aagagggcgg cgagcaggat   2220
cggagtagat caatcaggct ggtgaacggc ttcctggctc tggcatggga cgatctgcgc   2280
tctctgtgcc tgtttagtta ccaccatctg agggacctga tcctgattgc tgcacgcact   2340
gtgagcctgc tgggaagaag ggctgggag gcactgaagt acctgggcgg gctggtgcag   2400
tattggggga gagaactgaa gaaatccgcc atttctctgc tggacacagt ggctatcact   2460
gtcgcagagg gcaccgatag agtgatcgaa attgcccaga gattcggaag aggaatctgt   2520
aatatccccc gacgaatccg ccagggcttt gaagccgctc tgcagtgata a            2571
```

<210> SEQ ID NO 44
<211> LENGTH: 855
<212> TYPE: PRT
<213> ORGANISM: Artificial Sequence
<220> FEATURE:
<223> OTHER INFORMATION: pGX1024 - Env Clade C tier 2 ZM214M.PL15 Amino
      Acid Sequence

<400> SEQUENCE: 44

Met Arg Val Arg Gly Met Leu Arg Asn Cys Gln Gln Trp Trp Ile Trp
1 5 10 15

Gly Ile Leu Gly Phe Trp Met Leu Met Ile Cys Asn Gly Val Gly Asn
20 25 30

Leu Trp Val Thr Val Tyr Tyr Gly Val Pro Val Trp Arg Glu Ala Lys
35 40 45

Thr Thr Leu Phe Cys Ala Ser Asp Ala Lys Ala Tyr Glu Lys Glu Val
50 55 60

His Asn Val Trp Ala Thr His Ala Cys Val Pro Thr Asp Pro Asn Pro
65 70 75 80

Gln Glu Leu Val Leu Glu Asn Val Thr Glu Asn Phe Asn Met Trp Lys
85 90 95

Asn Asp Met Val Asn Gln Met His Glu Asp Ile Ile Ser Leu Trp Asp
100 105 110

Gln Ser Leu Lys Pro Cys Val Lys Leu Thr Pro Leu Cys Val Thr Leu
115 120 125

Asn Cys Ser Asn Val Asn Ile Asn Glu Thr Ser Ile Asp Phe Asn Val
130 135 140

Thr Ser Asn Ile Ser Met Lys Glu Glu Met Lys Asn Cys Ser Phe Lys
145 150 155 160

Val Asn Ser Glu Leu Arg Asp Lys Asn Arg Arg Glu His Ala Leu Phe
165 170 175

Tyr Lys Leu Asp Ile Val Gln Leu Asn Asp Glu Gly Asn Asp Ser Tyr
180 185 190

Ser Tyr Arg Leu Ile Asn Cys Asn Thr Ser Thr Ile Lys Gln Ala Cys
195 200 205

Pro Lys Val Ser Phe Glu Pro Ile Pro Ile His Tyr Cys Ala Pro Ala
210 215 220

Gly Tyr Ala Ile Leu Lys Cys Asn Asn Glu Thr Phe Asn Gly Ser Gly
225 230 235 240

Pro Cys Asn Asn Val Ser Thr Val Gln Cys Thr His Gly Ile Lys Pro
245 250 255

Val Val Ser Thr Gln Leu Leu Leu Asn Gly Ser Leu Ala Glu Lys Glu
260 265 270

Ile Met Ile Arg Ser Glu Asn Leu Thr Asn Asn Ala Lys Thr Ile Ile
275 280 285

Val Gln Leu Thr Glu Ala Val Asn Ile Thr Cys Met Arg Pro Gly Asn
290 295 300

Asn Thr Arg Arg Ser Val Arg Ile Gly Pro Gly Gln Thr Phe Tyr Ala
305 310 315 320

Thr Gly Glu Ile Ile Gly Asp Ile Arg Gln Ala His Cys Asn Ile Ser
325 330 335

Lys Asp Lys Trp Asn Gln Ile Leu Gln Asn Val Arg Ala Lys Leu Gly
340 345 350

Glu His Phe His Asp Lys Thr Ile Lys Phe Glu Pro Ser Ser Gly Gly
355 360 365

Asp Leu Glu Ile Thr Thr His Ser Phe Asn Cys Gly Gly Glu Phe Phe
370 375 380

Tyr Cys Asn Thr Thr Asn Leu Phe Ser Arg Thr Tyr Thr Asn Gly Ser
385 390 395 400

Asn Ser Asn Val Asn Ile Thr Ser Ala Thr Ile Thr Leu Pro Cys Arg

-continued

```
                405                 410                 415

Ile Lys Gln Ile Ile Asn Met Trp Gln Glu Val Gly Arg Ala Met Tyr
            420                 425                 430

Ala Pro Pro Ile Ala Gly Asn Ile Thr Cys Ile Ser Asn Ile Thr Gly
        435                 440                 445

Leu Leu Leu Thr Arg Asp Gly Gly Asn Gly Asn Asp Thr Asn Asp Thr
    450                 455                 460

Glu Thr Phe Arg Pro Ala Gly Gly Asp Met Arg Asp Asn Trp Arg Ser
465                 470                 475                 480

Glu Leu Tyr Lys Tyr Lys Val Val Glu Ile Lys Pro Leu Gly Ile Ala
                485                 490                 495

Pro Thr Lys Ala Lys Arg Arg Val Val Gly Arg Glu Lys Arg Ala Val
            500                 505                 510

Gly Ile Gly Ala Val Phe Leu Gly Phe Leu Gly Ala Ala Gly Ser Thr
        515                 520                 525

Met Gly Ala Ala Ser Ile Thr Leu Thr Val Gln Ala Arg Gln Leu Leu
    530                 535                 540

Ser Gly Ile Val Gln Gln Gln Asn Asn Leu Leu Arg Ala Ile Glu Ala
545                 550                 555                 560

Gln Gln His Leu Leu Gln Leu Thr Val Trp Gly Ile Lys Gln Leu Gln
                565                 570                 575

Ala Arg Val Leu Ala Ile Glu Arg Tyr Leu Lys Asp Gln Gln Leu Leu
            580                 585                 590

Gly Leu Trp Gly Cys Ser Gly Lys Leu Ile Cys Thr Thr Thr Val Ser
        595                 600                 605

Trp Asn Ser Ser Trp Ser Asn Lys Ser Val Asp Asp Ile Trp Gln Asn
    610                 615                 620

Met Thr Trp Met Gln Trp Asp Arg Glu Ile Asn Asn Tyr Thr Glu Ile
625                 630                 635                 640

Ile Tyr Arg Leu Leu Glu Val Ser Gln Asn Gln Gln Glu Lys Asn Glu
                645                 650                 655

Glu Asp Leu Leu Ala Leu Asp Lys Trp Asp Asn Leu Trp Asn Trp Phe
            660                 665                 670

Asp Ile Ser Lys Trp Leu Trp Tyr Ile Lys Ile Phe Ile Met Ile Val
        675                 680                 685

Gly Gly Leu Ile Gly Leu Arg Ile Ile Phe Ala Val Leu Ser Ile Val
    690                 695                 700

Asn Arg Val Arg Gln Gly Tyr Ser Pro Leu Ser Phe Gln Thr Leu Thr
705                 710                 715                 720

Pro Asn Pro Arg Glu Leu Asp Arg Leu Gly Arg Ile Glu Glu Glu Gly
                725                 730                 735

Gly Glu Gln Asp Arg Ser Arg Ser Ile Arg Leu Val Asn Gly Phe Leu
            740                 745                 750

Ala Leu Ala Trp Asp Asp Leu Arg Ser Leu Cys Leu Phe Ser Tyr His
        755                 760                 765

His Leu Arg Asp Leu Ile Leu Ile Ala Ala Arg Thr Val Ser Leu Leu
    770                 775                 780

Gly Arg Arg Gly Trp Glu Ala Leu Lys Tyr Leu Gly Gly Leu Val Gln
785                 790                 795                 800

Tyr Trp Gly Arg Glu Leu Lys Lys Ser Ala Ile Ser Leu Leu Asp Thr
                805                 810                 815

Val Ala Ile Thr Val Ala Glu Gly Thr Asp Arg Val Ile Glu Ile Ala
            820                 825                 830
```

```
Gln Arg Phe Gly Arg Gly Ile Cys Asn Ile Pro Arg Arg Ile Arg Gln
        835                 840                 845

Gly Phe Glu Ala Ala Leu Gln
    850                 855


<210> SEQ ID NO 45
<211> LENGTH: 2565
<212> TYPE: DNA
<213> ORGANISM: Artificial Sequence
<220> FEATURE:
<223> OTHER INFORMATION: pGX1029 Env Clade A tier 2 Q23ENV17 DNA
      sequence

<400> SEQUENCE: 45

atgagagtga tgggcattca gaggaactgt cagcacctgc tgacctgggg cattatgatt      60

ctggggacta ttatcttttg tagcgcagtg gagaacctgt gggtgactgt ctactatgga     120

gtgccagtct ggcgagacgc agataccaca ctgttctgcg ctagcgacgc taaggcatac     180

gaaacagaga aacacaacgt gtgggcaacc catgcctgcg tgcccacaga cccaaatccc     240

caggaaatcc acctggataa tgtcacagag aagtttaaca tgtggaagaa caacatggtg     300

gagcagatgc atactgacat catttctctg tgggatcaga gtctgaagcc ttgcgtgaaa     360

ctgactccac tgtgcgtcac cctgcactgt acaaatgtga cttccgtcaa cactaccggc     420

gacagagaag ggctgaagaa ttgttctttc aacatgacaa ctgagctgcg ggacaagaga     480

cagaaagtct acagcctgtt ttatcggctg gatatcgtgc ccattaatga aaaccagggc     540

agtgagtaca gactgatcaa ttgcaacact tcagctatta cccaggcatg tccaaaggtg     600

agcttcgagc ctatcccaat tcactattgc acccccgctg gcttcgcaat cctgaagtgt     660

aaagatgaag ggtttaatgg aacaggcctg tgcaaaaacg tgtctacagt ccagtgtact     720

catgggatta agcctgtggt ctcaacccag ctgctgctga atggaagcct ggccgagaag     780

aacatcacca ttaggagtga gaacatcaca aacaacgcta agatcatcat cgtgcagctg     840

gtccagcccg tgaccatcaa atgcattcgc cctaacaata acacacgcaa gagcatccga     900

attgggccag gacaggcctt ttacgctacc ggagacatta tcggcgatat ccggcaggcc     960

cactgtaacg tgactaggtc ccgctggaat aagaccctgc aggaagtggc cgagaaactg    1020

agaacttatt tcggcaacaa gaccattatc tttgccaata gctccggcgg ggacctggaa    1080

atcaccacac atagtttcaa ctgcggaggc gagttctttt actgtaatac ctcagggctg    1140

tttaacagca catggtacgt gaattcaact tggaacgaca ccgatagcac acaggagtcc    1200

aacgatacaa tcactctgcc ctgccgaatt aagcagatta tcaatatgtg gcagcgagca    1260

ggacaggcaa tgtacgctcc acctatccct ggcgtgatca agtgtgagag caacatcaca    1320

gggctgctgc tgactagaga cgggggaaag gataataacg tgaacgagac cttcaggcca    1380

ggaggaggag acatgcgaga taattggaga agcgaactgt acaagtataa agtggtcgaa    1440

atcgagccac tgggagtggc accaacaagg gctaaacgga gagtggtcga aagggagaag    1500

cgagctgtgg gaatcggagc agtcttcctg ggtttctgg gagccgctgg ctctaccatg     1560

ggcgcaacaa gtattaccct gacagtccag gctaggcagc tgctgtccgg gatcgtgcag    1620

cagcagaata acctgctgcg cgcaattgag gcccagcagc acctgctgaa gctgaccgtg    1680

tggggcatca aacagctgca ggcaagggtc ctggcagtgg agcgatatct gcgagaccag    1740

cagctgctgg gaatctgggg atgctccggc aaactgattt gtactaccaa tgtgccttgg    1800

aactctagtt ggtccaacaa gtctctggac gaaatctgga ataacatgac ttggctgcag    1860
```

```
tgggataaag agattaataa ctacacccag ctgatctatc gcctgattga ggaatctcag   1920

aatcagcagg aaaagaacga aaaagagctg ctggagctgg acaagtgggc caacctgtgg   1980

tcctggttcg atatttctaa ttggctgtgg tacatcaaga tcttcatcat cattgtgggc   2040

gggctgatcg gactgcggat tgtcttcgcc gtgctgtctg tcatcaaccg agtgcggcag   2100

ggctatagtc ctctgtcatt tcagactcat acccccaatc ctagaggact ggacagacca   2160

gaaaggatcg aggaagagga tggcgagcag ggaagaggca ggagtattcg cctggtgtca   2220

ggcttcctgg ccctggcttg ggacgatctg cgaagcctgt gcctgttctc ctaccaccgc   2280

ctgcgagact tcatcctgat tgcagccagg accgtggaac tgctggggca ttcaagcctg   2340

aaaggactgc gcctggggtg ggagggaatc aagtacctgt ggaacctgct gtcctattgg   2400

gggcgggaac tgaagatctc tgccattaat ctggtggaca caatcgcaat tgccgtcgct   2460

ggatggactg atagagtgat cgagattgcc cagcgcatcg gaagagctat tctgcatatc   2520

cccgtgagga ttcgccaggg actggaaaga gcactgctgt gataa                   2565
```

```
<210> SEQ ID NO 46
<211> LENGTH: 853
<212> TYPE: PRT
<213> ORGANISM: Artificial Sequence
<220> FEATURE:
<223> OTHER INFORMATION: pGX1029 Env Clade A tier 2 Q23ENV17 Amino Acid
      Sequence

<400> SEQUENCE: 46

Met Arg Val Met Gly Ile Gln Arg Asn Cys Gln His Leu Leu Thr Trp
1               5                   10                  15

Gly Ile Met Ile Leu Gly Thr Ile Ile Phe Cys Ser Ala Val Glu Asn
            20                  25                  30

Leu Trp Val Thr Val Tyr Tyr Gly Val Pro Val Trp Arg Asp Ala Asp
        35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Ile His Leu Asp Asn Val Thr Glu Lys Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

His Cys Thr Asn Val Thr Ser Val Asn Thr Thr Gly Asp Arg Glu Gly
    130                 135                 140

Leu Lys Asn Cys Ser Phe Asn Met Thr Thr Glu Leu Arg Asp Lys Arg
145                 150                 155                 160

Gln Lys Val Tyr Ser Leu Phe Tyr Arg Leu Asp Ile Val Pro Ile Asn
                165                 170                 175

Glu Asn Gln Gly Ser Glu Tyr Arg Leu Ile Asn Cys Asn Thr Ser Ala
            180                 185                 190

Ile Thr Gln Ala Cys Pro Lys Val Ser Phe Glu Pro Ile Pro Ile His
        195                 200                 205

Tyr Cys Thr Pro Ala Gly Phe Ala Ile Leu Lys Cys Lys Asp Glu Gly
    210                 215                 220

Phe Asn Gly Thr Gly Leu Cys Lys Asn Val Ser Thr Val Gln Cys Thr
```

-continued

```
225                 230                 235                 240

His Gly Ile Lys Pro Val Val Ser Thr Gln Leu Leu Leu Asn Gly Ser
                245                 250                 255

Leu Ala Glu Lys Asn Ile Thr Ile Arg Ser Glu Asn Ile Thr Asn Asn
            260                 265                 270

Ala Lys Ile Ile Ile Val Gln Leu Val Gln Pro Val Thr Ile Lys Cys
        275                 280                 285

Ile Arg Pro Asn Asn Asn Thr Arg Lys Ser Ile Arg Ile Gly Pro Gly
    290                 295                 300

Gln Ala Phe Tyr Ala Thr Gly Asp Ile Ile Gly Asp Ile Arg Gln Ala
305                 310                 315                 320

His Cys Asn Val Thr Arg Ser Arg Trp Asn Lys Thr Leu Gln Glu Val
                325                 330                 335

Ala Glu Lys Leu Arg Thr Tyr Phe Gly Asn Lys Thr Ile Ile Phe Ala
            340                 345                 350

Asn Ser Ser Gly Gly Asp Leu Glu Ile Thr Thr His Ser Phe Asn Cys
        355                 360                 365

Gly Gly Glu Phe Phe Tyr Cys Asn Thr Ser Gly Leu Phe Asn Ser Thr
    370                 375                 380

Trp Tyr Val Asn Ser Thr Trp Asn Asp Thr Asp Ser Thr Gln Glu Ser
385                 390                 395                 400

Asn Asp Thr Ile Thr Leu Pro Cys Arg Ile Lys Gln Ile Ile Asn Met
                405                 410                 415

Trp Gln Arg Ala Gly Gln Ala Met Tyr Ala Pro Pro Ile Pro Gly Val
            420                 425                 430

Ile Lys Cys Glu Ser Asn Ile Thr Gly Leu Leu Leu Thr Arg Asp Gly
        435                 440                 445

Gly Lys Asp Asn Asn Val Asn Glu Thr Phe Arg Pro Gly Gly Gly Asp
    450                 455                 460

Met Arg Asp Asn Trp Arg Ser Glu Leu Tyr Lys Tyr Lys Val Val Glu
465                 470                 475                 480

Ile Glu Pro Leu Gly Val Ala Pro Thr Arg Ala Lys Arg Arg Val Val
                485                 490                 495

Glu Arg Glu Lys Arg Ala Val Gly Ile Gly Ala Val Phe Leu Gly Phe
            500                 505                 510

Leu Gly Ala Ala Gly Ser Thr Met Gly Ala Thr Ser Ile Thr Leu Thr
        515                 520                 525

Val Gln Ala Arg Gln Leu Leu Ser Gly Ile Val Gln Gln Gln Asn Asn
    530                 535                 540

Leu Leu Arg Ala Ile Glu Ala Gln Gln His Leu Leu Lys Leu Thr Val
545                 550                 555                 560

Trp Gly Ile Lys Gln Leu Gln Ala Arg Val Leu Ala Val Glu Arg Tyr
                565                 570                 575

Leu Arg Asp Gln Gln Leu Leu Gly Ile Trp Gly Cys Ser Gly Lys Leu
            580                 585                 590

Ile Cys Thr Thr Asn Val Pro Trp Asn Ser Ser Trp Ser Asn Lys Ser
        595                 600                 605

Leu Asp Glu Ile Trp Asn Asn Met Thr Trp Leu Gln Trp Asp Lys Glu
    610                 615                 620

Ile Asn Asn Tyr Thr Gln Leu Ile Tyr Arg Leu Ile Glu Glu Ser Gln
625                 630                 635                 640

Asn Gln Gln Glu Lys Asn Glu Lys Glu Leu Leu Glu Leu Asp Lys Trp
                645                 650                 655
```

```
Ala Asn Leu Trp Ser Trp Phe Asp Ile Ser Asn Trp Leu Trp Tyr Ile
            660                 665                 670

Lys Ile Phe Ile Ile Ile Val Gly Gly Leu Ile Gly Leu Arg Ile Val
        675                 680                 685

Phe Ala Val Leu Ser Val Ile Asn Arg Val Arg Gln Gly Tyr Ser Pro
    690                 695                 700

Leu Ser Phe Gln Thr His Thr Pro Asn Pro Arg Gly Leu Asp Arg Pro
705                 710                 715                 720

Glu Arg Ile Glu Glu Glu Asp Gly Glu Gln Gly Arg Gly Arg Ser Ile
                725                 730                 735

Arg Leu Val Ser Gly Phe Leu Ala Leu Ala Trp Asp Asp Leu Arg Ser
            740                 745                 750

Leu Cys Leu Phe Ser Tyr His Arg Leu Arg Asp Phe Ile Leu Ile Ala
        755                 760                 765

Ala Arg Thr Val Glu Leu Leu Gly His Ser Ser Leu Lys Gly Leu Arg
    770                 775                 780

Leu Gly Trp Glu Gly Ile Lys Tyr Leu Trp Asn Leu Leu Ser Tyr Trp
785                 790                 795                 800

Gly Arg Glu Leu Lys Ile Ser Ala Ile Asn Leu Val Asp Thr Ile Ala
                805                 810                 815

Ile Ala Val Ala Gly Trp Thr Asp Arg Val Ile Glu Ile Ala Gln Arg
            820                 825                 830

Ile Gly Arg Ala Ile Leu His Ile Pro Val Arg Ile Arg Gln Gly Leu
        835                 840                 845

Glu Arg Ala Leu Leu
    850
```

<210> SEQ ID NO 47
<211> LENGTH: 2313
<212> TYPE: DNA
<213> ORGANISM: Artificial Sequence
<220> FEATURE:
<223> OTHER INFORMATION: pGX1004 MPol DNA sequence

<400> SEQUENCE: 47

```
atggactgga cctggattct gttcctggtg gccgctgcca ccagagtgca cagccctcag      60

atcaccctgt ggcagagacc tctggtgacc atcaagatcg gcggccagct gaaggaggcc     120

ctgctggccg acgacaccgt gctggaggag atcaacctgc ccggcaagtg gaagcctaag     180

atgatcggcg gcatcggggg cttcatcaaa gtgaggcagt acgaccagat cctgatcgag     240

atctgtggcc acaaggccat cggcacagtg ctggtcggcc ccacacccgt gaatatcatc     300

ggccggaaca tgctgaccca gatcggctgt accctgaact tccccatcag ccccatcgag     360

accgtgcctg tgaagctgaa gcctggcatg gatggcccta aggtgaagca gtggcccctg     420

accgaggaga agatcaaggc cctgacagag atctgtaccg agatggagaa ggagggcaag     480

atcagcaaga tcggccccga gaacccctac aacacccccg tgttcgccat caagaagaag     540

gacagcacca agtggcggaa actggtggac ttccgggagc tgaacaagag gacccaggac     600

ttctgggagg tgcagctggg catccctcac cctgccggcc tgaagaagaa gaagtccgtg     660

acagtgctgg atgtgggcga cgcctacttc agcgtgcccc tggacgagga cttcaggaag     720

tacaccgcct tcaccatccc cagcatcaac aacgagaccc ccggcatcag ataccagtac     780

aacgtgctgc ctcagggctg gaagggcagc cccgccatct tccagagcag catgaccaag     840

atcctggagc ccttcaggaa gcagaacccc gagatcgtga tctaccagct gtatgtgggc     900
```

```
agcgatctgg agatcggcca gcacagagcc aagatcgagg agctgaggga gcacctgctg    960

agatggggct tcaccacccc cgataagaag caccagaagg agccccctttt cctgtggatg   1020

ggctacgagc tgcaccctga caagtggacc gtgcagccca tcaagctgcc tgagaaggag   1080

agctggaccg tgaacgacat ccagaaactg gtgggcaagc tgaattgggc cagccagatc   1140

tacgccggca ttaaagtgag acagctgtgt aagctgctga gaggcgccaa agccctgacc   1200

gaagtggtgc ctctgacaga ggaggccgag ctggagctgg ccgagaacag ggagatcctg   1260

aaggagcccg tgcacggcgt gtactacgac cccagcaagg atctgatcgc cgagatccag   1320

aagcagggcc agggccagtg gacctaccag atctaccagg agcctttcaa gaacctgaaa   1380

accggcaagt acgccagaat gaggggagcc cacaccaacg atgtgaagca gctgaccgag   1440

gccgtgcaga aaatcgccat ggagagcatc gtgatctggg gcaagacacc caagttccgg   1500

ctgcccatcc agaaggagac ctgggaaacc tggtggaccg agtactggca ggccacctgg   1560

attcctgagt gggagttcgt gaacaccccc cctctggtga agctgtggta tcagctggag   1620

aaggaaccta tcgccggagc cgagaccttc tacgtggacg gagccgccaa tagagagacc   1680

aagctgggca aggccggcta cgtgaccgac agaggcagac agaaggtggt gtccctgacc   1740

gacaccacca accagaaaac cctgcaggcc atccacctgg ccctgcagga cagcggcctg   1800

gaggtgaaca tcgtgaccga ctcccagtac gccctgggca tcatccaggc ccagcccgac   1860

aagagcgaga gcgagctggt gtcccagatc atcgagcagc tgatcaagaa ggagaaggtg   1920

tacctgagct gggtgcccgc ccacaagggc attggcggca atgagcaggt ggacaagctg   1980

gtgtctagcg gcatccggaa ggtgctgtac ccctacgacg tgcccgatta cgcctgagaa   2040

ttcgtaagta agtgtcatat gggagagctc gactagactg gacagccaat gacgggtaag   2100

agagtgacat ttctcactaa cctaagacag gagggccgtc aaagctactg cctaatccaa   2160

tgacgggtaa tagtgacaag aaatgtatca ctccaaccta agacaggcgc agcctccgag   2220

ggatgtgtct tttgtttttt ataattaaaa agggtgacat gtccggagcc gtgctgcccg   2280

gatgatgtct tggcctctgt ttgctgcggc cgc                                2313
```

```
<210> SEQ ID NO 48
<211> LENGTH: 678
<212> TYPE: PRT
<213> ORGANISM: Artificial Sequence
<220> FEATURE:
<223> OTHER INFORMATION: pGX 1004 MPol Protein sequence

<400> SEQUENCE: 48

Met Asp Trp Thr Trp Ile Leu Phe Leu Val Ala Ala Ala Thr Arg Val
1               5                   10                  15

His Ser Pro Gln Ile Thr Leu Trp Gln Arg Pro Leu Val Thr Ile Lys
            20                  25                  30

Ile Gly Gly Gln Leu Lys Glu Ala Leu Leu Ala Asp Asp Thr Val Leu
        35                  40                  45

Glu Glu Ile Asn Leu Pro Gly Lys Trp Lys Pro Lys Met Ile Gly Gly
    50                  55                  60

Ile Gly Gly Phe Ile Lys Val Arg Gln Tyr Asp Gln Ile Leu Ile Glu
65                  70                  75                  80

Ile Cys Gly His Lys Ala Ile Gly Thr Val Leu Val Gly Pro Thr Pro
                85                  90                  95

Val Asn Ile Ile Gly Arg Asn Met Leu Thr Gln Ile Gly Cys Thr Leu
            100                 105                 110
```

-continued

```
Asn Phe Pro Ile Ser Pro Ile Glu Thr Val Pro Val Lys Leu Lys Pro
        115                 120                 125

Gly Met Asp Gly Pro Lys Val Lys Gln Trp Pro Leu Thr Glu Glu Lys
    130                 135                 140

Ile Lys Ala Leu Thr Glu Ile Cys Thr Glu Met Glu Lys Glu Gly Lys
145                 150                 155                 160

Ile Ser Lys Ile Gly Pro Glu Asn Pro Tyr Asn Thr Pro Val Phe Ala
                165                 170                 175

Ile Lys Lys Lys Asp Ser Thr Lys Trp Arg Lys Leu Val Asp Phe Arg
            180                 185                 190

Glu Leu Asn Lys Arg Thr Gln Asp Phe Trp Glu Val Gln Leu Gly Ile
        195                 200                 205

Pro His Pro Ala Gly Leu Lys Lys Lys Lys Ser Val Thr Val Leu Asp
    210                 215                 220

Val Gly Asp Ala Tyr Phe Ser Val Pro Leu Asp Glu Asp Phe Arg Lys
225                 230                 235                 240

Tyr Thr Ala Phe Thr Ile Pro Ser Ile Asn Asn Glu Thr Pro Gly Ile
                245                 250                 255

Arg Tyr Gln Tyr Asn Val Leu Pro Gln Gly Trp Lys Gly Ser Pro Ala
            260                 265                 270

Ile Phe Gln Ser Ser Met Thr Lys Ile Leu Glu Pro Phe Arg Lys Gln
        275                 280                 285

Asn Pro Glu Ile Val Ile Tyr Gln Leu Tyr Val Gly Ser Asp Leu Glu
    290                 295                 300

Ile Gly Gln His Arg Ala Lys Ile Glu Glu Leu Arg Glu His Leu Leu
305                 310                 315                 320

Arg Trp Gly Phe Thr Thr Pro Asp Lys Lys His Gln Lys Glu Pro Pro
                325                 330                 335

Phe Leu Trp Met Gly Tyr Glu Leu His Pro Asp Lys Trp Thr Val Gln
            340                 345                 350

Pro Ile Lys Leu Pro Glu Lys Glu Ser Trp Thr Val Asn Asp Ile Gln
        355                 360                 365

Lys Leu Val Gly Lys Leu Asn Trp Ala Ser Gln Ile Tyr Ala Gly Ile
    370                 375                 380

Lys Val Arg Gln Leu Cys Lys Leu Leu Arg Gly Ala Lys Ala Leu Thr
385                 390                 395                 400

Glu Val Val Pro Leu Thr Glu Glu Ala Glu Leu Glu Leu Ala Glu Asn
                405                 410                 415

Arg Glu Ile Leu Lys Glu Pro Val His Gly Val Tyr Tyr Asp Pro Ser
            420                 425                 430

Lys Asp Leu Ile Ala Glu Ile Gln Lys Gln Gly Gln Gly Gln Trp Thr
        435                 440                 445

Tyr Gln Ile Tyr Gln Glu Pro Phe Lys Asn Leu Lys Thr Gly Lys Tyr
    450                 455                 460

Ala Arg Met Arg Gly Ala His Thr Asn Asp Val Lys Gln Leu Thr Glu
465                 470                 475                 480

Ala Val Gln Lys Ile Ala Met Glu Ser Ile Val Ile Trp Gly Lys Thr
                485                 490                 495

Pro Lys Phe Arg Leu Pro Ile Gln Lys Glu Thr Trp Glu Thr Trp Trp
            500                 505                 510

Thr Glu Tyr Trp Gln Ala Thr Trp Ile Pro Glu Trp Glu Phe Val Asn
        515                 520                 525
```

-continued

```
Thr Pro Pro Leu Val Lys Leu Trp Tyr Gln Leu Glu Lys Glu Pro Ile
    530                 535                 540

Ala Gly Ala Glu Thr Phe Tyr Val Asp Gly Ala Ala Asn Arg Glu Thr
545                 550                 555                 560

Lys Leu Gly Lys Ala Gly Tyr Val Thr Asp Arg Gly Arg Gln Lys Val
                565                 570                 575

Val Ser Leu Thr Asp Thr Thr Asn Gln Lys Thr Leu Gln Ala Ile His
            580                 585                 590

Leu Ala Leu Gln Asp Ser Gly Leu Glu Val Asn Ile Val Thr Asp Ser
        595                 600                 605

Gln Tyr Ala Leu Gly Ile Ile Gln Ala Gln Pro Asp Lys Ser Glu Ser
    610                 615                 620

Glu Leu Val Ser Gln Ile Ile Glu Gln Leu Ile Lys Lys Glu Lys Val
625                 630                 635                 640

Tyr Leu Ser Trp Val Pro Ala His Lys Gly Ile Gly Gly Asn Glu Gln
                645                 650                 655

Val Asp Lys Leu Val Ser Ser Gly Ile Arg Lys Val Leu Tyr Pro Tyr
            660                 665                 670

Asp Val Pro Asp Tyr Ala
        675


<210> SEQ ID NO 49
<211> LENGTH: 2865
<212> TYPE: DNA
<213> ORGANISM: Artificial Sequence
<220> FEATURE:
<223> OTHER INFORMATION: pGX1016 pPK2C1 (PrimaryPOL) DNA sequence

<400> SEQUENCE: 49

atggattgga cttggatctt atttttagtt gctgctacta gagttcgctc tcctcagatc      60

acgctctggc agcggccgct cgtcacaata aagatcgggg ggcaactcaa ggaggcgctg     120

ctcgcggacg acacggtctt ggaggagatg tcgttgccgg ggcggtggaa gccgaagatg     180

atcgggggga tcgggggctt catcaaggtg cggcagtacg accagatcct catcgagatc     240

tgcgggcaca aggcgatcgg gacggtcctc gtcggcccga cgccggtcaa catcatcggg     300

cggaacctgt tgacccagat cggctgcacc ttgaacttcc ccatcagccc tattgagacg     360

gtgcccgtga agttgaagcc ggggatggac ggccccaagg tcaagcaatg gccattgacg     420

gaggagaaga tcaaggcctt agtcgaaatc tgtacagaga tggagaagga agggaagatc     480

agcaagatcg ggcctgagaa cccctacaac actccagtct tcgcaatcaa gaagaaggac     540

agtaccaagt ggagaaagct ggtggacttc agagagctga acaagagaac tcaggacttc     600

ggggaagttc agctgggcat cccacatccc gctgggttga agaagaagaa gtcagtgaca     660

gtgctggatg tgggtgatgc ctacttctcc gttcccttgg acgaggactt caggaagtac     720

actgccttca cgatacctag catcaacaac gagacaccag gcatccgcta ccagtacaac     780

gtgctgccac agggatggaa gggatcacca gccatctttc aatcgtcgat gaccaagatc     840

ctggagccct tccgcaagca aaacccagac atcgtgatct atcagctcta cgtaggaagt     900

gacctggaga tcgggcagca caggaccaag atcgaggagc tgagacagca tctgttgagg     960

tggggactga ccaccccaga caagaagcac cagaaggaac ctcccttcct gtggatgggc    1020

tacgaactgc atcctgacaa gtggacagtg cagcccatcg tgctgcctga gaaggacagc    1080

tggactgtga acgacataca gaagctcgtg ggcaagttga actgggcaag ccagatctac    1140

ccaggcatca aagttaggca gctgtgcaag ctgcttcgag gaaccaaggc actgacagaa    1200
```

-continued

```
gtgatcccac tgacagagga agcagagcta gaactggcag agaaccgaga gatcctgaag   1260

gagccagtac atggagtgta ctacgaccca agcaaggacc tgatcgcaga gatccagaag   1320

caggggcaag gccaatggac ctaccaaatc taccaggagc ccttcaagaa cctgaagaca   1380

ggcaagtacg caaggatgag gggtgcccac accaacgatg tgaagcagct gacagaggca   1440

gtgcagaaga tcaccacaga gagcatcgtg atctggggca agactcccaa gttcaagctg   1500

cccatacaga aggagacatg ggagacatgg tggaccgagt actggcaagc cacctggatc   1560

cctgagtggg agttcgtgaa cacccccttcc ctggtgaaac tgtggtatca gctggagaag   1620

gaacccatcg tgggagcaga gaccttctac gtggatgggg cagccaacag ggagaccaag   1680

ctgggcaagg caggctacgt gaccaaccga ggacgacaga aagtggtgac cctgactgac   1740

accaccaacc agaagactct gcaagccatc tacctagctc tgcaagacag cggactggaa   1800

gtgaacatcg tgacagactc acagtacgca ctgggcatca tccaagcaca accagaccaa   1860

tccgagtcag agctggtgaa ccagatcatc gagcagctga tcaagaagga gaaagtgtac   1920

ctggcatggg tcccggcgca caaggggatc ggggggaacg agcaggtcga caagttggtc   1980

tcggcgggga tccggaaggt gctgttcctg gacgggatcg ataaggccca agatgaacat   2040

gagaagtacc actccaactg gcgcgctatg gccagcgact tcaacctgcc gccggtcgtc   2100

gcgaaggaga tcgtcgccag ctgcgacaag tgccagctca aggggggaggc catgcacggg   2160

caagtcgact gcagtccggg gatctggcag ctgtgcacgc acctggaggg gaaggtgatc   2220

ctggtcgcgg tccacgtcgc cagcgggtat atcgaggcgg aggtcatccc ggctgagacg   2280

gggcaggaga cggcgtactt cctcttgaag ctcgcggggc ggtggccggt caagacgatc   2340

cacacgaacg ggagcaactt cacgggggcg acggtcaagg ccgcctgttg gtgggcggga   2400

atcaagcagg aatttggaat tccctacaat ccccaatcgc aaggagtcgt gagcatgaac   2460

aaggagctga agaagatcat cggacaaagg gatcaggctg agcacctgaa gacagcagtg   2520

cagatggcag tgttcatcca caacttcaaa agaaaagggg ggattggggg gtacagtgcg   2580

ggggaacgga tcgtggacat catcgccacc gacatccaaa ccaaggagct gcagaagcag   2640

atcaccaaga tccagaactt ccgggtgtac taccgcgaca gccgcaaccc actgtggaag   2700

ggaccagcaa agctcctctg gaagggagag gggcagtgg tgatccagga caacagtgac    2760

atcaaagtgg tgccaaggcg caaggccaag atcatccgcg actatggaaa acagatggca   2820

gggatgatt gtgtggcaag tagacaggat gaggatggcg cctag                    2865
```

<210> SEQ ID NO 50
<211> LENGTH: 954
<212> TYPE: PRT
<213> ORGANISM: Artificial Sequence
<220> FEATURE:
<223> OTHER INFORMATION: pGX1016 pPK2C1 (PrimaryPOL) Amino Acid sequence

<400> SEQUENCE: 50

```
Met Asp Trp Thr Trp Ile Leu Phe Leu Val Ala Ala Thr Arg Val Arg
1               5                   10                  15

Ser Pro Gln Ile Thr Leu Trp Gln Arg Pro Leu Val Thr Ile Lys Ile
            20                  25                  30

Gly Gly Gln Leu Lys Glu Ala Leu Leu Ala Asp Asp Thr Val Leu Glu
        35                  40                  45

Glu Met Ser Leu Pro Gly Arg Trp Lys Pro Lys Met Ile Gly Gly Ile
    50                  55                  60
```

-continued

```
Gly Gly Phe Ile Lys Val Arg Gln Tyr Asp Gln Ile Leu Ile Glu Ile
65                  70                  75                  80

Cys Gly His Lys Ala Ile Gly Thr Val Leu Val Gly Pro Thr Pro Val
                85                  90                  95

Asn Ile Ile Gly Arg Asn Leu Leu Thr Gln Ile Gly Cys Thr Leu Asn
            100                 105                 110

Phe Pro Ile Ser Pro Ile Glu Thr Val Pro Val Lys Leu Lys Pro Gly
        115                 120                 125

Met Asp Gly Pro Lys Val Lys Gln Trp Pro Leu Thr Glu Glu Lys Ile
    130                 135                 140

Lys Ala Leu Val Glu Ile Cys Thr Glu Met Glu Lys Glu Gly Lys Ile
145                 150                 155                 160

Ser Lys Ile Gly Pro Glu Asn Pro Tyr Asn Thr Pro Val Phe Ala Ile
                165                 170                 175

Lys Lys Lys Asp Ser Thr Lys Trp Arg Lys Leu Val Asp Phe Arg Glu
            180                 185                 190

Leu Asn Lys Arg Thr Gln Asp Phe Gly Glu Val Gln Leu Gly Ile Pro
        195                 200                 205

His Pro Ala Gly Leu Lys Lys Lys Lys Ser Val Thr Val Leu Asp Val
    210                 215                 220

Gly Asp Ala Tyr Phe Ser Val Pro Leu Asp Glu Asp Phe Arg Lys Tyr
225                 230                 235                 240

Thr Ala Phe Thr Ile Pro Ser Ile Asn Asn Glu Thr Pro Gly Ile Arg
                245                 250                 255

Tyr Gln Tyr Asn Val Leu Pro Gln Gly Trp Lys Gly Ser Pro Ala Ile
            260                 265                 270

Phe Gln Ser Ser Met Thr Lys Ile Leu Glu Pro Phe Arg Lys Gln Asn
        275                 280                 285

Pro Asp Ile Val Ile Tyr Gln Leu Tyr Val Gly Ser Asp Leu Glu Ile
    290                 295                 300

Gly Gln His Arg Thr Lys Ile Glu Glu Leu Arg Gln His Leu Leu Arg
305                 310                 315                 320

Trp Gly Leu Thr Thr Pro Asp Lys Lys His Gln Lys Glu Pro Pro Phe
                325                 330                 335

Leu Trp Met Gly Tyr Glu Leu His Pro Asp Lys Trp Thr Val Gln Pro
            340                 345                 350

Ile Val Leu Pro Glu Lys Asp Ser Trp Thr Val Asn Asp Ile Gln Lys
        355                 360                 365

Leu Val Gly Lys Leu Asn Trp Ala Ser Gln Ile Tyr Pro Gly Ile Lys
    370                 375                 380

Val Arg Gln Leu Cys Lys Leu Leu Arg Gly Thr Lys Ala Leu Thr Glu
385                 390                 395                 400

Val Ile Pro Leu Thr Glu Glu Ala Glu Leu Glu Leu Ala Glu Asn Arg
                405                 410                 415

Glu Ile Leu Lys Glu Pro Val His Gly Val Tyr Tyr Asp Pro Ser Lys
            420                 425                 430

Asp Leu Ile Ala Glu Ile Gln Lys Gln Gly Gln Gly Gln Trp Thr Tyr
        435                 440                 445

Gln Ile Tyr Gln Glu Pro Phe Lys Asn Leu Lys Thr Gly Lys Tyr Ala
    450                 455                 460

Arg Met Arg Gly Ala His Thr Asn Asp Val Lys Gln Leu Thr Glu Ala
465                 470                 475                 480

Val Gln Lys Ile Thr Thr Glu Ser Ile Val Ile Trp Gly Lys Thr Pro
```

```
                485                 490                 495

Lys Phe Lys Leu Pro Ile Gln Lys Glu Thr Trp Glu Thr Trp Trp Thr
            500                 505                 510

Glu Tyr Trp Gln Ala Thr Trp Ile Pro Glu Trp Glu Phe Val Asn Thr
        515                 520                 525

Pro Ser Leu Val Lys Leu Trp Tyr Gln Leu Glu Lys Glu Pro Ile Val
    530                 535                 540

Gly Ala Glu Thr Phe Tyr Val Asp Gly Ala Ala Asn Arg Glu Thr Lys
545                 550                 555                 560

Leu Gly Lys Ala Gly Tyr Val Thr Asn Arg Gly Arg Gln Lys Val Val
                565                 570                 575

Thr Leu Thr Asp Thr Thr Asn Gln Lys Thr Leu Gln Ala Ile Tyr Leu
            580                 585                 590

Ala Leu Gln Asp Ser Gly Leu Glu Val Asn Ile Val Thr Asp Ser Gln
        595                 600                 605

Tyr Ala Leu Gly Ile Ile Gln Ala Gln Pro Asp Gln Ser Glu Ser Glu
    610                 615                 620

Leu Val Asn Gln Ile Ile Glu Gln Leu Ile Lys Lys Glu Lys Val Tyr
625                 630                 635                 640

Leu Ala Trp Val Pro Ala His Lys Gly Ile Gly Gly Asn Glu Gln Val
                645                 650                 655

Asp Lys Leu Val Ser Ala Gly Ile Arg Lys Val Leu Phe Leu Asp Gly
            660                 665                 670

Ile Asp Lys Ala Gln Asp Glu His Glu Lys Tyr His Ser Asn Trp Arg
        675                 680                 685

Ala Met Ala Ser Asp Phe Asn Leu Pro Pro Val Val Ala Lys Glu Ile
    690                 695                 700

Val Ala Ser Cys Asp Lys Cys Gln Leu Lys Gly Glu Ala Met His Gly
705                 710                 715                 720

Gln Val Asp Cys Ser Pro Gly Ile Trp Gln Leu Cys Thr His Leu Glu
                725                 730                 735

Gly Lys Val Ile Leu Val Ala Val His Val Ala Ser Gly Tyr Ile Glu
            740                 745                 750

Ala Glu Val Ile Pro Ala Glu Thr Gly Gln Glu Thr Ala Tyr Phe Leu
        755                 760                 765

Leu Lys Leu Ala Gly Arg Trp Pro Val Lys Thr Ile His Thr Asn Gly
    770                 775                 780

Ser Asn Phe Thr Gly Ala Thr Val Lys Ala Ala Cys Trp Trp Ala Gly
785                 790                 795                 800

Ile Lys Gln Glu Phe Gly Ile Pro Tyr Asn Pro Gln Ser Gln Gly Val
                805                 810                 815

Val Ser Met Asn Lys Glu Leu Lys Lys Ile Ile Gly Gln Arg Asp Gln
            820                 825                 830

Ala Glu His Leu Lys Thr Ala Val Gln Met Ala Val Phe Ile His Asn
        835                 840                 845

Phe Lys Arg Lys Gly Gly Ile Gly Gly Tyr Ser Ala Gly Glu Arg Ile
    850                 855                 860

Val Asp Ile Ile Ala Thr Asp Ile Gln Thr Lys Glu Leu Gln Lys Gln
865                 870                 875                 880

Ile Thr Lys Ile Gln Asn Phe Arg Val Tyr Tyr Arg Asp Ser Arg Asn
                885                 890                 895

Pro Leu Trp Lys Gly Pro Ala Lys Leu Leu Trp Lys Gly Glu Gly Ala
            900                 905                 910
```

Val Val Ile Gln Asp Asn Ser Asp Ile Lys Val Val Pro Arg Arg Lys
915 920 925

Ala Lys Ile Ile Arg Asp Tyr Gly Lys Gln Met Ala Gly Asp Asp Cys
930 935 940

Val Ala Ser Arg Gln Asp Glu Asp Gly Ala
945 950

<210> SEQ ID NO 51
<211> LENGTH: 2565
<212> TYPE: DNA
<213> ORGANISM: Artificial Sequence
<220> FEATURE:
<223> OTHER INFORMATION: pGX1053 Env Clade B tier 1B NL43 DNA Sequence

<400> SEQUENCE: 51
atgagagtga aggaaaagta ccagcacctg tggagatggg gatggaagtg ggggactatg 60
ctgctgggga ttctgatgat ttgtagcgcc accgaaaagc tgtgggtgac agtctactat 120
ggcgtgccag tctggaaaga ggcaaccaca actctgttct gcgcctccga cgccaaggct 180
tacgatactg aggtgcacaa tgtctgggca actcatgcct gtgtgcccac cgacccaaat 240
ccccaggaag tggtcctggt gaacgtcacc gagaatttta acatgtggaa gaacgatatg 300
gtggaacaga tgcacgagga catcatttca ctgtgggatc agagcctgaa gccctgcgtg 360
aaactgacac ctctgtgcgt cagcctgaag tgtactgacc tgaaaaacga tactaatacc 420
aacagctcct ctggccgcat gatcatggaa aagggagaga tcaagaactg tagcttcaat 480
atctctacca gtattaggga caaggtgcag aaagaatacg ccttctttta taagctggac 540
atcgtgccaa ttgataatac atcctacaga ctgatcagct gcaacacatc cgtgattact 600
caggcatgtc caaaggtctc ttttgagcct atcccaattc actattgcgc acccgccggc 660
ttcgctatcc tgaagtgtaa caacaagacc tttaacggaa cagggccctg cactaatgtg 720
tccaccgtcc agtgtacaca tgggatcaga cctgtggtca gtacccagct gctgctgaac 780
ggctcactgg ccgaggaaga cgtggtcatc cggtctgcca acttcactga taatgctaaa 840
accatcattg tgcagctgaa cacatctgtc gagatcaatt gcacacgacc taacaataac 900
actaggaaga gtatcagaat ccagcggggc ccaggacgcg cttttgtgac aatcggaaaa 960
attgggaaca tgcgccaggc acactgtaat atcagccgag caaagtggaa cgccactctg 1020
aagcagattg cctccaaact gagggagcag ttcggcaata acaagactat catcttcaag 1080
cagagttcag gcggagaccc tgaaatcgtg acccatagct tcaattgcgg gggcgagttc 1140
ttttactgta acagtaccca gctgttcaac tcaacatggt ttaattccac ttggtctacc 1200
gaagggagca ataacaccga gggctccgat acaatcactc tgccatgccg catcaagcag 1260
ttcattaata tgtggcagga agtggggaaa gctatgtatg cacccccctat cagcggccag 1320 attaggtgta gctccaacat cacaggactg ctgctgacta gagatggagg gaataataat 1380
aacggctcag agatctttag acctggcgga ggggacatga gggataactg gagaagcgaa 1440
ctgtacaagt ataaagtggt caaaatcgag cctctgggag tggctccaac aaaggcaaaa 1500
aggagagtgg tccagcgaga gaagcgagca gtgggaatcg gagcactgtt cctgggcttt 1560
ctgggagccg ctgggtctac tatgggggca gccagtatga ccctgacagt gcaggcccga 1620
cagctgctgt ccgacatcgt ccagcagcag aataacctgc tgcgggccat tgaagctcag 1680
cagcacctgc tgcagctgac cgtgtgggga atcaagcagc tgcaggccag aatcctggct 1740
gtggagcggt acctgaaaga tcagcagctg ctgggcatct ggggatgcag tgggaagctg 1800

```
atttgtacca cagctgtgcc ctggaacgca tcatggagca ataagagcct ggagcagatc   1860

tggaataaca tgacctggat ggaatgggac cgggagatta ataactacac atctctgatc   1920

catagtctga ttgaggaatc ccagaaccag caggaaaaga atgaacagga gctgctggag   1980

ctggataaat gggcctctct gtggaattgg ttcaacatca ccaattggct gtggtacatt   2040

aagctgttta tcatgattgt gggcggactg gtcggactga ggatcgtgtt cgctgtcctg   2100

tctattgtga accgagtcag gcaggggtat agtcctctgt catttcagac acacctgcca   2160

atccctcgag gaccagaccg acccgaaggg attgaggaag agggaggaga gagagaccga   2220

gatcgatcca tccggctggt gaacggctct ctggccctga tttgggacga tctgcgctcc   2280

ctgtgcctgt tctcttacca tcgactgagg gatctgctgc tgatcgtgac cagaattgtc   2340

gaactgctgg gacgacgagg atgggaggcc ctgaaatact ggtggaatct gctgcagtat   2400

tggtcacagg agctgaagaa cagcgctgtg aacctgctga atgctactgc aatcgccgtg   2460

gctgaaggca ccgacagagt gatcgaggtc ctgcaggctg catatcgggc tattaggcac   2520

atcccaagac gcattagaca ggggctggaa cgcatcctgc tgtaa                   2565
```

<210> SEQ ID NO 52
<211> LENGTH: 854
<212> TYPE: PRT
<213> ORGANISM: Artificial Sequence
<220> FEATURE:
<223> OTHER INFORMATION: pGX1053 Env Clade B tier 1B NL43 Amino Acid Sequence

<400> SEQUENCE: 52

```
Met Arg Val Lys Glu Lys Tyr Gln His Leu Trp Arg Trp Gly Trp Lys
1               5                   10                  15

Trp Gly Thr Met Leu Leu Gly Ile Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Asp Lys Val Gln Lys Glu Tyr Ala Phe Phe
                165                 170                 175

Tyr Lys Leu Asp Ile Val Pro Ile Asp Asn Thr Ser Tyr Arg Leu Ile
            180                 185                 190

Ser Cys Asn Thr Ser Val Ile Thr Gln Ala Cys Pro Lys Val Ser Phe
        195                 200                 205

Glu Pro Ile Pro Ile His Tyr Cys Ala Pro Ala Gly Phe Ala Ile Leu
    210                 215                 220
```

-continued

```
Lys Cys Asn Asn Lys Thr Phe Asn Gly Thr Gly Pro Cys Thr Asn Val
225                 230                 235                 240

Ser Thr Val Gln Cys Thr His Gly Ile Arg Pro Val Val Ser Thr Gln
                245                 250                 255

Leu Leu Leu Asn Gly Ser Leu Ala Glu Glu Asp Val Val Ile Arg Ser
            260                 265                 270

Ala Asn Phe Thr Asp Asn Ala Lys Thr Ile Ile Val Gln Leu Asn Thr
        275                 280                 285

Ser Val Glu Ile Asn Cys Thr Arg Pro Asn Asn Asn Thr Arg Lys Ser
    290                 295                 300

Ile Arg Ile Gln Arg Gly Pro Gly Arg Ala Phe Val Thr Ile Gly Lys
305                 310                 315                 320

Ile Gly Asn Met Arg Gln Ala His Cys Asn Ile Ser Arg Ala Lys Trp
                325                 330                 335

Asn Ala Thr Leu Lys Gln Ile Ala Ser Lys Leu Arg Glu Gln Phe Gly
            340                 345                 350

Asn Asn Lys Thr Ile Ile Phe Lys Gln Ser Ser Gly Gly Asp Pro Glu
        355                 360                 365

Ile Val Thr His Ser Phe Asn Cys Gly Gly Glu Phe Phe Tyr Cys Asn
    370                 375                 380

Ser Thr Gln Leu Phe Asn Ser Thr Trp Phe Asn Ser Thr Trp Ser Thr
385                 390                 395                 400

Glu Gly Ser Asn Asn Thr Glu Gly Ser Asp Thr Ile Thr Leu Pro Cys
                405                 410                 415

Arg Ile Lys Gln Phe Ile Asn Met Trp Gln Glu Val Gly Lys Ala Met
            420                 425                 430

Tyr Ala Pro Pro Ile Ser Gly Gln Ile Arg Cys Ser Ser Asn Ile Thr
        435                 440                 445

Gly Leu Leu Leu Thr Arg Asp Gly Gly Asn Asn Asn Asn Gly Ser Glu
    450                 455                 460

Ile Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Lys Ala Lys Arg Arg Val Val Gln Arg Glu Lys Arg Ala Val Gly
            500                 505                 510

Ile Gly Ala Leu Phe Leu Gly Phe Leu Gly Ala Ala Gly Ser Thr Met
        515                 520                 525

Gly Ala Ala Ser Met Thr Leu Thr Val Gln Ala Arg Gln Leu Leu Ser
    530                 535                 540

Asp Ile Val Gln Gln Gln Asn Asn Leu Leu Arg Ala Ile Glu Ala Gln
545                 550                 555                 560

Gln His Leu Leu Gln Leu Thr Val Trp Gly Ile Lys Gln Leu Gln Ala
                565                 570                 575

Arg Ile Leu Ala Val Glu Arg Tyr Leu Lys Asp Gln Gln Leu Leu Gly
            580                 585                 590

Ile Trp Gly Cys Ser Gly Lys Leu Ile Cys Thr Thr Ala Val Pro Trp
        595                 600                 605

Asn Ala Ser Trp Ser Asn Lys Ser Leu Glu Gln Ile Trp Asn Asn Met
    610                 615                 620

Thr Trp Met Glu Trp Asp Arg Glu Ile Asn Asn Tyr Thr Ser Leu Ile
625                 630                 635                 640
```

```
His Ser Leu Ile Glu Glu Ser Gln Asn Gln Gln Glu Lys Asn Glu Gln
                645                 650                 655

Glu Leu Leu Glu Leu Asp Lys Trp Ala Ser Leu Trp Asn Trp Phe Asn
            660                 665                 670

Ile Thr Asn Trp Leu Trp Tyr Ile Lys Leu Phe Ile Met Ile Val Gly
        675                 680                 685

Gly Leu Val Gly Leu Arg Ile Val Phe Ala Val Leu Ser Ile Val Asn
    690                 695                 700

Arg Val Arg Gln Gly Tyr Ser Pro Leu Ser Phe Gln Thr His Leu Pro
705                 710                 715                 720

Ile Pro Arg Gly Pro Asp Arg Pro Glu Gly Ile Glu Glu Glu Gly Gly
                725                 730                 735

Glu Arg Asp Arg Asp Arg Ser Ile Arg Leu Val Asn Gly Ser Leu Ala
            740                 745                 750

Leu Ile Trp Asp Asp Leu Arg Ser Leu Cys Leu Phe Ser Tyr His Arg
        755                 760                 765

Leu Arg Asp Leu Leu Leu Ile Val Thr Arg Ile Val Glu Leu Leu Gly
    770                 775                 780

Arg Arg Gly Trp Glu Ala Leu Lys Tyr Trp Trp Asn Leu Leu Gln Tyr
785                 790                 795                 800

Trp Ser Gln Glu Leu Lys Asn Ser Ala Val Asn Leu Leu Asn Ala Thr
                805                 810                 815

Ala Ile Ala Val Ala Glu Gly Thr Asp Arg Val Ile Glu Val Leu Gln
            820                 825                 830

Ala Ala Tyr Arg Ala Ile Arg His Ile Pro Arg Arg Ile Arg Gln Gly
        835                 840                 845

Leu Glu Arg Ile Leu Leu
    850


<210> SEQ ID NO 53
<211> LENGTH: 2586
<212> TYPE: DNA
<213> ORGANISM: Artificial Sequence
<220> FEATURE:
<223> OTHER INFORMATION: pGX1054  Env Clade B tier 2 AC10.0.29 DNA
      Sequence

<400> SEQUENCE: 53

atgagagtcc gggagacacg aaaaaactat cagcacctgt ggtggaaatg gggaatgatg     60

ctgctgggaa tgctgatgat ctgttcagcc gtggaacaga cctgggtgac agtctactat    120

ggcgtgccag tctggaagga ggctaacacc acactgttct gcgcaagcga cgctaaagca    180

tacaacacag aggtgcacaa tgtctgggca actcatgcct gtgtgcccac cgatccaaat    240

ccccaggagg tggaactgga gaacgtcact gaaaacttca acatgtggaa gaacaacatg    300

gtggaccaga tgcacgagga tatcattagt ctgtgggacc agtcactgaa gccttgcgtg    360

aaactgaccc cactgtgcgt cactctgtca tgtaccgaca acgtggggaa tgatactagc    420

accaacaatt cccgctggga taagatggaa aaaggagaga tcaagaattg tagcttcaac    480

attactacca atatgcggga caagatgcag aaacagtacg ccctgtttta taagctggat    540

gtggtcccca tcgaggaagg gaaaaacaat aacagctcct tcaccgacta ccgcctgatc    600

tcttgcaata caagtgtgat tactcaggcc tgtcctaagg tcacatttga gcctatccca    660

attcactatt gcgccccagc tggattcgct ctgctgaagt gtaaagataa gaagttcaac    720

ggcactgggc cctgcaagaa cgtgagcacc gtccagtgta cacatggcat caaacctgtg    780
```

-continued

```
gtcagtaccc agctgctgct gaacgggtca ctggctgagg aagaggtggt catcagatca    840

gaaaatttca gcaataacgc aaggaccatc attgtgcagc tgaacacatc cgtcgagatc    900

aagtgcattc ggccaaataa caataccaga aaaggcatcc acattggacc cggccgggca    960

ttttacacaa ctggggacat cattggagat atcaggcagg cccattgtaa catttctcgc   1020

cagaattgga acaatacact gaagcagatc gccgaaaaac tgagagagca gttcgggaat   1080

aagactatcg tgtttaggaa ctctagtggc ggggaccctg agattgtgat gcacactttc   1140

aactgcgcag gagaattctt ttactgtaac accgccgagc tgtttaatag cacatggtat   1200

gctaacggca ctatctccat tggaggcggg aacaagacca atatcattct gccatgcaga   1260

atcaaacagt tcattaatat gtggcaggaa gtgggaaagg ctatgtatgc accccctatc   1320

agtggccaga ttaggtgttc aagcaacatc acaggactgc tgctgacccg ggacggagga   1380

cgaggaaacc agactgataa tcagaccgag atcttcagac ccgtgggggg agatatgaaa   1440

aacaattggc gcagcgaact gtacaagtat aaagtggtcc gaatcgagcc actgggaatt   1500

gcaccaaccc gggccaagcg aagagtggtc cagcgagaga aaagagccgt ggggatcgga   1560

gctctgttcc tgggatttct gggagcagct gggtccacaa tgggagcagc ctctatgaca   1620

ctgactgtgc aggcccgcct gctgctgtct gggatcgtgc agcagcagaa caatctgctg   1680

cgggccattg aagctcagca gcatctgctg cagctgaccg tgtggggcat caagcagctg   1740

caggctaggg tgctggcagt cgagaggtac ctgcgcgacc agcagctgct gggaatctgg   1800

ggctgcagcg ggaaactgat ttgtaccaca gccgtgcctt ggaacgtcag ctggaacaat   1860

agatccgtgg acgatatctg ggaaaatatg acatggatgc agtgggacag ggagatttcc   1920

aactacacct ctctgatcta tacactgatt gaagagtccc agaaccagca ggaaaagaat   1980

gaacaggagc tgctggcact ggataaatgg gccaacctgt ggaattggtt caacatcact   2040

gagtggctgt ggtacatcaa gatttttatc atgattgtgg gcgggctggt cggcctgaga   2100

atcgtgttcg ccgtcctgtc cattgtgaat cgagtccggc agggatattc ccccctgtct   2160

tttcagacac acctgcctgc tcagagagga ccagacaggc ctggaggaat cgaagaggaa   2220

gggggagagt ctgacagaga taggagtggc cgcctggtga acgggttcct ggccatcatt   2280

tggatcgacc tgcgatcact gtgcctgttt agctatcacc atctgcgaga tctgctgctg   2340

attgtgaccc ggatcgtcga aattctggga aggcgcggct gggagatcct gaagtactgg   2400

tggaacctgc tgcagtattg gattcaggag ctgaaaaata gtgccgtgtc actgctgaac   2460

gcaatcgcca ttgctgtggg cgaagggaag gatcgcatca ttgaggcctt ccgctctatc   2520

tttcgagcta tcctgcatat tccaacccgc attcgacagg gactggagcg aagtctgctg   2580

tgataa                                                              2586
```

<210> SEQ ID NO 54
<211> LENGTH: 860
<212> TYPE: PRT
<213> ORGANISM: Artificial Sequence
<220> FEATURE:
<223> OTHER INFORMATION: pGX1054 Env Clade B tier 2 AC10.0.29 Amino Acid Sequence

<400> SEQUENCE: 54

```
Met Arg Val Arg Glu Thr Arg Lys Asn Tyr Gln His Leu Trp Trp Lys
1               5                   10                  15

Trp Gly Met Met Leu Leu Gly Met Leu Met Ile Cys Ser Ala Val Glu
            20                  25                  30
```

```
Gln Thr Trp Val Thr Val Tyr Tyr Gly Val Pro Val Trp Lys Glu Ala
        35                  40                  45

Asn Thr Thr Leu Phe Cys Ala Ser Asp Ala Lys Ala Tyr Asn Thr Glu
    50                  55                  60

Val His Asn Val Trp Ala Thr His Ala Cys Val Pro Thr Asp Pro Asn
65                  70                  75                  80

Pro Gln Glu Val Glu Leu Glu Asn Val Thr Glu Asn Phe Asn Met Trp
                85                  90                  95

Lys Asn Asn Met Val Asp Gln Met His Glu Asp Ile Ile Ser Leu Trp
            100                 105                 110

Asp Gln Ser Leu Lys Pro Cys Val Lys Leu Thr Pro Leu Cys Val Thr
        115                 120                 125

Leu Ser Cys Thr Asp Asn Val Gly Asn Asp Thr Ser Thr Asn Asn Ser
    130                 135                 140

Arg Trp Asp Lys Met Glu Lys Gly Glu Ile Lys Asn Cys Ser Phe Asn
145                 150                 155                 160

Ile Thr Thr Asn Met Arg Asp Lys Met Gln Lys Gln Tyr Ala Leu Phe
                165                 170                 175

Tyr Lys Leu Asp Val Val Pro Ile Glu Glu Gly Lys Asn Asn Asn Ser
            180                 185                 190

Ser Phe Thr Asp Tyr Arg Leu Ile Ser Cys Asn Thr Ser Val Ile Thr
        195                 200                 205

Gln Ala Cys Pro Lys Val Thr Phe Glu Pro Ile Pro Ile His Tyr Cys
    210                 215                 220

Ala Pro Ala Gly Phe Ala Leu Leu Lys Cys Lys Asp Lys Lys Phe Asn
225                 230                 235                 240

Gly Thr Gly Pro Cys Lys Asn Val Ser Thr Val Gln Cys Thr His Gly
                245                 250                 255

Ile Lys Pro Val Val Ser Thr Gln Leu Leu Leu Asn Gly Ser Leu Ala
            260                 265                 270

Glu Glu Glu Val Val Ile Arg Ser Glu Asn Phe Ser Asn Asn Ala Arg
        275                 280                 285

Thr Ile Ile Val Gln Leu Asn Thr Ser Val Glu Ile Lys Cys Ile Arg
    290                 295                 300

Pro Asn Asn Asn Thr Arg Lys Gly Ile His Ile Gly Pro Gly Arg Ala
305                 310                 315                 320

Phe Tyr Thr Thr Gly Asp Ile Ile Gly Asp Ile Arg Gln Ala His Cys
                325                 330                 335

Asn Ile Ser Arg Gln Asn Trp Asn Asn Thr Leu Lys Gln Ile Ala Glu
            340                 345                 350

Lys Leu Arg Glu Gln Phe Gly Asn Lys Thr Ile Val Phe Arg Asn Ser
        355                 360                 365

Ser Gly Gly Asp Pro Glu Ile Val Met His Thr Phe Asn Cys Ala Gly
    370                 375                 380

Glu Phe Phe Tyr Cys Asn Thr Ala Glu Leu Phe Asn Ser Thr Trp Tyr
385                 390                 395                 400

Ala Asn Gly Thr Ile Ser Ile Gly Gly Gly Asn Lys Thr Asn Ile Ile
                405                 410                 415

Leu Pro Cys Arg Ile Lys Gln Phe Ile Asn Met Trp Gln Glu Val Gly
            420                 425                 430

Lys Ala Met Tyr Ala Pro Pro Ile Ser Gly Gln Ile Arg Cys Ser Ser
        435                 440                 445

Asn Ile Thr Gly Leu Leu Leu Thr Arg Asp Gly Gly Arg Gly Asn Gln
```

```
    450                 455                 460

Thr Asp Asn Gln Thr Glu Ile Phe Arg Pro Val Gly Gly Asp Met Lys
465                 470                 475                 480

Asn Asn Trp Arg Ser Glu Leu Tyr Lys Tyr Lys Val Val Arg Ile Glu
                485                 490                 495

Pro Leu Gly Ile Ala Pro Thr Arg Ala Lys Arg Arg Val Val Gln Arg
            500                 505                 510

Glu Lys Arg Ala Val Gly Ile Gly Ala Leu Phe Leu Gly Phe Leu Gly
        515                 520                 525

Ala Ala Gly Ser Thr Met Gly Ala Ala Ser Met Thr Leu Thr Val Gln
    530                 535                 540

Ala Arg Leu Leu Leu Ser Gly Ile Val Gln Gln Gln Asn Asn Leu Leu
545                 550                 555                 560

Arg Ala Ile Glu Ala Gln Gln His Leu Leu Gln Leu Thr Val Trp Gly
                565                 570                 575

Ile Lys Gln Leu Gln Ala Arg Val Leu Ala Val Glu Arg Tyr Leu Arg
            580                 585                 590

Asp Gln Gln Leu Leu Gly Ile Trp Gly Cys Ser Gly Lys Leu Ile Cys
        595                 600                 605

Thr Thr Ala Val Pro Trp Asn Val Ser Trp Asn Asn Arg Ser Val Asp
    610                 615                 620

Asp Ile Trp Glu Asn Met Thr Trp Met Gln Trp Asp Arg Glu Ile Ser
625                 630                 635                 640

Asn Tyr Thr Ser Leu Ile Tyr Thr Leu Ile Glu Glu Ser Gln Asn Gln
                645                 650                 655

Gln Glu Lys Asn Glu Gln Glu Leu Leu Ala Leu Asp Lys Trp Ala Asn
            660                 665                 670

Leu Trp Asn Trp Phe Asn Ile Thr Glu Trp Leu Trp Tyr Ile Lys Ile
        675                 680                 685

Phe Ile Met Ile Val Gly Gly Leu Val Gly Leu Arg Ile Val Phe Ala
    690                 695                 700

Val Leu Ser Ile Val Asn Arg Val Arg Gln Gly Tyr Ser Pro Leu Ser
705                 710                 715                 720

Phe Gln Thr His Leu Pro Ala Gln Arg Gly Pro Asp Arg Pro Gly Gly
                725                 730                 735

Ile Glu Glu Glu Gly Gly Glu Ser Asp Arg Asp Arg Ser Gly Arg Leu
            740                 745                 750

Val Asn Gly Phe Leu Ala Ile Ile Trp Ile Asp Leu Arg Ser Leu Cys
        755                 760                 765

Leu Phe Ser Tyr His His Leu Arg Asp Leu Leu Leu Ile Val Thr Arg
    770                 775                 780

Ile Val Glu Ile Leu Gly Arg Arg Gly Trp Glu Ile Leu Lys Tyr Trp
785                 790                 795                 800

Trp Asn Leu Leu Gln Tyr Trp Ile Gln Glu Leu Lys Asn Ser Ala Val
                805                 810                 815

Ser Leu Leu Asn Ala Ile Ala Ile Ala Val Gly Glu Gly Lys Asp Arg
            820                 825                 830

Ile Ile Glu Ala Phe Arg Ser Ile Phe Arg Ala Ile Leu His Ile Pro
        835                 840                 845

Thr Arg Ile Arg Gln Gly Leu Glu Arg Ser Leu Leu
    850                 855                 860
```

<210> SEQ ID NO 55

<211> LENGTH: 2610
<212> TYPE: DNA
<213> ORGANISM: Artificial Sequence
<220> FEATURE:
<223> OTHER INFORMATION: pGX1055 Env Clade B tier 2 QHO692.42 DNA Sequence

<400> SEQUENCE: 55
atgcgcgtca agggaattag aaggaactgg caggggctgt ggagatgggg aactatgctg 60
ctgggaatgc tgatgatttg tagggctgcc gaaaatctgt gggtgactgt ctactatggg 120
gtgcctgtct ggaaagaggc taccacaact ctgttctgcg catctgatgc taaggcatac 180
gaaacagaga aacacaacgt gtgggccact catgcttgcg tgccaaccga cccaaatccc 240
caggaagtgg tcctgggcaa cgtgaccgag aactttaata tgtggaagaa caatatggtg 300
gaacagatgc atgaggatat cattagcctg tgggacgagt ccctgaagcc ctgcgtgaaa 360
ctgacacctc tgtgcgtcac tctgaattgt accgatgaag tgaagacatc ctacgccaac 420
aaaacttcta atgagactta taagacctct aatgaaacct tcggggagat caaaaactgt 480
agcttttccg tgccaacagg aattaaggat aaagtgcaga acgtctacgc cctgttctat 540
aagctggacg tgatccccat tgacgataac aacaacagct ccaagaacaa caacggaagc 600
tactctagtt acagactgat caactgcaat acatcagtga ttactcaggc ttgtcctaag 660
gtcagctttg agcctatccc aattcattac tgcgccccag ctggcttcgc aatcctgaag 720
tgtaacaaca agaccttcaa cggaacaggc ccctgcacta acgtgtctac cgtccagtgt 780
acacacggca ttagacctgt ggtctctacc cagctgctgc tgaatgggag tctggcagag 840
gaagaggtgg tcatcaggag tgaaaacttc actaacaatg ccaaaaccat cattgtgcac 900
ctgaagaaaa gtgtcgagat taactgcacc cggccaggca acaatacaag aaagtcaatc 960
catattggac caggaagggc cttctacgca accggggata tcattggaga catccgccag 1020
gcccactgta atctgtcaag cgtgcagtgg aacgatacac tgaagcagat cgtgatcaag 1080
ctgggcgagc agttcgggac aaataagact attgctttta accagtcctc tggcggggac 1140
cccgaaatcg tgatgcatag cttcaattgc ggaggcgagt tcttttactg taataccaca 1200
cagctgttca actccacatg ggaatttcac ggcaactgga caagatctaa cttcaccgag 1260
tctaacagta ctaccattac tctgccttgc aggatcaagc agattgtgaa catgtggcag 1320
gaagtcggga aagctatgta tgcacccccct atcaggggac agattcgctg tagttcaaat 1380
atcaccggcc tgctgctgac aagagacggg ggagtgaacg gaacccgaga gacattccgg 1440
cccggcgggg gagatatgag agacaactgg aggagcgaac tgtacaagta taaagtggtc 1500
aaaatcgagc ctctgggggt ggcaccaacc aaggccaaac ggagagtggt ccagcgcgag 1560
aagcgagcag tgggcactat tggggccatg ttcctgggat ttctgggagc agctgggagt 1620
accatgggag cagcctcaat caccctgaca gtgcaggcac gacagctgct gtccggaatc 1680
gtgcagcagc agaacaatct gctgcgggcc attgaagctc agcagcacat gctgcagctg 1740
accgtgtggg gcatcaagca gctgcaggct agggtgctgg cagtcgagcg gtacctgaga 1800
gatcagcagc tgctgggaat ctggggctgc agcgggaagc tgatttgtac aactgccgtg 1860
ccatggaatg cttcatggag caacaaatcc caggattata tctggaacaa tatgacatgg 1920
atgcagtggg acaaggaaat caacaactac actaatctga tctactctct gctggaagac 1980
agtcagaatc agcaggagaa gaacgaacat gagctgctgg agctggataa atgggccagc 2040
ctgtggaact ggttcgacat cacccgctgg ctgtggtaca tcaagatctt catcatgatt 2100

-continued

```
gtgggcgggc tgatcggact gcgaatcgtc attgccgtgg tctccattgt gaacagagtc   2160

aggcagggat attcccctat ctctctgcag acccacttcc cagctcctcg cggaccagat   2220

cgaccagagg gaatcgaaga gggaggcggg gaccgagatc gagaccggag cctgcgactg   2280

gtgcacggct ccctggccct gatctgggac gatctgaggt cactgtgcat cttcagctac   2340

catagactga gggacctgct gctgatcgtg gcccgcgtgg tcgaaattct gggaaggcgc   2400

ggctgggagg ctctgaagta ctggtggaat ctgctgcagt attggtccca ggagctgaaa   2460

aacagtgcag tgtcactgct ggatgcaact gccatcgctg tggcagaagg caccgaccgg   2520

atcattgaga tcattcgacg ggctttccgc gccatcctgc atattcctac ccgcatccga   2580

cagggactgg agagagcact gctgtgataa                                    2610
```

<210> SEQ ID NO 56
<211> LENGTH: 868
<212> TYPE: PRT
<213> ORGANISM: Artificial Sequence
<220> FEATURE:
<223> OTHER INFORMATION: pGX1055  Env Clade B tier 2 QHO682.42 Amino
      Acid Sequence

<400> SEQUENCE: 56

```
Met Arg Val Lys Gly Ile Arg Arg Asn Trp Gln Gly Leu Trp Arg Trp
1               5                   10                  15

Gly Thr Met Leu Leu Gly Met Leu Met Ile Cys Arg Ala Ala Glu Asn
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Val Val Leu Gly Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Glu Ser Leu Lys Pro Cys Val Lys Leu Thr Pro Leu Cys Val Thr Leu
        115                 120                 125

Asn Cys Thr Asp Glu Val Lys Thr Ser Tyr Ala Asn Lys Thr Ser Asn
    130                 135                 140

Glu Thr Tyr Lys Thr Ser Asn Glu Thr Phe Gly Glu Ile Lys Asn Cys
145                 150                 155                 160

Ser Phe Ser Val Pro Thr Gly Ile Lys Asp Lys Val Gln Asn Val Tyr
                165                 170                 175

Ala Leu Phe Tyr Lys Leu Asp Val Ile Pro Ile Asp Asp Asn Asn Asn
            180                 185                 190

Ser Ser Lys Asn Asn Asn Gly Ser Tyr Ser Ser Tyr Arg Leu Ile Asn
        195                 200                 205

Cys Asn Thr Ser Val Ile Thr Gln Ala Cys Pro Lys Val Ser Phe Glu
    210                 215                 220

Pro Ile Pro Ile His Tyr Cys Ala Pro Ala Gly Phe Ala Ile Leu Lys
225                 230                 235                 240

Cys Asn Asn Lys Thr Phe Asn Gly Thr Gly Pro Cys Thr Asn Val Ser
                245                 250                 255

Thr Val Gln Cys Thr His Gly Ile Arg Pro Val Val Ser Thr Gln Leu
            260                 265                 270
```

```
Leu Leu Asn Gly Ser Leu Ala Glu Glu Glu Val Val Ile Arg Ser Glu
        275                 280                 285

Asn Phe Thr Asn Asn Ala Lys Thr Ile Ile Val His Leu Lys Lys Ser
    290                 295                 300

Val Glu Ile Asn Cys Thr Arg Pro Gly Asn Asn Thr Arg Lys Ser Ile
305                 310                 315                 320

His Ile Gly Pro Gly Arg Ala Phe Tyr Ala Thr Gly Asp Ile Ile Gly
                325                 330                 335

Asp Ile Arg Gln Ala His Cys Asn Leu Ser Ser Val Gln Trp Asn Asp
            340                 345                 350

Thr Leu Lys Gln Ile Val Ile Lys Leu Gly Glu Gln Phe Gly Thr Asn
        355                 360                 365

Lys Thr Ile Ala Phe Asn Gln Ser Ser Gly Gly Asp Pro Glu Ile Val
    370                 375                 380

Met His Ser Phe Asn Cys Gly Gly Glu Phe Phe Tyr Cys Asn Thr Thr
385                 390                 395                 400

Gln Leu Phe Asn Ser Thr Trp Glu Phe His Gly Asn Trp Thr Arg Ser
                405                 410                 415

Asn Phe Thr Glu Ser Asn Ser Thr Thr Ile Thr Leu Pro Cys Arg Ile
            420                 425                 430

Lys Gln Ile Val Asn Met Trp Gln Glu Val Gly Lys Ala Met Tyr Ala
        435                 440                 445

Pro Pro Ile Arg Gly Gln Ile Arg Cys Ser Ser Asn Ile Thr Gly Leu
    450                 455                 460

Leu Leu Thr Arg Asp Gly Gly Val Asn Gly Thr Arg Glu Thr Phe Arg
465                 470                 475                 480

Pro Gly Gly Gly Asp Met Arg Asp Asn Trp Arg Ser Glu Leu Tyr Lys
                485                 490                 495

Tyr Lys Val Val Lys Ile Glu Pro Leu Gly Val Ala Pro Thr Lys Ala
            500                 505                 510

Lys Arg Arg Val Val Gln Arg Glu Lys Arg Ala Val Gly Thr Ile Gly
        515                 520                 525

Ala Met Phe Leu Gly Phe Leu Gly Ala Ala Gly Ser Thr Met Gly Ala
    530                 535                 540

Ala Ser Ile Thr Leu Thr Val Gln Ala Arg Gln Leu Leu Ser Gly Ile
545                 550                 555                 560

Val Gln Gln Gln Asn Asn Leu Leu Arg Ala Ile Glu Ala Gln Gln His
                565                 570                 575

Met Leu Gln Leu Thr Val Trp Gly Ile Lys Gln Leu Gln Ala Arg Val
            580                 585                 590

Leu Ala Val Glu Arg Tyr Leu Arg Asp Gln Gln Leu Leu Gly Ile Trp
        595                 600                 605

Gly Cys Ser Gly Lys Leu Ile Cys Thr Thr Ala Val Pro Trp Asn Ala
    610                 615                 620

Ser Trp Ser Asn Lys Ser Gln Asp Tyr Ile Trp Asn Asn Met Thr Trp
625                 630                 635                 640

Met Gln Trp Asp Lys Glu Ile Asn Asn Tyr Thr Asn Leu Ile Tyr Ser
                645                 650                 655

Leu Leu Glu Asp Ser Gln Asn Gln Gln Glu Lys Asn Glu His Glu Leu
            660                 665                 670

Leu Glu Leu Asp Lys Trp Ala Ser Leu Trp Asn Trp Phe Asp Ile Thr
        675                 680                 685
```

```
Arg Trp Leu Trp Tyr Ile Lys Ile Phe Ile Met Ile Val Gly Gly Leu
    690                 695                 700

Ile Gly Leu Arg Ile Val Ile Ala Val Val Ser Ile Val Asn Arg Val
705                 710                 715                 720

Arg Gln Gly Tyr Ser Pro Ile Ser Leu Gln Thr His Phe Pro Ala Pro
                725                 730                 735

Arg Gly Pro Asp Arg Pro Glu Gly Ile Glu Glu Gly Gly Gly Asp Arg
            740                 745                 750

Asp Arg Asp Arg Ser Leu Arg Leu Val His Gly Ser Leu Ala Leu Ile
        755                 760                 765

Trp Asp Asp Leu Arg Ser Leu Cys Ile Phe Ser Tyr His Arg Leu Arg
    770                 775                 780

Asp Leu Leu Leu Ile Val Ala Arg Val Val Glu Ile Leu Gly Arg Arg
785                 790                 795                 800

Gly Trp Glu Ala Leu Lys Tyr Trp Trp Asn Leu Leu Gln Tyr Trp Ser
                805                 810                 815

Gln Glu Leu Lys Asn Ser Ala Val Ser Leu Leu Asp Ala Thr Ala Ile
            820                 825                 830

Ala Val Ala Glu Gly Thr Asp Arg Ile Ile Glu Ile Ile Arg Arg Ala
        835                 840                 845

Phe Arg Ala Ile Leu His Ile Pro Thr Arg Ile Arg Gln Gly Leu Glu
    850                 855                 860

Arg Ala Leu Leu
865
```

<210> SEQ ID NO 57
<211> LENGTH: 2562
<212> TYPE: DNA
<213> ORGANISM: Artificial Sequence
<220> FEATURE:
<223> OTHER INFORMATION: pGX1034 - Env Clade B tier 2 CAAN5342.A2 DNA Sequence

<400> SEQUENCE: 57

```
atgagagtga aagagattag gaagaactat cggcacctgt ggaaatgggg gattatgctg     60

ctgggaatgc tgatgatttg tagcgccaca gagaatctgt gggtgactgt ctactatggg    120

gtgcccgtct ggaaggaagc caccacaact ctgttctgcg ctagcgacgc aaagggatac    180

gagaaagaag tgcacaacgt ctgggccacc catgcttgcg tgcctacaga tccaaatccc    240

caggaagtgg tcctggagaa cgtgaccgaa aacttcaaca tgtggaaaaa caatatggtg    300

gagcagatgc acgaagatat catttcactg tgggaccaga gcctgaagcc ttgcgtgaaa    360

ctgactccac tgtgcgtcac cctgaattgt agtgacgtga acaccacatc agtcaatact    420

accgccagct ccatggaagg cggggagatc aagaattgtt ccttcaacac aactaccagt    480

atgtcagaca agatgcagaa agagtacgct ctgttttata ccctggatgt ggtccccatc    540

gtgaaggaaa acaatacata ccggctgatc agttgcaaca catcagtgat tactcaggcc    600

tgtccaaaag tcagcttcga gcctatccca attcactatt gcgctcccgc aggcttcgct    660

atcctgatgt gcaacaataa gacatttgat ggcaaagggc cttgcaacaa cgtgagcacc    720

gtccagtgta cacatggaat caagccagtg gtctcaaccc agctgctgct gaatggcagc    780

ctggctgagg aagaggtggt cattaggtcc gataatttca cagacaacgc aaagactatc    840

attgtgcacc tgaacgaatc tatcgagatt acttgcacca ggcccaacaa taacaccagc    900

aaatccatca caattggacc tggacgagcc ttctacgcaa ccggacgaat cattggcgac    960
```

-continued

```
atccggaagg cacactgtaa tattagcggg gagaaatggc ataacgccct ggaacagatc   1020

gtgaagaaac tgggagaaaa gttcgagaat gccacaacta tcaggtttaa ccagtctagt   1080

ggaggcgatc aggagattgt gatgcatacc ttcaactgcg ggggagaatt cttttactgt   1140

aacagcactc agctgtttaa ttccacctgg tggccaaacg gcaccacaac tgagtggagc   1200

aatgaaacct ccaacgggac aatcactctg ccctgccgca ttaagcagat cattaatatg   1260

tggcaggaag tgggcaaagc tatgtatgca ccccctatct ctgggcctat tagttgttca   1320

agcaacatca caggactgct gctggtgcga gatggcggga atgacaacga gactaatggc   1380

accgaaacat tcagaccagg aggcggggat atgcgggaca actggagatc cgagctgtac   1440

aagtataaag tggtcaagat cgaaccactg gggtggcac ccacaaaggc caaacggaga   1500

gtggtccaga gagagaaaag ggccgtgggg ctgggagcta tgttcctggg ctttctggga   1560

gcagctggat ctaccatggg agcagccagt atcactctga ccgtgcaggc caggctgctg   1620

ctgtctggga tcgtccagca gcagaataac ctgctgcgcg ccattgaggc tcagcagcac   1680

ctgctgcagc tgaccgtgtg gggcatcaag cagctgcagg ctagagtcct ggcaattgag   1740

aggtacctga aggaccagca gctgctggga atctggggat gctccggaaa actgatttgt   1800

accacagccg tgccctggaa ctcctcttgg tctaataaga gtctgaaatg gatctgggac   1860

aatatgactt ggatggagtg ggaaaaggag attgataatt acaccggcat catctacaac   1920

ctgctggaag agagtcagaa ccagcaggat aagaatgaaa aagagctgct ggagctggac   1980

aagtgggcct cactgtggac ttggttcgat atcaccaatt ggctgtggta catcaaaatc   2040

ttcatcatga ttgtgggagg cctggtcgga ctgcggatcg tgttcgcagt cctgtctatt   2100

gtgaacaggg tccgccaggg ctattcaccc ctgagctttc agacacgact gccagcacct   2160

agggggctgg accgacctga gggaaccgaa gaggaagggg gagacagaga taaggaccgc   2220

agtatccgac tggtggatgg cttcctggct ctgatttggg acgatctgag atccctgtgc   2280

ctgttttctt atcaccgact gcgggacctg ctgctgatcg tggcacgggt ggtcgagatt   2340

ctgggccata gagggtggga aatcctgaag tactggtgga acctgctgca gtattggagc   2400

caggagctga aaaattccgc cgtgtctctg ctgaacgcca cagctatcgc agtggccgag   2460

ggcactgatc gcatcattga agtgctgcag cgaattggac gagccatcct gcacatcccc   2520

acccgaatta gacagggcct ggaaagagca ctgctgtgat aa                       2562
```

```
<210> SEQ ID NO 58
<211> LENGTH: 852
<212> TYPE: PRT
<213> ORGANISM: Artificial Sequence
<220> FEATURE:
<223> OTHER INFORMATION: pGX1034 - Env Clade B tier 2 CAAN5342.A2 Amino
      Acid Sequence

<400> SEQUENCE: 58

Met Arg Val Lys Glu Ile Arg Lys Asn Tyr Arg His Leu Trp Lys Trp
1               5                   10                  15

Gly Ile Met Leu Leu Gly Met Leu Met Ile Cys Ser Ala Thr Glu Asn
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Gly Tyr Glu Lys Glu Val
    50                  55                  60

His Asn Val Trp Ala Thr His Ala Cys Val Pro Thr Asp Pro Asn Pro
65                  70                  75                  80
```

```
Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Ser Asp Val Asn Thr Thr Ser Val Asn Thr Thr Ala Ser Ser
    130                 135                 140

Met Glu Gly Gly Glu Ile Lys Asn Cys Ser Phe Asn Thr Thr Thr Ser
145                 150                 155                 160

Met Ser Asp Lys Met Gln Lys Glu Tyr Ala Leu Phe Tyr Thr Leu Asp
                165                 170                 175

Val Val Pro Ile Val Lys Glu Asn Asn Thr Tyr Arg Leu Ile Ser Cys
            180                 185                 190

Asn Thr Ser Val Ile Thr Gln Ala Cys Pro Lys Val Ser Phe Glu Pro
        195                 200                 205

Ile Pro Ile His Tyr Cys Ala Pro Ala Gly Phe Ala Ile Leu Met Cys
    210                 215                 220

Asn Asn Lys Thr Phe Asp Gly Lys Gly Pro Cys Asn Asn Val Ser Thr
225                 230                 235                 240

Val Gln Cys Thr His Gly Ile Lys Pro Val Val Ser Thr Gln Leu Leu
                245                 250                 255

Leu Asn Gly Ser Leu Ala Glu Glu Glu Val Val Ile Arg Ser Asp Asn
            260                 265                 270

Phe Thr Asp Asn Ala Lys Thr Ile Ile Val His Leu Asn Glu Ser Ile
        275                 280                 285

Glu Ile Thr Cys Thr Arg Pro Asn Asn Asn Thr Ser Lys Ser Ile Thr
    290                 295                 300

Ile Gly Pro Gly Arg Ala Phe Tyr Ala Thr Gly Arg Ile Ile Gly Asp
305                 310                 315                 320

Ile Arg Lys Ala His Cys Asn Ile Ser Gly Glu Lys Trp His Asn Ala
                325                 330                 335

Leu Glu Gln Ile Val Lys Lys Leu Gly Glu Lys Phe Glu Asn Ala Thr
            340                 345                 350

Thr Ile Arg Phe Asn Gln Ser Ser Gly Gly Asp Gln Glu Ile Val Met
        355                 360                 365

His Thr Phe Asn Cys Gly Gly Glu Phe Phe Tyr Cys Asn Ser Thr Gln
    370                 375                 380

Leu Phe Asn Ser Thr Trp Trp Pro Asn Gly Thr Thr Thr Glu Trp Ser
385                 390                 395                 400

Asn Glu Thr Ser Asn Gly Thr Ile Thr Leu Pro Cys Arg Ile Lys Gln
                405                 410                 415

Ile Ile Asn Met Trp Gln Glu Val Gly Lys Ala Met Tyr Ala Pro Pro
            420                 425                 430

Ile Ser Gly Pro Ile Ser Cys Ser Ser Asn Ile Thr Gly Leu Leu Leu
        435                 440                 445

Val Arg Asp Gly Gly Asn Asp Asn Glu Thr Asn Gly Thr Glu Thr Phe
    450                 455                 460

Arg Pro Gly Gly Gly Asp Met Arg Asp Asn Trp Arg Ser Glu Leu Tyr
465                 470                 475                 480

Lys Tyr Lys Val Val Lys Ile Glu Pro Leu Gly Val Ala Pro Thr Lys
                485                 490                 495
```

```
Ala Lys Arg Arg Val Val Gln Arg Glu Lys Arg Ala Val Gly Leu Gly
            500                 505                 510

Ala Met Phe Leu Gly Phe Leu Gly Ala Ala Gly Ser Thr Met Gly Ala
        515                 520                 525

Ala Ser Ile Thr Leu Thr Val Gln Ala Arg Leu Leu Leu Ser Gly Ile
    530                 535                 540

Val Gln Gln Gln Asn Asn Leu Leu Arg Ala Ile Glu Ala Gln Gln His
545                 550                 555                 560

Leu Leu Gln Leu Thr Val Trp Gly Ile Lys Gln Leu Gln Ala Arg Val
                565                 570                 575

Leu Ala Ile Glu Arg Tyr Leu Lys Asp Gln Gln Leu Leu Gly Ile Trp
            580                 585                 590

Gly Cys Ser Gly Lys Leu Ile Cys Thr Thr Ala Val Pro Trp Asn Ser
        595                 600                 605

Ser Trp Ser Asn Lys Ser Leu Lys Trp Ile Trp Asp Asn Met Thr Trp
    610                 615                 620

Met Glu Trp Glu Lys Glu Ile Asp Asn Tyr Thr Gly Ile Ile Tyr Asn
625                 630                 635                 640

Leu Leu Glu Glu Ser Gln Asn Gln Gln Asp Lys Asn Glu Lys Glu Leu
                645                 650                 655

Leu Glu Leu Asp Lys Trp Ala Ser Leu Trp Thr Trp Phe Asp Ile Thr
            660                 665                 670

Asn Trp Leu Trp Tyr Ile Lys Ile Phe Ile Met Ile Val Gly Gly Leu
        675                 680                 685

Val Gly Leu Arg Ile Val Phe Ala Val Leu Ser Ile Val Asn Arg Val
    690                 695                 700

Arg Gln Gly Tyr Ser Pro Leu Ser Phe Gln Thr Arg Leu Pro Ala Pro
705                 710                 715                 720

Arg Gly Leu Asp Arg Pro Glu Gly Thr Glu Glu Glu Gly Gly Asp Arg
                725                 730                 735

Asp Lys Asp Arg Ser Ile Arg Leu Val Asp Gly Phe Leu Ala Leu Ile
            740                 745                 750

Trp Asp Asp Leu Arg Ser Leu Cys Leu Phe Ser Tyr His Arg Leu Arg
        755                 760                 765

Asp Leu Leu Leu Ile Val Ala Arg Val Val Glu Ile Leu Gly His Arg
    770                 775                 780

Gly Trp Glu Ile Leu Lys Tyr Trp Trp Asn Leu Leu Gln Tyr Trp Ser
785                 790                 795                 800

Gln Glu Leu Lys Asn Ser Ala Val Ser Leu Leu Asn Ala Thr Ala Ile
                805                 810                 815

Ala Val Ala Glu Gly Thr Asp Arg Ile Ile Glu Val Leu Gln Arg Ile
            820                 825                 830

Gly Arg Ala Ile Leu His Ile Pro Thr Arg Ile Arg Gln Gly Leu Glu
        835                 840                 845

Arg Ala Leu Leu
    850
```

<210> SEQ ID NO 59
<211> LENGTH: 2580
<212> TYPE: DNA
<213> ORGANISM: Artificial Sequence
<220> FEATURE:
<223> OTHER INFORMATION: Env Clade B 6535.3 DNA Sequence

<400> SEQUENCE: 59

-continued

```
atgaaggtga aggggacccg caaaaactac cagagactgt ggagatgggg caacatgctg      60
acaatgctgc tgggaatgct gatgatttgc tccgccacag agaagctgtg ggtgactgtc     120
tactatggcg tgcctgtctg gaaagaagct accacaactc tgttctgcgc atctgaggct     180
aaggcatacg acacagaagt gcacaacgtc tgggcaaccc atgcctgcgt gccaacagat     240
ccaaaccccc aggaagtgga gctggggaat gtcactgaga acttcaacat gtggaaaaat     300
gacatggtgg agcagatgca cgaagacatc attagtctgt gggatcagtc actgaagcct     360
tgcgtgcggc tgaccccact gtgcgtcaca ctggactgta ctgatctgaa caataccaca     420
aacactaaca atactaccaa taccaacagc tccaagatcg agggcgggga aatgaagaac     480
tgttcattca acatcacaac taatcgcgga gacaagcgac agaaagagta cgccctgctg     540
tataggactg atatcgtgag cattgaaaac acctctagtt cataccgcct gatctcatgc     600
aataccagcg tgattacaca ggcctgtcct aaggtcacat ttgagcctat cccaattcac     660
tattgcgccc cagctggctt cgctatcctg aagtgtaacg aggataagtt caacggcacc     720
gggccctgca aaaacgtgtc cactgtccag tgtacccatg gcattcggcc tactgtgagt     780
acccagctgc tgctgaatgg gtcactggcc aaggaggaag tgatcattag atccgccaac     840
ctgtctgaca atgctaagat cattatcgtg cagctgaaag atcccgtcga gatcaactgc     900
acacgaccta acaacaacac tcggaagagt attaatctgg gacccggcag ggctttctat     960
gcaacaggag acattatcgg cgatatccgg caggcccact gtaacattag cagagctaaa    1020
tggaatgaca ctctgaggga gatcgctaag aaactggcag aacagttcaa taaccgcacc    1080
atcgtgttta accagagctc cggaggcgat cctgagattg tgatgcattc tttcaattgc    1140
gccggcgaat tcttttactg tgacaccagc cagctgttta actccacatg gaattcaaac    1200
agcacatgga atgatactaa taacaataac tccaccgaga agattatcct gtcttgccgg    1260
atcagacaga ttatcaacag gtggcaggaa gtgggcaagg ccatgtatgc tccccctatc    1320
agcgggccca tcaagtgttc tagtaatatc acaggactgc tgctggctag ggacgggga     1380
aatgagacta acgtgacaga aacttttcgc ccagcaggag gggacatgcg agataactgg    1440
agaagcgagc tgtacaagta taaagtggtc cagatcgaac cactgggcat tgcccccaca    1500
aaggctaaac ggagagtggt ccagagagag aagagggcag tggggatgct gggagccatg    1560
ttcctgggct ttctgggggc cgctggatca accatcggag cagccagcat gaccctgaca    1620
gtgcaggcca ggcagctgct gagcggcatc gtgcagcagc agaataacct gctgcgcgca    1680
attgaggccc agcagcatat gctgcagctg accgtgtggg gcatcaaaca gctgcaggca    1740
agagtgctgg ccgtcgagag gtacctgaaa gaccagcagc tgctgggcat ctgggggtgc    1800
tctggaaagc tgatttgtac cacagccgtg ccctggaaca cctcctggtc taacaagagt    1860
ctgaattata tctgggacaa catgacatgg atggaatggg agcgggaaat tgataattac    1920
accagcctga tctatacact gattgaggaa tcccagaacc agcaggagaa gaatgagctg    1980
gaactgctgg aactggataa atggggctcc ctgtggaact ggttcagtat ctcaaattgg    2040
ctgtggtaca tccggatctt catcatcatt gtgggaggcc tggtcgggct gagaatcgtg    2100
ttcaccgtcc tgtctattgt gaaccgagtc cggcagggat atagcccact gtcctttcag    2160
actcgactgc cagcaaccca gaggggacag ccagaccgcc ctgagggaat cgaggaagag    2220
gggggagaaa gagacagggc acgctccatt cggctggtgg atgggttcct ggccctgttt    2280
tgggacgatc tgagatctct gtgcctgttc agttaccacc gactgcggga tctgctgctg    2340
atcgtggctc gcattgtcga gctgctgggc catcgagggt gggaaatcct gaagtactgg    2400
```

tggaacctgc tgcagtattg gagacaggag ctgaagaaat ctgcagtgag tctgctgaat 2460
actaccgcta tcgtggtcgc agagggcacc gaccgcatca ttgaagtggt ccagcgagct 2520
taccgagctt ttctgcatat tccccgccgc atccgacagg gactggagag agcactgctg 2580

<210> SEQ ID NO 60
<211> LENGTH: 860
<212> TYPE: PRT
<213> ORGANISM: Artificial Sequence
<220> FEATURE:
<223> OTHER INFORMATION: Env Clade B 6535.3 Amino Acid Sequence

<400> SEQUENCE: 60

Met Lys Val Lys Gly Thr Arg Lys Asn Tyr Gln Arg Leu Trp Arg Trp
1 5 10 15

Gly Asn Met Leu Thr Met Leu Leu Gly Met Leu Met Ile Cys Ser Ala
20 25 30

Thr Glu Lys Leu Trp Val Thr Val Tyr Tyr Gly Val Pro Val Trp Lys
35 40 45

Glu Ala Thr Thr Thr Leu Phe Cys Ala Ser Glu Ala Lys Ala Tyr Asp
50 55 60

Thr Glu Val His Asn Val Trp Ala Thr His Ala Cys Val Pro Thr Asp
65 70 75 80

Pro Asn Pro Gln Glu Val Glu Leu Gly Asn Val Thr Glu Asn Phe Asn
85 90 95

Met Trp Lys Asn Asp Met Val Glu Gln Met His Glu Asp Ile Ile Ser
100 105 110

Leu Trp Asp Gln Ser Leu Lys Pro Cys Val Arg Leu Thr Pro Leu Cys
115 120 125

Val Thr Leu Asp Cys Thr Asp Leu Asn Asn Thr Thr Asn Thr Asn Asn
130 135 140

Thr Thr Asn Thr Asn Ser Ser Lys Ile Glu Gly Gly Glu Met Lys Asn
145 150 155 160

Cys Ser Phe Asn Ile Thr Thr Asn Arg Gly Asp Lys Arg Gln Lys Glu
165 170 175

Tyr Ala Leu Leu Tyr Arg Thr Asp Ile Val Ser Ile Glu Asn Thr Ser
180 185 190

Ser Ser Tyr Arg Leu Ile Ser Cys Asn Thr Ser Val Ile Thr Gln Ala
195 200 205

Cys Pro Lys Val Thr Phe Glu Pro Ile Pro Ile His Tyr Cys Ala Pro
210 215 220

Ala Gly Phe Ala Ile Leu Lys Cys Asn Glu Asp Lys Phe Asn Gly Thr
225 230 235 240

Gly Pro Cys Lys Asn Val Ser Thr Val Gln Cys Thr His Gly Ile Arg
245 250 255

Pro Thr Val Ser Thr Gln Leu Leu Leu Asn Gly Ser Leu Ala Lys Glu
260 265 270

Glu Val Ile Ile Arg Ser Ala Asn Leu Ser Asp Asn Ala Lys Ile Ile
275 280 285

Ile Val Gln Leu Lys Asp Pro Val Glu Ile Asn Cys Thr Arg Pro Asn
290 295 300

Asn Asn Thr Arg Lys Ser Ile Asn Leu Gly Pro Gly Arg Ala Phe Tyr
305 310 315 320

Ala Thr Gly Asp Ile Ile Gly Asp Ile Arg Gln Ala His Cys Asn Ile
325 330 335

-continued

```
Ser Arg Ala Lys Trp Asn Asp Thr Leu Arg Glu Ile Ala Lys Lys Leu
            340                 345                 350

Ala Glu Gln Phe Asn Asn Arg Thr Ile Val Phe Asn Gln Ser Ser Gly
        355                 360                 365

Gly Asp Pro Glu Ile Val Met His Ser Phe Asn Cys Ala Gly Glu Phe
    370                 375                 380

Phe Tyr Cys Asp Thr Ser Gln Leu Phe Asn Ser Thr Trp Asn Ser Asn
385                 390                 395                 400

Ser Thr Trp Asn Asp Thr Asn Asn Asn Asn Ser Thr Glu Lys Ile Ile
                405                 410                 415

Leu Ser Cys Arg Ile Arg Gln Ile Ile Asn Arg Trp Gln Glu Val Gly
            420                 425                 430

Lys Ala Met Tyr Ala Pro Pro Ile Ser Gly Pro Ile Lys Cys Ser Ser
        435                 440                 445

Asn Ile Thr Gly Leu Leu Leu Ala Arg Asp Gly Gly Asn Glu Thr Asn
    450                 455                 460

Val Thr Glu Thr Phe Arg Pro Ala Gly Gly Asp Met Arg Asp Asn Trp
465                 470                 475                 480

Arg Ser Glu Leu Tyr Lys Tyr Lys Val Val Gln Ile Glu Pro Leu Gly
                485                 490                 495

Ile Ala Pro Thr Lys Ala Lys Arg Arg Val Val Gln Arg Glu Lys Arg
            500                 505                 510

Ala Val Gly Met Leu Gly Ala Met Phe Leu Gly Phe Leu Gly Ala Ala
        515                 520                 525

Gly Ser Thr Ile Gly Ala Ala Ser Met Thr Leu Thr Val Gln Ala Arg
    530                 535                 540

Gln Leu Leu Ser Gly Ile Val Gln Gln Gln Asn Asn Leu Leu Arg Ala
545                 550                 555                 560

Ile Glu Ala Gln Gln His Met Leu Gln Leu Thr Val Trp Gly Ile Lys
                565                 570                 575

Gln Leu Gln Ala Arg Val Leu Ala Val Glu Arg Tyr Leu Lys Asp Gln
            580                 585                 590

Gln Leu Leu Gly Ile Trp Gly Cys Ser Gly Lys Leu Ile Cys Thr Thr
        595                 600                 605

Ala Val Pro Trp Asn Thr Ser Trp Ser Asn Lys Ser Leu Asn Tyr Ile
    610                 615                 620

Trp Asp Asn Met Thr Trp Met Glu Trp Glu Arg Glu Ile Asp Asn Tyr
625                 630                 635                 640

Thr Ser Leu Ile Tyr Thr Leu Ile Glu Glu Ser Gln Asn Gln Gln Glu
                645                 650                 655

Lys Asn Glu Leu Glu Leu Leu Glu Leu Asp Lys Trp Gly Ser Leu Trp
            660                 665                 670

Asn Trp Phe Ser Ile Ser Asn Trp Leu Trp Tyr Ile Arg Ile Phe Ile
        675                 680                 685

Ile Ile Val Gly Gly Leu Val Gly Leu Arg Ile Val Phe Thr Val Leu
    690                 695                 700

Ser Ile Val Asn Arg Val Arg Gln Gly Tyr Ser Pro Leu Ser Phe Gln
705                 710                 715                 720

Thr Arg Leu Pro Ala Thr Gln Arg Gly Gln Pro Asp Arg Pro Glu Gly
                725                 730                 735

Ile Glu Glu Glu Gly Gly Glu Arg Asp Arg Ala Arg Ser Ile Arg Leu
            740                 745                 750
```

```
Val Asp Gly Phe Leu Ala Leu Phe Trp Asp Asp Leu Arg Ser Leu Cys
        755                 760                 765

Leu Phe Ser Tyr His Arg Leu Arg Asp Leu Leu Leu Ile Val Ala Arg
    770                 775                 780

Ile Val Glu Leu Leu Gly His Arg Gly Trp Glu Ile Leu Lys Tyr Trp
785                 790                 795                 800

Trp Asn Leu Leu Gln Tyr Trp Arg Gln Glu Leu Lys Lys Ser Ala Val
                805                 810                 815

Ser Leu Leu Asn Thr Thr Ala Ile Val Val Ala Glu Gly Thr Asp Arg
            820                 825                 830

Ile Ile Glu Val Val Gln Arg Ala Tyr Arg Ala Phe Leu His Ile Pro
        835                 840                 845

Arg Arg Ile Arg Gln Gly Leu Glu Arg Ala Leu Leu
    850                 855                 860
```

<210> SEQ ID NO 61
<211> LENGTH: 2622
<212> TYPE: DNA
<213> ORGANISM: Artificial Sequence
<220> FEATURE:
<223> OTHER INFORMATION: Env Clade B THRO.18 DNA Sequence

<400> SEQUENCE: 61

```
atgagagtca aaggaatcaa gaagagtttt cagcactggt ggaaatgggg aacaatgctg     60

ctgggaatcc tgatgatctg tagcgccact gacaagctgt gggtgaccgt ctactatggc    120

gtgcctgtct ggaaagaagc tgtgaccaca ctgttttgcg caagcgacgc taaggcatac    180

gatacagagg tgcacaatgt ctgggccaca catgcttgcg tgccaactga cccagatccc    240

caggaggtgg tcctggaaaa cgtgactgag aatttcaaca tgtggaagaa caatatggtg    300

gaacagatgc acgaggacat catttcactg tgggatcaga gcctgaagcc ctgcgtgaaa    360

ctgacacctc tgtgcgtcac cctgaattgt acagattata acaatacagc cactaacact    420

accagctccg ctacaactac cgcatctagt gccaacaaga ccgctaaaga ggaagcagtg    480

atgaagaact gttcctttaa tatcacaact aacgtgcggg acaaggtcaa aagagaatac    540

gccctgttct ataatctgga tgtggtcaaa ctggaggaag gggagacttc ttacagactg    600

gtgagctgca acacttccgt ggtcacccag gcttgtccca agatcacctt tgagcctatc    660

ccaattcact attgcgcccc tgctggcttc gcaattctga agtgtaacaa caagaccttc    720

aacgggactg gaccatgcac caacgtgagt acagtccagt gtactcatgg catcaaaccc    780

gtggtctcta cccagctgct gctgaatggg agtctggccg agggcgggga agtgatgatt    840

cgcagcgcaa acttcactaa caatgccaag accatcattg tgcagctgtc aaaaagcgtc    900

gccatcaact gcacccggcc taacaataac acatccaagt ctattcacat gggcccagga    960

ggcgctttct ttgcaaccgg gaggatcatt ggagacatcc gcaaagccta ctgtaccgtg   1020

aatggcacag agtggaacac cacactgagg cagattgtgg aaaagttcaa gaaacagttt   1080

ggggagaata agaccatcgt gttcaaacca tcagccgggg gagatcccga aattgtgaca   1140

catagcttta actgcggcgg ggagttcttt tactgtaata ctaccaacct gttcaattca   1200

agctccacag agctgaatag cacttggtcc ggaaattcta acgacaccgg caagaacgat   1260

accatcacac tgccatgccg gatcaagcag atcattaata tgtggcagca agtgggcaag   1320

gccatgtatg ctccccctat cagcgggaaa attaattgtc tgtccaacat caccggactg   1380

ctgctgacaa gggacggagg ctctgatggg ggaagtaaaa attctagtaa aaacgaaact   1440
```

-continued

```
ggaaccgaga tcttccgccc tggcggggga gacatgagag ataactggag gtccgaactg   1500

tacaagtata aagtggtccg gatcgagcct ctgggagtgg caccaacaaa ggctaaacgg   1560

agagcagtcc agcgagagaa gcgagacctg ggactggggg ctctgttcct gggatttctg   1620

ggagcagctg ggagtaccat gggagcagcc tcagtgacac tgactgtcca ggccagacag   1680

ctgctgtctg gcatcgtgca gcagcagaat aacctgctga gggcaattga agcccagcag   1740

cacctgctgc agctgaccgt gtggggcatc aagcagctgc aggcacgact gctggctgtg   1800

gagcggtacc tgaaagacca gcagctgctg ggaatctggg gctgcagcgg gaagctgatt   1860

tgtacaacta ccgtgccctg gaataacagt tggtcaaaga acaaaaacata cgagtatatc   1920

tggaataaca tgacttggat cgaatgggag cgcgaaattg ataattacac aggcctgatc   1980

tataacctga ttgaaaaaag ccagaatcag caggagaaga acgagaaaga actgctggag   2040

ctggacaagt gggatagtct gtggtcatgg ttcagcatca ccaattggct gtggtacatc   2100

aagatcttca tcatgattgt gggcgggctg atcgggctga gaatcgtgtt cgctgtcctg   2160

tccatcgtga acagggtccg ccagggatat tccccccctgt ctttccagac caggctgcca   2220

gcacctcgcg ggccagaccg acccgaagga atcgaggaag agggaggcga gcgagaccgg   2280

gatagatctg gccctctggt gaatgggttc ctggccctga tttgggtcga cctgcggtcc   2340

ctgtgcctgt tttcttacca taggctgcgc gatctgctgc tgatcgtggc acgcattgtc   2400

gaactgctgg gactgcgagg atgggaggcc ctgaaatact ggtggaacct gctgcagtat   2460

tggtcccagg agctgaagaa tagtgccgtg tcactgctga acgcaactgc catcgctgtc   2520

gcagaaggca ccgatagaat cattgagatt ctgcagaggg tgggacgcgc cattctgcat   2580

atccccaccc gcattcgcca gggactggaa agagctctgc tg                      2622
```

<210> SEQ ID NO 62
<211> LENGTH: 874
<212> TYPE: PRT
<213> ORGANISM: Artificial Sequence
<220> FEATURE:
<223> OTHER INFORMATION: Env Clade B THRO.18 Amino Acid Sequence

<400> SEQUENCE: 62

```
Met Arg Val Lys Gly Ile Lys Lys Ser Phe Gln His Trp Trp Lys Trp
1               5                   10                  15

Gly Thr Met Leu Leu Gly Ile Leu Met Ile Cys Ser Ala Thr Asp Lys
            20                  25                  30

Leu Trp Val Thr Val Tyr Tyr Gly Val Pro Val Trp Lys Glu Ala Val
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asp Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Tyr Asn Asn Thr Ala Thr Asn Thr Thr Ser Ser Ala
    130                 135                 140

Thr Thr Thr Ala Ser Ser Ala Asn Lys Thr Ala Lys Glu Glu Ala Val
145                 150                 155                 160
```

-continued

```
Met Lys Asn Cys Ser Phe Asn Ile Thr Thr Asn Val Arg Asp Lys Val
                165                 170                 175

Lys Arg Glu Tyr Ala Leu Phe Tyr Asn Leu Asp Val Val Lys Leu Glu
            180                 185                 190

Glu Gly Glu Thr Ser Tyr Arg Leu Val Ser Cys Asn Thr Ser Val Val
        195                 200                 205

Thr Gln Ala Cys Pro Lys Ile Thr Phe Glu Pro Ile Pro Ile His Tyr
    210                 215                 220

Cys Ala Pro Ala Gly Phe Ala Ile Leu Lys Cys Asn Asn Lys Thr Phe
225                 230                 235                 240

Asn Gly Thr Gly Pro Cys Thr Asn Val Ser Thr Val Gln Cys Thr His
                245                 250                 255

Gly Ile Lys Pro Val Val Ser Thr Gln Leu Leu Leu Asn Gly Ser Leu
            260                 265                 270

Ala Glu Gly Gly Glu Val Met Ile Arg Ser Ala Asn Phe Thr Asn Asn
        275                 280                 285

Ala Lys Thr Ile Ile Val Gln Leu Ser Lys Ser Val Ala Ile Asn Cys
    290                 295                 300

Thr Arg Pro Asn Asn Asn Thr Ser Lys Ser Ile His Met Gly Pro Gly
305                 310                 315                 320

Gly Ala Phe Phe Ala Thr Gly Arg Ile Ile Gly Asp Ile Arg Lys Ala
                325                 330                 335

Tyr Cys Thr Val Asn Gly Thr Glu Trp Asn Thr Thr Leu Arg Gln Ile
            340                 345                 350

Val Glu Lys Phe Lys Lys Gln Phe Gly Glu Asn Lys Thr Ile Val Phe
        355                 360                 365

Lys Pro Ser Ala Gly Gly Asp Pro Glu Ile Val Thr His Ser Phe Asn
    370                 375                 380

Cys Gly Gly Glu Phe Phe Tyr Cys Asn Thr Thr Asn Leu Phe Asn Ser
385                 390                 395                 400

Ser Ser Thr Glu Leu Asn Ser Thr Trp Ser Gly Asn Ser Asn Asp Thr
                405                 410                 415

Gly Lys Asn Asp Thr Ile Thr Leu Pro Cys Arg Ile Lys Gln Ile Ile
            420                 425                 430

Asn Met Trp Gln Gln Val Gly Lys Ala Met Tyr Ala Pro Pro Ile Ser
        435                 440                 445

Gly Lys Ile Asn Cys Leu Ser Asn Ile Thr Gly Leu Leu Leu Thr Arg
    450                 455                 460

Asp Gly Gly Ser Asp Gly Gly Ser Lys Asn Ser Ser Lys Asn Glu Thr
465                 470                 475                 480

Gly Thr Glu Ile Phe Arg Pro Gly Gly Gly Asp Met Arg Asp Asn Trp
                485                 490                 495

Arg Ser Glu Leu Tyr Lys Tyr Lys Val Val Arg Ile Glu Pro Leu Gly
            500                 505                 510

Val Ala Pro Thr Lys Ala Lys Arg Arg Ala Val Gln Arg Glu Lys Arg
        515                 520                 525

Asp Leu Gly Leu Gly Ala Leu Phe Leu Gly Phe Leu Gly Ala Ala Gly
    530                 535                 540

Ser Thr Met Gly Ala Ala Ser Val Thr Leu Thr Val Gln Ala Arg Gln
545                 550                 555                 560

Leu Leu Ser Gly Ile Val Gln Gln Gln Asn Asn Leu Leu Arg Ala Ile
                565                 570                 575
```

-continued

```
Glu Ala Gln Gln His Leu Leu Gln Leu Thr Val Trp Gly Ile Lys Gln
            580                 585                 590

Leu Gln Ala Arg Leu Leu Ala Val Glu Arg Tyr Leu Lys Asp Gln Gln
        595                 600                 605

Leu Leu Gly Ile Trp Gly Cys Ser Gly Lys Leu Ile Cys Thr Thr Thr
    610                 615                 620

Val Pro Trp Asn Asn Ser Trp Ser Lys Asn Lys Thr Tyr Glu Tyr Ile
625                 630                 635                 640

Trp Asn Asn Met Thr Trp Ile Glu Trp Glu Arg Glu Ile Asp Asn Tyr
                645                 650                 655

Thr Gly Leu Ile Tyr Asn Leu Ile Glu Lys Ser Gln Asn Gln Gln Glu
            660                 665                 670

Lys Asn Glu Lys Glu Leu Leu Glu Leu Asp Lys Trp Asp Ser Leu Trp
        675                 680                 685

Ser Trp Phe Ser Ile Thr Asn Trp Leu Trp Tyr Ile Lys Ile Phe Ile
    690                 695                 700

Met Ile Val Gly Gly Leu Ile Gly Leu Arg Ile Val Phe Ala Val Leu
705                 710                 715                 720

Ser Ile Val Asn Arg Val Arg Gln Gly Tyr Ser Pro Leu Ser Phe Gln
                725                 730                 735

Thr Arg Leu Pro Ala Pro Arg Gly Pro Asp Arg Pro Glu Gly Ile Glu
            740                 745                 750

Glu Glu Gly Gly Glu Arg Asp Arg Asp Arg Ser Gly Pro Leu Val Asn
        755                 760                 765

Gly Phe Leu Ala Leu Ile Trp Val Asp Leu Arg Ser Leu Cys Leu Phe
    770                 775                 780

Ser Tyr His Arg Leu Arg Asp Leu Leu Leu Ile Val Ala Arg Ile Val
785                 790                 795                 800

Glu Leu Leu Gly Leu Arg Gly Trp Glu Ala Leu Lys Tyr Trp Trp Asn
                805                 810                 815

Leu Leu Gln Tyr Trp Ser Gln Glu Leu Lys Asn Ser Ala Val Ser Leu
            820                 825                 830

Leu Asn Ala Thr Ala Ile Ala Val Ala Glu Gly Thr Asp Arg Ile Ile
        835                 840                 845

Glu Ile Leu Gln Arg Val Gly Arg Ala Ile Leu His Ile Pro Thr Arg
    850                 855                 860

Ile Arg Gln Gly Leu Glu Arg Ala Leu Leu
865                 870
```